US011613767B2

(12) United States Patent
Sun et al.

(10) Patent No.: US 11,613,767 B2
(45) Date of Patent: *Mar. 28, 2023

(54) PRIMARY ALCOHOL PRODUCING ORGANISMS

(71) Applicant: Genomatica, Inc., San Diego, CA (US)

(72) Inventors: Jun Sun, San Diego, CA (US); Anthony P. Burgard, Elizabeth, PA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,976

(22) Filed: May 27, 2020

(65) Prior Publication Data

US 2021/0108232 A1   Apr. 15, 2021

Related U.S. Application Data

(63) Continuation of application No. 16/233,018, filed on Dec. 26, 2018, now abandoned, which is a continuation of application No. 14/987,489, filed on Jan. 4, 2016, now Pat. No. 10,208,320, which is a continuation of application No. 13/168,833, filed on Jun. 24, 2011, now Pat. No. 9,260,729, which is a continuation of application No. 12/398,996, filed on Mar. 5, 2009, now Pat. No. 7,977,084.

(60) Provisional application No. 61/110,500, filed on Oct. 31, 2008, provisional application No. 61/090,171, filed on Aug. 19, 2008, provisional application No. 61/034,146, filed on Mar. 5, 2008.

(51) Int. Cl.

| | |
|---|---|
| *C12P 7/04* | (2006.01) |
| *C12N 9/04* | (2006.01) |
| *C12N 9/02* | (2006.01) |
| *C12N 9/10* | (2006.01) |
| *C12N 9/88* | (2006.01) |
| *C12P 7/02* | (2006.01) |
| *C12N 15/52* | (2006.01) |

(52) U.S. Cl.
CPC ............... *C12P 7/04* (2013.01); *C12N 9/001* (2013.01); *C12N 9/0006* (2013.01); *C12N 9/0008* (2013.01); *C12N 9/1029* (2013.01); *C12N 9/88* (2013.01); *C12N 15/52* (2013.01); *C12P 7/02* (2013.01); *C12Y 101/01001* (2013.01); *C12Y 101/01035* (2013.01); *C12Y 102/0105* (2013.01); *C12Y 203/01009* (2013.01); *C12Y 203/01016* (2013.01); *C12Y 402/01017* (2013.01)

(58) Field of Classification Search
CPC .... C12Y 203/01009; C12Y 203/01016; C12Y 101/01001; C12Y 101/01035; C12Y 402/01017; C12Y 102/0105; C12N 9/0006; C12N 9/1029; C12N 9/88; C12N 9/0008; C12N 9/001; C12N 15/52; C12P 7/02; C12P 7/04
See application file for complete search history.

(56) References Cited

U.S. PATENT DOCUMENTS

| | | | |
|---|---|---|---|
| 3,513,209 A | 5/1970 | Clement Ra | |
| 3,965,182 A | 6/1976 | Worrel | |
| 4,048,196 A | 9/1977 | Broecker et al. | |
| 4,082,788 A | 4/1978 | Mims | |
| 4,301,077 A | 11/1981 | Pesa et al. | |
| 4,652,685 A | 3/1987 | Cawse et al. | |
| 5,079,143 A | 1/1992 | Klein et al. | |
| 5,143,833 A | 9/1992 | Datta | |
| 5,143,834 A | 9/1992 | Glassner et al. | |
| 5,168,055 A | 12/1992 | Datta | |
| 5,173,429 A | 12/1992 | Gaddy et al. | |
| 5,182,199 A | 1/1993 | Hartley | |
| 5,192,673 A | 3/1993 | Jain et al. | |
| 5,403,721 A | 4/1995 | Ward, Jr. et al. | |
| 5,413,922 A | 5/1995 | Matsuyama et al. | |
| 5,416,020 A | 5/1995 | Severson et al. | |
| 5,457,040 A | 10/1995 | Jarry et al. | |
| 5,478,952 A | 12/1995 | Schwartz | |
| 5,487,987 A | 1/1996 | Frost et al. | |
| 5,504,004 A | 4/1996 | Guettler et al. | |
| 5,512,465 A | 4/1996 | Matsuyama et al. | |
| 5,521,075 A | 5/1996 | Guettler et al. | |
| 5,573,931 A | 11/1996 | Guettler et al. | |
| 5,616,496 A | 4/1997 | Frost et al. | |
| 5,686,276 A | 11/1997 | Lafend et al. | |

(Continued)

FOREIGN PATENT DOCUMENTS

| | | |
|---|---|---|
| CN | 1 358 841 | 7/2002 |
| EP | 0 494 078 | 7/1992 |

(Continued)

OTHER PUBLICATIONS

Blank et al., Large-scale 13C-flux analysis reveals mechanistic principles of metabolic network robustness to null mutations in yeast. Genome Biology, 2005, vol. 6:R49, pp. 1-16. (Year: 2005).*

Blasig et al., Degradation of long-chain n-alkanes by yeast Candida maltosa. Appl. Microbiol. Biotechnol., 1988, vol. 28: 589-597. (Year: 1988).*

David et al., Metabolic network driven analysis of genome-wide transcription data from Aspergillus nidulans. (Genome Biology, 2006, vol. 7:RI 08, pp. 1-16. (Year: 2006).*

(Continued)

*Primary Examiner* — Ganapathirama Raghu

(74) *Attorney, Agent, or Firm* — Greenberg Traurig, LLP

(57) ABSTRACT

The invention provides a non-naturally occurring microbial organism having a microbial organism having at least one exogenous gene insertion and/or one or more gene disruptions that confer production of primary alcohols. A method for producing long chain alcohols includes culturing these non-naturally occurring microbial organisms.

28 Claims, 25 Drawing Sheets

(56) References Cited

U.S. PATENT DOCUMENTS

| | | |
|---|---|---|
| 5,700,934 A | 12/1997 | Wolters et al. |
| 5,770,435 A | 6/1998 | Donnelly et al. |
| 5,807,722 A | 9/1998 | Gaddy et al. |
| 5,869,301 A | 2/1999 | Nghiem et al. |
| 5,908,924 A | 6/1999 | Burdette et al. |
| 5,958,745 A | 9/1999 | Gruys et al. |
| 6,117,658 A | 9/2000 | Dennis et al. |
| 6,133,014 A | 10/2000 | Mukouyama et al. |
| 6,136,577 A | 10/2000 | Gaddy et al. |
| 6,159,738 A | 12/2000 | Donnelly et al. |
| 6,187,569 B1 | 2/2001 | Bramucci et al. |
| 6,214,592 B1 | 4/2001 | Crouzet et al. |
| 6,274,790 B1 | 8/2001 | Kunst et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,353,100 B1 | 3/2002 | Guit et al. |
| 6,432,686 B1 | 8/2002 | Bulthuis et al. |
| 6,448,061 B1 | 9/2002 | Pan et al. |
| 6,455,284 B1 | 9/2002 | Gokarn et al. |
| 6,660,857 B2 | 12/2003 | Agterberg et al. |
| 6,686,194 B1 | 2/2004 | Mutzel et al. |
| 6,686,310 B1 | 2/2004 | Kourtakis et al. |
| 6,743,610 B2 | 6/2004 | Donnelly et al. |
| 6,852,517 B1 | 2/2005 | Suthers et al. |
| 7,127,379 B2 | 10/2006 | Palsson et al. |
| 7,186,541 B2 | 3/2007 | Gokarn et al. |
| 7,223,567 B2 | 5/2007 | Ka-Yiu et al. |
| 7,241,594 B2 | 7/2007 | Lee et al. |
| 7,244,610 B2 | 7/2007 | San et al. |
| 7,256,016 B2 | 8/2007 | San et al. |
| 7,262,046 B2 | 8/2007 | Ka-Yiu et al. |
| 7,285,402 B2 | 10/2007 | Gaddy et al. |
| 7,309,597 B2 | 12/2007 | Liao et al. |
| 7,371,558 B2 | 5/2008 | Cervin et al. |
| 7,393,676 B2 | 7/2008 | Gorkarn et al. |
| 7,432,091 B2 | 10/2008 | Yukawa et al. |
| 7,569,375 B2 | 8/2009 | Stampfer et al. |
| 7,569,380 B2 | 8/2009 | San et al. |
| 7,901,915 B2 | 3/2011 | Symes et al. |
| 7,923,225 B2 | 4/2011 | Mueller et al. |
| 7,943,356 B2 | 5/2011 | Daussmann et al. |
| 7,947,483 B2 * | 5/2011 | Burgard .............. C12P 7/18 435/252.1 |
| 8,110,093 B2 | 2/2012 | Friedman et al. |
| 8,110,670 B2 * | 2/2012 | Hu .................. C12N 9/001 536/23.2 |
| 8,129,154 B2 | 3/2012 | Burk et al. |
| 8,183,028 B2 | 5/2012 | Alibhai et al. |
| 9,260,729 B2 * | 2/2016 | Sun .................. C12N 15/52 |
| 10,208,320 B2 * | 2/2019 | Sun .................. C12P 7/04 |
| 2002/0012939 A1 | 1/2002 | Palsson et al. |
| 2002/0040123 A1 | 4/2002 | Patil et al. |
| 2002/0106358 A1 | 8/2002 | Hopwood et al. |
| 2002/0168654 A1 | 11/2002 | Maranas |
| 2003/0028915 A1 | 2/2003 | Tilton et al. |
| 2003/0032153 A1 | 2/2003 | Yamamoto et al. |
| 2003/0059792 A1 | 3/2003 | Palsson et al. |
| 2003/0087381 A1 | 5/2003 | Gokarn |
| 2003/0113886 A1 | 6/2003 | Brzostowicz et al. |
| 2003/0170836 A1 | 9/2003 | Bramucci et al. |
| 2003/0182678 A1 | 9/2003 | Mitsky et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0152159 A1 | 8/2004 | Causey et al. |
| 2005/0042736 A1 | 2/2005 | San et al. |
| 2005/0079482 A1 | 4/2005 | Maranas et al. |
| 2005/0250135 A1 | 11/2005 | Klaenhammer et al. |
| 2005/0287655 A1 | 12/2005 | Tabata et al. |
| 2006/0035348 A1 | 2/2006 | Gulevich et al. |
| 2006/0073577 A1 | 4/2006 | Ka-Yiu et al. |
| 2006/0099578 A1 | 5/2006 | Wallace et al. |
| 2006/0110810 A1 | 5/2006 | Rajgarhia et al. |
| 2006/0172399 A1 | 8/2006 | Nomoto et al. |
| 2006/0281156 A1 | 12/2006 | Aoyama et al. |
| 2007/0022497 A1 | 1/2007 | Cirpus et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto |
| 2007/0092957 A1 | 4/2007 | Donaldson et al. |
| 2007/0111294 A1 | 5/2007 | Burgard et al. |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0261230 A1 | 10/2008 | Liao et al. |
| 2008/0274522 A1 | 11/2008 | Bramucci et al. |
| 2008/0293060 A1 | 11/2008 | Schirmer et al. |
| 2008/0293125 A1 | 11/2008 | Subbian et al. |
| 2009/0047718 A1 | 2/2009 | Blaschek et al. |
| 2009/0061493 A1 | 3/2009 | Trimbur et al. |
| 2009/0068207 A1 | 3/2009 | Breitbart et al. |
| 2009/0075351 A1 | 3/2009 | Burk et al. |
| 2009/0081746 A1 | 3/2009 | Liao et al. |
| 2009/0191593 A1 | 7/2009 | Burk et al. |
| 2009/0246842 A1 | 10/2009 | Hawkins et al. |
| 2009/0305364 A1 | 12/2009 | Burgard et al. |
| 2010/0009419 A1 | 1/2010 | Burk et al. |
| 2010/0068773 A1 | 3/2010 | Marx et al. |
| 2010/0071259 A1 | 3/2010 | Hu et al. |
| 2010/0099925 A1 | 4/2010 | Kharas |
| 2010/0168481 A1 | 7/2010 | Farmer et al. |
| 2010/0199548 A1 | 8/2010 | Cardayre et al. |
| 2010/0221798 A1 | 9/2010 | Schirmer et al. |
| 2010/0235934 A1 | 9/2010 | Friedman et al. |
| 2010/0242345 A1 | 9/2010 | Keasling et al. |
| 2010/0248233 A1 * | 9/2010 | Muller .............. C12P 7/16 435/6.13 |
| 2010/0249470 A1 | 9/2010 | Schirmer et al. |
| 2010/0251601 A1 | 10/2010 | Hu et al. |
| 2010/0274033 A1 | 10/2010 | Sanchez-Riera et al. |
| 2011/0151530 A1 | 6/2011 | Soucaille et al. |
| 2011/0196180 A1 | 8/2011 | Alibhai et al. |
| 2011/0256599 A1 | 10/2011 | Hu et al. |
| 2012/0142979 A1 | 6/2012 | Keasling et al. |

FOREIGN PATENT DOCUMENTS

| | | |
|---|---|---|
| EP | 1 075 482 | 2/2001 |
| EP | 1 473 368 | 11/2004 |
| EP | 1 647 594 | 4/2006 |
| EP | 2017344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 1982/03854 | 11/1982 |
| WO | WO 1999/06532 | 2/1999 |
| WO | WO 1999/058686 | 11/1999 |
| WO | WO 2001/16346 | 3/2001 |
| WO | WO 2002/042418 | 5/2002 |
| WO | WO 2002/055995 | 7/2002 |
| WO | WO 2002/090312 | 11/2002 |
| WO | WO 2003/010322 | 2/2003 |
| WO | WO 2003/106691 | 12/2003 |
| WO | WO 2003/106998 | 12/2003 |
| WO | WO 2004/018621 | 3/2004 |
| WO | WO 2004/062763 | 7/2004 |
| WO | WO 2005/026338 | 3/2005 |
| WO | WO 2005/047498 | 5/2005 |
| WO | WO 2005/068643 | 7/2005 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/041269 | 4/2007 |
| WO | WO 2007/050671 | 5/2007 |

(56) References Cited

FOREIGN PATENT DOCUMENTS

| | | |
|---|---|---|
| WO | WO 2007/136762 | 11/2007 |
| WO | WO 2007/141208 | 12/2007 |
| WO | WO 2008/013996 | 1/2008 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/052991 | 5/2008 |
| WO | WO 2008/080124 | 7/2008 |
| WO | WO 2008/089102 | 7/2008 |
| WO | WO 2008/098227 | 8/2008 |
| WO | WO 2008/119082 | 10/2008 |
| WO | WO 2008/121701 | 10/2008 |
| WO | WO 2008/131286 | 10/2008 |
| WO | WO 2008/137403 | 11/2008 |
| WO | WO 2008/143704 | 11/2008 |
| WO | WO 2008/152016 | 12/2008 |
| WO | WO 2009/013158 | 1/2009 |
| WO | WO 2009/013159 | 1/2009 |
| WO | WO 2009/013160 | 1/2009 |
| WO | WO 2009/014437 | 1/2009 |
| WO | WO 2009/023493 | 2/2009 |
| WO | WO 2009/031766 | 3/2009 |
| WO | WO 2009/049274 | 4/2009 |
| WO | WO 2009/103026 | 8/2009 |
| WO | WO 2009/111513 | 9/2009 |
| WO | WO 2009/111672 | 9/2009 |
| WO | WO 2009/113853 | 9/2009 |
| WO | WO 2009/113855 | 9/2009 |
| WO | WO 2009/131040 | 10/2009 |
| WO | WO 2010/023206 | 3/2010 |
| WO | WO 2010/062480 | 6/2010 |

OTHER PUBLICATIONS

Herrgard MJ., Reconstruction and Systems Analysis of Genome-Scale Metabolic and Regulatory Networks in *Saccharomyces cerevisiae*. Doctoral Thesis, 2004, Univ., California, San Diego, pp. 1-364. (Year: 2004).*

Jenkins et al., Subcellular Fractionation of Candidu stellatoidea after Growth with Glucose or n-Hexadecane. J. Gen. Microbiol., 1983, 1171-1185. (Year: 1983).*

Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).

Abe et al., "Discovery of amide (peptide) bond synthetic activity in Acyl-CoA synthetase," *J. Biol. Chem.* 283(17):11312-11321 (2008).

Aberhart et al., "Stereospecific hydrogen loss in the conversion of [21-1-7]isobutyrate to 0-hydroxyisobutyrate in Pseudomonas putida. The stereochemistry of [3-hydroxyisobutyrate dehydrogenase," *J. Chem. Soc.* [Perkin]] 6:1404-1406 (1979).

Abiko et al., "Localization of Nad-isocitrate dehydrogenase and glutamate dehydrogenase in rice roots: candidates for providing carbon skeletons to Nadh-glutamate synthase," *Plant Cell Physiol* 46:1724-1734 (2005).

Abo-Dalo et al., "A novel member of the Gcns-related N-acetyltransferase superfamily from Caenorhabditis elegans preferentially catalyses the N-acetylation of thialysine [S-(2-aminoethyl)-L-cysteine]," *Biochem. J.* 384:129-137 (2004).

Adams et al., "Oxidoreductase-type enzymes and redox proteins involved in fermentative metabolisms of hyperthermophilic Archaea," *Adv. Protein Chem.* 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri et al., "Enoyl-CoA Hydratase: Reaction, Mechanism, and Inhibition," *Bioorg. Med. Chem.* 11(1):9-20 (2003).

Ahmed et al., "Fermentation of Biomass-Generated Synthesis Gas: Effects of Nitric Oxide," *Biotechol. Bioeng* 97:1080-1086 (2007).

Ahmed et al., "Effects of biomass-generated producer gas constituents on cell growth, product distribution and hydrogenase activity of Clostridium carboxidivorans P7T," *Biomass Bioenergy* 30(7):665-672 (2006).

Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).

Akatsuka et al., "The Serratia marcescens bioH gene encodes an esterase," *Gene* 302(1-2):185-192 (2003).

Akhtar et al., "Construction of a synthetic YdbK-dependent pyruvate:H2 pathway in *Escherichia coli* BL21(DE3)," *Metab. Eng.* 11(3):139-147 (2009).

Alam et al., "Anaerobic Fermentation Balance of Escherichia coli as Observed by in Vivo Nuclear Magnetic Resonance Spectroscopy," *J. Bacteriol.* 171(11):6213-6217 (1989).

Alber et al., "3-Hydroxypropionyl-coenzyme a synthetase from Metallosphaera sedula, an enzyme involved in autotrophic CO2 fixation," *J. Bacteriol.* 190:1383-1389 (2008).

Alber et al., "Malonyl-coenzyme a reductase in the modified 3-hydroxypropionate cycle for autotrophic carbon fixation in archaeal Metallosphaera and Sulfolobus spp.," *J. Bacteriol.* 188(24):8551-8559 (2006).

Alber et al., "Propionyl-coenzyme a synthase from Chloroflexus aurantiacus, a key enzyme of the 3-hydroxypropionate cycle for autotrophic CO2 fixation," *J. Biol. Chem.* 277:12137-12143 (2002).

Alber et al., "Study of an alternate glyoxylate cycle for acetate assimilation by Rhodobacter sphaeroides," *Mol. Microbiol.* 61(2):297-309 (2006).

Alberty, Biochemical thermodynamics. *Biochim. Biophys. Acta* 1207:1-11 (1994).

Aldor et al., "Metabolic engineering of poly(3-hydroxybutyrate-co-3-hydroxyvalerate) composition in recombinant Salmonella enterica serovar typhimurium," *Biotechnol. Bioeng.* 76(2):108-114 (2001).

Aldor et al., "Metabolic Engineering of a Novel Propionate-Independent Pathway for the Production of Poly(3-Hydroxybutyrate-co-3-Hydroxyvalerate) in Recombinant Salmonella enterica Serovar Typhimurium," *Appl. Environ. Microbiol.* 68(8):3848-3854 (2002).

Aldrich Catalog, Sigma-Aldrich Company, Milwaukee, WI, p. 481 (2002).

Aldrich et al., "Cloning and complete nucleotide sequence determination of the catB gene encoding cis,cis-muconate lactonizing enzyme," *Gene* 52:185-195 (1987).

Alexeeva et al., "Requirement of ArcA for redox regulation in escherichia coli under microaerobic but not anaerobic or aerobic conditions," *J. Bacteriol* 185(1):204-209 (2003).

Alexson et al., "Nadh-sensitive propionyl-coA hydrolase in brown-adipose-tissue mitochondria of the rat," *Biochim. Biophys. Acta* 1005(1):13-19 (1989).

Alhapel et al., "Molecular and functional analysis of nicotinate catabolism in Eubacterium barkeri," *Proc. Natl. Acad. Sci. USA* 103(33):12341-12346 (2006).

Allan et al., "y-hydroxybutyrate accumulation in Arabidopsis and tobacco plants is a general response to abiotic stress: putative regulation by redox balance and glyoxylate reductase isoforms," *J. Exp. Bot.* 59(9):2555-2564 (2008).

Alper et al., "Construction of lycopene-overproducing E. coli strains by combining systematic and combinatorial gene knockout targets," *Nat. Biotechnol.* 23(5):612-616.

Alper et al., "Identifying gene targets for the metabolic engineering of lycopene biosynthesis in *Escherichi coli*," *Metab. Eng*, 7(3):155-164 (2005).

Alper et al., "Engineering yeast transcription machinery for improved ethanol tolerance and production," *Science* 314(5805):1565-1568 (2006).

Altamirano et al., "Decoupling cell growth and product formation in Chinese hamster ovary cells through metabolic control," *Biotechnol. Bioeng*, 76(4):351-360 (2001).

Altmiller et al., "Purification and properties of dihydroxy acid dehydratase from soluble and mitochondrial fractions of Neurospora crassa," *Arch. Biochem. Biophys.* 138:160-170 (1970).

Amann et al., "Tightly regulated tac promoter vectors useful for the expression of unfused and fused proteins in *Escherichia coli*," *Gene* 69:301-315 (1988).

Andersen et al., "Cloning of the IysA gene from Mycobacterium tuberculosis," *Gene* 124(1):105-109 (1993).

(56) References Cited

OTHER PUBLICATIONS

Andersen et al., "A gene duplication led to specialized 17-aminobutyrate and β-alanine aminotransferase in yeast," *Febs J.* 274:1804-1817 (2007).
Anderson et al., "Occurrence, metabolism, metabolic role, and industrial uses of bacterial polyhydroxyalkanoates," *Microbiol. Rev.* 54(4):450-472 (1990).
Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).
Andersson et al., "Effect of different carbon sources on the production of succinic acid using metabolically engineered *Escherichia coli*," *Biotechnol. Prog.* 23(2):381-388 (2007).
Andreesen et al., "Formate Dehydrogenase of Clostridium thermoaceticum: Incorporation of Selenium-75, and the Effects of Selenite, Molybate, and Tungstate on the Enzyme," *J. Bacteriol.* 116(2):867-873 (1973).
Aneja et al., "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).
Angrand et al., "Simplified generation of targeting constructs using ET recombination," *Nucleic Acids Res.* 27(17):e16 (1999).
Ansorge et al., "Production of Recombinant L-Leucine Dehydrogenase from Bacillus cereus in Pilot Scale Using the Runaway Replication System E. coli[pIET98]," *Biotechnol. Bioeng.* 68:557-562 (2000).
Aoshima et al., "A novel biotin protein required for reductive carboxylation of 2-oxoglutarate by isocitrate dehydrogenase in Hydrogenobacter thermophilus TK-6," *Mol. Microbiol.* 51(3):791-798 (2004).
Aoshima et al., "Nondecarboxylating and decarboxylating isocitrate dehydrogenases: oxalosuccinate reductas as an ancestral form of isocitrate dehydrogenase," *J. Bacteriol.* 190(6):2050-2055 (2008).
Aoshima et al., "A novel enzyme, citryl-CoA lyase, catalysing the second step of the citrate cleavage reaction in Hydrogenobacter thermophilus Tk-6," *Mol. Microbiol.* 52(3):763-770 (2004).
Aoshima et al., "A novel enzyme, citryl-CoA synthetase, catalysing the first step of the citrate cleavage reaction in Hydrogenobacter thermophilus Tk-6," *Mol. Microbiol.* 52(3):751-761 (2004).
Aoshima et al., "A novel oxalosuccinate-forming enzyme involved in the reductive carboxylation of 2-oxoglutarate in Hydrogenobacter thermophilus Tk-6," *Mol. Microbiol.* 62(3):748-759 (2006).
Aoshima, "Novel enzyme reactions related to the tricarboxylic acid cycle: phylogenetic/functional implications and biotechnological applications," *Appl. Microbiol. Biotechnol.* 75(2):249-255 (2007).
Aragon et al., "A survey of Enzymes Which Generate or Use Acetoacetyl Thioesters in Rat Liver," *J. Biol. Chem.* 258(8):4725-4733 (1983).
Arendsen et al., "Nitrate-Dependent Regulation of Acetate Biosynthesis and Nitrate Respiration by clostridium thermoaceticum," *J. Bacteriol.* 181:1489-1495 (1999).
Argyrou et al., "Kinetic and chemical mechanism of Mycobacterium tuberculosis 1-deoxy-D-xylulose-5-phosphate isomeroreductase," *Biochemistry* 43:4375-4384 (2004).
Arikawa et al., "Soluble fumarate reductase isoenzymes from Saccharomyces cerevisiae are required for anaerobic growth," *Fems Microbiol. Lett.* 165:111-116 (1998).
Aristidou et al., "Metabolic Engineering of Escherichia coli to Enhance Recombinant Protein Production through Acetate Reduction," *Biotechnol. Prog,* 11(4):475-478 (1995).
Aristidou et al., "Metabolic flux analysis of *Escherichia coli* expressing the Bacillus subtilis Acetolactate Synthase in Batch and Continuous Cultures," *Biotechnol Bioeng.* 63(6):737-749 (1999).
Armstrong et al., "Steroselectivity and sterospecificity of the a,(3-dihydroxyacid dehydratase from Salmonella typhimurium," *Biochim. Biophys. Acta* 498:282-293 (1977).
Arps et al., "Genetics of serine pathway enzymes in Methylobacterium extorquens AM1: phosphoenolpyruvate carboxylase and malyl coenzyme a lyase," *J. Bacteriol.* 175:3776-. 3783 (1993).

Asano et al., "Crystalline 3-methylaspartase from a facultative anaerobe, *Escherichia coli* strain YG1002," *Fems Microbiol. Lett.* 118(3):255-258 (1994).
Asano et al., "Alteration of substrate specificity of aspartase by directed evolution,"*Biomol. Eng,* 22(1-3):95-101 (2005).
Asanuma et al., "Characterization and transcription of the genes encoding enzymes involved in butyrate production in Butyrivibrio fibrisolvens," *Curr. Microbiol.* 45:203-207.
Ashiuchi et al., "Biochemical evidence that Escherichia coli hyi (orf b0508, gip) gene encodes hydroxypyruvate isomerase," *Biochim. Biophys. Acta.* 1435(1-2):153-159 (1999).
Asuncion et al., "Overexpression, purification, crystallization and data collection of 3-methylaspartase from Clostridium tetanomorphum," *Acta. Crystallogr. D. Biol. Crystallogr.* 57(Pt 5):731-733 (2001).
Asuncion, et al., "The structure of 3-methylaspartase from Clostridium tetanomorphum functions via the common enolase chemical step," *J. Biol. Chem.* 277(10):8306-8311.
Atsumi et al., "Metabolic engineering of Escherichia coli for 1-butanol production," *Metab. Eng,* 10(6):305-311 (2007).
Atsumi et al., "Non-fermentative pathways for synthesis of branched-chain higher alcohols as biofuels," *Nature* 451(7174):86-89 (2008).
Atteia et al., "Pyruvate formate-lyase and a novel route of eukaryotic Atp synthesis in Chlamydomonas mitochondria," *J. Biol. Chem.* 281:9909-9918 (2006).
Auerbach et al., "Lactate dehydrogenase from the hyperthermophilic bacterium thermotoga maritima: the crystal structure at 2.1 a resolution reveals strategies for intrinsic protein stabilization," *Structure* 6:769-781 (1998).
Baba et al., "Construction of Escherichia coli K-12 in-frame, single-gene knockout mutants: the Keio collection," *Mol. Syst. Biol.* 2:2006.0008 (2006).
Bachmann et al., "0-Lactam synthetase: a new biosynthetic enzyme," *Proc. Natl. Acad. Sci. USA* 95(16):9082-9086 (1998).
Bai et al., "Lewis-acid assisted cross metathesis of acrylonitrile with functionalized olefins catalyzed by phosphine-free ruthenium carbene complex," *Org. Biomol. Chem.* 3:4139-4142 (2005).
Bailey et al., "Identification, cloning, purification, and enzymatic characterization of Mycobacterium tuberculosis 1-deoxy-D-xylulose 5-phosphate synthase," *Glycobiology* 12:813-820 (2002).
Baird et al., "Enzymes involved in acetoacetate formation in various bovine tissues," *Biochem. J.* 117(4):703-709 (1970).
Baker et al., "Purification and properties of L-erythro-3,5-diaminohexanoate dehydrogenase from Clostridium sticklandii," *Biochemistry* 13(2):292-299 (1974).
Baker et al., "Purification and properties of L-erythro-3,5-diaminohexanoate dehydrogenase from a lysine-fermenting Clostridium," *J. Biol. Chem.* 247:7724-7734.
Bakker et al., "Stoichiometry and compartmentation of NADH metabolism in Saccharomyces cerevisiae," *Fems Microbiol. Rev.* 25: 15-37 (2001).
Banerji et al., "The cloning and characterization of the arom gene of Pneumocystis carinii," *J. Gen. Microbiol.* 139:2901-2914 (1993).
Barber et al., "Structure and regulation of acetyl-CoA carboxylase genes of metazoa," *Biochimica. Biophysica. Acta* 1733:1-28 (2005).
Barker et al., "Microbial synthesis of p-hydroxybenzoic acid from glucose," *Biotechnol. Bioeng.* 76:376-390 (2001).
Barker et al., "Butyryl-CoA:Acetoacetate CoA-transferase from Lysine-fermenting clostridium," *J. Biol. Chem.* 253(4):1219-1225 (1978).
Barker et al., "Pathway of Lysine Degradation in Fusobacterium nucleatum," *J. Bacteriol.* 152(1):201-207 (1982).
Barrick, et al., "Quantitative analysis of ribosome binding sites in E.coli," *Nucleic Acids Res.* 22(7):1287-1295 (1994).
Barrowman et al., "Immunological comparison of microbial Tpp-dependent nonoxidative a-keto acid decarboxylases," *FEMS Microbiol. Lett.* 34:57-60 (1986).
Barthelmebs et al., "Exression of Escherichia coli of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).
Barthelmebs et al., "Inducible metabolism of phenolic acids in Pediococcus pentosaecus is encoded by an autoregulated operon

(56) References Cited

OTHER PUBLICATIONS which involves a new class of negative transcriptional regulator," J. Bacteriol. 182:6724-6731 (2000).
Bartsch et al., "Molecular analysis of two genes of the Escherichia coli gab cluster: nucleotide sequence of the glutamate: succinic semialdehyde transaminase gene (gabT) and characterization of the succinic semialdehyde dehydrogenase gene (gabD)," J Bacteriol. 172(12):7035-7042 (1990).
Bartsch et al., "Only plant-type (GLYK) glycerate kinases produce d-glycerate 3-phosphate," Febs Lett. 582(20):3025-3028 (2008).
Basset et al., "Folate synthesis in plants: the p-aminobenzoate branch is initiated by a bifunctional PabA-PabB protein that is targeted to plastids," Proc. Natl. Acad. Sci U. S. A. 101:1496-1501 (2004).
Battaile et al., "Structures of isobutyryl-CoA dehydrogenase and enzyme-product complex: comparison with isovaleryl- and short-chain acyl-CoA dehydrogenases," J. Biol. Chem. 279:16526-16534 (2004).
Baudin et al., "A simple and efficient method for direct gene deletion in Saccharomyces cerevisiae," Nucleic Acids Res. 21(14):3329-3330 (1993).
Bauer et al., "Improved Expression of Human Interleukin-2 in High-Cell-Density Fermentor Cultures of Escherichia coli K-12 by a Phosphotransacetylase Mutant," Appl. Environ. Microbiol. 56:1296-1302 (1990).
Beatrix et al., "The biotin-dependent sodium ion pump glutaconyl-CoA decarboxylase from Fusobactevium nucleatum (subsp. nucleatum). Comparison with the glutaconyl-CoA decarboxylases from gram-positive bacteria," Arch. Microbiol. 154(4):362-369 (1990).
Beckers et al., "Large-scale mutational analysis for the annotation of the mouse genome," Curr. Opin. Chem. Biol. 6:17-23 (2001).
Benner et al., "Stereospecificity and sterochemical infidelity of acetoacetate decarboxylase (AAD)," J. Am. Chem. So. 103:993-994 (1981).
Benning et al., "New reactions in the crotonase superfamily: structure of methylmalonyl CoA decarboxylase from Escherichia coli," Biochemistry 39:4630-4639 (2000).
Berg et al., "A 3-Hydroxypropionate/4-Hydroxybutyrate Autotrophic Carbon Dioxide Assimilation Pathway in Archaea," Science 318(5857) 1782-1786 (2007).
Bergquist and Gibbs, "Degenerate oligonucleotide gene shuffling," Meth. Mol. Biol. 352:191-204 (2007).
Bergquist et al., "Degenerate oligonucleotide gene shuffling (DOGS) and random drift mutagenesis (Rndm): two complementary techniques for enzyme evolution," Biomol. Eng. 22:63-72 (2005).
Berkovitch et al., "A locking mechanism preventing radical damage in the absence of substrate, as revealed by the x-ray structure of lysine 5,6-aminomutase," Proc. Natl. Acad. Sci. USA 101:15870-15875 (2004).
Berman et al., "The pathway of myo-inositol degradation in Aerobacter aerogenes," J. Biol. Chem. 241(4):800-806 (1966).
Bermejo et al., "Expression of Clostridium acetobutylicum ATCC 824 Genes in Escherichia coli for Acetone Production and Acetate Detoxification," Appl. Environ. Microbiol. 64(3):1079-1085 (1998).
Berrios-Rivera, et al., "Metabolic Engineering of Escherichia coli: Increase of Nadh Availability by Overexpressing an Nad(+)-Dependent Formate Dehydrogenase" Metab Eng 4(3):217-229 (2002).
Berthold et al., "Structure of the branched-chain keto acid decarboxylase (KdcA) from Lactococcus lactis provides insights into structural basis for the chemoselective enantioselective carboligation reaction," Acta Cryst. D63:1217-1224 (2007).
Biellmann et al., "Aspartate-fl-semialdehyde dehydrogenase from Escherichia coli. Purification and general properties," Eur. J. Biochem. 104(1):53-58 (1980).
Binieda et al., "Purification, characterization, DNA sequence and cloning of a pimeloyl-CoA synthetase from Pseudomonas mendocina 35," Biochem. J. 340:793-801 (1999).
Binstock and Schulz, "Fatty acid oxidation complex from Escherichia coli," Methods Enzymol. 71(Pt C):403-411 (1981).

Birch et al., "Cloning, sequencing, and expression of the gene encoding methylmalonyl-coenzyme a mutase from Streptomyces cinnamonensis," J. Bacteriol. 175(11):3511-3519.
Birrer et al., "Electro-transformation of Clostridium beijerinckii Nrrl B-592 with shuttle plasmid pHR106 and recombinant derivatives," Appl. Microbiol. Biotechnol. 41(1):32-38 (1994).
Bisswanger, "Substrate specificity of the Pyruvate Dehydrogenase Complex from Escherichia coli," J. Biol. Chem. 256(2):815-822 (1981).
Bister et al., "Abyssomicin C-A polycyclic antibiotic from a marine Verrucosispora strain as an inhibitor of the p-aminobenzoic acid/tetrahydrofolate biosynthesis pathway," Angew Chem. Int. Ed. Engl. 43(19):2574-2576 (2004).
Blanco et al., "Critical catalytic functional groups in the mechanism of aspartate-fl-semialdehyde dehydrogenase," Acta Cryst. D60:1808-1815 (2004).
Blanco et al., "The role of substrate-binding groups in the mechanism of aspartate-fl-semialdehyde dehydrogenase," Acta Crysta. D60:1388-1395 (2004).
Blaschkowski et al., "Routes of flavodoxin and ferredoxin reduction in Escherichia coli. CoA-acylating pyruvate: flavodoxin and Nadph: flavodoxin oxidoreductases participating in the activation of pyruvate formate-lyase," Eur. J. Biochem. 123(3):563-569.
Blazquez et al., "Identification and analysis of a glutaryl-CoA dehydrogenase-encoding gene and its cognate transcriptional regulator from Azoarcus sp. CIB," Environ. Microbiol. 10(2):474-482 (2008).
Blombach et al., "Corynebacterium glutamicum tailored for high-yeild L-valine production," Appl. Microbiol. Biotechnol. 79(3):471-479 (2008).
Blomqvist et al., "Characterization of the genes of the 2,3-butanediol operons from Klebsiella terrigena and Enterobacter aerogenes," J. Bacteriol. 175:1392-1404 (1993).
Bobik et al., "Hplc assay for methylmalonyl-CoA epimerase," Anal. Bioanal. Chem. 375(3):344-349 (2003).
Bobik et al., "Identification of the human methylmalonyl-CoA racemase gene based on the analysis of prokaryotic gene arrangements. Implications for decoding the human genome," J. Biol. Chem. 276(40):37194-37198 (2001).
Bobik et al., "Propanediol Utilization Genes (pdu) of Salmonella typhimurium: Three Genes for the Propanediol Dehydratase," J. Bacteriol. 179(21):6633-6639 (1997).
Bock et al., "Purification and characterization of two extremely thermostable enzymes, phosphate acetyltransferase and acetate kinase, from the hyperthermophilic eubacterium Thermotoga maritima," J. Bacteriol. 181:1861-1867 (1999).
Boiangiu et al., "Sodium Ion Pumps and Hydrogen Production in Glutamate Fermenting Anaerobic Bacteria," J. Mol. Microbiol. Biotechnol. 10:105-119 (2005).
Boles et al., "Characterization of a glucose-repressed pyruvate kinase (Pyk2p) in Saccharomyces cerevisiae that is catalytically insensitive to fructose-1,6-bisphosphate," J. Bacteriol. 179:2987-2993 (1997).
Bonnarme et al., "Itaconate biosynthesis in Aspergillus terreus," J. Bacteriol. 177(12):3573-3578 (1995).
Bonner et al., "Purification and properties of fatty acyl thioesterase I from Escherichia coli," J. Biol. Chem. 247(10):3123-3133 (1972).
Booth et al., "Structural basis of substrate specificity in human glyoxylate reductase/hydroxypyruvate reductase," J. Mol. Biol. 360(1):178-189 (2006).
Boronat et al., "Experimental evolution of a metabolic pathway for ethylene glycol utilization by Escherichia coli," J. Bacteriol. 153(1):134-139 (1983).
Boronin, et al., "Plasmids specifying c-caprolactam degradation in Pseudomonas strains," Fems Microbiol Lett, 22(3):167-170 (1984).
Bose et al., "Genetic analysis of the methanol- and methylamine-specific methyltransferase 2 genes of Methanosarcina acetivorans C2A," J. Bacteriol. 190(11):4017-. 4026 (2008).
Bott et al., "Methylmalonyl-CoA decarboxylase from Propionigenium modestum. Cloning and sequencing of the structural genes and purification of the enzyme complex," Eur. J. Biochem. 250:590-599 (1997).

(56) References Cited

OTHER PUBLICATIONS

Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).
Bottomley et al., "Cloning, sequencing, expression, purification and preliminary characterization of type Ii dehydroquinase from Helicobacter pylori," *Biochem. J.* 319:559-. 565 (1996).
Bower et al., "Cloning, sequencing, and characterization of the Bacillus subtilis biotin biosynthetic operon," *J. Bacteriol.* 178(14):4122-4130 (1996).
Boylan et al., "L-Threonine Dehydrogenase of *Escherichia Coli* K-12," *Biochem. Biophys. Res. Commun.* 85(1):190-197 (1978).
Boynton et al., "Cloning, sequencing, and expression of clustered genes encoding beta-hydroxybutyryl-coenzyme a (CoA) dehydrogenase, crotonase, and butyryl-CoA dehydrogenase from Clostridium acetobutylicum Atcc 824," *J. Bacteriol.* 178(11):3015-3024 (1996).
Brachmann et al., "Designer deletion strains derived from Saccharomyces cerevisiae S288C: a useful set of strains and plasmids for Pcr-mediated gene disruption and other applications," *Yeast* 14(2):115-132 (1998).
Bradford, "A rapid and sensitive method for the quantitation of microgram quantities of protein utilizing the principle of protein-dye binding," *Anal. Biochem.* 72:248-254.
Branlant, "Nucleotide sequence of Escherichia coli gap gene. Different evolutionary behavior of the Nad+-binding domain and of the catalytic domain of D-glyceraldehyde-3-phosphate dehydrogenase," *Eur. J. Biochem.* 150:61-66 (1985).
Brasen et al., "Unusual Adp-forming acetyl-coenzyme a synthetases from the mesophilic halophilic euryarchaeon Haloarcula marismortui and from the hyperthermophilic crenarchaeon Pyrobaculum aerophilum," *Arch. Microbiol.* 182(4):277-287 (2004).
Braune et al., "The sodium ion translocating glutaconyl-CoA decarboxylase from Acidaminococcus fermentans: cloning and function on the genes forming a second operon," *Mol. Microbiol.* 31(2):473-487 (1999).
Bravo et al., "Reliable, sensitive, rapid and quantitative enzyme-based assay for gamma-hydroxybutyric acid (GHB)," *J. Forensic Sci.* 49:379-387 (2004).
Bredwell et al., "Reactor Design Issues for Synthesis-Gas Fermentations," *Biotechnol. Prog.* 15(5):834-844 (1999).
Breese et al., "Genes coding for the benzoyl-CoA pathway of anaerobic aromatic metabolism in the bacterium Thauera aromatica," *Eur. J. Biochem.* 256(1):148-154 (1998).
Breitkruez et al., "A novel y-hydroxybutyrate dehydrogenase: Identification and expression of an Arabidopsis cDNA and potential role under oxygen deficiency," *J. Biol. Chem.* 278:41552-41556 (2003).
Bremer, "Pyruvate Dehydrogenase, Substrate Specificity and Product Inhibition," *Eur. J. Biochem.* 8:535-540 (1969).
Brey et al., "Cloning of multiple genes involved with cobalamin (Vitamin B12) biosynthesis in Bacillus megaterium," *J. Bacteriol.* 167:623-630 (1986).
Bro et al., "In silico aided metabloic engineering of Saccharomyces cerevisiae for improved bioethanol production," *Metab. Eng* 8(2):102-111 (2006).
Brooke et al., "Gams: a User's Guide. Gams Development Corporation" (1998).
Broun et al., "Catalytic plasticity of fatty acid modification enzymes underlying chemical diversity of plant lipids," *Science* 282:1315-1317 (1998).
Brown et al., "A role for pabAB, a p-aminobenzoate synthase gene of Streptomyces venezuelae ISP5230, in chloramphenicol biosynthesis," *Microbiol.* 142 ( Pt 6):1345-1355.
Brown et al., "Comparative structural analysis and kinetic properties of lactate dehydrogenases from the four species of human malarial parasites," *Biochemistry* 43:6219-6229 (2004).
Brown et al., "The enzymic interconversion of acetate and acetyl-coenzyme a in Escherichia coli," *J. Gen. Microbiol.* 102(2):327-336 (1977).

Browner et al., "Sequence analysis, biogenesis, and mitochondrial import of the a-subunit of rat liver propionyl-CoA carboxylase," *J. Biol. Chem.* 264:12680-12685 (1989).
Bu et al., "The exon-intron organization of the genes (GAD1 and GAD2) encoding two human glutamate decarboxylases (GAD67 and GAD65) suggests that they derive from a common ancestral Gad," *Genomics* 21:222-228 (1994).
Bu et al., "Two human glutamate decarboxylases, 65-kDa Gad and 67-kDa Gad, are each encoded by a single gene," *Proc Natl.Acad Sci U S.A.* 89:2115-2119 (1992).
Buchanan et al., "An extremely thermostable aldolase from Sulfolobus solfataricus with specificity for non-phosphorylated substrates," *Biochem. J.* 343:563-570 (1999).
Buck et al., "Primary structure of the succinyl-CoA synthetase of *Escherichia coli*," *Biochem.* 24(22):6245-6252 (1985).
Buckel et al., "Two pathways of glutamate fermentation by anaerobic bacteria," *J. Bacteriol.* 117(3):1248-1260 (1974).
Buckel et al., "Radical enzymes in anaerobes," *Annu. Rev. Microbiol.* 60:27-49 (2006).
Buckel et al., "Radical species in the catalytic pathways of enzymes from anaerobes," FEMS Microbiol. Rev. 22(5):523-541 (1999).
Buckel et al., "ATPP-Driven electron transfer in enzymatic radical reactions," *Curr. Opin. Chem. Biol.* 8:462-467 (2004).
Buckel et al., "Glutaconate CoA-Transferase from Acidaminococcus fermentans," *Eur. J. Biochem.* 118:315-321 (1981).
Buckel et al., "Radical-mediated dehydration reactions in anaerobic bacteria," *Biol. Chem.* 386:951-959 (2005).
Buckel, "Sodium ion-translocating decarboxylases," *Biochimica. Biophysica. Acta.* 1505:15-27 (2001).
Bueding et al., "Production of a-methylbutyric acid by bacteria-free Ascaris lumbricoides," *J. Biol. Chem.* 193:411-423 (1951).
Buhler and Simon, "On the kinetics and mechanism of enoate reductase," *Hoppe Seylers. Z. Physiol. Chem.* 363(6):609-625 (1982).
Bunch, et al., "The ldhA gene encoding the fermentative lactate dehydrogenase of *Escherichia coli*," *Microbiol.* 143:187-195 (1997).
Burgard and Maranas, "Probing the performance limits of the Escherichia coli metabolic network subject to gene additions or deletions," *Biotechnol. Bioeng.* 74:364-375.
Burgard et al., "Minimal Reaction Sets for *Escherichia coli* Metabolism under Different Growth Requirements and Uptake Environments." *Biotechnol. Prog,* 17:791-797 (2001).
Burgard et al., "Optknock: a bilevel programming framework for identifying gene knockout strategies for microbial strain optimization," *Biotechnol. Bioeng.* 84(6):647-657.
Burke et al, "The Isolation, Characterization, and Sequence of the Pyruvate Kinase Gene of Saccharomyces cerevisiae," *J. Biol. Chem.* 258(4):2193-2201 (1983).
Burks et al., "Stereochemical and Isotopic Labeling Studies of 2-Oxo-hept-4-ene-1, 7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Achlp, in Saccharomyces cerevisiae," *J. Biol. Chem.* 278:17203-17209 (2003).
Buzenet et al., "Purification and properties of 4-Aminobutyrate 2-Ketoglutarate Aminotransferase From Pig Liver," *Biochimica Biophysica Acta* 522:400-411 (1978).
Byrnes et al., "Thermodynamics of reactions catalyzed by anthranilate synthase," *Biophys. Chem.* 84:45-64 (2000).
Cahyanto et al., "Regulation of aspartokinase, asparate semialdehyde dehydrogenase, dihydrodipicolinate synthease and dihydropdipicolinate reductase in Lactobacillus plantarum," *Microbiology.* 152 (Pt 1): 105-112 (2006).
Caldovic et al., "N-Acetylglutamate and its changing role through evolution," *Biochem. J.* 372:279-290 (2003).
Calhoun et al., "Threonine deaminase from Eschericiha coli. I. Purification and properties," *J. Biol. Chem.* 248(10):3511-3516 (1973).
Camara et al., "Characterization of a Gene Cluster Involved in 4-Chlorocatechol Degradation by Pseudomonas reinekei MT1," *J. Bacteriol.* 191(15):4905-4915 (2009).
Campbell et al., "The enigmatic Escherichia coli fadE gene is yafH," *J. Bacteriol.* 184(13):3759-3764 (2002).

(56) References Cited

OTHER PUBLICATIONS

Campbell et al., "A complete shikimate pathway in Toxoplasma gondii: an ancient eukaryotic innovation," *Int. J. Parasitol.* 34:5-13 (2004).
Campbell et al., "A new *Escherichia coli* metabolic competency: growth on fatty acids by a novel anaerobic I3-oxidation pathway," *Mol. Microbiol.* 47(3):793-805 (2003).
Canovas et al., "Characterization of the genes for the biosynthesis of the compatible solute ecotine in the moderately haliphilic bacterium Halomonas elongata Dsm 3043," *Syst. Appl. Microbiol.* 21:487-497 (1998).
Cao et al., "Simultaneous Production and recovery of Fumaric Acid from Immobilized Rhizopus oryzae with a Rotary biofilm Contactor and an Adsorption Column," *Appl. Environ. Microbiol.* 62(8):2926-2931 (1996).
Carlini et al., "Guerbet condensation of methanol with n-propanol to isobutyl alcohol over heterogeneous copper chromite/Mg—Al mixed oxides catalysts," J. Molecular Catalysis. A: *Chemical* 220:215-220 (2004).
Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A: Chem.* 206:409-418 (2003).
Carlini et al., "Selective synthesis of isobutanol by means of the Guebet reaction Part 1. Methanol/n-propanol condensation by using copper based catalytic systems," *J. Mol. Catal. A: Chem.* 184:273-280 (2002).
Carlini et al., "Selective synthesis of isobutanol by means of the Guerbet reaction Part 2. Reaction of methanol/ethanol and methanol/ethanol/n-propanol mixtures over copper based Me0Na catalytic systems," *J. Mol. Catal. A: Chemical* 200:137-146 (2003).
Carpenter et al., "Structure of dehydroquinate synthase reveals an active site capable of multistep catalysis," *Nature* 394:299-302 (1998).
Carretero-Paulet et al., "Expression and molecular analysis of the Arabidopsis Dxr gene encodingl-deoxy-D-xylulose 5-phosphate reductoisomerase, the firszt committed enzyme of the 2-C-methyl-D-erythritiol 4-phosphate pathway," *Plant Physiol.* 129:1581-1591 (2002).
Carta et al., "Production of fumaric acid by fermentation of enzymatic hydrolysates derived from Cassava bagasse," *Biores. Tech.* 68:23-28 (1999).
Cary et al., "Cloning and Expression of Clostridium acetobutylicum Atcc 824 Acetoacetyl-coenzyme a:Acetate/Butyrate:Coenzyme A-Transferase in *Escherichia coli,*" *App. Environ. Microbiol.* 56(6):1576-1583 (1990).
Cary et al., "Cloning and expression of Clostridium acetobutylicum phosphotransbutyrylase and butyrate kinase genes in *Escherichia coli,*" *J. Bacteriol.* 170(10):4613-4618 (1988).
Casero et al., "Spermidine/spermine N1-acetyltransferase-the turning point in polyamine metabolism," *Faseb J.* 7:653-661 (1993).
Caspi et al., "MetaCyc: a multiorganism database of metabolic pathways and enzymes," *Nucleic Acids Res.* 34(Database issue):D511-D516 (2006).
Cavin et al., "Gene cloning, transcriptional analysis, purification, and characterization of phenolic acid decarboxylase from bacillus subtilis," *Appl. Environ. Microbiol.* 64(4):1466-1471 (1998).
Cha et al., "Stereo- and regiospecific cis,cis-muconate cycloisomerization by Rhodococcus rhodochrous N75," *Fems Microbiol. Lett.* 224:29-34 (2003).
Cha et al., "Succinic Thiokinase. I. Purification of the Enzyme from Pig Heart," *J. Biol. Chem.* 239:1961-1967 (1964).
Chandra et al. "Pyruvate decarboxylase: a key enzyme for the oxidative metabolism of lactic acid by Acetobacter pasteurianus," *Arch. Microbiol.* 176:443-451 (2001).
Chang et al., "p-Aminobenzoic acid and chloramphenicol biosynthesis in Streptomyces venezuelae: gene sets for a key enzyme, 4-amino-4-deoxychorismate synthase," *Microbiology* 147:2113-2126 (2001).

Chang et al., "Effects of deletions at the carboxyl terminus of Zymomonas mobills pyruvate decarboxylase on the kinetic properties and substrate specificity," *Biochemistry.* 39(31):9430-9437 (2000).
Chang et al., "Glutarate semialdehyde dehydrogenase of Pseudomonas. Purification, properties, and relation to 1-lysine catabolism," *J. Biol. Chem.* 252(22):7979-7986 (1977).
Chang et al., "Molecular cloning, DNA sequencing, and biochemical analyses of Escherichia coli glyoxylate carboligase. An enzyme of the acetohydroxy acid synthase-pyruvate oxidase family," *J. Biol. Chem.* 268(6):3911-3919 (1993).
Chao et al., "The effects of wall populations on coexistence of bacteria in the liquid phase of chemostat cultures," *J. Gen. Microbiol.* 131(5):1229-1236 (1985).
Chaparro-Riggers et al., "Comparison of Three Enoate Reductases and their Potential Use for Biotransformations," *Adv. Synth. Catal.* 349:1521-1531 (2007).
Charles et al., "The isolation and nucleotide sequence of the complex Arom locus of Aspergillus nidulans," *Nucleic Acids Res.* 14:2201-2213 (1986).
Charmer et al., "A novel class of CoA-transferase involved in short-chain fatty acid metabolism in butyrate-producing human colonic bacteria," *Microbiology* 152:179-185.
Chatterjee et al., "A general model for selectively in olefin cross methathesis," *J. Am. Chem. Soc.* 125(37):11360-11370 (2003).
Chatterjee et al., "Mutation of the ptsG Gene Results in Increased Production of Succinate in Fermentation of Glucose by *Escherichia coli,*" *Appl. Env. Microbiol.* 67:148-.154 (2001).
Chaudhuri et al., "Identification of the active-site lysine residues of two biosynthetic 3-dehydroquinases," *Biochem. J.* 275:1-6 (1991).
Chen et al., "Acetone-Butanol-Isopropanol Production by *Clostridium beijerinckii* (Synonym, Clostridium Butylicum)," *Biotechnology Letters* 8(5):371-376 (1986).
Chen et al., "A novel lysine 2,3-aminomutase encoded by the yodO gene of Bacillus subtilis: characterization and the observation of organic radical intermediates," *Biochem. J.* 348:539-549 (2000).
Chen et al., "Cloning, Sequencing, Heterologous Expression, Purification, and Characterization of Adenosylcobalamin-dependent D-Ornithine Aminomutase from *Clostridium sticklandii,*" *J. Biol. Chem.* 276:44744-44750 (2001).
Chen et al., "The control region of the pdu/cob regulon in Salmonella typhimurium," *J. Bacteriol.* 176:5474-5482 (1994).
Cheng et al., "Mammalian wax biosynthesis. I. Identification of two fatty acyl-Coenzyme a reductases with different substrate specificities and tissue distributions," *J Biol Chem.* 279(36): 37789-37797 (2004).
Cheng et al., "Mammalian wax biosynthesis. II. Expression cloning of wax synthase cDNAs encoding a member of the acyltransferase enzyme family," *J Biol Chem.* 279(36):37798-37807 (2004).
Cheng et al., "Genetic Analysis of a Gene Cluser for Cyclohexanol Oxidation in Acinetobacter sp. Strain SE19 by in Vitro Transportation," *J. Bacteriol.* 182(17):4744-4751 (2000).
Cheng et al., "Structural basis for shikimate-binding specificity of Helicobacter pylori shikimate kinase," *J. Bacteriol.* 187:8156-8163 (2005).
Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).
Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).
Chistoserdova et al., "Methylotrophy in Methylobacterium extorquens AM1 from a genomic point of view," *J. Bacteriol.* 185(10):2980-2987 (2003).
Chistoserdova et al., "Purification and characterization of hydroxypyruvate reductase from the facultative methylotroph Methylobacterium extorquens AM1," *J. Bacteriol.* 173(22):7228-7232 (1991).
Cho et al., "Critical residues for the coenzyme specificity of Nad-dependent 15-hydroxyprostaglandin dehydrogenase," *Arch. Biochem. Biophys.* 419:139-146 (2003).

(56) References Cited

OTHER PUBLICATIONS

Choi et al, "Olefin Metathesis Involving Ruthenium Enoic Carbene Complexes," *J. Am. Chem. Soc.* 123(42):10417-10418 (2001).
Choi et al., "Enhanced production of cis,cis-muconate in a cell-recycle bioreactor," *J. Ferment. Bioeng.* 84:70-76 (1997).
Choi-Rhee et al., "The biotin carboxylase-biotin carboxyl carrier protein complex of Escherichia coli acetyl-CoA carboxylase," *J. Biol. Chem.* 278:30806-30812 (2003).
Chopra et al., "Expression, purification, and biochemical characterization of Mycobacterium tuberculosis aspartate decarboxylase, PanD," *Protein Expr. Purif.* 25:533- 540 (2002).
Chou et al., "Effect of Modulated Glucose Uptake on High-Level Recombinant Protein Production in a Dense Escherichia coli Culture," *Biotechnol. Prog.* 10:644-647 (1994).
Chowdhury et al., "3-Hydroxyisobutyrate dehydrogenase from Pseudomonas putida E23: purification and characterization," *Biosci Biotechnol Biochem*, 60(12):2043-2047.
Chowdhury et al., "Cloning and overexpression of the 3-hydroxyisobutyrate dehydrogenase gene from pseudomonas putida E23," *Biosci. Biotechnol. Biochem.* 67(2):438-441 (2003).
Christenson et al., "Kinetic analysis of the 4-methylideneimidazole-5-one-containing tyrosine aminomutase in enediyne antitumor antibiotic C-1027 biosynthesis," *Biochemistry.* 42:12708-12718 (2003).
Chuakrut et al., "Characterization of a bifunctional archael acyl coenzyme a carboxylase," *J. Bacteriol.* 185:938-947 (2003).
Chumakov et al., "Genetic and physiological data implicating the new human gene G72 and the gene for D-amino acid oxidase in schizophrenia," *Proc. Natl. Acad. Sci. U. S. A.* 99(21):13675-13680 (2002).
Clark et al., "Purification and properties of 5,10-methylenetetrahydrofolate reductase from Clostridium formicoaceticum," *Methods Enzymol.* 122:392-399 (1986).
Clark et al., "Purification and Properties of 5,10-Methylenetetrahydrofolate Reductase, an Iron-sulfur Flavoprotein from Clostridium formicoaceticum," *J. Biol. Chem.* 259(17)10845-10849 (1984).
Clark, et al., "Mutants of *Escherichia coli* defective in acid fermentation," *Appl. Biochem. Biotechnol.* 17:163-173 (1988).
Clark, Progress Report for Department of Energy Grant De-FG02-88ER13941, "Regulation of Alcohol Fermentation in *Escherichia coli*," pp. 1-7 for the period: Jul. 1991-Jun. 1994.
Clarke et al., "Rational construction of a 2-Hydroxyacid Dehydrogenase With New Substrate Specificity," *Biochem. Biophys. Res. Commun.* 148:15-23 (1987).
Clausen et al., "PAD1 encodes phenylarcrylic acid decarboxylase which confers resistance to cinnamic acid in Saccharomyces cerevisiae," *Gene* 142:107-112 (1994).
Cluster ID ELL00000108 Aldehyde dehydrogenase related cluster Aldehyde dehydrogenase, mitochondrial precursor related cluster nr Name Bacillus halodurans genomic DNA, section 2/14 nr Blast Score 4e-55 Sequence Length 2153 No. of ESTs 39 Last Modified Date Jan. 30, 2006.
Cluster ID ELL00000206 L-3-hydroxyacyl-CoA dehydrogenase subunit precursor related cluster Short chain 3-hydroxyacyl-CoA dehydrogenase, mitochondrial precursor related cluster Euglena gracilis L-3-hydroxyacyl-CoA dehydrogenase subunit precursor, mRNA, complete cds Sequence Length 844 No. of ESTs 10 Last Modified Date Jan. 3. 2006.
Cluster ID ELL00000789 Acetyl-CoA acetyltransferase related cluster 3-ketoacyl-CoA thiolase, mitochondrial related cluster Bacillus cereus ATCC 14579 section 14 of 18 of the complete genome Sequence Length 802 No. of ESTs 1 Last Modified Date Dec. 10, 2003.
Cluster ID ELL00001952 Trifunctional enzyme alpha subunit, mitochondrial-like protein related cluster Trifunctional enzyme alpha subunit, mitochondrial precursor (TP-alpha) (78 kDa gastrin- binding prot Shewanella oneidensis Mr-1 section 294 of 457 of the complete genome Sequence Length 1255 No. of ESTs 2 Last Modified Date Dec. 10, 2003.
Cluster ID ELL00002199 Trans-2-enoyl-CoA reductase, mitochondrial precursor related cluster 2-enoyl thioester reductase related cluster Anopheles gambiae ENSANGP00000020213 (ENSANGG00000017724) mRNA, partial cds Sequence Length 1371 No. of ESTs 5 Last Modified Date Jan. 30, 2006.
Cluster ID ELL00002235 pot.cp-encoded menB_367493 naphthoate synthase Cyanidium_caldarium MNL12.10 enoyl-CoA hydratase/isomerase family [Ec:5.3.3.-] Pseudomonas putida KT2440 section 16 of 21 of the complete genome Sequence Length 728 No. of ESTs 3 Last Modified Date Dec. 10, 2003.
Cluster ID ELL00002335 Trans-2-enoyl-CoA reductase, mitochondrial precursor related cluster 2-enoyl thioester reductase related cluster Anopheles gambiae ENSANGP00000020213 (ENSANGG00000017724) mRNA, partial cds Sequence Length 820 No. of ESTs 6 Last Modified Date Jan. 30, 2006.
Cluster ID ELL00002419 L-3-hydroxyacyl-CoA dehydrogenase subunit precursor related cluster Short chain 3-hydroxyacyl-CoA dehydrogenase, mitochondrial precursor related cluster Euglena gracilis L-3-hydroxyacyl-CoA dehydrogenase subunit precursor, mRNA, complete cds Sequence Length 1124 No. of ESTs 10 Last Modified Date Jan. 30, 2006.
Cluster ID ELL00002493 Acetyl-CoA acetyltransferase related cluster 3-ketoacyl-CoA thiolase, mitochondrial related cluster Clostridium acetobutylicum megaplasmid pSOL1, complete sequence Sequence Length 1262 No. of ESTs 10 Last Modified Date Jan. 30, 2006.
Cluster ID ELL00002550 Acetyl-CoA acetyltransferase related cluster 3-ketoacyl-CoA thiolase, mitochondrial related cluster Clostridium tetani E88, section 1 of 10 of the complete genome Sequence Length 1423 No. of ESTs 15 Last Modified Date Jan. 30, 2006.
Cluster ID ELL00002572 aldehyde dehydrogenase Neurospora crassa strain OR74A Aldehyde dehydrogenase related cluster Aldehyde dehydrogenase, mitochondrial precursor related cluster Neurospora crassa strain OR74A Sequence Length 2081 No. of ESTs 45 Last Modified Date Jan. 30, 2006.
Cluster ID ELL00002581 Aldehyde dehydrogenase related cluster Aldehyde dehydrogenase, mitochondrial precursor related cluster Oryza sativa (japonica cultivar-group) cDNA clone:J033038G01, full insert sequence Sequence Length 1934 No. of ESTs 41 Last Modified Date Jan. 30, 2006.
Cluster ID ELL00002648 Trans-2-enoyl-CoA reductase, mitochondrial precursor related cluster Vibrio parahaemolyticus DNA, chromosome 1, complete sequence, 5/11 Sequence Length 670 No. of ESTs 1 Last Modified Date Dec. 10, 2003.
Cluster ID ELL00005926 Trifunctional enzyme alpha subunit, mitochondrial-like protein, putative related cluster Cluster related to UPI0000383599 COG1250: 3-hydroxyacyl-CoA dehydrogenase Photorhabdus luminescens subsp. laumondii TTO1 complete genome; segment 11/17 Sequence Length 467 No. Of ESTs 5 Last Modified Date 2006-01-30.
Cluster ID ELL00006206 pot.cp-encoded menB_9295936 naphthoate synthase Cyanidioschyzon_merolae_strain_10D Cluster related to UPI0000384342 COG1024: Enoyl-CoA hydratase/carnitine racemase Trypanosoma brucei chromosome 3 clone RPCI93-48K5, complete sequence Sequence Length 900 No. Of ESTs 2 Last Modified Date 2006-01-30.
Cluster ID ELL00006286 L-3-hydroxyacyl-CoA dehydrogenase subunit precursor related cluster Short chain 3-hydroxyacyl-CoA dehydrogenase, mitochondrial precursor related cluster Euglena gracilis L-3-hydroxyacyl-CoA dehydrogenase subunit precursor, mRNA, complete cds Sequence Length 813 No. Of ESTs 3 Last Modified Date 2006-01-30.
Cluster ID ELL00006656 L-3-hydroxyacyl-CoA dehydrogenase subunit precursor related cluster Short chain 3-hydroxyacyl-CoA dehydrogenase, mitochondrial precursor related cluster Euglena gracilis L-3-hydroxyacyl-CoA dehydrogenase subunit precursor, mRNA, complete cds Sequence Length 416 No. Of ESTs 1 Last Modified Date 2006-01-30.
Coco et al., "DNA shuffling method for generating highly recombined genes and evolved enzymes," *Nat. Biotechnol.* 19:354-359 (2001).
Coggins et al., "The arom multifunctional enzyme from Neurospora crassa," *Methods Enzymol.* 142:325-341 (1987).

(56) References Cited

OTHER PUBLICATIONS

Colby et al., "Purification and properties of 3-hydroxybutyryl-coenzyme a dehydrogenase from Clostridium beijerinckii ("Clostridium butylicum") NRRL B593," *Appl. Environ. Microbiol.* 58:3297-3302 (1992).
Coleman, "Expression of a glutamate decarboxylase homologue is required for normal oxidative stress tolerance in Saccharomyces cerevisiae," *J. Biol. Chem.* 276:244-250.
Coleman, "Structure and mechanism of alkaline phosphatase," *Annu. Rev. Biophys. Biomol. Struct.* 21:441-483 (1992).
Conrad et al., "D- and L-Isoleucine Metabolism and Regulation of Their Pathways in Pseudomonas Putida," *J. Bacteriol.* 118(1):103-111 (1974).
Cooper, "Glutamate-γ-aminobutyrate transaminase," *Methods Enzymol* 113:80-82.
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.* 272(41):25659-25667 (1997).
Couturier et al., "A Cyclometalated Aryloxy(chloro)neopentylidenetungsten Complex: a Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1992).
Cox, et al., "Development of a metabolic network design and optimization framework incorporating implementation constraints: a succinate production case study," *Metab. Eng.* 8(1):46-57 (2006).
Craney et al., "A synthetic luxCDABE gene cluster optimized for expression in high-Gc bacteria," *Nucleic Acids Res.* 35(6):e46 (2007).
Cunningham et al., "Transcriptional regulation of the aconitase genes (acnA and acnB) of *Escherichia coli*," *Microbiology* 143(Pt 12):3795-3805 (1997).
Cusa et al., "Genetic analysis of a chromosomal region containing genes required for assimilation of allantoin nitrogen and linked glyoxylate metabolism in *Escherichia coli*," *J. Bacteriol.* 181(24):7479-7484 (1999).
Dai et al., "Highly Selective Diels-Alder Reactions of directly Connected Enzyne Dienphiles," *J. Am. Chem. Soc.* 129:645-657 (2007).
Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).
Dal et al., "Transcriptional Organization of Genes for Protocatechuate and quinate Degradation from Acinetobacter sp. Strain ADP1," *Appl. Environ. Microbiol.* 71(2):1025-1034 (2005).
Dangel et al., "Anaerobic metabolism of cyclohexanol by denitrifying bacteria," *Arch. Microbiol.* 150(4):358-362 (1988).
Dangel et al., "Enzyme reactions involved in anaerobic cyclohexanol metabolism by a dentitrifying Psedomonas species," *Arch. Microbiol.* 152:273-279 (1989).
D'Art et al., "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from Escherichia coli," *J. Biol. Chem.* 266(35):23953-23958 (1991).
Das et al., "Characterization of a corrinoid protein involved in the Cl metabolism of strict anaerobic bacterium Moorella thermoacetica," *Proteins* 67(1):167-176 (2007).
Database Reaxys [Online] Elsevier Properties SA; RX-ID nos. 715357 and 5957085; Volmar: Comptes Rendus Hebdomadaires Des Seances De L'Academie Des Sciences, vol. 181; (1925); p. 467 (document printed 04-112011).
Datar et al., "Fermentation of biomass-generated producer gas to ethanol," *Biotechnol. Bioeng.* 86(5):587-594 (2004).
Datsenko et al., "One-step inactivation of chromosomal genes in *Escherichia coli* K-12 using PCR products," *Proc. Natl. Acad. Sci. USA* 97:6640-6645 (2000).
Datta et al., "Covalent structure of biodegradative threonine dehydratase of *Escherichi coli*: homology with other dehydratases," *Proc. Natl. Acad. Sci. USA* (84(2):393-397.
Davey et al., "The metabolism of trans-cyclohexan-1,2-diol by an Acinetobacter species," *Eur. J. Biochem.* 74(1):115-127 (1977).
Davids et al, "Characterization of the N-acetyltransferases respectively responsible for arylalkylamine and diamine acetylation in Ascaris suum," *Mol. Biochem. Parasitol.* 64(2):341-344 (1994).
Davie et al., "Expression and assembly of a functional El component (a2132) of mammalian branched-chain a-ketoacid dehydrogenase complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr Purif* 8:430-438 (1996).
De Bok et al., "Two W-containing formate dehydrogenases ($CO_2$-reductases) involving syntrophic propionate oxidation by Syntrophobacter fumaroxidans," *Eur. J. Biochem.* 270:2476-2485 (2003).
De Crecy et al., "Development of a novel continuous culture device for experimental evolution of bacterial populations," *Appl. Microbiol. Biotechnol.* 77(2): 489-496 (2007).
De La Plaza et al., "Biochemical and molecular characterization of alpha-ketoisovalerate decarboxylase, an enzyme involved in the formation of aldehydes from amino acids by Lactococcus lactis," *Fems Microbiol. Lett.* 238(2):367-374 (2004).
De La Torre et al., "Identification and functional analysis of a prokaryotic-type aspartate aminotransferase: implications for plant amino acid metabolism," *Plant. J.* 46(3):414-425 (2006).
De Mata et al., "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).
De Mendonca et al., "Functional characterization by genetic complementation of aroB-encoded dehydroquinate synthase from Mycobacterium tuberculosis H37Rv and its heterologous expression and purification," *J. Bacteriol.* 189:6246-6252 (2007).
De Miranda et al., "Human serine racemase: molecular cloning, genomic organization and functional analysis," *Gene* 256(1-2):183-188 (2000).
De Smidt, et al., "The alcohol dehydrogenases of Saccharomyces cerevisiae: a comprehensive review," *FEMS Yeast Res.* 8(7):967-78 (2008).
DeWindt et al., "Purification and some properties of hydroxypyruvate isomerase of Bacillus fastidiosus," *Biochim. Biophys. Acta.* 613(2):556-562 (1980).
Deana, "Substrate specificity of a dicarboxyl-CoA: dicarboxylic acid coenzyme a transferase from rat liver mitochondria," *Biochem. Int.* 26(4):767-773 (1992).
Defeyter et al., "Purification and properties of shikimate kinase II from *Escherichia coli* K-12," *J. Bacteriol.* 165:331-333 (1986).
Del Campillo-Campbell et al., "Biotin-requiring Mutants of *Escherichia coli* K-12," *J. Bacteriol.* 94(6):2065-2066 (1967).
Dellomonaco et al., "Engineered reversal of the (3-oxidation cycle for the synthesis of fuels and chemicals," *Nature* 476(7360):355-359 (Published online Aug. 10, 2011).
Dellomonaco et al., "Engineered reversal of the (3-oxidation cycle for the synthesis of fuels and chemicals," Supplementary Information (14 pp.) for: *Nature* 476(7360):355-359 (Published online Aug. 10, 2011).
Deno, "The Diels-Alder Reaction with a, 13, y, 6-Unsaturated Acids," *J. Am. Chem. Soc.* 72:4057-4059 (1950).
Department of Energy, "Top value added chemicals from biomass. Volume I—Results of Screening for Potential Candidates from Sugars and Synthesis Gas," *Biomass.* Aug. 2004.
Desvaux, "Clostridium cellulolyticum: model organism of mesophilic cellulolytic clostridia," *FEMS Microbiol. Rev.* 29(4):741-764 (2005).
Devos et al., "Practical limits of function prediction," *Proteins* 41:98-107 (2000).
Di Gennaro, "Styrene lower catabolic pathway in Pseudomonas fluorescens St: identification and characterization of genes for phenylacetic acid degradation," *Arch. Microbiol.* 188(2):117-125 (2007).

(56) References Cited

OTHER PUBLICATIONS

Diad et al., "Crystal structure of butyrate kinase 2 from Thermotoga maritima, a member of the Askha superfamily of phosphotransferases," *J. Bacteriol.* 191:2521-2529 (2009).

Diad et al., "Crystallization of the butyrate kinase 2 from Thermotoga maritima mediated by vapor diffusion of acetic acid," *Acta Cryst.* D59:1100-1102 (2003).

Dias et al., "Well-Defined Ruthenium Olefin Metathesis Catalyst: Mechanism and Activity," *J. Am. Chem. Soc.* 119(17):3887-3897 (1997).

Diaz et al., "Gene cloning, heterologous overexpression and optimized refolding of the NAD-glutamate dehydrogenase from *Haloferax mediterranei*," *Extremophiles* 10:105-115.

Diderichsen et al., "Cloning of aldB, Which Encodes a-Acetolactate Decarboxylase, an Exoenzyme from bacillus brevis," *J. Bacteriol.* 172(8):4315-4321 (1990).

Dittrich, et al., "Redistribution of Metabolic Fluxes in the Central Aerobic Metabolic Pathway of E. coli Mutant Strains with Deletion of the ackA-pta and poxB Pathways for the Synthesis of Isoamyl Acetate," *Biotechnol Prog* 21(2):627-631 (2005).

Dixon et al., "D-Amino Acid Oxidase. II. Specificity, Competitive Inhibition and Reaction Sequence," *Biochim. Biophys. Acta.* 96: 368-382.

Do et al., "Engineering Escherichia coli for fermentative dihydrogen production: potential role of Nadh-ferredoxin oxidoreductase from the hydrogenosome of anaerobic protozoa," *Appl. Biochem. Biotechnol.* 153(1-3):21-33 (2009).

Do et al., "Growth of rhodospirillum rubrum on synthesis gas: conversion of Co to H2 and Poly-13-hydroxyalkanoate," *Biotechnol. Bioeng* 97(2):279-286 (2007).

Dobbek et al., "Crystal structure of a carbon monoxide dehydrogenase reveals a [Ni-4Fe-5S] cluster," *Science* 293(5533):1281-1285 (2001).

Dombek and Ingram, "Ethanol production during batch fermentation with Saccharomyces cerevisiae: Changes in glycolytic enzymes and internal pH," *Appl Environ Microbiol.* 53:1286-1291 (1987).

Donnelly et al., "Succinic semialdehyde dehydrogenases of Escherichia coli: Their role in the degradation of p-hydroxyphenylacetate and y-aminobutyrate," *Eur. J. Biochem.* 113:555-561 (1981).

Donnelly et al., "Two succinic semialdehyde dehydrogenases are induced when *Escherichia coli* K-12 Is grown on y-aminobutyrate," *J. Bacteriol.* 145:1425-1427 (1981).

Donnelly et al., "A novel fermentation pathway in an *Escherichia coli* mutant producing succinic acid, acetic acid, and ethanol," *App. Biochem. Biotech.* 70-72:187-198.

Dosselaere et al., "A Metabolic Node in Action: Chorismate-Utilizing Enzymes in Microorganisms," *Crit. Rev. Microbiol.* 27(2):75-131 (2001).

Doten et al., "Cloning and Genetic Organization of the pca Gene cluster from Acinetobacter calcoaceticus," *J. Bacteriol.* 169(7):3168-3174 (1987).

Doughty et al., "Purification and properties of d-glycerate 3-kinase from *Escherichia coli*," *J. Biol. Chem.* 241(3):568-572 (1966).

Doyle et al., "Structural Basis for a Change in substrate Specificity: Crystal Structure of S113E Isocitrate Dehydrogenase in a Complex with Isopropylmalate, $Mg^{2+}$ and NAPD," *Biochemistry* 40:4234-4241 (2001).

Drake et al., "Physiology of the thermophilic acetogen Moorella thermoacetica," *Res. Microbiol.* 155(10):869-883 (2004).

Drake, "Acetogenesis, acetogenic bacteria, and the acetyl-CoA "Wood/Ljungdahl" pathway: past and current perspectives," in *Acetogenesis*, H. L. Drake, (ed.), Chapman &. Hall, New York, p. 3-60 (1994).

Drake, "Demonstration of hydrogenase in extracts of the homoacetate-fermenting bacterium Clostridium thermoaceticum," *J. Bacteriol.* 150(2):702-709 (1982).

Draths et al., "Environmentally compatible synthesis of adipic acid from D-glucose," *J. Am. Chem. Soc.* 116:399-400 (1994).

Drevland et al., "Enzymology and Evolution of the Pyruvate Pathway to 2-Oxobutyrate in Methanocaldococcus jannachii," *J. Bacteriol.* 189(12):4391-4400 (2007).

Drewke et al., "4-O-Phosphoryl-L-threonine, a substrate of the pdxC(serC) gene product involved in vitamin B6 biosynthesis," *Febs Lett.* 390:179-182 (1996).

Drewke et al., "Ethanol formation in adh0 mutants reveals the existence of a novel acetaldehyde-reducing activity in Saccharomyces cerevisiae," *J. Bacteriol.* 172:3909-3917.

Driscoll et al., "Sequence Organization and Regulation of the bacillus subtilis menBE Operon," *J. Bacteriol.* 174(15):5063-5071 (1992).

Drummond et al., "Enzymes of ketone body metabolism. II. Properties of an acetoacetate-synthesizing enzyme prepared from ox liver," *J. Biol. Chem.* 235:318-325.

Du et al., "Succinic acid production from wheat using a biorefining strategy," *Appl. Microbiol. Biotechnol.* 76:1263-1270 (2007).

Duarte et al., "Reconstruction and validation of Saccharomyces cerevisiae iND750, a fully compartmentalized genome-scale metabolic model," *Genome Res.* 14(7):1298-1309.

Duckworth et al., "The Binding of Reduced Nicotinamide Adenine Dinucleotide to Citrate Synthase of *Escherichia coli* K12," *Biochemistry* 15(1):108-114 (1976).

Duff et al., "Purification, characterization, and subcellular localization of an acid phosphatase from black mustard cell-suspension cultures: comparison with phosphoenolpyruvate phosphatase," *Arch. Biochem. Biophys.* 286(1):226-232 (1991).

Duncan et al., "The pentafunctional arom enzyme of Saccharomyces cerevisiae is a mosaic of monofunctional domains," *Biochem. J.* 246:375-386 (1987).

Duncan et al., "Acetate utilization and butyryl coenzyme a (CoA):acetate-CoA transferase in butyrate-producing bacteria from the human large intestine," *Appl. Environ. Microbiol.* 68(10):5186-5190 (2002).

Duncombe et al., "Molecular and catalytic properties of the acetoacetyl-coenzyme a thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anerobic mitochondria of the parasitic nematode Ascaris suum," *J. Biol. Chem.* 268(30):22391-. 22396 (1993).

Durner et al., "Accumulation of Poly[(R)-3-Hydroxyalkanoates] Pseudomonas oleovorans during Growth with Octanoate in continuous culture at Different Dilution Rates," *Appl. Environ. Microbiol.* 66(8):3408-3414 (2000).

Durre et al., "Microbial Production of Acetone/Butanol/Isopropanol," in Biotechnology Volume 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Durre et al., "Solventogenic enzymes of Clostridium acetobutylicum: catalytic properties, genetic organization, and transcriptional regulation," *FEMS Microbiol. Rev.* 17:251-262.

Durre, "Biobutanol: an attractive biofuel," *Biotechnol. J.* 2(12):1525-1534 (2007).

Durre, "New insights and novel developments in clostridial acetone/butanol/isopropanol fermentation," *Appl. Microbiol. Biotechnol.* 49:639-648 (1998).

Dusch et al., "Expression of the Corynebacterium glutamicum panD gene encoding 1, aspartate-a-decarboxylase leads to pantothenate overproduction in *Escherichia coli*," *Appl. Environ. Microbiol.* 65(4) 1530-1539 (1999).

Dutscho et al., "Cloning and sequencing of the genes of 2-hydroxyglutaryl-CoA dehydratase from Acidaminococcus fermentans," *Eur. J. Biochem.* 181(3):741-746 (1989).

Dwiarti et al., "Purification and characterization of cis-aconitic acid decarboxylase from Aspergillus terreus TN484-M1," *J. Biosci Bioeng.* 94(1):29-33 (2002).

Dwyer et al., "Proton Abstraction reaction, Steady-State kinetics, and Oxidation-Reduction Potential of Human Glutaryl-CoA Dehydrogenase," *Biochemistry* 39:11488-11499 (2000).

Dykhuizen, "Chemostats used for studying natural selection and adaptive evolution," *Methods Enzymol.* 224:613-631 (1993).

(56) References Cited

OTHER PUBLICATIONS

Eberhard et al., "Evolution of Function in the Crotonase Superfamily: the Stereochemical course of the Reaction catalyzed by 2-Ketocyclohexanecarboxyl-CoA Hydrolase," *J. Am. Chem. Soc.* 126:7188-7189 (2004).

Edegger et al., "Biocatalytic deuterium- and hydrogen-transfer using over-expressed Adh-'A'. enhanced steroselectivity and 2H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol.* 55:296-300 (2001).

Edwards et al., "Metabolic flux balance analysis and the in silico analysis of *Escherichia coli* K-12 gene deletions," *BMC Bioinform.* 1:1 (2000).

Edwards et al., "Systems properties of the Haemophilus influenzae Rd metabolic genotype," *J. Biol. Chem.* 274(25):17410-17416 (1999).

Edwards et al., "The Escherichia coli MG1655 in silico Metabolic Genotype: Its Definition, Characteristics, and Capabilities," *Proc. Natl. Acad. Sci. USA* 97(10):5528-5533 (2000).

Edwards et al., "Metabolic modelling of microbes: the flux-balance approach," *Environ. Microbiol.* 4(3):133-140 (2002).

Edwards et al., "In Silico Predictions of Escherichia coli metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol Bioeng* 99:1392-1406 (2008).

Egland et al., "A cluster of bacterial genes for anaerobic benzene ring biodegradation," *Proc. Natl. Acad. Sci. USA* 94:6484-6489 (1997).

Eikmanns et al., "The phosphoenolpyruvate carboxylase gene of Corynebacterium glutamicum: molecular cloning, nucleotide sequence, and expression." *Mol. Gen. Genet.* 218:330-339 (1989).

Elshahed et al., "Metabolism of Benzoate, Cyclohex-l-ene Carboxylate, and Cyclohexane Carboxylate by "Syntrophus aciditrophicus" Strain Sb in Syntrophic Association with Hz-Using Microorganisms," *Appl. Environ. Microbiol.* 67(4):1728-1738.

Engel, "Butyryl-CoA Dehydrogenase from Megasphaera elsdenii," *Methods Enzymol.* 71:359-366 (1981).

Enomoto et al., "Cloning and sequencing of the gene encoding the soluble fumarate reductase from Saccharomyces cerevisiae," *DNA Res.* 3:263-267 (1996).

Ensign et al., "Characterization of the Co Oxidation/Hz Evolution System of Rhodospirillum rubrum. Role of a 22-kDa iron-sulfur protein in mediating electron transfer between carbon monoxide dehydrogenase and hydrogenase," *J. Biol. Chem.* 266(27)18395-18403 (1991).

Eschmann et al., "Inhibition of Purine Utilization by Adenine in Alcaligenes eutrophus H16," *Arch. Microbiol.* 125:29-34 (1980).

Estevez et al., "X-ray crystallographic and kinetic correlation of a clinically observed human fumarase mutation," *Protein Sci.* 11(6):1552-1557 (2002).

Eulberg et al., "Characterization of a protocatechuate catabolic gene cluster from Rhodococcus opacus 1CP: evidence for a merged enzyme with 4-carboxymuconolactone-cecarboxylating and 3-oxoadipate enol-lactone-hydrolyzing activity," *J. Bacteriol.* 180:1072-1081 (1998).

Evans et al., "Specificity of substrate recognition by type II dehydroquinases as revealed by binding of polyanions," *Febs Lett.* 530(1-3):24-30 (2002).

Evans et al., "113C propionate oxidatin in wild-type and citrate synthase mutant *Escherichia coli*: evidence for multiple pathways of propionate utilization," *Biochem. J.* 291(Pt 3):927-932 (1993).

Ezeji et al., "Butanol fermentation research: upstream and downstream manipulations," *Chem. Rec.* 4(5):305-314 (2004).

Faehnle et al., "A New Branch in the Family: Structure of Aspartate-β-semialdehyde Dehydrogenase from Methanococcus jannaschii," *J. Mol. Biol.* 353:1055-1068 (2005).

Fallon et al., "2-phosphoglyceric acid phosphatase: identification and properties of the beef-liver enzyme," *Biochim. Biophys. Acta.* 105(1):43-53 (1965).

Feist et al., "Modeling methanogenesis with a genome-scale metabolic reconstruction of Methanosarcina barkeri," *Mol. Syst. Biol.* 2:2006.0004 (2006).

Feldberg et al., "L-threonine deaminase of Rhodospirillum rubrum. Purification and characterization," *Eur. J. Biochem.* 21(3):438-446 (1971).

Fell et al., "Fat Synthesis in Adipose Tissue. An Examination of Stoichiometric Constraints," *Biochem. J.* 238(3):781-786 (1986).

Fernandez-Canon et al., "Characterization of a fungal maleylacetoacetate isomerase gene and indentification of its human homologue," *J. Biol. Chem.* 273:329-337 (1998).

Fernandez-Valverde et al., "Purification of Pseudomonas putida Acyl Coenzyme a Ligase Active with a Range of aliphatic and Aromatic substrates," *Appl. Environ. Microbiol.* 59(4):1149-1154 (1993).

Fischer et al., "Metabolic flux profiling of *Escherichi coli* mutants in central carbon metabolism using Gc-Ms," *Eur. J. Biochem.* 270(5):880-891 (2003).

Fish et al., "2-Keto-3-deoxy-D-glucarate aldolase," *Methods Enzymol.* 9:529-534 (1966).

Fishbein et al., "Purification and properties of an enzyme in human blood and rat liver microsomes catalyzing the formation and hydrolysis of y-lactones. I. Tissue localization, stoichiometry, specificity, distinction from esterase," *J. Biol. Chem.* 241:4835-4841 (1966).

Fishbein et al., "Purification and properties of an enzyme in human blood and rat liver microsomes catalyzing the formation and hydrolysis of y-lactones. II. Metal ion effects, kinetics, and equilibria," *J. Biol. Chem.* 241:4842-4847 (1966).

Fitzgerald et al., "Characterization and sequence analysis of the human ornithine decarboxylase gene," *DNA* 8:(9):623-634 (1989).

Flint et al., "The role and properties of the iron-sulfur cluster in Escherichia coli dihydroxy-acid dehydratase," *J. Biol. Chem.* 268:14732-14742 (1993).

Flint, "Initial kinetic and mechanistic characterization of *Escherichia coli* fumarase a," *Arch. Biochem. Biophys.* 311(2):509-516 (1994).

Fochi, "Selective catalytic dehydrogenation of 1,4-cyclohexadiene to benzene. 1. Radical anions derived from transition-metal arene complexes as promoters," *Organometallics.* 7:2255-2256 (1988).

Fomine et al., "Cross-methathesis of dimethyl maleate and ethylene catalyzed by second generation ruthenium carbene complexes: B3LYP and MPW1K comparison study," *J. Org. Chem.* 691:5189-5196 (2006).

Fong et al., "Metabolic gene-deletion strains of *Escherichia coli* evolve to computationally predicted growth phenotypes," *Nat. Genet.* 36(10):1056-1058 (2004).

Fong et al., "Description and Interpretation of Adaptive Evolution of *Escherichia coli* K12 MG1655 by Using a Genome-Scale in Silico Metabolic Model," *J. Bacteriol.* 185:6400-. 6408 (2003).

Fong et al., "In Silico design and adaptive evolution of *escherichia coli* for production of lactic acid," *Biotechnol. Bioeng.* 91(5):643-648 (2005).

Fonknechten et al., "A conserved gene cluster rules anaerobic oxidative degradation of L-ornithine," *J. Bacteriol.* 191(9):3162-3167 (2009).

Fontaine et al., "Molecular charcterization and transcriptional analysis of adhE2, the. gene encoding the Nadh-dependent aldehyde/ alcohol dehydrogenase responsible for butanol production in alcohologenic cultures of Clostridium acetobutylicum ATCC 824," *J. Bacteriol.* 184:821-830 (2002).

Fontaine et al., "A New Type of Glucose Fermentation by Clostridium thermoaceticum n. Sp.," *J. Bacteriol.* 43(6):701-715 (1942).

Ford et al., "Molecular properties of the lys1+ gene and the regulation of a-aminoadipate reductase in Schizosaccharomyces pombe," *Curr. Genet.* 28:131-137 (1995).

Forouhar et al., "Structural and Functional Evidence for Bacillus subtilis PaiA as a Novel N'-Spermidine/spermine Acetyltransferase," *J. Biol. Chem.* 280(48):40328-40336.

Förster et al., "Genome-scale reconstruction of the Saccharomyces cerevisiae metabolic network," *Genome Res.* 13(2):244-253 (2003).

(56) References Cited

OTHER PUBLICATIONS

Fox et al., "Isolation and characterization of homogeneous acetate kinase from Salmonella typhimurium and *Escherichia coli*," *J. Biol. Chem.* 261(29):13487-13497 (1986).
Fox et al., "Characterization of the region encoding the Co-induced hydrogenase of Rhodospirillum rubrum," *J. Bacdteriol.* 178(21):6200-6208 (1996).
Freiberg, et al., "Identification and characterization of the first class of potent bacterial acetyl-CoA carboxylase inhibitors with antibacterial activity," *J. Biol. Chem.* 279:26066-26073 (2004).
Freidrich et al., "The complete stereochemistry of the enzymatic dehydration of 4-hydroxybutyryl coenzyme a to crontonyl coenzyme a," *Angew. Chem. Int. Ed.* 47:3254-3257 (2008).
Frerman et al.,"Studies on the subunits of *Escherichia coli* coenzyme a transferase. Reconstitution of an active enzyme," *Biochim. Biophys. Acta* 580(2):289-297 (1979).
Frey et al., "S-Adenosylmethionine: a wolf in sheep's clothing, or a rich man's adenosylcobalamin?" *Chem. Rev.* 103(6):2129-2148 (2003).
Fries et al., "Reaction Mechanism of the heterotetrameric (a2(32) El Component of 2-Oxo Acid Dehydrogenase Multienzyme Complexes," *Biochemistry* 42:6996-7002 (2003).
Frost et al., "Synthesis of adipic acid from biomass-derived carbon sources," *Biotechnol. Adv.* 15(1):294 (1997).
Frost et al., "Dehydroquinate synthase from *Escherichia coli*: purification, cloning, and construction of overproducers of the enzyme" *Biochemistry* 23:4470-4475 (1984).
Frost, "Redefining chemical manufacture. Replacing petroleum with plant-derived feedstocks," *Ind. Biotechnol.* 1(1):23-24 (2005).
Fu et al., "Crystal structures of human glutaryl-CoA dehydrogenase with and without an alternate substrate: structural bases of dehydrogenation and decarboxylation reactions," *Biochemistry* 43(30):9674-9684 (2004).
Fujii et al., "Characterization of L-lysine 6-aminotransferase and its structural gene from Flavobacterium lutescens IFO3084," *J. Biochem.* 128:391-397 (2000).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 32:e145 (2004).
Fujii, T. et al. "Molecular Cloning, Sequence Analysis, and Expression of the Yeast Alcohol Acetyltransferase Gene," *Appl. Environ. Microbiol.* 60:2786-2792 (1994).
Fujishiro et al., "Crystallization and Some Properties of Acetylpolyamine Amidohydrolase From Mycoplana Bullata," *Biochem. Biophys. Res. Commun.* 157(3):1169-1174 (1988).
Fujita et al., "Novel Substrate Specificity of Designer 3-Isopropylmalate Dehydrogenase Derived from Thermus thermophilus HB8," *Biosci. Biotechnol. Biochem.* 65(12):2695-2700 (2001).
Fukao et al., "Succinyl-CoA:3-ketoacid CoA transferase (Scot): cloning of the human Scot gene, tertiary structural modeling of the human Scot monomer, and characterization of three pathogenic mutations," *Genomics* 68:144-151 (2000).
Fukuda et al., "Substrate recognition by 2-oxoacid:ferredoxin oxidoreductase from Sulfolobus sp. Strain 7," *Biochim. Biophys. Acta* 1597:74-80 (2002).
Fukuda et al., "Role of a highly conserved Ypitp motif in 2-oxoacid:ferredoxin oxidoreductase Heterologous expression of the gene from Sulfolobus sp. Strain 7, and characterization of the recombinant and variant enzymes," *Eur. J. Biochem.* 268:5639-5646.
Fukui et al., "Engineering of Ralstonia eutropha for production of poly(3-hydroxybutyrate-co-3-hydroxyhexanoate) from fructose and solid-state properties of the copolymer," *Biomacromolecules*, 3(3):618-624 (2002).
Fukumura et al, "Hydrolysis of cyclic and linear oligomers of 6-aminocaproic acid by a bacterial cell extract," *J. Biochem.* 59(6):531-536 (1966).
Fukumura et al., "Purification and properties of a novel enzyme, L-a-amino-c-caprolactamase from Cryptococcus laurentii," *Febs Lett.* 89(2):298-300 (1978).
Fuller et al., "Proton transfer in methylmalonyl-CoA epimerase from Propionibacterium shermanii. The reaction of (2R)-methylmalonyl-CoA in tritiated water," *Biochem. J.* 213(3):643-650 (1983).
Furdui et al., "The role of pyruvate ferredoxin oxidoreductase in pyruvate synthesis during autotrophic growth by the Wood-Ljungdahl pathway," *J. Biol. Chem.* 275(37):28494-28499 (2000).
Furukawa et al., "Increased alcohol acetyltransferase activity by inositol limitation in Saccharomyces cerevisiae in sake mash," *J Biosci Bioeng.* 96(4):380-386 (2003).
Furuyoshi et al., "Purification and characterization of a new Nad(+)-dependent enzyme, L-tartrate decarboxylase, from Pseudomonas sp. group Ve-2," *J. Biochem.* 110(4):520-525 (1991).
Galagan et al., "The genome of M. acetivorans reveals extensive metabolic and physiological diversity," *Genome Res.* 12(4):532-542 (2002).
Gallagher et al., "The crystal structure of chorismate lyase shows a new fold and a tightly retained product," *Proteins* 44:304-311 (2001).
Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).
Garras et al., "Subcellular localisation and induction of Nadh-sensitive acetyl-CoA hydrolase and propionyl-CoA hydrolase activities in rat liver under lipogenic conditions after treatment with sulfur-substituted fatty acids," *Biochim. Biophys Acta* 1255(2):154-160.
Garvie, "Bacterial lactate dehydrogenases," *Microbiol. Rev.* 44:106-139 (1980).
Gay et al., "Cloning Structural Gene sacB, Which Codes for Exoenzyme Levansucrase of Bacillus subtilis: Expression of the Gene in *Escherichia coli*," *J. Bacteriol.* 153(3):1424-1431 (1983).
Genbank Accession No. AAC45217.1 GI:1684886 (Dec. 20, 2007).
Genbank Accession No. AAD38039.1 G:5020215 (Mar. 30, 2000).
Genbank Accession No. AAD38041.1 GI:5020219 (Mar. 30, 2000).
Genbank Accession No. AAG13130.1 GI:10121328 (Sep. 14, 2000).
Genbank Accession No. AA072312.1 GI:29293591 (Mar. 27, 2003).
Genbank Accession No. ABF82233.1 Gi:106636093 (Aug. 2, 2007).
Genbank Accession No. ABF82234.1 GI:106636094 (Aug. 2, 2007).
Genbank Accession No. ABF82235.1 GI:106636095 (Aug. 2, 2007).
Genbank Accession No. ABF82246.1 GI:106636106 (Aug. 2, 2007).
Genbank Accession No. ABK24445.1 GI:116787282 (Dec. 1, 2007).
Genbank Accession No. BAA03892.1 GI:425213 (Feb, 16, 2008).
Genbank Accession No. BAB12273.1 GI:9967138 (Mar. 18, 2005).
Genbank Accession No. BAB85476.1 GI:18857901 (Mar. 18, 2005).
Genbank Accession No. CAA43226.1 GI:45683 (Apr. 18, 2005).
Genbank Accession No. CAG11476.1 GI:47219943 (Mar. 17, 2004).
Genbank Accession No. Np 001003515.1 GI:51011113 (Aug. 5, 2007).
Genbank Accession No. Np 001011073.1 GI:58331907 (Nov. 18, 2006).
Genbank Accession No. NP 001016371.1 GI:62858535 (Jan. 30, 2008).
Genbank Accession No. NP 014032.1 GI:6323961 (Feb. 11, 2008).
Genbank Accession No. NP_070026.1 GI:11498797 (Dec. 3, 2007).
Genbank Accession No. NP_149242.1 GI:15004782 (Dec. 4, 2007).
Genbank Accession No. NP_349314.1 GI:15895965 (Dec. 4, 2007).
Genbank Accession No. NP_349317.1 GI:15895968 (Dec. 4, 2007).
Genbank Accession No. NP_349318.1 GI:15895969 (Dec. 4, 2007).
Genbank Accession No. NP_349476.1 GI:15896127 (Dec. 4, 2007).
Genbank Accession No. NP_349891.1 GI:15896542 (Dec. 4, 2007).
Genbank Accession No. NP_349892.1 GI:15896543 (Dec. 4, 2007).
Genbank Accession No. NP_414884.2 Gi:90111116 (Dec. 20, 2007).
Genbank Accession No. NP_415423.1 Gi:16128870 (Dec. 20, 2007).
Genbank Accession No. NP_415705.1 GI:16129150 (Dec. 20, 2007).
Genbank Accession No. NP_415757.1 GI:16129202 (Dec. 20, 2007).
Genbank Accession No. NP_415905.1 GI:16129348 (Dec. 20, 2007).

(56) References Cited

OTHER PUBLICATIONS

Genbank Accession No. NP_415911.1 Gi:16129354 (Dec. 20, 2007).
Genbank Accession No. NP_415912.1 GI:16129355 (Dec. 20, 2007).
Genbank Accession No. NP_415913.1 GI:16129356 (Dec. 20, 2007).
Genbank Accession No. NP_416728.1 GI:16130161 (Dec. 20, 2007).
Genbank Accession No. NP_416843.1 GI:16130274 (Dec. 20, 2007).
Genbank Accession No. NP_416844.1 GI:16130275 (Dec. 20, 2007).
Genbank Accession No. NP_417321.2 GI:90111494 (Dec. 20, 2007).
Genbank Accession No. NP_417484.1 GI:16130909 (Dec. 20, 2007).
Genbank Accession No. NP_418288.1 GI:16131692 (Dec. 20, 2007).
Genbank Accession No. NP_509584.1 GI:17549919 (Mar. 23, 2007).
Genbank Accession No. NP_745413.1 GI:26989988 (Nov. 30, 2007).
Genbank Accession No. NP_745425.1 GI:26990000 (Nov. 30, 2007).
Genbank Accession No. NP_745426.1 GI:26990001 (Nov. 30, 2007).
Genbank Accession No. NP_745427.1 GI:26990002 (Nov. 30, 2007).
Genbank Accession No. NP_781017.1 GI:28210073 (Dec. 2, 2007).
Genbank Accession No. NP_971211.1 GI:42526113 (Jan. 25, 2008).
Genbank Accession No. P38947.1 GI:730847 (Feb. 5, 2008).
Genbank Accession No. P38947.2 GI:172046062 (Nov. 4, 2008).
Genbank Accession No. P40353.2 GI:2506980 (Oct. 2, 2007).
Genbank Accession No. P53296.1 GI:1723729 (Oct. 2, 2007).
Genbank Accession No. Q5EU90.1 GI:62287512 (Jul. 24, 2007).
Genbank Accession No. Q5I6B5 GI:75105208 (Oct. 31, 2006).
Genbank Accession No. Q8GGG1 GI:81478805 (Oct. 31, 2006).
Genbank Accession No. XP_001113746.1 GI:109000274 (Jun. 14, 2006).
Genbank Accession No. XP_001638329.1 GI:156398707 (Aug. 26, 2007).
Genbank Accession No. XP_001639469.1 GI:156402181 (Aug. 26, 2007).
Genbank Accession No. XP_001648220.1 GI:157104018 (Jan. 9, 2008).
Genbank Accession No. XP_001655993.1 GI:157132312 (Jan. 9, 2008).
Genbank Accession No. XP_001679449.1 GI:157751474 (Apr. 2, 2008).
Genbank Accession No. XP_001749481.1 GI:167535615 (Feb. 8, 2008).
Genbank Accession No. XP_320682.4 GI:158300867 (Oct. 16, 2007).
Genbank Accession No. XP_395130.3 GI:110762648 (Jul. 27, 2006).
Genbank Accession No. XP_535334.2 GI:73950497 (Aug. 30, 2005).
Genbank Accession No. XP_572875.1 GI:58271438 (Apr. 24, 2006).
Genbank Accession No. XP_640315.1 GI:66812272 (Jan. 30, 2008).
Genbank Accession No. XP_642118.1 GI:66816217 (Jan. 30, 2008).
Genbank Accession No. XP_787188.2 GI:115733116 (Oct. 7, 2006).
Genbank Accession No. XP_802711.1 GI:71399112 (Jan. 4, 2008).
Genbank Accession No. XP_806421.1 GI:71407979 (Jan. 4, 2008).
Genbank Accession No. XP_844077.1 GI:72387305 (Mar. 4, 2008).
Genbank Accession No. XP_973042.1 GI:91088569 (Apr. 5, 2006).
Genbank Accession No. XP_974428.1 GI:91089675 (Jul. 21, 2008).
Genbank Accession No. YP_001172441.1 GI:146282288 (Dec. 8, 2007).
Genbank Accession No. Yp 001322360.1 Gi:150392311 (06-Dec-2007).
Genbank Accession No. Yp 001394464.1 Gi:153953699 (12-Dec-2007).
Genbank Accession No. Yp 001394497.1 Gi:153953732 (12-Dec-2007).
Genbank Accession No. Yp 001397054.1 Gi:153956289 (12-Dec-2007).
Genbank Accession No. Yp 001511817.1 Gi:158319310 (06-Dec-2007).
Genbank Accession No. Yp 001530041.1 Gi:158522171 (30-Nov-2007).
Genbank Accession No. Yp 001585327.1 Gi:161522398 (04-Dec-2007).
Genbank Accession No. Yp 001588758.1 Gi:161614793 (05-Dec-2007).
Genbank Accession No. Yp 001646648.1 Gi:163941764 (27-Dec-2007).
Genbank Accession No. Yp 001669856.1 Gi:167034625 (06-Feb-2008).
Genbank Accession No. Yp 026272.1 Gi:49176430 (20-Dec-2007).
Genbank Accession No. Yp 047869.1 Gi:50086359 (29-Nov-2007).
Genbank Accession No. Yp 267463.1 Gi:71280300 (30-Nov-2007).
Genbank Accession No. Yp 419997.1 Gi:83309733 (11-Dec-2007).
Genbank Accession No. Yp 467905.1 Gi:86356013 (27-Jan-2008).
Genbank Accession No. Yp 633978.1 Gi:108761238 (03-Dec-2007).
Genbank Accession No. Yp 641317.1 Gi:108801120 (30-Nov-2007).
Genbank Accession No. Yp 693524.1 Gi:110834665 (09-Dec-2007).
Genbank Accession No. Yp 694462.1 Gi:110835603 (09-Dec-2007).
Genbank Accession No. Yp 725941.1 Gi:113867452 (08-Dec-2007).
Genbank Accession No. Yp 959434.1 Gi:120555083 (06-Dec-2007).
Genbank Accession No. Zp 01114282.1 Gi:88798699 (24-Feb-2006).
Genbank Accession No. Zp 01163033.1 Gi:89076755 (01-Mar-2006).
Genbank Accession No. Zp 01443601.1 Gi:114764375 (18-Sep-2006).
Genbank Accession No. Zp 01485509.1 Gi:116220059 (16-Oct-2006).
Genbank Accession No. Zp 01645699.1 Gi:119878825 (22-Dec-2006).
Genbank Accession No. Zp 01732824.1 Gi:126661825 (07-Mar-2007).
Genbank Accession No. Zp 01860900.1 Gi:149182424(20-Jun-2007).
Genbank Accession No. ZP_02012479.1 GI:153891468 (Jul. 25, 2007).
Genbank Accession No. ZP_02133627.1 GI:163726110 (Dec. 20, 2007).
Genda et al., "Purification and characterization of fumarase from *Corynebacterium glutamicum*," *Biosci. Biotechnol. Biochem.* 70:1102-1109 (2006).
Gene Bridges, "Quick & Easy Bac Modification Kit by Red /Et Recombination," Technical Protocol, Cat. No. K001, Version 2.6 (2007).
Gerhardt et al. "Fermentation of 4-aminobutyrate by Clostridium aminobutyricum: cloning of two genes involved in the formation dehydration of 4-hydroxybutyrl-CoA," *Arch. Microbiol.* 174:189-199 (2000).
Gerischer et al., "mRNA Analysis of the *adc* Gene Region of *Clostridium acetobutylicum* during the Shift to Solventogenesis," *J. Bacteriol.* 174(2):426-433 (1992).
Gescher et al., "Genes coding for a new pathway of aerobic benzoate metabolism in *Azoarcus evansii*," *J Bacteriol.* 184(22):6301-6315 (2002).
Giaever et al., "Functional profiling of the Saccharomyces cerevisiae genome," *Nature*. 418(6896):387-391 (2002).

(56) References Cited

OTHER PUBLICATIONS

Gibbs et al., "Degenerate olignucleotide gene shuffling (DOGS): a method for enhancing the frequence of recombination with family shuffling," *Gene* 271:13-20 (2001).
Gibson (née Thomas) et al., "Cross metathesis of the amino acid homoallylglycine," *Chem. Commun.* 1107-1108 (1997).
Gibson et al., "Physical and genetic interactions of cytosolic malate dehydrogenase with other gluconeogenic enzymes," *J. Biol. Chem.* 278:25628-25636 (2003).
Giesel et al., "On the occurrence of enoate reductase and 2-oxo-carboxylate reductase in clostridia and some observations on the amino acid fermentation by Peptostreptococcus anaerobius," *Arch. Microbiol.* 135(1):51-57 (1983).
Gillyon et al., "Putrescine Breakdown in the Yeast Candida boidinii: Subcellular Location of Some of the Enzymes Involved and Properties of Two Acetamidoaldehyde Dehydrogenases," *J. of Gen. Microbiol.* 133:2477-2485 (1987).
Glasemacher et al., "Purification and properties of acetyl-CoA synthetase (ADP_forming), an archael enzyme of acetate formation and Atp synthesis, from the hyperthermophile Pyrococcus furiosus," *Eur. J. Biochem.* 244:561-567 (1997).
Gobel et al., "Degradation of Aromatics and Chloroaromatics by Pseudomonas sp. Strain B13: Cloning, Characterization, and analysis of Sequences Encoding 3-Oxoadipate:Succinyl-Coenzyme a (CoA) Transferase and 3-oxoaipyl-CoA Thiolase," *J. Bacteriol.* 184(1):216-223 (2002).
Goda et al., "Cloning, sequencing, and expression in *Escherichia coli* of the Clostridium tetanomorphum gene encoding 0-methylaspartase and characterization of the recombinant protein," *Biochemistry* 31(44):10747-10756 (1992).
Gokarn et al., "Expression of pyruvate carboxylase enhances succinate production in *Escherichia coli* without affecting glucose uptake" *Biotechnol. Lett.* 20:795-798 (1998).
Gokarn et al., "Metabolic Analysis of Escherichia coli in the Presence and Absence of the Carboxylating Enzymes Phosphoenolpyruvate Carboxylase and Pyruvate Carboxylase," *Appl. Environ. Microbiol.* 666:1844-1850 (2000).
Gokarn, et al., "The physiological effects and metabolic alterations caused by the expression of Rhizobium etli pyruvate carboxylase in *Escherichia coli*," *Appl. Microbiol. Biotechnol.* 56(1-2):188-195 (2001).
Gokulan et al., "Crystal structure of Mycobacterium tuberculosis diaminipimelate decarboxylase, an essential enzyme in bacterial lysine biosynthesis," *J. Biol. Chem.* 278(20):18588-18596 (2003).
Goldberg et al., "Improved Conversion of Fumarate to Succinate by *Escherichia coli* Strains Amplified for Fumarate Reductase," *Appl. Environ. Microbiol.* 45:1838-1847.
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
Gonzalez et al., "Genetic analysis of Carboxydothermus hydrogenoformans carbon monoxide dehydrogenase genes cooF and cooS," *Fems Microbiol. Lett.* 191(2):243-247.
Gonzalez et al., "Characterization of a (2R,3R)-2,3-Butanediol Dehydrogenase as the Saccharomyces cerevisiae YAL060W Gene Product," *J. Biol. Chem.* 275(46):35876-35885.
Gonzalez-Pajuelo et al., "Metabolic engineering of *Clostridium acetobutylicum* for the industrial production of 1,3-propanediol from glycerol," *Met. Eng.* 7:329-336 (2005).
Gordon et al., "Purification, properties and immunological relationship of L(+)-lactate dehydrogenase from Lactobacillus casei," *Eur. J. Boichem.* 67:543-555 (1976).
Goupil et al., "Imbalance of Leucine Flux in Lactococcus lactis and Its Use for the Isolation of Diacetyl-Overproducing Strains," *Appl. Environ. Microbiol.* 62(7):2636-2640.
Goupil-Feuillerat et al., "Transcriptional and Translational Regulation of a-Acetolactate Decarboxylase of Lactococcus lactis subsp. Lactis," *J. Bacteriol.* 182(19):5399-5408 (2000).

Gourley et al., "The two types of 3-dehydroquinase have distinct structures but catalyze the same overall reaction," *Nat. Struct. Biol.* 6:521-525 (1999).
Grant et al.. "The non-oxidative decarboxylation of p-hydroxybenzoic acid, gentisic acid, protocatechuic acid and gallic acid by *Klebsiella aerogenes (Aerobacter aerogenes)*," *Antonie Van Leeuwenhoek* 35:325-343 (1969).
Green et al., "Genetic manipulation of acid and solvent formation in clostridium acetobutylicum ATCC 824," *Biotechnol. Bioeng.* 58(2-3):215-221 (1998).
Green et al., "p-Aminobenzoate biosynthesis in *Escherichia coli*. Purification of aminodeoxychorismate lyase and cloning of pabC," *J. Biol. Chem.* 266:12971-12975.
Green et al., "Catabolism of a-ketoglutarate by a sucA mutant of Bradyrhizobium japonicum: evidence for an alternative tricarboxylic acid cycle," *J. Bacteriol.* 182:2838-2844 (2000).
Green et al., "Characterization and sequence of *Escherichia coli* pabC, the gene encoding aminodeoxychorismate lyase, a pyridoxal phosphate-containing enzyme," *J Bacteriol.* 174:5317-5323 (1992).
Grethlein et al., "Bioprocessing of coal-derived synthesis gases by anaerobic bacteria," *Trends Biotech.* 10:418-423 (1992).
Grochowski et al., "Identification of lactaldehyde dehydrogenase in *Methanocaldococcus jannaschii* and its involvement in production of lactate for F420 biosynthesis," *J. Bacteriol.* 188(8):2836-2844 (2006).
Grolle et al., "Isolation of the dxr gene of Zymomonas mobilis and characterization of the 1-deoxy-D-xylulose 5-phosphate reductoisomerase," *FEMS Microbiol. Lett.* 191:131-137 (2000).
Grubbs "Olefin Meethathesis," *Tetrahedron* 60:7117-7140 (2004).
Gruez et al., "Crystal structure and kinetics identify *Escherichia coli* YdcW gene product as a medium-chain aldehyde dehydrogenase," *J. Mol. Biol.* 343(1):29-41 (2004).
Gu et al., "Crystal structure of shikimate kinase from Mycobacterium tuberculosis reveals the dynamic role of the LID domain in catalysis," *J. Mol. Biol.* 319:779-789 (2002).
Gueldener et al., "A second set of loxP marker cassettes for Cre-mediated multiple gene knockouts in budding yeast," *Nucleic Acids Res.* 30(6):e23 (2002).
Guerra et al., "Role of transmembrane segment M8 in the biogenesis and function of yeast plasma-membrane HtATPase," *Biochim. Biophys Acta* 1768:2383-2392 (2007).
Guest et al., "The fumarase genes of *Escherichia coli*: location of the fumB gene and discovery of a new gene (fumC)," *J. Gen. Microbiol.* 131(11):2971-2984 (1985).
Guettler et al., "Actinobacillus succinogenes sp. nov., a novel succinic-acid-producing strain from the bovine rumen," *Int. J. Syst. Bacteriol.* 49 :207-216 (1999).
Guirard et al., "Purification and properties of ornithine decarboxylase from Lactobacillus sp. 30a," *J. Biol. Chem.* 255:5960-5964 (1980).
Gulick et al., "The 1.75 a crystal structure of acetyl-CoA synthetase bound to adenosine-5'-propylphosphate and coenzyme a," *Biochemistry* 42(10):2866-2873 (2003).
Guo et al., "Posttranslational activation, site-directed mutation and phylogenetic analyses of the lysine biosynthesis enzymes a-aminoadipate reductase Lyslp (Aar) and the phosphopantetheinyl transferase Lys7p (PPTase) from Schizosaccharomyces pombe," *Yeast* 21:1279-1288 (2004).
Guo et al., "Site-directed mutational analysis of the novel catalytic domains of a-aminoadipate reductase (Lys2p) from candida albicans," *Mol. Gen. Gemonics* 269:271-279.
Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).
Gutierrez et al., "A mutant D-amino acid aminotransferase with broad substrate specificity: construction by replacement of the interdoman loop Pro 119-Arg120-Pro121 by Gly-Gly-Gly," *Protein Eng.* 11:53-58 (1998).
Gutknecht, R., et al., "The dihydroxyacetone kinase of Escherichia coli utilizes a phosphoprotein instead of ATP as phosphoryl donor," *Embo J.* 20(10):2480-2486 (2001).
Guyer, et al., "Identification of a sex-factor-affinity site in E. coli as 76," *Cold Spring. Harbor Symp. Quant. Biol.*45:135-140 (1981).

(56) References Cited

OTHER PUBLICATIONS

Guzman et al., "Tight regulation, modulation, and high-level expression by vectors containing the arabinose Pba D promoter," *J. Bacteriol.* 177:4121-4130 (1995).

Haarasilta et al., "On the activity and regulation of anaplerotic and gluconeogenetic enzymes during the growth process of baker's yeast. The biphasic growth," *Eur. J. Biochem.* 52:1-7 (1975).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from Escherichia coli, a Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. USA*, 103(50):18917-18922 (2006).

Hagishita et al., "Cloning and expression of the gene for serine-glyoxylate aminotransferase from an obligate methylotroph Hyphomicrobium methylovorum GM2," *Eur. J. Biochem.* 241(1):1-5 (1996).

Hahm et al., "Characterization and evaluation of apta (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hambraeus and Nyberg, "Enzymatic Hydrogenation of trans-2-Nonenal in Barley," *J. Agric. Food Chem.* 53:8714-8721 (2005).

Hamilton-Kemp et al., "Production of the long-chain alcohols octanol, decanol, and dodecanol by *Escherichia coli*," *Curr. Microbiol.* 51:82-86 (2005).

Hammer et al., "Purification and characterization of an inducible L-lysine:2-oxoglutarate 6-aminotransferase from Candida utilis," *J. Basic Microbiol.* 32:21-27 (1992).

Han et al., "Biochemical characterization and inhibitor discovery of shikimate dehydrogenase from Helicobacter pylori," *FEBS J.* 273:4682-4692 (2006).

Han et al., "Comparative characterization of Aedes 3-hydroxykynurenine transaminase/alanine glyoxylate transaminase and Drosophila serine pyruvate aminotransferase," *FEBS Lett.* 527(1-3):199-204 (2002).

Hanai et al., "Engineered synthetic pathway for isopropanol production in *Escherichia coli*," *Appl. Environ. Microbiol.* 73(24):7814-7818 (2007).

Hansen et al., "De novo biosynthesis of vanillin in fission yeast (*Schizosaccharomyces pombe*) and baker's yeast (*Saccharomyces cerevisiae*)," *Appl. Environ. Microbiol.* 75(9):2765-2774 (2009).

Hansford, "Control of mitochondrial substrate oxidation," *Curr. Top Bioenergy* 10:217-278 (1980).

Harder, "Anaerobic degradation of cyclohexane-1,2-diol by a new Azoarcus species," *Arch. Microbiol.* 168:199-204 (1997).

Hardison et al., "Globin Gene Server: a prototype E-Mail Database Server Featuring Extensive Multiple Alignments and Data Compilation for Electronic Genetic Analysis," *Genomics* 21:344-353 (1994).

Harker et al., "Expression of prokaryotic 1-deoxy-D-xylulose-5-phosphatases in *Escherichia coli* increases carotenoid and ubiquinone biosynthesis," *FEBS Lett.* 448:115-119 (1999).

Harms et al., "Methylcobalamin: coenzyme M methyltransferase isoenzymes MtaA and MtbA from Methanosarcina barkeri. Cloning, sequencing and differential transcription of the encoding genes, and functional overexpression of the mtaA gene in *Escherichia coli*," *Eur. J. Biochem.* 235(3):653-659 (1996).

Harrison et al., "The pimFABCDE operon from Rhodopseudomonas palustris mediates dicarboxylic acid degradation and participates in anaerobic benzoate degradation," *Microbiology* 151:727-736 (2005).

Hartel et al., "Purification of glutaryl-CoA dehydrogenase from Pseudomonas sp., an enzyme involved in the anaerobic degradation of benzoate," *Arch. Mirobiol.* 159:174-181.

Harwood et al., "The β-ketoadipate pathway and the biology of self-identity," *Annu. Rev. Microbiol.* 50:553-590 (1996).

Harwood et al., "Anaerobic metabolism of aromatic compounds via the benzoyl-CoA pathway," *FEMS Microbiol. Rev.* 22:439-458 (1999).

Harwood et al., "Identification of the pcaRKF Gene cluster from Pseudomonas putida: Involvement in Chemotaxis, Biodegradation, and Transport of 4-Hydroxybenzoate," *J. Bacteriol.* 176(21):6479-6488 (1994).

Hasan et al., "Dehydroquinate synthase in Bacillus subtilis. An enzyme associated with chorismate synthase and flavin reductase," *J. Biol. Chem.* 253:4999-5004 (1978).

Hasegawa et al., "Transcriptional regulation of ketone body-utilizing enzyme, acetoacetyl-CoA synthetase, by C/EBPa during adipocyte differentiatiion," *Biochimica. Biophysica. Acta* 1779:414-419 (2008).

Haselbeck et al., "Isolation, nucleotide sequence, and disruption of the Saccharomyces cerevisiae gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).

Hashimoto et al., "Activation of L-Lysine c-Dehydrogenase from Agrobacterium tumefaciens by Several Amino Acids and Monocarboxylates," *J. Biochem.* 106:76-80.

Hasson et al., "The crystal structure of benzoylfomate decarboxylase at 1.6 a resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from Serratia marcescens, " *Biosci. Biotechnol. Biochem.* 64:1477-1485 (2000).

Hatakeyama et al., "Gene Cloning and Characterization of Maleate cis-trans Isomerase from Alcaligenes faecalis," *Biochem. Biophys. Res. Comm.* 239:74-79 (1997).

Hawes et al., "Primary structure and tissue-specific expression of human (3-hydroxyisobutyryl-coenzyme a hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from Fusobacterium," *J. Nihon. Univ. Sch. Dent.* 28(1):12-21 (1986).

Hayden et al., "Glutamate dehydrogenase of Halobacterium salinarum: evidence that the gene sequence currently assigned to the Nadp±-dependent enzyme is in fact that of the NADtdependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. USA* 99(25):15926-15931.

Hayes et al., "The Biofine Process: Production of Levulinic Acid, Furfural and Formic Acid from Lignocellulosic Feedstocks," in Biorefineries: *Industrial Proceses and Products*, Wiley, Weinheim, Germany, 139-164. (2006).

Haywood et al., "4-Acetamidobutyrate Deacetylase in the Yeast Candida boidinii Grown on Putrescine or Spermidine as Sole Nitrogen, Source and Its Probable Role in Polyamine Catabolism," *J. Gen. Microbiol.* 132:7-14 (1986).

Haywood et al., "Characterization of two 3-ketothiolases possessing differing substrate specificities in the polyhydroxyalkanoate synthesizing organism Alcaligenes eutrophus," *FEMS Microbiol. Lett.* 52:91-96 (1988).

He et al.. "Purification and characterization of an oxygen-sensitive reversible 4-hydroxybenzoate decarboxylase from *Clostridium hydroxybenzoicum*," *Eur. J Biochem.* 229:77-82 (1995).

Heidlas et al., "Purification and Properties of two oxidoreductases catalyzing the enantioselective reduction of diacetyl and other diketones from baker's yeast," *Eur. J. Biochem.* 188:165-174 (1990).

Heipieper et al., "Ethanol tolerance and membrane fatty acid adaptation in adh multiple and null mutants of Kluyveromyces lactis," *Res. Microbiol.* 151:(9):777-84 (2000).

(56) References Cited

OTHER PUBLICATIONS

Helin et al., "The refined x-ray structure of muconate lactonizing enzyme from Pseudomonas putida PRS2000 at 1.85 a resolution," *J. Mol. Biol.* 254:918-941 (1995).
Heller et al., "Cloning and expression of the gene for the vitamin B12 receptor protein in the outer membrane of *Escherichia coli*," *J. Bacteriol.* 161:896-903 (1985).
Hemschemeier et al., "Biochemical and physiological characterization of the pyruvate formate-lyase Pfl 1 of Chlamydomonas reinhardtii, a typically bacterial enzyme in eukaryotic alga, " *Eukaryot. Cell* 7:518-526 (2008).
Hendrick et al., "The Nonoxidative Decarboxylation of Hydroxypyruvate in Mammalian Systems," *Arch. Biochem. Biophys.* 105:261-269 (1964).
Henne, et al., "Construction of environmental DNA libraries in *Escherichia coli* and screening for the presence of genes conferring utilization of 4-hydroxybutyrate," *Appl. Environ. Microbiol.* 65(9):3901-3907 (1999).
Hennessy, et al., "The reactivity of gamma-hydroxybutyric acid (GHB) and gamma-butyrolactone (Gbl) in alcoholic solutions," J. Forensic. Sci. 49(6):1220-1229 (2004). (provided electronically by publisher as pp. 1-10).
Henning et al., "Identification of novel benzoylformate decarboxylases by growth selection," *Appl. Environ. Microbiol.* 72:7510-7517 (2006).
Henriksson et al., "The 1.9 a resolution structure of Mycobacterium tuberculosis 1-deoxy-D-xylulose 5-phosphate reductoisomerase, a potential drug target," *Acta Cryst.* D62:807-813 (2006).
Henstra et al., "Microbiology of synthesis gas fermentation for biofuel production," *Curr. Opin. Biotechnol.* 18:200-206 (2007).
Hermes et al., "Searching sequence space by definably random mutagenesis: Improving the catalytic potency of an enzyme," *Proc. Natl. Acad. Sci USA* 87:696-700 (1990).
Herrmann et al., "Energy Conservation via Electron-Transferring Flavoprotein in Anaerobic Bacteria," *J. Bacteriol.* 190(3):784-791 (2008).
Herrmann et al., "Two beta-alanyl-CoA:ammonia lyases in Clostridium propionicum," *Febs J.* 272:813-821 (2005).
Hespell et al., "Stabilization of pet Operon Plasmids and Ethanol Production in Escherichia coli Strains Lacking Lactate Dehydrogenase and Pyruvate Formate-Lyase Activities," *Appl. Environ. Microbiol.* 62:4594-4597 (Dec. 1996).
Hesslinger et al., "Novel keto acid formate-lyase and propionate kinase enzymes are components of an anaerobic pathway in Escherichia coli that degrades L-threonine to propionate," *Mol. Microbiol.* 27(2):477-492 (1998).
Hester et al., "Purification of active Ela202 of Pseudomonas putida branched-chain-oxoacid dehydrogenase," *Eur. J. Biochem.* 233:828-836 (1995).
Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).
Heydari et al., "Highly Stable L-Lysine 6-Dehydrogenase from the thermophile Geobacillus stearothermophilus Isolated from a Japanese Hot Spring: characterization, Gene Cloning and sequencing, and Expression," *Appl. Environ. Microbiol.* 70(2):937-942.
Hibbert et al., "Directed evolution of biocatalytic processes," *Biomol. Eng.* 22:11-19.
Highbarger et al., "Mechanism of the reaction catalyzed by acetoacetate decarboxylase. Importance of lysine 116 in determining the pKa of active-site lysine 115," *Biochemistry* 35(1):41-46 (1996).
Hijarrubia et al., "Domain Structure Characterization of the Multifunctional a-Aminoadipate Reductase from Penicillium chrysogenum by Limited Proteolysis," *J. Biol. Chem.* 278(10):8250-8256 (2003).
Hill et al., "PCR based gene engineering of the Vibrio harveyi lux operon and the *Escherichia coli* trp operon provides for biochemically functional native and fused gene products," *Mol. Gen. Genet.* 226:41-48 (1991).

Hillmer et al., "Particulate Nature of Enzymes Involved in the Fermentation of Ethanol and Acetate by Clostridium Kluyveri," *Febs Lett.* 21(3):351-354 (1974).
Hillmer et al., "Solubilization and partial characterization of particulate dehydrogenases from Clostridium kluyveri," *Biochim. Biophys. Acta.* 334:12-23 (1974).
Hirano et al., "Purification and characerization of the Alcohol Dehydrogenase with a Broad Substrate Specificy Originated from 2-Phenylethanol-Assimilating Brevibacterium sp. Ku 1309," *J. Biosci. Bioeng,* 100(3): 318-322 (2005).
Hirata et al., "Stereochemistry of reduction of the endocyclic double bond of (-)-carvone with the enzyme preparation from cultured cells of Nicotiana tabacum," *Phytochemistry.* 28(12):3331-3333 (1989).
Hiser et al., "ERG10 from Saccharomyces cerevisiae encodes acetoacetyl-CoA thiolase," *J. Biol. Chem.* 269:31383-31389 (1994).
Ho et al., "Regulation of serine biosynthesis in Arabidopsis. Crucial role of plastidic 3-phosphoglycerate dehydrogenase in non-photosynthetic tissues," *J. Biol. Chem.* 274:397.
Hoang et al., "A broad-host-range Flp-Frt recombination system for site-specific excision of chromosomally-located DNA sequences: application for isolation of unmarked Pseudomonas aeruginosa mutants," *Gene* 212(1):77-86 (1998).
Hoffmann et al., "Sterochemistry of the methylmalonyl-CoA decarboxylation reaction," *Febs Lett.* 220:121-125 (1987).
Hoffmeister et al., "Mitochondrial trans-2-enoyl-CoA reductase of wax ester fermentation from Euglena gracilis defines a new family of enzymes involved in lipid synthesis," *J. Biol. Chem.* 280:4329-4338 (2005).
Hofmeister et al., "(R)-lactyl-CoA dehydratase from Clostridium propionicum. Stereochemistry of the dehydration of (R)-2-hydroxybutyryl-CoA to crotonly-CoA," *Eur. J. Biochem.* 206(2):547-552 (1992).
Hofmeister et al., "Cloning and expression of the two genes coding for L-serine dehydratase from Peptostreptococcus asaccharolyticus: relationship of the iron-sulfur protein to both L-serine dehydratases from *Escherichia coli*," *J. Bacteriol.* 179(15):4937-4941 (1997).
Hogan et al., "Improved Specificity toward Substrates with Positively Charged Side chains by Site-Directed Mutagenesis of the L-Lactate Dehydrogenase of Bacillus stearothermophilus," *Biochemistry* 34:4225-4230 (1995).
Holden et al., "Chorismate lyase: kinetics and engineering for stability," *Biochim. Biophys. Acta.* 1594(1):160-167 (2002).
Holloway et al., "Adenosylcobalamin-dependent glutamate mutase from Clostridium tetanomorphum. Overexpression in *Escherichia coli*, purification, and characterization of the recombinant enzyme," *J. Biol. Chem.* 269(32):20425-20430 (1994).
Holms, "The central metabolic pathways in Escherichia coli: relationship between flux and control at a branch point, efficiency of conversion to biomass, and excretion of acetate," *Curr. Top Cell. Regul.* 28:69-105 (1986).
Hong et al., "Metabolic flux analysis for succinic acid production by recombinant *Escherichia coli* with amplified malic enzyme activity," *Biotechnol. Bioeng.* 74(2):89-95.
Hong et al "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).
Hong et al., "The genome sequence of the capnophilic rumen bacterium Mannheimia. succiniciproducens." *Nat. Biotechnol.* 22(10):1275-1281 (2004).
Hong et al., "Importance of redox balance on the production of succinic acid by metabolically engineered *Escherichia coli*," *Appl. Microbiol. Biotechnol.* 58:286-290.
Hoover et al., "Kinetic mechanism of a recombinant Arabidopsis glyoxylate reductase: studies of initial velocity, dead-end inhibition and product inhibition," *Can. J. Bot.* 85:896-902 (2007).
Horswill et al., "In vitro conversion of propionate to pyruvate by Salmonella enterica enzymes: 2-methylcitrate dehydratase (PrpD) and aconitas Enzymes catalyze the conversion of 2-methylcitrate to 2-methylisocitrate," *Biochemistry* 40(15):4703-4713.
Horton et al., "Heterologous expression of the Saccharomyces cerevisiae alcohol acetyltransferase genes in Clostridium acetobutylicum

(56) References Cited

OTHER PUBLICATIONS and *Escherichia coli* for the production of isoamyl acetate," *J. Ind. Microbiol. Biotechnol.* 30(7):427-432 (2003).
Howard et al., "Titanium Metallacarbene-Metallacylobutane Reactions: Stepwise Metathesis," *J. Am. Chem. Soc.* 102:6876-6878 (1980).
Hsu et al., "Expression of an aromatic-dependent decarboxylase which provides growth-essential CO2 equivalents for the acetogenic (Wood) pathway of *Clostridium thermoaceticum*," *J Bacteriol.* 172:5901-5907 (1990).
Hu et al., "The catalytic intermediate stabilized by a "down" active site loop for diaminopimelate decarboxylase from Helicobacter pylori. Enzymatic characterization with crystal structure analysis," *J. Biol. Chem.* 283(30):21284-21293 (2008).
Huang et al., "Genetic characterization of the resorcinol catabolic pathway in Corynebacterium glutamicum," *Appl. Environ. Microbiol.* 72:7238-7245 (2006).
Huang et al., "Purification and characterization of a ferulic acid decarboxylase from Pseudomonas fluorescens," *J. Bacteriol.* 176:5912-5918 (1994).
Huang et al., "Identification and characterization of a second butyrate kinase from Clostridium acetobutylicum ATCC 824," *J. Mol. Microbiol. Biotechnol.* 2(1):33-38 (2000).
Hubner et al., "The mechanism of substrate activation of pyruvate decarboxylase: a first approach," *Eur. J. Biochem.* 92:175-181 (1978).
Huder et al., "Sequence of the sodium ion pump methylmalonyl-CoA decarboxylase from Veillonella paryula," *J. Biol. Chem.* 268:24564-24571 (1993).
Hudson et al., "Nucleotide sequence and transcription of the phenylalanine and tyrosine operons of *Escherichia coli* K12," *J. Mol. Biol.* 180(4):1023-1051 (1984).
Hughes et al., "Cloning and expression of pca genes from Pseudomonas putida in *Escherichia coli*," *J. Gen. Microbiol.* 134:2877-2887 (1988).
Hughes et al.," Evidence for isofunctional enzymes in the degradation of phenol, m- and p-toluate, and p-cresol via catechol meta-cleavage pathways in Alcaligenes eutrophus," *J. Bacteriol.* 158(1):79-83 (1984).
Hugler et al., "Malonyl-coenzyme a Reductase from Chloroflexus aurantiacus, a Key Enzyme of the 3-Hydroxypropionate Cycle for Autotrophic CO2 Fixation," *J. Bacteriol.* 184(9):2404-2410 (2002).
Huh et al., "Global analysis of protein localization in budding yeast," *Nature* 425:686-691.
Huisman et al., "Enzyme evolution for chemical process applications," in R.N. Patel (ed.), Biocatalysis in the pharmaceutical and biotechnology industries, CRC Press, p. 717-742 (2007).
Huo et al., "Substrate Specificity and Identification of Functional Groups of Homoserine Kinase from *Escherichia coli*," *Biochemistry* 5:16180-16185 (1996).
Husain et al., "Partial purification and characterization of glutaryl-coenzyme a dehydrogenase, electron transfer flavoprotein, and electron transfer flavoprotein-Q oxidoreductase from Paracoccus denitrificans," *J. Bacteriol.* 163:709-715 (1985).
Hustede et al., "Cloning of poly(3-hydroxybutyric acid) synthase genes of Rhodobacter sphaeroides and Rhodospirillum rubum and heterologous expression in Alcaligenes eutrophys," *FEMS Microbiol. Lett.* 93:285-290 (1992).
Ibarra et al., "*Escherichia coli* K-12 undergoes adaptive evolution to achieve in silico predicted optimal growth," *Nature* 420(6912):186-189 (2002).
Ichikawa et al. Catalytic reaction of 1,3-butanediol over solid acids, *J. Mol. Catalysis A Chem.* 256:106-112 (2006).
Ichikawa et al., "Pio study on 1,3-butanediol dehydration over CeO2 (1 1 1) surface," *J. Mol. Catalysis a Chem.* 231:181-189 (2005).
Ichiyama et al., "Oxalate synthesis in mammals: properties and subcellular distribution of serine:pyruvate/alanine:glyoxylate aminotransferase in the liver," *Mol. Urol.* 4(4):333.

Iffland et al., "Directed Molecular Evolution of Cytochrome c Peroxidase," *Biochemistry* 39:10790-10798 (2000).
Ikai et al., "Identification and analysis of a gene encoding L-2,4-diaminobutyrate:2-ketoglutarate 4-aminotransferase involved in the 1,3-diaminopropane production pathway in Acinetobacter baummanni," *J. Bacteriol.* 179:5118-5125 (1997).
Imai and Ohno, "Measurement of yeast intracellular pH by image processing and the change it undergoes during growth phase," *J.Biotechnol.* 38:165-172 (1995).
Ingoldsby et al., "The discovery of four distinct glutamate dehydrogenase genes in a strain of Halobacterium salinarum," *Gene* 349:237-244 (2005).
Ingram and Vreeland, "Differential-Effects of Ethanol and Hexanol on the Escherichia-coli Cell-Envelope," *J. Bacteriol.* 144:481-488 (1980).
Inui et al., "Occurrence of Oxygen-Sensitive, Nadp+-Dependent Pyruvate-Dehydrogenase in Mitochondria of Euglena-Gracilis," *J. Biochem.* 96:931-934 (1984).
Inui et al., "Pyruvate-Nadp+Oxidoreductase from Euglena-Gracilis - the Kinetic-Properties of the Enzyme," *Arch. Biochem. Bipophys.* 274:434-442 (1989).
Inui et al., "Wax Ester Fermentation in euglena-Gracilis," *Febs Lett.* 150:89-93 (1982).
Inui et al., "Fatty acid synthesis in mitochondria of Euglena gracilis," *Euro. J. Biochem.* 142(1):121-126 (1984).
Inui et al., "Production and Composition of Wax Esters by Fermentation of Euglena gracilis," *Air. Biol. Chem.* 47(11):2669-2671 (1983).
Inui et al., "Purification and characterization of pyruvate:Nadp+ oxidoreductase in Euglena gracilis," *J. Biol. Chem.* 262(19):9130-9135 (1987).
Inui et al., "Pyruvate:Nadp+oxidoreductase from Euglena gracilis: mechanism of 02-inactivation of the enzyme and its stability in the aerobe," *Arch. Biochem. Biophys.* 280:292-298 (1990).
Inui et al., "The physiological role of oxygen-sensitive pyruvate dehydrogenase in mitochondrial fatty acid synthesis in Euglena gracilis," *Arch. Biochem. Biophys.* 237(2):423-429 (1985).
Ishida et al., "Efficient production of L-Lactic acid by metabolically engineered Saccharomyces cerevisiae with a genome-integrated L-lactate dehydrogenase gene. *Appl. Envirom. Microbiol.* 71:1964-1970 (2005).
Ishige et al., "Wax ester production from n-alkanes by Acinetobacter sp. strain M-1: ultrastructure of cellular inclusions and role of acyl coenzyme a reductase," *Appl. Environ. Microbiol.* 68(3):1192-1195 (2002).
Ishigi et al., "Long-chain aldehyde dehydrogenase that participates in n-alkane utilization and wax ester synthesis in Acinetobacter sp strain M-1," *Appl. Environ. Microbiol.* 66:3481-3486 (2000).
Ismaiel et al., "Purification and Characterization of a Primary-Secondary Alcohol Dehydrogenase from Two Strains of Clostridium beijerinckii," *J. Bacteriol.* 175(16):5097- 5105 (1993).
Ismail et al., "Functional genomics by Nmr spectroscopy. Phenylacetate catabolism in *Escherichia coli*," *Eur. J. Biochem.* 270(14):3047-3054 (2005).
Ito et al., "Anthranilate synthetase, an enzyme specified by the tryptophan operon of *Escherichia coli*: Comparative studies on the complex and the subunits," *J Bacteriol.* 97:734-742 (1969).
Ito et al., "Colistin nephrotoxicity: report of a case with light and electron microscopic studies," *Acta Pathol. Jpn.* 19:55-67 (1969).
Ito et al., "D-3-hydroxybutyrate dehydrogenase from Pseudomonas fragi: molecular cloning of the enzyme gene and crystal structure of the enzyme," *J. Mol. Biol.* 355(4):722- 733 (2006).
Iverson et al., "Structure of the *Escherichia coli* fumarate reductase respiratory complex," *Science* 284(5422):1961-1966 (1999).
Iwakura et al., "Studies on regulatory functions of malic enzymes. Vi. Purification and molecular properties of Nadp-linked malic enzyme from *Escherichia coli* W," *J. Biochem.* 85:1355-1365 (1979).
Izard et al., "Crystal structures of the metal-dependent 2-dehydro-3-deoxy-galacarate aldolase suggest a novel reaction mechanism," *Embo J.* 19:3849-3856 (2000).
Izumi et al., "Structure and Mechanism of HpcG, a Hydratase in the Homoprotocatechuate Degradation Pathway of *Escherichia coli*," *J. Mol. Biol.* 370:899-911 (2007).

(56) References Cited

OTHER PUBLICATIONS

Jacobi et al., "The hyp operon gene products are required for the maturation of catalytically active hydrogenase isoenzymes in *Escherichia coli*," *Arch. Microbiol.* 158(6):444-451 (1992).
Jacques et al., "Characterization of yeast homoserine dehydrogenase, an antifungal target: the invariant histidine 309 is important for enzyme integrity," *Biochem. Biophys. Acta* 1544:28-41 (2001).
Jager et al., "Die Alanatreduktion von b-Carbonyl-oxalylsaure-estern," *Chem. Ber.* 92:2492-2499 (1959).
James et al., "Expression of two Escherichia coli acetyl-CoA carboxylase subunits is autoregulated," *J. Biol. Chem.* 279:2520-2527 (2004).
James et al., "Production and characterization of bifunctional enzymes. Domain swapping to produce new bifunctional enzymes in the aspartate pathway," *Biochemistry.* 41(11) 3720-3725 (2002).
Jansen et al., "L-2-hydroxylutarate dehydrogenase: identification of a novel enzyme activity in rat and human liver. Implications for L-2-hydroxyglutaric academia," *Biochim, Biophys. Acta* 1225(1):53-56 (1993).
Janssen, "Propanol as an end product of theonine fermentation," *Arch. Microbiol.* 182:482-486 (2004).
Jantama et al., "Combining metabolic engineering and metabolic evolution to develop nonrecombinant strains of *Escherichia coli*C that produce succinate and malate," *Biotechnol. Bioeng,* 99(5):1140-1153 (2008).
Jantama et al "Eliminating Side Products and Increasing succinate Yields in Engineered Strains of *Escherichia coli*C," *Biotechnol. Bioeng.* 101(5) 881-893 (2008).
Javid-Majd et al., "Mechanistic Analysis of the argE-Encoded N-Acetylornithine Deacetylase," *Biochemistry* 39:1285-1293 (2000).
Jeng et al., "Ornithine degradation in Clostridium sticklandii; pyridoxial phosphate and coenzyme a dependent thiolytic cleavage of 2-amino-4-ketopentanoate to alanine and acetyl coenzyme a," *Biochemistry* 13(14):2898-2903 (1974).
Jenkins et al., "Genetic and molecular characterization of the genes involved in short-chain fatty acid degradation in Escherichia coli: the ato system," *J. Bacteriol.* 169(1):42-52.
Jennert et al., "Gene transfer to Clostridium cellulolyticum ATCC 35319," *Microbiol.* 146:3071-3080 (2000).
Jenssen et al., "A literature network of human genes for high-throughput analysis of gene expression," *Nat. Gene.* 28:21-28 (2001).
Jeon et al., "Heterologous expression of the alcohol dehydrogenase (adhl) gene from Geobacillius thermoglucosidasius strain M10EXG," *J. Biotechnol.* 135:127-133 (2008).
Jewell et al., "Bioconversion of propionic, valeric and 4-hydroxybutyric acids into the corresponding alcohols by Clostridium acetobutylicum Nrrl 527," *Curr. Microbiol.* 13(4):215-219 (1986).
Jiang et al., "De Novo Computational Design of Retro-Aldol Enzymes," *Science* 319: 1387-1391 (2008).
Jin et al., "Characterization of the major citrate synthase of Bacillus subtilis," *J. Bacteriol.* 178(12):3658-3660 (1996).
Jogl et al., "Crystal structure of yeast acetyl-coenzyme a synthetase in complex with Amp," *Biochemistry* 43(6):1425-1431 (2004).
Johanson et al., "Strain engineering for steroselective bioreduction of dicarbonyl compounds by yeast reductases," *FEMS Yeast Res.* 5:513-525 (2005).
Johnson et al., "Alteration of a single amino acid changes the substrate specificity of dihydroflavonol 4-reductase," *Plant J.* 25(3):325-333 (2001).
Johnston et al., "Structure of naphthoate synthase (MenB) from Mycobacterium tuberculosis in both native and product-bound forms," *Acta Cryst* D61:1199-1206 (2005).
Jojima et al., "Production of isopropanol by metabolically engineered *Escherichia coli*," *Appl. Microbiol. Biotechnol.* 77:1219-1224 (2008).
Jones et al.,"Acetone-butanol fermentation revisited," *Microbiol. Rev.* 50(4):484-524.
Jones et al., "Molecular cloning, characterization and analysis of the regulation of the ARO2 gene, encoding chorismate synthase, of Saccharomyces cerevisiae," *Mol. Microbiol.* 5(9):2143-2152 (1991).
Junker et al., "Involvement of the cis/trans isomerase Cti in solvent resistance of Pseudomonas putida Dot-T1E," *J. Bacteriol.* 181:5693-5700 (1999).
Junker et al., "Characterization of the p-toluenesulfonate operon tsaMBCD and tsaR in Comamonas testosteroni T-2," *J. Bacteriol.* 179(3):919-927 (1997).
Kaclikova et al., "Fumaric acid overproduction in yeast mutants deficient in fumarase," *Fems Microbiol. Lett.* 91(2):101-106 (1992).
Kahng et al., "Characterization of strain HY99, a novel microorganism capable of aerobic and anaerobic degradation of aniline," *Fems Microbiol Lett.* 190:215-221 (2000).
Kai et al., "Phosphoenolpyruvate carboxylase: three-dimensional structure and molecular mechanisms," *Arch. Biochem. Biophys.* 414:170-179 (2003).
Kakimoto et al., 13-aminoisobutyrate-a-ketoglutarate transaminase in relation to (3-aminoisobutyric aciduria, *Biochim. Biophys. Acta* 156(2):374-380 (1968).
Kalousek et al., "Isolation and characterization of propionyl-CoA carboxylase from normal human liver. Evidence for a protomeric tetramer of nonidentical subunits," *J. Biol. Chem.* 255:60-65 (1980).
Kalpos, "On the mammalian acetone metabolism: from chemistry to clinical implications," *Biochim. Biophys. Acta* 1621(2):122-139 (2003).
Kalscheuer et al., "A novel bifunctional wax ester synthase/acyl-CoA:diacylglycerol acyltransferase mediates wax ester and triacylglycerol biosynthesis in Acinetobacter calcoaceticus ADP1," *J. Biol. Chem.* 278(10):8075-8082 (2003).
Kalscheuer et al., "Analysis of storage lipid accumulation in Alcanivorax borkumensis: Evidence for alternative triacylglycerol biosynthesis routs in bacteria," *J. Bacteriol.* 189(3):918-928 (2007).
Kanagawa, et al., "Characterization of the 6-aminohexanoate-dimer hydrolase from Pseudomonas sp. NK87," *J Gen Microbiol,* 139(4):787-795 (1993).
Kanamasa et al., "Cloning and functional characterization of the cis-aconitic acid decarboxylase (CAD) gene from Aspergillus terreus," *Appl. Microbiol. Biotechnol.* 80(2):223-229 (2008).
Kanao et al., "Characterization of isocitrate dehydrogenase from the green sulfur bacterium Chlorbium limicola. A carbon dioxide-fixing enzyme in the reductive tricarboxylic acid cycle," *Eur. J. Biochem.* 269(7):1926-1931 (2002).
Kanaujia et al., "Cloning, expression, purification, crystallization and preliminary X-ray. crystallographic study of DHNA synthetase from Geobacillus kaustophilus," *Acta Cryst* F63:103-105 (2007).
Kanehisa et al., "Kegg: Kyoto Encyclopedia of Genes and Genomes database," *Nucleic Acids Res.* 28(1):27-30 (2000).
Kapatral et al., "Genome Sequence and Analysis of the Oral Bacterium Fusobacterium nucleatum Strain ATCC 25586," *J. Bacteriol.* 184(7):2005-2018 (2002).
Karyakin et al., "Kinetic properties of L-lysine-2-monooxygenase from Pseufomonas putida and its application to biosensors for L-lysine," *Prikladnaya Biokhimiya I Mikrobiologiya* 27:825-832 (1991).
Kasberg et al., "Cloning, characterization, and sequence analysis of the cicE gene encoding the maleylacetate reductase of Pseufomonas sp. Strain B13," *J. Bacteriol.* 179:3801-3803 (1997).
Kaschabek et al., "Degradation of chloroaromatics: purification and characterization of maleylacetate reductase from Pseudomonas sp. Strain B13," *J. Bacteriol.* 175:6075-6081.
Kaschabek et al., "Maleylacetate reductase of Pseufomonas sp. Strain B13: specificity of substrate conversion and halide elimination," *J. Bacteriol.* 177:320-325 (1995).
Kaschabek et al., "Degradation of aromatics and chloroaromatics by Pseudomonas sp. strain B13: purification and characterization of 3-oxoadipate:succinyl-coenzyme a (CoA) transferase and 3-oxoadipyl-CoA thiolase," *JBacteriol,* 184(1):207-215 (2002).
Kashket and Cao, "Isolation of a Degeneration-Resistant Mutant of clostridium acetobutylicum NCIMB 8052," *Appl. Environ. Microbiol.* 59:4198-4202 (1993).

(56) References Cited

OTHER PUBLICATIONS

Kato et al., "3-Methylaspartate ammonia-lyase as a marker enzyme of the mesaconate pathway for (S)-glutamate fermentation in Enterobacteriaceae," *Arch. Microbiol.* 168(6):457-463 (1997).
Katti, et al., "Crystal structure of muconolactone isomerase at 3.3 a resolution," *J. Mol. Biol.* 205:557-571 (1989).
Katz et al., "Screening of two complementary collections of Saccharomyces cerevisiae to identify enzymes involved in stereoselective reductions of specific carbonyl compounds: an alternative to protein purification," *Enzyme Microb. Technol.* 33:163-172 (2003).
Kawabata et al., "The Effect of Growth Temperature on Wax Ester Content and Composition of *Euglena gracilis*," *J. Gen. Microbiol.* 135: 1461-1467 (1989).
Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).
Kefala et al., "Cloning, expression, purification, crystallization and preliminary x-ray diffraction analysis of LysA (Rv1293) from Mycobacterium tuberculosis," *Acta. Cryst.* F61:782-784 (2005).
Kehrer et al., "Glycerate kinase of the hyperthermophilic archaeon Thermoproteus tenax: new insights into the phylogenetic distribution and physiological role of members of the three different glycerate kinase classes," *BMC Genomics* 8:301 (2007).
Kellum et al., "Effects of cultivation gas phase on hydrogenase of the acetogen Clostridium thermoaceticum," *J. Bacteriol.* 160(1):466-469 (1984).
Kenealy et al., "Biochemical Aspects of Fumaric Acid Accumulation by *Rhizopus arrhizus*," *Appl. Environ. Microbiol.* 52:128-133 (1986).
Keng et al., "Specificity of Aspartokinase III from *Escherichia coli* and Examination of Important Catalytic Residues," *Arch. Biochem. Biophys.* 335(1):73-81 (1996).
Kenklies et al., "Proline biosynthesis from L-ornithine in Clostridium sticklandii: purification of A1-pyrroline-5-carboxylate reductase, and sequence and expression of encoding gene, proC," *Microbiology* 145(Pt 4):819-826 (1999).
Kerby et al., "Carbon Monoxide-Dependent Growth of Rhodospirillum rubrum, " *J. Bacteriol.* 177:2241-2244 (1995).
Kerby, et al., "Genetic and physiological characterization of the Rhodospirillum rubrum carbon monoxide dehydrogenase system," *J Bacteriol*, 174(16):5284-5294 (1992).
Kern et al., "Isoamyl alcohol-induced morphological change in Saccharomyces cerevisiae involves increases in mitochondria and cell wall chitin content," *FEMS Yeast Res.* 5:43-49.
Kessler et al., "Pyruvate-formate-lyase-deactivase and acetyl-CoA reductase activities of *Escherichia coli* reside on a polymeric protein particle encoded by adhE," *Febs Lett.* 281(1-2):59-63 (1991).
Khan et al., "Molecular Properties and Enhancement of Thermostability by Random. Mutagenesis of Glutamate Dehydrogenase from Bacillus subtilis," *Biosci. Biotechnol. Biochem.* 69(10):1861-1870 (2005).
Kikuchi et al., "Mutational analysis of the feedback sites of phenylalanine-sensitive 3-deoxy-D-arabino-heptulosonate-7-phosphate synthase of *Escherichia coli*," *Appl. Environ. Microbiol.* 63(2):761-762 (1997).
Killenberg-Jabs et al., "Active oligomeric states of pyruvate decarboxylase and their functional characterization," *Eur. J. Biochem.* 268:1698-1704 (2001).
Kim et al., "Catalytic promiscuity in dihydroxy-acid dehydratase from the thermoacidophilic archaeon Sulfolobus solfataricus," *J. Biochem.* 139(3):591-596 (2006).
Kim et al, "Effect of Overexpression of Actinobacillus succinogenes Phosphoenolpyruvate Carboxykinase on Succinate Production in *Escherichia coli*," *Appl. Env. Microbiol.* 70(2). 1238-1241 (2004).
Kim et al., "2-Hydroxyisocaproyl-CoA dehydratase and its activator from Clostridium difficile," *Febs J.* 272:550-561 (2005).
Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).
Kim et al., "Dihydrolipoamide dehydrogenase mutation alters the NADH sensitivity of pyruvate dehydrogenase complex of *Escherichia coli* K-12," *J. Bacteriol.* 190:3851-3858.
Kim et al., "Studies of the hyperthermophile *Thermotoga maritima* by random sequencing of cDNA and genomic libraries. Identification and sequencing of the *trpEG* (D) operon," *J Mol. Biol.* 231:960-981 (1993).
Kim, "Purification and Properties of a diamine a-Ketoglutarate Transminase from *Escherichia coli*," *J. Biol. Chem.* 239(3):783-786 (1964).
Kinghorn et al., "The cloning and analysis of the aroD gene of E. coli K-12," *Gene* 14(1-2):73-80 (1981).
Kino et al. Synthesis of Dl-tryptophan by modified broad specificity amino acid racemase from Pseudomonas putida IFO 12996, *Appl. Microbiol. Biotechnol.* 73:1299-1305 (2007).
Kinoshita et al., "Purification and characterization of 6-aminohexanoic-acid-oligomer hydrolase of Flavobacterium sp. KI72," *Eur. J. Biochem.* 116(3):547-551 (1981).
Kinoshita, "Purification of two alcohol dehydrogenases from Zymomonas mobilis and their properties," *Appl. Microbiol. Biotechnol.* 22:249-254 (1985).
Kisselev L., "Polypeptide release factors in prokaryotes and eukaryotes: same function, different structure," *Structure* 10:8-9 (2002).
Kitzing et al., "Spectroscopic and kinetic characterization of the bifunctional chorismate synthase from Neurospora crassa: evidence for a common binding site for 5-enolpyruvylshikimate 3-phosphate and Nadph," *J. Biol. Chem.* 276(46):42658-42666.
Kizer et al., "Application of Functional Genomics to Pathway Optimization for Increased Isoprenoid Production," *Appl. Environ. Microbiol.* 74(10):3229-3241 (2008).
Klasson, et al., "Biological conversion of coal and coal-derived synthesis gas," *Fuel* 72(12):1673-1678 (1993).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Kleanthous et al., "A comparison of the enzymological and biophysical properties of two distinct classes of dehydroquinase enzymes," *Biochem. J.* 282(Pt3):687-695 (1992).
Klyosov, "Kinetics and specificity of human liver aldehyde dehydrogenases toward aliphatic, aromatic, and fused polycyclic aldehydes," *Biochemistry* 35(14):4457-4467.
Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).
Knappe et al., "A radical-chemical route to acetyl-CoA: the anaerobically induced pyruvate formate-lyase system of *Escherichia coli*," *FEMS. Microbiol. Rev.* 75:383-398 (1990).
Knappe et al., "Post-translational activation introduces a free radical into pyruvate formate-lyase," *Proc. Natl. Acad. Sci. USA* 81:1332-1335 (1984).
Knothe, "'Designer' Biodiesel: Optimizing Fatty Ester Composition to Improve Fuel Properties," *Energy Fuels* 22:1358-1364 (2008).
Kobayashi et al., "Physicochemical, catalytic, and immunochemical properties of fumarases crystallized separately from mitochondrial and cytosolic fractions of rat liver," *J. Biochem.* 89(6):1923-1931 (1981).
Koch et al., "Enzymatic reduction of benzoyl-CoA to alicyclic compounds, a key reaction in anaerobic aromatic metabolism," *Eur. J. Biochem.* 205:195-202 (1992).
Koch et al., "Products of enzymatic reduction of benzoyl-CoA, a key reaction in anaerobic aromatic metabolism," *Eur. J. Biochem.* 211:649-661 (1993).
Koland et al., "Proximity of Reactive Cysteine Residue and Flavin in *Escherichia coli* Pyruvate Oxidase As Estimated by Flourescence Energy Transfer," *Biochemistry* 21:4438-4442 (1982).
Kollmann-Koch et al.,"Nicotinic acid metabolism. Dimethylmaleate hydratase," *Hoppe Seylers Z Physiol Chem.* 365:s.847-857 (1984).

(56) References Cited

OTHER PUBLICATIONS

Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).

Korbert et al., "Crystallization of the Nadp±-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase a-subunit structure using 3.4 a Mad and 1.9 a native data," *Acta Cryst.* D58:2116-2121 (2002).

Korotkova et al., "Connection between poly-P-hydroxybutyrate biosynthesis and growth on C1 and C2 compounds in the methylotroph Methylobacterium extorquens AM1," *J. Bacteriol.* 183(3):1038-1046 (2001).

Korotkova et al., "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium Thermotoga maritima: molecular characterization and phylogenetic implications," *Extremophiles* 52-60 (1997).

Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).

Koshiba et al., "Purification and Properties of Flavin- and Molybdenum-Containing Aldehyde Oxidase from Coleoptiles of Maize," *Plant Physiol.* 110(3):781-789 (1996).

Kosjaek et al., "Purification and characterization of a chemotolerant alcohol dehydrogenase application to coupled redox reactions," *Biotechnol. Bioeng.* 86:55-62.

Kouzarides, "Acetylation: a regulatory modification to rival phosphorylation?" *EMBO. J.* 19(6):1176-1179 (2000).

Kovachy et al., "Recognition, Isolation, and Characterization of Rat Liver D-Methylmalonyl Coenzyme a Hydrolase," *J. Biol. Chem.* 258(18):11415-11421 (1983).

Kowalchuk et al., "Contrasting patterns of evolutionary divergence within the Acinetobacter calcoaceticus pca operon," *Gene* 146:23-30 (1994).

Kraus et al., "Biosynthesis and mitochondrial processing of the 13 subunit of propionyl coenzyme a carboxylase from rat liver," *J. Biol. Chem.* 258:7245-7248 (1983).

Kreimeyer et al., "Identification of the Last Unknown Genes in the Fermentation Pathway of Lysine," *J. Biol. Chem.* 282(10):7191-7197 (2007).

Krell et al., "Biochemical and X-ray crystallographic studies on shikimate kinase: the important structural role of the P-loop lysine," *Protein Sci.* 10(6):1137-1149 (2001).

Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).

Kress et al., "Tungsten(VI) and molybdenum(VI) oxo-alkyl species. Their role in the metathesis of olefins," *J. Chem. Soc., Chem. Commun.* 431-432 (1980).

Kretovich et al., "The enzyme catalyzing the reductive amination of oxypyruvate," *Izv. Akad. Nauk. SSSR Biol.* 2:295-301 (1966).

Kretz et al., "Gene site saturation mutagenesis: a comprehensive mutagenesis approach," *Methods Enzymol.* 388:3-11 (2004).

Krieger et al., "Pyruvate decarboxylase from Kluyveromyces lactis an enzyme with an extraordinary substrate activation behaviour," *Eur. J. Biochem.* 269:3256-3263 (2002).

Krishna, et al., "Enzymatic synthesis of isoamyl acetate using immobilized lipase from *Rhizomucor miehei*," *J. Biotechnol.* 87:193-201 (2001).

Kuchta et al., "Lactate Reduction in Clostridium propionicum Purification and properties of lactyl-CoA dehydratase" *J. Biol Chem.* 260(24):13181-13189 (1985).

Kuhnl et al., "Functional analysis of the methylmalonyl-CoA epimerase from Caenorhabditis elegans," *FEBS J.* 272(6):1465-1477 (2005).

Kulkarni et al., "Bioremediation of c-caprolactum from nylon-6 wastewater by use of Pseudomonas aeruginosa MCM B-407," *Curr. Microbiol.* 37(3):191-194 (1998).

Kumamaru et al "Enhanced degradation of polychlorinated biphenyls by directed evolution of biphenyl dioxygenase," *Nat. Biotechnol.* 16:663-666 (1998).

Kumari et al., "Cloning, Characterization, and Functional Expression of acs, the Gene Which Encodes Acetyl Coenzyme a Synthetase in *Escherichia coli*," *J. Bacteriol.* 177(10):2878-2886 (1995).

Kuntze et al., "6-Oxocyclohex-1-ene-1-carbonyl-coenzyme a hydrolases from obligately anaerobic bacteria: characterization and indentification of its gene as a functional marker for aromatic compounds degrading anaerobes," *Environ. Microbiol.* 10(6):1547-1556.

Kurihara et al., "A Novel Putrescine Utilization Pathway Involves 17-Glutamylated Intermediates of *Escherichia coli* K-12," *J. Biol. Chem.* 280(6):4602-4608 (2005).

Kurihara et al., "y-Glutamyputrescine synthetase in the putrescine utilization pathway of *Escherichia coli* K-12," *J. Biol. Chem.* 283(29)19981-19990 (2008).

Kuznetsova et al., "Enzyme genomics: Application of general enzymatic screens to discover new enzymes," *FEMS Microbiol. Rev.* 29(2):263-279 (2005).

Kwok et al., "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in Escherichi coli under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium Thauera aromatica," *Eur. J. Biochem.* 263(2):420-429 (1999).

Laivenieks et al., "Cloning sequencing, and overexpression of the Anaerobiospirillum succinicproducens phosphoenolpyruvate carboxykinase (pckA) gene," *Appl. Environ. Microbiol.* 63:2273-2280 (1997).

Lam et al., "Metabolic Relationships between Pyridoxine (Vitamin B6) and Serine Biosynthesis in *Escherichia coli* K-12," *J. Bacteriol.* 171(11):6518-6528 (1990).

Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem J*, 395(1):147-155.

Lamed et al., "Novel NADP-linked alcohol-aldehyde/ketone oxidoreductase in thermophilic ethanologenic bacteria," *Biochem. J.* 195:183-190 (1981).

Lardizabal, et al., "Purification of a jojoba embryo wax synthase, cloning of its cDNA, and production of high levels of wax in seeds of transgenic arabidopsis," *Plant Physiol.* 122(3):645-655 (2000).

Lawrence et al., "Evolution of coenzyme B12 synthesis among enteric bacteria: evidence for loss and reacquisition of a multigene complex," *Genetics* 142(1):11-24 (1996).

Lawrence et al., "The cobalamin (coenzyme $B_{12}$) biosynthetic genes of *Escherichia coli*," *J. Bacteriol.* 177(22):6371-6380 (1995).

Lebbink et al., "Engineering activity and stability of Thermotoga maritima glutamate dehydrogenase I. Introduction of a six-residue ion-pair network in the hinge region," *J. Mol. Biol.* 280:287-296 (1998).

Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee et al., "Identification of essential active-site residues in ornithine decarboxylase of Nicotiana glutinosa decarboxylating both L-ornithine and L-lysine," *Biochem. J.* 360:657-665 (2001).

(56) References Cited

OTHER PUBLICATIONS

Lee et al., "A new approach to directed gene evolution by recombined extension on truncated templates (RETT)," *J. Molec. Catalysis* 26:119-129 (2003).
Lee et al., "Batch and continuous cultivation of Anaerobiospirillum succiniciproducens for the production of succinic acid from whey," *Appl. Microbiol. Biotechnol.* 54(1):23-27.
Lee et al., "Biological conversion of wood hydrolysate to succinic acid by Anaerobiospirillum succiniciproducens. *Biotechnol. Lett.* 25(2):111-114 (2003).
Lee et al., "Biosynthesis of enantiiopure (S)-3-hydroxybutyric acid in metabolically engineered *Escherichia coli*," *App. Microbiol. Biotechnol.* 79:633-641 (2008).
Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).
Lee et al., "Cloning and Characterization of Mannheimia succiniciproducens MBEL55E. Phosphoenolpyruvate Carboxykinase (pckA) Gene," *Biotechnol. Bioprocess Eng.* 7:95-99 (2002).
Lee et al., "Cloning and characterization of the dxs gene, encoding 1-deoxy-D-xylulose 5-phosphate synthase from *Agrobacterium tumefaciens*, and its overexpression in *Agrobacterium tumefaciens*," *J. Biotechnol.* 128(3):555-566 (2007).
Lee et al., "Crystal structure of the type II 3-dehydroquinase from Helicobacter pylori," *Proteins* 51(4):616-617 (2003).
Lee et al., "Fermentative production of chemicals that can be used for polymer synthesis," *Macromol. Biosci.* 4:157-164 (2004).
Lee et al., "Genome-based metabolic engineering of Mannheimia succiniciproducens for. succinic acid productiion," *Appl. Environ. Microbiol.* 72(3):1939-1948 (2006).
Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).
Lee et al., "Phylogenetic diversity and the structural basis of substrate specificity in the β/a-barrel fold basic amino acid decarboxylases," *J. Biol. Chem.* 282:27115-27125 (2007).
Lee et al., "Metabolic engineering of *Escherichia coli* for enhanced production of succinic. acid, based on genome comparison and in silico gene knockout simulation," *Appl Environ. Microbiol.* 71(12):7880-7887 (2005).
Lehtiö et al., "The pyruvate format lyase family: sequences, structures and activation," *Protein Eng. Des.Sel.* 17:545-552 (2004).
Lehtiö et al., "Crystal structure of glycyl radical enzyme from Archaeoglobus fulgidus," *J. Mol. Biol.* 357(1):221-235 (2006).
Lei et al., "A shared binding site for NAD+ and coenzyme a in an acetaldehyde dehydrogenase involved in bacterial degradation of aromatic compounds," *Biochemistry* 47:6870-6882 (2008).
Lemoine et al., "Microcorrespondence: Monofunctional biosynthetic peptidoglycan transglycosylases," *Mol. Microbiol.* 19(3):639-647 (1996).
Lemonnier and Lane, "Expression of the second lysine decarboxylase gene of *Escherichia coli,*" *Microbiology* 144(Pt 3):751-760 (1998).
Lenski et al., "Dynamics of adaptation and diversification: a 10,000-generation experiment with bacterial populations," *Proc. Natl. Acad. Sci. USA* 91(15):6808-6814.
Leonardo et al., "Anaerobic Regulation of the adhE gene, Encoding the Fermentative Alcohol Dehydrogenase of *Escherichia coli*," *J. Bacteriology* 175(3):870-878 (1993).
Lepore et al., "The x-ray crystal structure of lysine-2,3-aminomutase from Clostridium subterminale," *Proc. Natl. Acad. Sci USA* 102:13819-13824 (2005).
Leppanen et al., "Pyruvate formate lyase is structurally homologous to type I ribonucleotide reductase," *Structure* 7:733-744 (1999).
Lessner et al., "An unconventional pathway for reduction of CO2 to methane in Co-grown Methanosarcina acetivorans revealed by proteomics," *Proc. Natl. Acad. Sci. USA* 103(47):17921-17926 (2006).

Leutwein et al., "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).
Levanon S. S., et al., "Effect of Oxygen on the *Escherichia coli* ArcA and Fnr Regulation Systems and Metabolic Responses," *Biotechnol Bioeng* 89(5):556-564 (2005).
Li et al., "Effects of substitution of tryptophan 412 in the substrate activation pathway of yeast pyruvate decarboxylase," *Biochemistry* 38:10004-10012 (1999).
Li et al., "Properties of Nicotinamide Adenine Dinucleotide Phosphate-Dependent Formate Dehydrogenase from Clostridium thermoaceticum," *J. Bacteriol.* 92(2):405-412 (1966).
Li et al., "Purification, crystallization and preliminary crystallographic studies on 2-dehydro-3-deoxygalactarate aldolase from Leptospira interrogans," *Acta Cryst.* F62:1269-1270 (2006).
Li, "Development of a reporter system for the study of gene expression for solvent production in Clostridium beijerinckii Nrrl B592 and Clostridium acetobutylicum ATCC 824," Dissertation, Department of Biochemestry, Virginia Polytechnic Institute and State. University (Sep. 1998).
Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).
Liepman et al., "Peroxisomal alanine : glyoxylate aminotransferase (AGT1) is a photorespiratory enzyme with multiple substrates in Arabidopsis thaliana," *Plant J.* 25(5):487-498 (2001).
Lin et al., "Chemostat culture characterization of Escherichia coli mutant strains metabolically engineered for aerobic succinate production: a study of the modified metabolic network based on metabolite profile, enzyme activity, and gene expression profile," *Metab. Eng.* 7(5-6):337-352 (2005).
Lin et al., "Functional Expression of Horseradish Peroxidase in E. coli by Directed Evolution," *Biotechnol. Prog.* 15:467-471 (1999).
Lin et al., "Effect of carbon sources differing in oxidation state and transport route on succinate production in metabolically engineered *Escherichia coli*," *J. Ind. Microbiol. Biotechnol.* 32:87-93 (2005).
Lin et al., "Fed-batch culture of a metabolically engineered *Escherichia coli* strain designed for high-level succinate production and yield under aerobic conditions," *Biotechnol. Bioeng.* 90:775-779 (2005).
Lin et al., "Genetic Reconstruction of the Aerobic Central Metabolism in *Escherichia coli* for the Absolute Aerobic Production of Succinate," *Biotechnol. Bioeng.* 89(2):148-156 (2005).
Lin et al., "Increasing the Acetyl-CoA pool in the Presence of Overexpressed Phosphoenolpyruvate Carboxylase or Pyruvate Carboxylase Enhances Succinate. Production in *Escherichia coli*," *Biotechnol Prog,* 20(5):1599-1604 (2004).
Lin et al., "Metabolic engineering of aerobic succinate production systems in *Escherichia coli* to improve process productivity and achieve the maximum theoretical succinate yield," *Metab Eng.* 7(2):116-127 (2005).
Lin, "Metabolic Network Design and Engineering in *Escherichia coli*" Ph.D. Thesis, Rice University, Dept. f Bioengineering (2005).
Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl Microbiol Biotechnol.* 67(4): 515-523 (2005).
Lingen et al., "Alteration of the substrate specificity of benzoylformate decarboxylase from Pseudomonas putida by directed evolution," *Chembiochem.* 4:721-726 (2003).
Lingen et al., "Improving the carboligase activity of benzoylformate decarboxylase from Pseudomonas putida by a combination of directed evolution and site-directed mutagenesis," *Protein Eng.* 15:585-593 (2002).
Link et al., "Methods for generating precise deletions and insertions in the genome of wild-type *Eshcerichia coli*: application to open reading frame characterization," *J. Bacteriol.* 179:6228-6237 (1997).
Liou et al., "Clostridium carboxidivorans sp. nov., a solvent-producing clostridium isolated from an agricultural settling lagoon, and reclassification of the acetogen Clostridium scatologenes strain SL1 as Clostridium drakei sp. nov," *Int. J. Syst. Evol. Microbiol.* 55(Pt 5):2085-2091 (2005).

(56) References Cited

OTHER PUBLICATIONS

Liu et al., "Kinetic and crystallographic analysis of active site mutants of Escherichia coli y-aminobutyrate aminotransferase," Biochemistry, 44(8):2982-2992 (2005).
Liu et al., "Microbial production of R-e-hydroxybutyric acid by recombinant E. coli harboring genes of phbA, phbB, and tesB," Appl. Microbiol. Biotechnol. 76:811-818.
Liu et al., "Purification and characterization of ornithine acetyltransferase from Saccharomyces cerevisiae," Eur. J. Biochem. 228:291-296 (1995).
Liu et al., "A Mofrl family glycerate kinase from the thermophilic crenarchaeon, Sulfolobus tokodaii, with unique enzymatic properties," Biotechnol. Lett. 31(12):1937-1941 (2009).
Liu et al., "Crystal structures of unbound and aminooxyacetate-bound Escherichia coli y-aminobutyrate aminotransferase," Biochemistry 43(34):10896-10905 (2004).
Liu et al., "Economical succinic acid production from cane molasses by Actinobacillus succinogenes." Bioresour Technol 99(6):1736-1742 (2008).
Ljungdahl et al., "Formate dehydrogenase, a selenium-tungsten enzyme from Clostridium thermoaceticum," Methods Enzymol. 53:360-372 (1978).
Ljungdahl et al., "Tungsten, a component of active formate dehydrogenase from Clostridium thermoacetium," Febs Lett. 54:279-282 (1975).
Ljungdahl, "The Autotrophic Pathway of Acetate Synthesis in Acetogenic Bacteria," Ann. Rev. Microbiol. 40:415-450 (1986).
Lloyd-Jones et al., "Rate Enhancement by Ethylene in the Ru-Catalyzed Ring-Closing. Metathesis of Enynes: Evidence for an "Ene-then-Yne" Pathway that Diverts through a Second Catalytic Cycle," Angew Chem Int Ed. 44(45):7442-7447 (2005).
Lobner-Olesen et al., "Identification of the Gene (aroK) Encoding Shikimic Acid Kinase I of Escherichia coli," J. Bacteriol. 174(2):525-529 (1992).
Locher et al., "4-Toluene Sulfonate Methyl-Monooxygenase from Comamonas testosteroni T-2: Purification and Some Properties of the Oxygenase Component," J. Bacteriol. 173(12):3741-3748 (1991).
Locher et al., "Crystal structure of the Acidaminococcus fermentans 2-hydroxyglutaryl-CoA dehydratase component a" J. Mol. Biol. 307(1):297-308 (2001).
Lokanath et al., "Crystal structure of novel NADP-dependent 3-hydroxyisobutyrate dehydrogenase from Thermus thermophilus HB8," J. Mol. Biol. 352(4):905-917 (2005).
Loke et al., "Active acetyl-CoA synthase from Clostridium thermoaceticum obtained by cloning and heterologous expression of acsAB in Escherichia coli," Proc Natl Acad Sci U S. A. 97:12503-12535 (2000).
Longtine et al., "Additional modules for versatile and economical Pcr-based gene deletion and modification in Saccharomyces cerevisiae," Yeast 14(10):953-961 (1998).
Lopez-Barragan et al., "The bzd gene cluster, coding for anaerobic benzoate catabolism, in Azoarcus sp. Strain Cib," J. Bacteriol. 186(17):5762-5774 (2004).
Louie et al., "Cloning and characterization of the gamma-glutamyl phosphate reductase gene of Campylobacter jejuni," Mol. Gen. Genet. 240:29-35 (1993).
Louis et al., "Restricted distribution of the butyrate kinase pathway among butyrate-producing bacteria from the human colon," J. Bacteriol. 186:2099-2106 (2004).
Lovell et al., "Cloning and expression in escherichia coli of the Clostridium thermoaceticum gene encoding thermostable formyltetrahydrofolate synthetase," Arch. Microbiol. 149(4):280-285 (1988).
Lovell, et al., "Primary structure of the thermostable formyltetrahydrofolate synthetase from Clostridium thermoaceticum," Biochemistry 20(29):5687-5694 (1990).
Low et al., "Mimicking somatic hypermutation: affinity maturation of antibodies displayed on baceriophage using a bacterial mutator strain," J. Mol. Biol. 260(3):359-368 (1996).
Lu et al., "Controlled Poetntial Enzymology of Methyl Transfer Reactions Involved in Acetyl-CoA Synthesis by Co Dehydrogenase and the Corrinoid/Iron-Sulfur Protein from Clostridium thermoaceticum," J. Biol. Chem. 265(6):3124-3133 (1990).
Lu et al., "Functional Analysis and Regulation of the Divergent spuABCDEFGH-spuI Operons for Polyamine Uptake and Utilization in Pseudomonas aeruginosa PAO1," J. Bacteriol. 184(14):3765-3773 (2002).
Lu et al., "Sequence and expression of the gene encoding the corrinoid/iron-sulfur protein from Clostridium thermoaceticum and reconstitution of the recombinant protein to full activity," J. Biol. Chem. 268(8):5605-5614 (1993).
Luersen, "Leishmania major thialsine Ne-acetyltransferase: Identification of amino acid residues crucial for substrate binding," Febs Lett. 579:5347-5352 (2005).
Luli et al., et al., "Comparison of Growth, Acetate Production, and Acetate Inhibition of Escherichia coli Strains in Batch and Fed-Batch Fermentations," Appl Environ Microbiol. 56:1004-1011 (1990).
Lupa et al., "Distribution of genes encoding the microbial non-oxidative reversible hydroxyarylic acid decarboxylases/phenol carboxylases," Genomics 86:342-351 (2005).
Lupa et al., "Properties of the reversible nonoxidative vanillate/4-hydroxybenzoate decarboxylase from Bacillus subtilis," Can. J Microbiol 54:75-81 (2008).
Lütke-Eversloh et al., "Biochemical and molecular characterization of a succinate semialdehyde dehydrogenase involved in the catabolism of 4-hydroxybutyric acid in Ralstonia eutropha," Fems Microbiol. Lett. 181(1):63-71 (1999).
Lutz et al., "Independent and tight regulation of transcriptional units in Escherichia coli via the LacR/O, the TetR/0 and AraC/Ii-I2 regulatory elements," Nucleic Acids Res. 25(6):1203-1210 (1997).
Lutz et al., "Creating multiple-crossover Dna libraries independent of sequence identity," Proc. Natl. Acad. Sci USA 98:11248-11253 (2001).
Lutz et al., "Dissecting the functional program of Escherichia coli promoters: the combined mode of action of Lac repressor and AraC activator," Nucleic Acids Res. 29(18):3873-3881 (2001).
Lutz et al., "Rapid generation of incremental truncation libraries for protein enginering using a-phosphothioate nucleotides," Nucleic Acids Res. 29:E16 (2001).
Lynch et al., "SCALEs: multiscale analysis of library enrichment," Nat. Methods. 4(1):87-93 (2007).
Lynd et al., "Microbial Cellulose Utilization: Fundamentals and Biotechnology," Microbiol. Mol. Biol. Rev. 66:506-577 (2002).
Lynn et al., "Living Ring-Opening Metathesis Polymerization in Aqueous Media Catalyzed by Well-Defined Ruthenium Carbene Complexes," J. Am. Chem. Soc. 118(4):784-790 (1996).
Lynn et al., "Living Ring-Opening Metathesis Polymerization in Water," J. Am. Chem. Soc. 120(7):1627-1628 (1998).
Ma et al., "Induced rebuilding of aspartase conformation," Ann. NY Acad. Sci. 672:60-65.
Macheroux et al., "A unique reaction in a common pathway: mechanism and function of chorismate synthase in the shikimate pathway," Planta 207(3):325-334 (1999).
Macis et al., "Properties and sequence of the coenzyme Biz-dependent glycerol dehydratase of Clostridium pasteruianum," FEMS Microbiol. Lett. 164:21-28 (1998).
Mack et al., "Conversion of glutaconate CoA-transferase from Acidaminococcus fermentans into an acyl-CoA hydrolase by site-directed mutagenesis," Febs Lett. 405(2):209-212 (1997).
Mack et al., "Location of the two genes encoding glutaconate coenzyme A-transferase at the beginning of the hydroxyglutarate operon in Acidaminococcus fermentans," Eur. J. Biochem. 226:41-51 (1994).
Maclean et al., "The Structure of Chorismate Synthase Reveals a Novel Flavin Binding Site Fundamental to a Unique Chemical Reaction," Structure 11(12):1499-1511 (2003).
Maeda et al "Enhanced hydrogen production from glucose by metabolically engineered Escherichia coli," Appl. Microbiol. Biotechnol. 77:879-890 (2007).
Maeder et al., "The Methanosarcina barkeri genome: comparative analysis with Methanosarcina acetivorans and Methanosarcina mazei

(56) References Cited

OTHER PUBLICATIONS reveals extensive rearrangement within methanosarcinal genomes," J. Bacteriol. 188(22):7922-7931 (2006).

Maes et al., "Crystallization of ornithine acetyltransferase from yeast by counter-diffusion and preliminary x-ray study," Acta Cryst F62:1294-1297 (2006).

Mahadevan et al., "The effects of alternate optimal solutions in constraint-based genome-scale metabolic models," Metab. Eng, 5(4):264-276 (2003).

Mahan et al., "Genetic analysis of the proBA genes of Salmonella typhimurium: physical and genetic analyses of the cloned proB+ a+genes of *Escherichia coli* and of a mutant allele that confers proline overproduction and enhanced osmotolerance," J. Bacteriol. 156:1249-. 1262 (1983).

Mai et al., "Purification and characterization of two reversible and Adp-dependent acetyl coenzyme a synthetases from the hyperthermophilic archaeon Pyrococcus furiosus," J. Bacteriol. 178:5897-5903 (1996.).

Maicas, S. et al., "Nad(P)H regeneration is the key for heterolactic fermentation of hexoses in Oenococcus oeni," Microbiology 148: 325-332 (2002).

Maitra et al., "5-Dehydro-3-deoxy-D-arabino-heptulosonic acid 7-phosphate. An intermediate in the 3-dehydroquinate synthase reaction," J Biol. Chem. 253:5426-5430.

Majewski et al., "Simple Constrained-Optimization View of Acete Overflow in E. Coli," Biotechnol. Bioeng, 35(7):732-738 (1990).

Maklashina et al., "Anaerobic expression of Escherichia coli succinate dehydrogenase: functional replacement of fumarate reductase in the respiratory chain during anaerobic growth," J. Bacteriol. 180(22):5989-5996 (1998).

Manjasetty et al., "Crystallization and preliminary X-ray analysis of dmpFG-encoded 4-hydroxy-2-ketovalerate aldolase--aldehyde dehydrogenase (acylating) from Pseudomonas sp strain CF600," Acta Crystallogr. D. Biol. Crystallogr. 57:582-585 (2001).

Manning et al., "Tracer studies of the interconversion of R- and S-methylmalonic semialdehydes in man," Biochem. J. 231(2):481-484 (1985).

Marco-Marin et al., "Site-directed Mutagenesis of Escherichia coli Acetylglutamate Kinase and Aspartokinase III Probes the Catalytic and Substrate-binding Mechanisms of these Amino Acid Kinase Family Enzymes and Allows Three-dimensional Modelling of Aspartokinase," J. Mol. Biol. 334:459-476 (2003).

Marek et al., "Cloning and expression of the *Escherichia coli* K-12 sad gene," J. Bacteriol. 170:991-994 (1988).

Marks et al., "Molecular cloning and characterization of (R)-3-hydroxybutyrate dehydrogenase from human heart," J. Biol. Chem. 267(22):15459-15463 (1992).

Martin et al., "Engineering a mevalonate pathway in *Escherichia coli* for production of terpenoids," Nat. Biotechnol. 21:796-802 (2003).

Martin et al., "Nematode.net update 2008: improvements enabling more efficient data mining and comparative nematode genomics," Nucleic Acids Res. 37:D571-D578 (2009).

Martinez-Blanco, et al, "Purification and biochemical characterization of phenylacetyl-CoA ligase from Pseudomonas putida. A specific enzyme for the catabolism of phenylacetic acid," J. Biol. Chem. 265(12):7084-7090 (1990).

Martinez-Carrion et al., "D-Alanine-D-glutamate transminase. I. Purification and characterization," J. Biol. Chem. 240(9):3538-3546 (1965).

Martins et al., "Crystal structure of 4-hydroxybutyryl-CoA dehydratase: radical catalysis involving a [4Fe-4S] cluster and flavin," Proc. Natl. Acad. Sci. USA 101(44):15645-15649.

Mason et al., "Alcohol acetyltransferases and the significance of ester synthesis in yeast," Yeast 16(14):1287-1298 (2000).

Matiasek et al., "Volatile ketone formation in bacteria: release of 3-oxopentanoate by soil pseudomonads during growth on heptanoate," Curr. Microbiol. 42:276-281 (2001).

Mat-Jan et al., "Mutants of *Escherichia coli* Deficient in the Fermentative Lactate Dehydrogenase," J. Bacteriol. 171(1):342-348 (1989).

Matsumura et al., "Constitutive expression of catABC genes in the aniline-assimilating bacterium Rhodococcus species An-22: production, purification, characterization and gene analysis of CatA, CatB and CatC," Biochem. J. 393:219-226 (2006).

Matsushima et al., "An enone reductase from Nicotiana tabacum: cDNA cloning,. expression in *Escherichia coli*, and reduction of enones with the recombinant proteins," Bioorg. Chem. 36:23-28 (2008).

Matsuyama et al., "Industrial production of (R) -1,3-butanediol by new biocatalysts," J. Mol. Catal. B: Enzym. 11:513-521 (2001).

Matta et al., "Interactions of the antizyme AtoC with regulatory elements of the *Escherichia coli* atoDAEB operon," J. Bacteriol. 189(17):6324-6332 (2007).

Mattevi et al., "Atomic structure of the cubic core of the pyruvate dehydrogenase multienzyme complex," Science 255(5051):1544-1550 (1992).

Matthies et al., "Reciprocal Isomerization of Butyrate and Isobutyrate by the Strictly Anaerobic Bacterium Strain WoG13 and Methanogenic Isobutyrate Degradation by a Defined Triculture," Appl. Environ. Microbiol. 58(5):1435-1439 (1992).

Maurus, et al., "Insights into the Evolution of Allosteric Properties. The Nadh Binding Site of Hexameric Type II Citrate Synthases," Biochemistry 42:5555-5565 (2003).

Mavrovouniotis, Estimation of standard Gibbs energy changes of biotransformations, J. Biol. Chem. 266:14440-14445 (1991).

Maynard et al., "Autocatalytic activation of acetyl-CoA synthase," J. Biol. Inorg. Chem. 9:316-322 (2004).

Mazur et al., "Cis,cis-muconate lactonizing enzyme from Trichosporon cutaneum: evidence for a novel class of cycloisomerases in eucaryotes," Biochemistry 33:1961-1970.

McAlister-Henn et al., "Isolation and expression of the gene encoding yeast mitochondrial malate dehydrogenase," J. Bacteriol. 169:5157-5166 (1987).

McCarthy et al., "Crystal structure of methylmalonyl-coenzyme a epimerase from P. shermanii: a novel enzymatic function on an ancient metal binding scaffold," Structure. 9(7):637-646 (2001).

McCullough et al., "Enzymatic decarboxylation of the aminobenzoates," J. Am. Chem. Soc. 79:628-630 (1957).

McGregor et al., "argE-Encoded N-Acetyl-L-Ornithine Deacetylase from *Escherchia coli* Contains a Dinuclear Metalloactive Site," J. Am. Chem. Soc. 127:14100-14107 (2005).

McInerney et al., "The genome of Syntrophus aciditrophicus: Life at the thermodynamic limit of microbial growth," Proc. Natl. Acad. Sci USA 104:7600-7605 (2007).

McPherson et al., "Complete nucleotide sequence of the *Escherichia coli* gdhA gene," Nucleic Acids Res. 11:5257-5266 (1983).

McPherson et al., "Multiple interactions of lysine-128 of Escherichia coli glutamate dehydrogenase revealed by site-directed mutagenesis studies," Protein Eng. 2(2):147-152.

Meagher, "Purification and partial amino acid sequence of the cyanogen bromide fragments of muconolactone isomerase from Pseudomonas putida," Biochim. Biophys. Acta 494:33-47 (1977).

Mechichi et al., "Alicycliphilus denitrificans gen. nov., sp. nov., a cyclohexanol-degrading, nitrate-reducing fl-proteobacterium," Int. J. Syst. Evol. Microbiol. 53:147-152.

Megraw et al., "Formation of lactyl-coenzyme a and pyruvyl-coenzyme a from lactic acid by Escherichia coli," J. Bacteriol. 90(4):984-988 (1965).

Mehdi et al., "Dehydroquinate synthase from *Escherichia coli*, and its substrate 3-deoxy-D-arabino-heptulosonic acid 7-phosphate," Methods Enzymol. 142:306-314 (1987).

Meinnel et al., "Structural and Biochemical Characterization of the *Escherichia coli* argE Gene Product," J. Bacteriol. 174(7):2323-2331 (1992).

Melchiorsen et al., "The level of pyruvate-formate lyase controls the shift from homolactic to mixed-acid product formation in Lactococcus lactis," Appl. Microbiol. Biotechnol. 58:338-344 (2002).

(56) References Cited

OTHER PUBLICATIONS

Meng et al., "Site-directed Mutagenesis and Functional Analysis of the Active-Site Residues of the E2 Component of Bovine Branched-Chain a-Keto Acid Dehydrogenase Complex," *Biochemistry* 33:12879-12885 (1994).

Meng et al.i, "Cloning, expression and characterization of a thiolase gene from Clostridium pasteurianum," *Biotechnol. Lett.* 28(16):1227-1232 (2006).

Menon et al., "Mechanism of the Clostridium thermoaceticum pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of Klebsiella pneumoniae," *J. Biotech.* 56:135-142 (1997).

Menzel et al., "Kinetic, dynamic, and pathway studies of glycerol metabolism by Klebsiella pneumoniae in anaerobic continuous culsutre: Iv. Enzynmes and fluxes of pyruvate metabolism," *Botechnol. Bioeng,* 60(5):617-626 (1998).

Merkel et al., "Characterization and sequence of the *Escherichia coli* panBCD gene cluster," *FEMS Microbiol. Lett.* 143(2-3):247-252 (1996).

Mermelstein et al., "Metabolic Engineering of *Clostridium acetobutylicum* ATCC 824 for Increased Solvent Production by Enhancement of Acetone Formation Enzyme Activities. Using a Synthetic Acetone Operon," *Biotechnol. Bioeng.* 42(9):1053-1060 (1993).

Metz et al., "Purification of a jojoba embryo fatty acyl-Coenzyme a reductase and expression of its cDNA in high erucic acid rapeseed," *Plant Phy.* 122:635-644 (2000).

Meynial-Salles, I., et al., "A new process for the continuous production of succinic acid from glucose at high yield, titer and productivity," *Biotechnol. Bioeng.* 99(1):129-135.

Michel et al., "Structures of Shikimate Dehydrogenase AroE and its Paralog YdiB. A Common Structural Framework for Different Activities," *J. Biol. Chem.* 278(21):19463-19472 (2003).

Millard et al "Enhanced production of succinic acid by overexpression of phosphoenolpyruvate carboxylase in *Escherichia coli*," *Appl. Environ. Microbiol.* 62(5):1808-1810 (1996).

Miller et al., "Enzymology of butyrate Formation by Butyrivibrio-Fibrisolvens," *J. Bacteriol.* 138:99-104 (1979).

Miller et al., "Structure of 0-lactam synthetase reveals how to synthesize antibiotics instead of asparagine," *Nat. Struct. Biol.* 8(8):684-689 (2001).

Miller et al., "The catalytic cycle of 0-lactam synthetase observed by x-ray crystallographic snapshots," *Proc. Natl. Acad. Sci. USA* 99(23):14752-14757 (2002).

Minard et al., "Isolation, nucleotide sequence analysis, and disruption of the MDH2 gene from Saccharomyces cerevisiae: evidence for three isozymes of yeast malate dehydrogenase," *Mol. Cell. Biol.* 11:370-380 (1991).

Misono et al., "Occurrence of L-Lysine c-Dehydrogenase in Agrobacterium tumefaciens," *J. Bacteriol.* 150(1):398-401 (1982).

Misono et al., "Properties of L-lysine c-dehydrogenase from Agrobacterium tumefaciens," *J. Biochem.* 105(6):1002-1008 (1989).

Miura et al., "Molecular Cloning of the nemA Gene Encoding N-Ethylmaleimide Reductase from *Escherichia Coli*," *Biol. Pharm. Bull.* 20(1):110-112 (1997).

Miyazaki et al., "a-Aminoadipate aminotransferase from an extremely thermophilic bacterium, Thermus thermophilus," *Microbiology* 150:2327-2334 (2004).

Mizobata et al., "Purification and characterization of a thermostable class II fumarase from Thermus thermophilus," *Arch. Biochem. Biophys.* 355(1):49-55 (1998).

Mizugaki et al. "Studies on the metabolism of unsaturated fatty acids. Ix. Stereochemical studies of the reaction catalyzed by trans-2-enoyl-coenzyme a reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Mohammadi et al., "Preliminary report of NAD+-dependent amino acid dehydrogenase producing bacteria isolated from soil," *Iran Biomed. J.* 11(2):131-135 (2007).

Momany et al., "Crystallization of diaminopimelate decarboxylase from *escherichia coli*, a stereo specific D-amino-acid decarboxylase," *Acta Cryst.* D58:549-552 (2002).

Momany et al., "Crystallographic Structure of Plp-Dependent Ornithine Decarboxylase from Lactobacillus 30a to 3.0 a Resolution," *J. Mol. Biol.* 252:643-655 (1995).

Monastiri et al., "I3-Ketothiolase (2-methylacetoacetyl-CoA thiolase) deficiency: a frequent disease in Tunisia?" *J. Inher. Metab. Dis.* 22:932-933 (1999).

Monnet et al., "Regulation of branched-chain amino acid biosynthesis by a-acetolactate decarboxylase in *Streptococcus thermophilus*," *Lett. Appl. Microbiol.* 36(6):399-405.

Monterrubio et al., "A common regulator for the operons encoding the enzymes involved in d-galactarate, d-glucarate, and d-glycerate utilization in *Escherichia coli*," *J. Bacteriol.* 182(9):2672-2674 (2000).

Moon et al., "Metabolic engineering of *Escherichia coli* for the production of malic acid, "*Biochem. Eng. J.* 40(2):312-320 (2008).

Moore et al., "Efficient independent activity of a monomeric, monofunctional dehydroquinate synthase derived from the N-terminus of the pentafunctional Arom protein of *Aspergillus nidulans*," *Biochem. J.* 301 ( Pt 1):297-304 (1994).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris et al., "Nucleotide sequence of the LYS2 gene of Saccharomyces cerevisiae: homology to Bacillus brevis tyrocidine synthetase 1," *Gene* 98:141-145 (1991).

Morsomme et al., "Single point mutations in various domains of a plant plasma membrane HtATPase expressed in Saccharomyces cerevisiae increase H+-pumping and permit yeast growth at low pH," *EMBO. J.* 15(20):5513-5526 (1996).

Morton et al., "Cloning, sequencing, and expressions of genes encoding enzymes of the autotrophic acetyl-CoA pathway in the acetogen Clostridium thermoaceticum," in M. Sebald (ed.), *Genetics and molecular biology of anaerobic bacteria*, Springer Verlag, New. York, 389-406 (1992).

Morton et al., "The primary structure of the subunits of carbon monoxide dehydrogenase/acetyl-CoA synthase from Clostridium thermoaceticum," *J. Biol. Chem.* 266(35):23824-23828 (1991).

Moskowitz et al., "Metabolism of poly-P-hydroxybutyrate. Ii. Enzymatic synthesis of D-(-)-(3hydroxybutyryl coenzyme a by an enoyl hydrase from rhodospirillum rubrum," *Biochemistry* 8:2748-2755 (1969).

Moszer, "The complete genome of Bacillus subtilis: from sequence annotation to data management and analysis," *FEBS Lett.* 430:28-36 (1998).

Mouttaki et al., "Cyclohexane Carboxylate and Benzoate Formation from Crotonate in Syntrophus aciditrophicus," *Appl. Environl. Microbiol.* 73(3):930-938 (2007).

Muh et al., "4-Hydroxybutyryl-CoA dehydratase from Clostridium aminobutyricum: characterization of Fad and iron-sulfur clusters involved in an overall non-redox reaction," *Biochemistry* 35:11710-11718 (1996).

Muh et al., "Mössbauer study of 4-hydroxybutyryl-CoA dehydratase probing the role of an iron-sulfur cluster in an overall non-redox reaction," *Eur. J. Biochem.* 248:380-384 (1997).

Mukhopadhyay et al., "Pyruvate carboxylase from Mycobacterium smegmatis: stabilization, rapid purification, moleculare and bio-

(56) References Cited

OTHER PUBLICATIONS chemical characterization and regulation of the cellular level," *Biochim. Biophys. Acta* 1475(3):191-206 (2000).
Muller et al., "Activation of (R)-2-hydroxyglutaryl-CoA dehydratase from Acidaminococcus fermentans" *Eur. J. Biochem.* 230(2):698-704 (1995).
Muller et al., "Nucleotide exchange and excisiion technology (NExT) Dna shuffling; a robust method for DNA fragmentation and directed evolution," *Nucleic Acids Res.* 33:e117.
Muller, "Energy Conservation in Acetogenic Bacteria," *Appl. Environ. Microbiol.* 69:6345-6353 (2003).
Murakami et al., "Purification and characterization of two muconate cycloisomerase isozymes from aniline-assimilating Frateuria species Ana-18," *Biosci. Biotechnol. Biochem.* 62:1129-1133 (1998).
Muratsubaki et al., "One of the fumarate reductase isoenzymes from Saccharomyces cerevisiae is encoded by the OSM1 gene, " *Arch. Biochem. Biophys.* 352:175-181 (1998).
Musfeldt et al., "Novel type of ADP-forming acetyl coenzyme a synthetase in hyperthermophilic archaea: heterologous expression and characterization of isoenzymes from the sulfate reducer Archaeoglobus fulgidus and the methanogen Methanococcus jannaschii," *J. Bacteriol.* 184(3):636-644 (2002).
Muyrers et al., "Rapid modification of bacterial artificial chromosomes by Et-recombination," *Nucleic Acids Res.* 27:1555-1557 (1999).
Nagasawa et al., "Cloning and Nucleotide Sequence of the Alcohol Acetyltransferase II gene (ATF2) from Saccharomyces cerevisiae Kyokai No. 7," *Biosci. Biotechnol. Biochem.* 62:1852-1857 (1998).
Nagata et al., "Gene cloning, purification, and characterization of thermostable and halophilic leucine dehydrogenase from a halophilic thermophile, Bacillus licheniformis TSN9," *Appl. Microbiol. Biotechnol.* 44:432-438 (1995).
Nagata et al., "Assay of alanine:glyoxylate aminotransferase in human liver by its serine: glyoxylate aminotransferase activity," *Biomed. Res.* 30(5):295-301 (2009).
Naggert et al., "Cloning, sequencing, and characterization of Escherichia coli thioesterase II," *J. Biol. Chem.* 266(17):11044-11050 (1991).
Nahvi et al., "Genetic Control by a Metabolite Binding mRNA," *Chem. Biol.* 9:1043-1049 (2002).
Naidu et al., "Characterization of a three-component vanillate 0-demethylase from Moorella thermoacetica," *J. Bacteriol.* 183(11):3276-3281 (2001).
Najafpour et al., "Ethanol and acetate synthesis from waste gas using batch culture of Clostridium ljungdahlii," *Enzyme Microb. Technol.* 38:223-228 (2006).
Najmudin et al., "Purification, crystallization and preliminary X-ray crystallographic studies on acetolactate decarboxylase," *Acta Cryst* D59:1073-1075 (2003).
Nakahigashi and Inokuchi, "Nucleotide sequence of the fadA and fadB genes from Escherichia coli," *Nucleic Acids Res.* 18(16):4937 (1990).
Nakamura et al., "Metabolic engineering for the microbial production of 1,3-propanediol," *Curr. Opin. Biotechnol.* 15(5) 454-459 (2003).
Nakano et al., "Characterization of Anaerobic Fermentative Growth of Bacillus subtilis: Identification of Fermentation End Products and Genes Required for Growth," *J. Bacteriol.* 179(21):6749-6755 (1997).
Nakazawa et al., "Studies on monooxygenases. V. Manifestation of amino acid oxidase activity by L-lysine monooxygenase," *J. Biol. Chem.* 247:3439-3444 (1972).
Namba et al., "Coenzyme A- and Nicotinamide Adenine Dinucleotide-dependent Branched Chain a-Keto Acid Dehydrogenase," *J. Biol. Chem.* 244(16):4437-4447 (1969).
Neidhart et al., "Mandelate racemase and muconate lactonizing enzyme are mechanistically distinct and structurally homologous," *Nature* 347:692-694 (1990).
Ness et al., "Synthetic shuffling expands functional protein diversity by allowing amino acids to recombine independently," *Nat. Biotechnol.* 20:1251-1255 (2002).

Nichols et al., "para-Aminobenzoate Synthesis from Chorismate Occurs in Two Steps," *J. Biol. Chem.* 264(15):8597-8601 (1989).
Nicolaou et al., "The Diels-Alder Reaction in Total Synthesis," *Angew Chemie Int Ed.* 41:1668-1698 (2002).
Nicolaou et al., "Total Synthesis of Abyssomicin C, Atrop-abyssomicin C, and Abyssomicin D: Implications for Natural Origins of Atrop-abyssomicin C," *J. Am. Chem. Soc.* 129(2):429-440 (2007).
Niegemann et al., "Molecular organization of the Escherichia coli gab cluster: nucleotide sequence of the structural genes gabD and gabP and expression of the Gaba permease gene," *Arch.Microbiol* 160:454-460 (1993).
Nimmo, "Kinetic mechanism of *Escherichia coli* isocitrate dehydrogenase and its inhibition by glyoxylate and oxaloacetate," *Biochem. J.* 234(2):317-323 (1986).
Nishimaki et al., "Studies on the Metabolism of Unsaturated Fatty Acids. Xiv. Purification and Properties of Nadph-Dependent trans-2-Enoyl-CoA Reductase of *Escherichia coli* K-12," *J. Biochem.* 95(5):1315-1321 (1984).
Nishizawa et al., "Gene expression and characterization of two 2-oxoacid:ferredoxin oxidoreductases from Aeropyrum pernix Kl," *FEBS Lett.* 579:2319-2322 (2005).
Nissen et al., "Expression of a cytoplasmic transhydrogenase in Saccharomyces cerevisiae results in formation of 2-oxoglutarate due to depletion of the Nadph pool." *Yeast* 18:19.
Niu et al., "Benzene-free synthesis of adipic acid," *Biotechnol. Prog.* 18:201-211 (2002).
Njau et al., "Novel I3-hydroxyacid dehydrogenases in *Escherichia coli* and *Haemophilus influenza*," *J. Biol. Chem.* 275(49):38780-38786 (2000).
Nogales et al., "Characterization of the last step of the aerobic phenylacetic acid degradation pathway," *Microbiology* 153(Pt 2):357-365 (2007).
Noichinda et al., "Subcellular Localization of Alcohol Acetyltransferase in Strawberry Fruit," *Food Sci. Technol. Res.* 5(3):239-242 (1999).
Nolling et al., "Genome sequence and comparative analysis of the solvent-producing bacterium Clostridium acetobutylicum," *J. Bacteriol.* 183(16):4823-4838 (2001).
Norton, "The Diels-Alder Diene Synthesis," *Chem. Rev.* 31:319-523 (1942).
Nowicki et al., "Recombinant tyrosine aminotransferase from Trypanosoma cruzi: structural characterization and site directed mutagenesis of a broad substrate specificity enzyme," *Biochima Biophysica Acta* 1546:268-281 (2001).
Nu&Ez et al., "Biochemical characterization of the 2-ketoacid reductases encoded by ycdW and yiaE genes in *Escherichia coli*," *Biochem. J.* 354(Pt 3):707-715 (2001).
Obradors et al., "Site-directed mutagenesis studies of the metal-binding center of the iron-dependent propanediol oxidoreductase from *Escherichia coli*," *Eur. J. Biochem.* 258(1):207-213 (1998).
O'Brien et al., "Studies of the Thiamin Pyrophosphate Binding Site of *Escherichia coli*. Pyruvate Oxidase," *J. Biol. Chem.* 255(8):3302-3307 (1980).
O'Brien et al, "Regulation by Lipids of Cofactor Binding to a Peripheral Membrane Enzyme: Binding of Thiamin Pyrophosphate to Pyruvate Oxidase," *Biochemistry.* 16(14):3105-3109 (1977).
O'Brien et al., "Chemical, physical and enzymatic comparisons of formyltetrahydrofolate synthetases from thermo- and mesophilic clostridia," *Experientia. Suppl.* 26:249-262.
O'Brien et al., "Insight into the Mechanism of the Biz-Independent Glycerol Dehydratase from Clostridium butyricum: Preliminary Biochemical and Structural Characterization," *Biochemistry* 43:4635-4645 (2004).
Oda et al., "In vitro association with peroxisomes and conformational change of peroxisomal serine:pyruvate/alanine:glyoxylate aminotransferase in rat and human livers," *Biochem. Biophys. Res. Commun.* 228(2):341-346 (1996).
Oda et al., "Purification and characterization of the active serine: pyruvate aminotransferase of rat liver mitochondria expressed in *Escherichia coli*," *J. Biochem.* 106(3):460-467 (1989).
Ofman et al., "2-Methyl-3-hydroxybutyryl-CoA dehydrogenase deficiency is caused by mutations in the HADH2 gene, " *Am. J. Hum. Genet.* 72:1300-1307 (2003).

(56) References Cited

OTHER PUBLICATIONS

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-0-Lysine by Pseudomonas. Purification and Properties of a Deacetylase-Thiolestrerase Utilizing 4-Acetamidobutyryl CoA and Related Compounds," *J. Biol. Chem.* 256(14):7642-7651 (1981).

Okino et al., "An effeicient succinic acid production process in a metabolically engineered Corynebacterium glutamicum strain," *Appl. Microbiol. Biotechnol.* 81(3):459-464 (2008).

Oku et al., "Biosynthesis of branched-chain fatty acids in bacillus subtilis. A decarboxylase is essental for branched-chain fatty acid synthetase," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism." *Enzyme Protein.* 47:136-148 (1993).

Olczak et al., "Purification and characterization of acid phosphatase from yellow lupin (Lupinus luteus) seeds," *Biochim. Biophys. Acta.* 1341(1):14-25 (1997).

Oliveira et al., "Cloning and overexpression in soluble form of functional shikimate kinase and 5-enolpyruvylshikimate 3-phosphate synthase enzymes from Mycobacterium tuberculosis," *Protein Expr. Purif.* 22(3):430-435 (2001).

Olivera et al., "Molecular characterization of the phenylacetic acid catabolic pathway in Pseudomonas putida U: the phenylacetyl-CoA catabolon," *Proc. Natl. Acad. Sci. USA* 95(11):6419-6424 (1998).

One page from home page URL: http://toxnet.nlm.nih.gov/cgi-bin/sis/search/r?dbs+hsdb: @term+@rn+@rel+79-10-7;and Fifty-four pages off text document downloaded from website Sep. 2, 2011.

One page from URL: <www.dtu.dk/English/Service/Phonebook.aspx?lg=showcommon&id=193466> Containing 182 p. document: Patil, Ph.D. Thesis, "Systems Biology of Metabolic Networks: Uncovering Regulatory and stoichiometric Principles," 2006. (Printed from the Internet Jun. 8, 2011).

Onuffer et al., "Redesign of the substrate specificity of *Escherichia coli* aspartate aminotransferase to that of Escherichia coli tyrosine aminotransferase by homology modeling and site-directed mutagenesis," *Protein Sci.* 4:1750-1757 (1995).

O'Reilly et al., "Sequence and analysis of the citrulline biosynthetic operon argC-F from Bacillus subtilis," *Microbiology* 140:1023-1025 (1994).

Orencio-Trejo et al., "Metabolic regluation analysis of an ethanologenic *Escherichia coli* strain based on Rt-Pcr and enzymatic activities," Biotechnol. Biofuels 1:8 (2008). (provided electronically by publisher as pp. 1-13).

Oshima et al., "Regulation of phosphatase synthesis in Saccharomyces cerevisiae—a review," *Gene* 179(1):171-177 (1996).

Osipiuk et al., "X-ray crystal structure of GarR-tartronate semialdehyde reductase from Salmonella typhimurium," *J. Struct. Funct. Genomics* 10(3):249-253 (2009).

Ostermeier et al., "A Combinatorial approach to hybrid enzymes independent of Dna homology," *Nat. Biotechnol.* 17:1205-1209 (1999).

Ostermeier et al., "Combinatorial protein engineering by incremental truncation," *Proc. Natl. Acad. Sci. USA* 96:3562-3567 (1999).

O'Sullivan et al., "Purification and characterisation of acetolactate decarboxylase from Leuconostoc lactis NCW1," *FEMS Microbiol. Lett* 194(2):245-249 (2001).

Otten et al., "Directed evolution:selecting today's biocatalysts," *Biomol. Eng.* 22:1-9.

Overkamp et al., "Functional analysis of structural genes for NADtdependent formate dehydrogenase in Saccharomyces cerevisiae," *Yeast* 19:509-520 (2002).

Overkamp et al., "In vivo analysis of the mechanism for oxidation of cytosolic Nadh by Saccharomyces cerevisiae mitochondria," *J. Bacteriol.* 182:2823-2830 (2000).

Overkamp et al., "Metabolic engineering of glycerol production in Saccharomyces cerevisiae," *Appl. Environ. Microbiol.*, 68(6):2814-2821 (2002).

Padovani et al., "Assembly and protection of the radical enzyme, methylmalonyl-CoA mutase, by its chaperone," *Biochem.* 45(30):9300-9306 (2006).

Paik et al., "Enzymic syntehsis of c-N-Acetyl-L-Lysine," *Arch. Biochem. Biophys.* 108:221-229 (1964).

Palosaari et al., "Purification and Properties of the Inducible Coenzyme A-Linked Butyraldehyde Dehydrogenase from Clostridium acetobutylicum," *J. Bacteriol.* 170(7):2971-2976 (1988).

Parales et al., "Characterization of the Genes Encoding 0-Ketoadipate: Succinyl-Coenzyme a Transferase in Pseudomonas putida," *J. Bacteriol.* 174(14):4657-4666 (1992).

Park et al., "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).

Park et al., "Identification and characterization of a new enoyl Coenzyme a hydratase involved in biosynthesis of medium-chain-length polyhydroxyalkanoates in recombinant *Escherichia coli*," *J. Bacteriol.* 185(18):5391-5397 (2003).

Park et al., "New FadB homologous enzymes and their use in enhanced biosynthesis of. medium-chain-length polyhydroxyalkanoates in FadB mutant *Escherichia coli*," *Biotechnol. Bioeng.* 86(6):681-686 (2004).

Park et al., "Metabolic engineering of Escherichia coli for the production of L-valine based on transcriptome analysis and in silico gene knockout simulation," *Proc. Natl. Acad. Sci. USA* 104(19):7797-7802 (2007).

Park et al., "Regulation of succinate dehydrogenase (sdhCDAB) operon expression in Escherichia coli in response to carbon supply and anaerobiosis: role of ArcA and Fnr," *Mol. Microbiol.* 15(3):473-482 (1995).

Park et al., "Utilization of Electrically Reduced Neutral Red by Actinobacillus succinogenes: Physiological Function of Neutral Red in Membrane-Driven Fumarate Reduction and Energy Conservation," *J. Bacteriol* 181(8):2403-2410 (1999).

Parke et al., "Cloning and Genetic Characterization of *dca* Genes Required for 13-Oxidation of Straight-Chain Dicarboxylic Acids in *Acinetobacter sp.* Strain ADP1," *Appl. Environ. Microbiol.* 67(10):4817-4827 (2001).

Parkin et al., "Rapid and efficient electrocatalytic $CO_2$/C0 interconversions by Carboxydothermus hydrogenoformans Co dehydrogenase I on an electrode," *J. Am. Chem. Soc.* 129(34):10328-10329 (2007).

Parsot et al., "Nucleotide sequence of Escherichia coli argB and argC genes: comparison of N-acetylglutamate kinase and N-acetylglutamate-r-semialdehyde dehydrogenase with homologous and analogous enzymes," *Gene* 68:275-283 (1988).

Patel et al., "Acetoacetate metabolism in rat brain. Development of acetoacetyl-coenzyme a deacylase and 3-hydroxy-3-methylglutaryl-coenzyme a synthase," *Biochem J.* 176(3):951-958 (1978).

Patel et al., "I3-ketoadipate enol-lactone hydrolases I and II from Acinetobacter calcoaceticus," J. Biol. Chem. 250:6567-6577 (1975).

Patil et al., "Use of genome-scale microbial models for metabolic engineering," *Curr. Opin. Biotechnol.* 15(1)64-69 (2004).

Patnaik et al., "Genome shuffling of Lactobacillus for improved acid tolerance" *Nat. Biotechnol.* 20:707-712 (2002).

Pauli et al., "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of Saccharomyces cerevisiae allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier et al., "2-Ketocyclohexanecarboxyl Coenzyme a Hydrolase, the Ring cleavage Enzyme Required for Anaerobic Benzoate Degradation of Rhodopseudomonas palustris," *J. Bacteriol.* 180(9):2330-2336 (1998).

(56) References Cited

OTHER PUBLICATIONS

Peoples et al., "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peres et al., "Biodegradation of nitrobenzene by its simultaneous reduction into aniline and mineralization of the aniline formed," *Appl. Microbiol. Biotechnol.* 49(3):343-349.

Peretz et al., "Amino acid sequence of alcohol dehydrogenase from the thermophilic bacterium Thermoanaerobium brockii," *Biochemistry* 28(16):6549-6555 (1989).

Peretz et al., "Molecular cloning, nucleotide sequencing, and expression of genes encoding alcohol dehydrogenases from the thermophile Thermoanaerobacter brockii and the mesophile Clostridium beijerinckii," *Anaerobe.* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior, et al., "Reactivity of lactones and Ghb formation," *J. Org. Chem.* 70:420.

Pestka et al., "2-phosphoglycerate phosphatase and serine biosynthesis in Veillonella alcalescens," *Can. J. Microbiol.* 27(8):808-814 (1981).

Petersen et al., "Purification of acetoacetate decarboxylase from clostridium acetobutylicum ATCC 824 and cloning of the acetoacetate decarboxylase gene in *Escherichia coli*," *Appl. Environ. Microbiol.* 56:3491-3498 (1990).

Petitdemange et al., "Regulation of the Nadh and Nadph-ferredoxin oxidoreductases in clostridia of the butyric group," *Biochim. Biophys. Acta* 421(2):334-347.

Pfanner et al., "Versatility of the mitochondrial protein import machinery," *Nat. Rev. Mol. Cell. Biol.* 2(5):339-349 (2001).

Pfluger et al., "Lysine-2,3-Aminomutase and 0-Lysine Acetyltransferase Genes of Methanogenic Archaea Are Salt Induced and Are Essential for the Biosynthesis of Ne-Acetyl-(3-Lysine and Growth at High Salinity," *Appl. Environ. Microbiol.* 69(10):6047-6055 (2003).

Phalip et al., "Purification and properties of the a-acetolactate decarboxylase from lactococcus lactis subsp. Lactis NCDO 2118," *FEBS Lett.* 351(1):95-99 (1994).

Pharkya et al., "OptiStrain: a computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400-2, 404, 406 (2000).

Pierce et al., "The Complete Genome Sequence of Moorella thermoacetia (f. Clostridum thermoaceticum)," *Environ. Microbiol.* 10(10):2550-2573 (2008).

Pieulle et al., "Isolation and analysis of the gene encoding the pyruvate-ferredoxin oxidoreductase of Desulfovibrio africanus, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in Bacillus sphericus," *Biochem. J.* 287:685-690 (1992).

Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).

Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium Ralstonia eutropha H16," *Nat. Biotechnol.* 24(10):1257-1262 (2006).

Pollard et al., "Purification, characterisation and reaction mechanisms of monofunctional 2-hydroxypentadienoic acid hydratase from *Escherichia coli*," *Eur. J. Biochem. FEBS* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from Escherichia coli: the relative roles of these enzymes in pyruvate biosynthesis," *J Bacteriol.* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from Pseudomonas sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Priestman et al., "5-Enolpyruvylshikimate-3-phosphate synthase from *Staphylococcus aureus* is insensitive to glyphosate," *FEBS Lett.* 579(3):728-732 (2005).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509.

Pritchett et al., "Genetic, physiological and biochemical characterization of multiple methanol methyltransferase isozymes in Methanosarcina acetivorans C2A," *Mol. Microbiol.* 56(5):1183-1194 (2005).

Pronk et al., "Pyruvate metabolism in Saccharomyces cerevisiae," *Yeast* 12:1607-1633.

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant Nad(H)-dependent glutamate dehydrogenase activity in transgenic tobacco via alteration of 13 subunit levels," *Planta.* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qi et al., "Saturation-mutagenesis in two positions distant from active site of a Klebsiella pneumoniae glycerol dehydratase identifies some highly active mutants," *J. Biotechnol.* 144(1):43-50 (2009).

Qian et al., "Metabolic engineering of *Escherichia coli* for the production of putrescine: a four carbon diamine," *Biotechnol. Bioeng.* 104(4)651-662 (2009).

Qiu et al, "Metabolic engineering of Aeromonas hydrophila for the enhanced production of. poly(3-hydroxybutyrate-co-3-hydroxyhexanoate)," *Appl. Microbiol. Biotechnol.* 69(5):537-. 542 (2006).

Qu et al., "Inhibition of human ornthine decarboxylase activity by enantiomers of difluoromethylornithine," *Biochem. J.* 375:465-470 (2003).

Quail et al., "Purification, characterization and mode of action of pdhR, the transcriptional repressor of the PdhR-aceEF-lpd operon of *Escherichia coli*," *Mol. Microbiol.* 15(3):519-529 (1995).

(56) References Cited

OTHER PUBLICATIONS

Rado et al., "Phosphotransacetylase from Bacillus subtilis: purification and physiological studies," *Biochim. Biophys. Acta* 321:114-125 (1973).
Ragsdale et al., "Acetogenesis and the Wood-Ljungdahl pathway of CO2 fixation," *Biochimica. Biophysica. Acta* 1784(12):1873-1898 (2008).
Ragsdale, "Enzymology of the wood-Ljungdahl pathway of acetogenesis," *Ann. NY. Acad Sci.* 1125:129-136 (2008).
Ragsdale, "Life with carbon monoxide," *Crit. Rev. Biochem. Mol. Biol.* 39(3):165-195.
Ragsdale, "Pyruvate ferredoxin oxidoreductase and its radical intermediate," *Chem. Rev.* 103(6):2333-2346 (2003).
Rajpal et al., "A general method for greatly improving the affinity of antibodies by using combinatorial libraries," *Proc. Natl. Acad. Sci. USA* 102:8466-8471 (2005).
Ramjee et al., "*Escherichia coli* L-aspartate-a-decarboxylase: preprotein processing and observation of reaction intermediates by electrospray mass spectrometry," *Biochem. J.* 323(Pt 3):661-669 (1997).
Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).
Ramos et al., "Mutations affecting the enzymes involved in the utilization of 4-aminobutyric acid as nitrogen source by the yeast Saccharomyces cerevisiae," *Eur.J. Biochem.* 149:401-404 (1985).
Ran et al., "Directed evolution of 2-keto-3-deoxy-6-phosphogalactonate aldolase to replace 3-deoxy-D-arabino-heptulosonic acid 7-phosphate synthase," *J. Am. Chem. Soc.* 129(19):6130-6139 (2007).
Randall et al., "3-Phosphoglycerate phosphatase in plants. I. Isolation and characterization from sugarcane leaves," *J. Biol. Chem.* 246(17):5510-5517 (1971).
Randall et al., "3-Phosphoglycerate Phosphatase in Plants: III. Activity Associated with Starch Particles," Plant Physiol. 48(4):488-492 (1971).
Rangarajan et al., "Structure of [NiFe] hydrogenase maturation protein HypE from *Escherichia coli* and its interaction with HypF," *J. Bacteriol.* 190(4):1447-1458 (2008).
Rasmussen, L.J., et al. "Carbon Metabolism Regulates Expression of the pfl (Pyruvate-Formate-Lyase) Gene in *Escherichia coli*," *J. Bacteriol* 173(20):6390-6397 (1991).
Rathinasabapathi, "Propionate, a source of β-alanine, is an inhibitor of β-alanine methylation in Limonium latifoilium Plunbaginaces," *J. Plant Physiol.* 159:671-674 (2002).
Ratnatilleke et al., "Cloning and sequencing of the coenzyme B(12)-binding domain of isobutyryl-CoA mutase from Streptomyces cinnamonensis, reconstitution of mutase activity, and characterization of the recombinant enzyme produced in *Escherichia coli*," *J. Biol. Chem.* 274(44):31679-31685 (1999).
Raux et al., "The role of Saccharomyces cerevisiae Metlp and Met8p in sirohaem and cobalamin biosynthesis," *Biochem. J.* 338 (pt. 3):701-708 (1999).
Raux et al., "Salmonella typhimurium cobalamin (vitamin B12) biosynthetic genes: functional studies in S. typhimurium and *Escherichia coli*," *J. Bacteriol.* 178(3):753-767.
Ravagnani et al., "SpoOA directly controls the switch from acid to solvent production in solvent-forming clostridia," *Mol. Microbiol.* 37(5):1172-1185 (2000).
Raybuck et al., "Kinetic characterization of the carbon monoxide-acetyl-CoA (carbonyl group) exchange activity of the acetyl-CoA synthesizing Co dehydrogenase from Clostridium thermoaceticum," *Biochemistry* 27(20):7698-7702 (1988).
Raynaud et al., "Molecular characterization of the 1,3-propanediol (1,3-Pd) operon of clostridium butyricum," *Proc. Natl. Acad. Sci USA* 100:5010-5015 (2003).
Rea et al., "Structure and Mechanism of HpcH: a Metal Ion Dependent Class Ii Aldolase from the Homoprotocatechuate Degradation Pathway of *Escherichia coli*," *J. Mol. Biol.* 373:866-876 (2007).

Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reda et al., "Reversible interconversion of carbon dioxide and formate by an electroactive enzyme," *Proc. Natl. Acad. Sci. USA* 105:10654-10658 (2008).
Reed et al., "An expanded genome-scale model of *Escherichia coli* K-12 (iJR904 GSM/GPR)," *Genome Biol.* 4(9):R54 (2003).
Reetz and Carballeira, "Iterative saturation mutagenesis (ISM) for rapid directed evolution of functional enzymes, " *Nat. Protoc.* 2:891-903 (2007).
Reetz et al., "Creation of Enantioselective Biocatalysts for Organic Chemistry by in Vitro Evolution," *Angew. Chem. Int. Ed. Engl.* 36:2830-2832 (1997).
Reetz et al., "Directed Evolution of an Enantioselective Enzyme through Combinatorial Multiple-Cassette Mutagenesis, "*Angew. Chem. Int. Ed. Engl.* 40:3589-3591 (2001).
Reetz et al., "Expanding the Range of Substrate Acceptance Enzymes: Cominatorial Active-Site Saturation Test," *Angew. Chem. Int. Ed.* 44:4192-4196 (2005).
Reetz et al., "Iterative saturation mutagenesis on the basis of B factors as a strategy for incresing protein thermostability," *Angew. Chem. Int. Ed.* 45:7745-7751 (2006).
Regev-Rudzki et al., "Yeast Aconitase in Two Locations and Two Metabolic Pathways: Seeing Small Amounts Is Believing," *Mol. Biol. Cell* 16:4163-4171 (2005).
Reher et al., "Characterization of glycerate kinase (2-phosphoglycerate forming), a key enzyme of the nonphosphorylative Entner-Doudoroff pathway, from the thermoacidophilic euryarchaeon Picrophilus torridus," *Fems Microbiol. Lett.* 259(1):113-119 (2006).
Reidhaar-Olson et al., "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Reiser et al., "Isolation of mutants of Acinetobacter calcoaceticus deficient in wax ester synthesis and complementation of one mutation with a gene encoding a fatty acyl coenzyme a reductase," *J. Bacteriol.* 179(9):2969-2975 (1997).
Reitzer et al., "Crystallization and preliminary X-ray analysis of recombinant glutamate mutase and of the isolated component S from Clostridium cochlearium," *Acta Cryst.* D54:1039-1042 (1998).
Repetto et al., "Structure and Regulation of KGD1, the Structural Gene for Yeast a-Ketoglutarate Dehydrogenase," *Mol. Cell. Biol.* 9(6):2695-2705 (1989).
Reshetnikov, et al., "Characterization of the ectoine biosynthesis genes of haloalkalotolerant obligate methanotroph 'Methylomicrobium alcaliphilum 20Z'," *Arch. Microbiol.* 184:286-297 (2006).
Resnekov et al., "Organization and regulation of the Bacillus subtilis odhAB operon, which encodes two of the subenzymes of the 2-oxoglutarate dehydrogenase complex, " *Mol. Gen. Genet.* 234:285-296 (1992).
Rhodes et al., "Production of fumaric acid by *Rhizopus arrhuzus*," *Appl. Microbiol.* 7:74-80 (1959).
Rhodes et al., "Production of Fumaric Acid in 20-Liter Fermentors," *Appl. Microbiol.* 10(1)9-15 (1962).
Rigden et al., "A cofactor-dependent phosphoglycerate mutase homolog from Bacillus stearothermophilus is actually a broad specificity phosphatase," *Protein Sci.* 10:1835-1846.
Ringer et al., "Monoterpene double-bond reductases of the (-)-menthol biosynthetic pathway: isolation and characterization of cDNAs encoding (-)-isopiperitenone reductase and (+)-pulegone reductase of peppermint," *Arch. Biochem. Biophys.* 418(1):80-92 (2003).
Ringquist et al., "Translation initiation in *Escherichia coli*: sequences within the ribosome-binding site," *Mol. Microbiol.* 6(9):1219-1229 (1992).
Rintala et al., "The ORF YNL274c (GOR1) codes for glyoxylate reductase in Saccharomyces cerevisiae," *Yeast* 24(2):129-136 (2007).

(56) References Cited

OTHER PUBLICATIONS

Riondet et al., "Measurement of the intracellular pH in *Escherichia coli* with the internally conjugated fluorescent probe 5- (and 6-)carboxyfluorescein succinimidyl ester." *Biotechnol. Tech.* 11:735-738 (1997).
Rioux et al., "Two outer membrane transport systems for vitamin $B_{12}$ in *Salmonella typhimurium*," *J. Bacteriol.* 171:2986-2993 (1989).
Rioux et al., "Vitamin B12 transport in *Escherichia coli* K12 does not require the *btuE* gene of the *btuCED* operon," *Mol. Gen. Genet.* 217:301-308 (1989).
Riviere et al., "Acetyl:succinate CoA-transferase in procyclic Trypanosoma brucei. Gene identification and role in carbohydrate metabolism." *J. Biol. Chem.* 279:45337-45346.
Roa Engel et al., "Fumaric acid production by fermentation," *Appl. Microbiol. Biotechnol.* 78(3):379-389 (2008).
Roberts et al, "The Role of Enoyl-coA Hydratase in the Metabolism of Isoleucine by Pseudomonas putida," *Arch. Microbiol.* 117:99-108 (1978).
Roberts et al., "Acetyl-coenzyme a synthesis from methyltetrahydrofolate, CO, and coenzyme a by enzymes purified from Clostridium thermoaceticum: attainment of in vivo rates and identification of rate-limiting steps," *J. Bacteriol.* 174(14):4667-4676 (1992).
Roberts et al., "Cloning and expression of the gene cluster encoding key proteins involved in acetyl-CoA synthesis in Clostridium thermoaceticum: Co dehydrogenase, the corrinoid/Fe-S protein, and methyltransferase," *Proc. Natl. Acad. Sci. USA* 86(1):32-36.
Robinson et al., "Studies on Rat Brain Acyl-Coenzyme a Hydrolase (Short Chain)," *Biochem. Biophys. Res. Commun.* 71(4):959-965 (1976).
Roca et al., "Metabolic engineering of ammonium assimilation in xylose-fermenting *Saccharomyces cerevisiae* improves ethanol production," *Appl Environ Microbiol* 69:4732-4736 (2003).
Rodich et al., "Isoprenoid biosynthesis in plants—2C-methyl-D-erythritol-4-phosphate synthase (IspC protein) of *Arabidopsis thaliana*," *FEBS J.* 273(19):4446-4458 (2006).
Rodriguez et al., "Characterization of the p-Coumaric Acid Decarboxylase from *Lactobacillus plantarium* CECT 748T," *J. Agric. Food Chem.* 56:3068-3072 (2008).
Rofe et al., "Hepatic oxalate production: the role of hydroxypyruvate," *Biochem. Med. Metab. Biol.* 36(2):141-150 (1986).
Roffia et al., "Byproduct Identification in the Terepthalic Acid Production Process and Possible Mechanisms of their Formation," *Ind. Eng. Chem. Prod. Res. Dev.* 23:629-634.
Rohdich et al., "Enoate reductases of Clostridia. Cloning, sequencing, and expression," *J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).
Romero et al., "Partial purification and characterization and nitrogen regulation of the lysine c-aminotransferase of Streptomyces clavuligers, " *J. Ind. Microbiol. Biotechnol.* 18:241-246 (1997).
Rontein et al., "Plants synthesize ethanolamine by direct decarboxylation of serine using a pyridoxal phosphate enzyme," *J. Biol. Chem.* 276(38):35523-35529 (2001).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rose et al., "The role of the allosteric B site in the fumarase reaction," *Proc. Natl. Acad. Sci. USA* 101(10):3393-3397 (2004).
Rose et al., "Enzymatic phosphorylation of acetate," *J. Biol. Chem.* 211(2):737-756.
Rosenberg, "A Comparison of Lipid Patterns in Photosynthesizing and Nonphotosynthesizing Cells of Euglena Gracilis," *Biochem.* 2:1148-1154 (1963).
Roszak et al., "The Structure and Mechanism of the Type II Dehydroquinase from Streptomyces coelicolor," *Structure* 10:493-503 (2002).
Roth et al., "Characterization of the cobalamin (vitamin B12) biosynthetic genes of *Salmonella typhimurium*," *J. Bacteriol.* 175:3303-3316 (1993).
Rother et al., "Anaerobic growth of Methanosarcina acetivorans C2A on carbon monoxide: an unusual way of life for a methanogenic archaeon," *Proc. Natl. Acad. Sci. USA* 101(48):16929-16934 (2004).
Rother et al., "Genetic and proteomic analyses of Co utilization by Methanosarcina acetivorans," *Arch. Microbiol.* 188(5):463-472 (2007).
Rous, "On the occurrence of enzymes of ketone-body metabolism in human adipose tissue," *Biochem. Biophys. Res. Commun.* 69(1):74-78 (1976).
Roux et al., "p-aminobenzoate synthesis in *Escherichia coli*: kinetic and mechanistic characterization of the amidotransferase PabA," *Biochemistry* 31:6904-6910 (1992).
Roux et al., "p-Aminobenzoate synthesis in *Escherichia coli*: mutational analysis of three conserved amino acid residues of the amidotransferase PabA," *Biochemistry* 32:3763-3768.
Roy et al., "Cloning and Characterization of the gene Encoding Lipoamide Dehydrogenase in Saccharomyces cerevisiae," *J. Gen. Microbiol.* 133:925-933 (1987).
Roymoulik et al., "Rearrangement of L-2-hydroxyglutarate to L-threo-3-methylmalate catalyzed by adenosylcobalamin-dependent glutamate mutase," *Biochem.* 39(33):10340-10346 (2000).
Rozell et al., "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).
Rudman et al., "Transamination in *Escherichia coli*," *J. Biol. Chem.* 200(2):591-604.
Ruldeekulthamrong et al., "Molecular characterization of lysine 6-dehydrogenase from Achromobacter denitrificans," *BMB Reports* 790-795 (2008).
Sabo et al., "Purification and physical properties of inducible *Escherichia coli* lysine decarboxylase," Biochemistry 13:622-670 (1974).
Sadowski, "The Flp recombinase of the 2- um plasmid of Saccharomyces cerevisiae," *Prog. Nucleic Acid Res. Mol. Biol.* 51:53-91 (1995).
Saegesser et al., "Stability of broad host range cloning vectors in the phototrophic bacterium Rhodospirillum rubrum," *FEMS Microbiol. Lett.* 95:7-11 (1992).
Saito et al., "Microbial synthesis and properties of poly(3-hydroxybutyrate-co-4-hydroxybutyrate) in Comamonas acidovorans," *Int. J Biol Macromol.* 16:99-104 (1994).
Sakai et al, "Acetate and Ethanol Production from H2 and CO2 by Morrella sp. Using a Repeated Batch Culture," *J. Biosci. Bioeng.* 99:252-258 (2005).
Sakanyan et al., "A re-examination of the pathway for ornithine biosynthesis in a thermophilic and two mesophilic Bacillus species," *J. Gen. Microbiol.* 138:125-130 (1992).
Sakurada et al., "Acetylpolyamine Amidohydrolase from Mycoplana ramosa: Gene Cloning and Characterization of the Metal-Substituted Enzyme," *J. Bacteriol.* 178(19):5781-5786 (1996).
Salmon et al., "Global gene expression profiling in *Escherichia coli* K12. Effects of oxygen availability and ArcA," J. Biol. Chem. 280(15):15084-15096 (2005).
Saltzgaber-Muller et al., "Nuclear genes coding the yeast mitochondrial adenosine. triphosphatase complex. Isolation of ATP2 coding the Fi-ATPase 0 subunit," *J. Bio. Chem.* 258(19):11465-11470 (1983).
Samanta et al., "Use of Rhodopseudomonas palustris genome sequence to identify a single amino acid that contributes to the activity of coenzyme a ligase with chlorinated substrates," *Mol. Microbiol.* 55(4):1151-1159 (2005).
Samsonova et al., "Molecular cloning and characterization of *Escherichia coli* K12 ygjG gene, " *BMC Microbiol.* 3:2 (2003).
Samuelov et al., "Whey fermentation by anaerobiospirillum succiniciproducens for production of a succinate-based animal feed additive," *Appl. Environ. Microbiol.* 65(5):2260-2263 (1999).
San et al., "Metabolic Engineering through Cofactor Manipulation and its Effects on Metabolic Flux Redistribution in *Escherichia coli*," Metab Eng 4(2):182-192 (2002).
Sanchez et al., "Efficient succinic acid production from glucose through overexpression of pyruvate carboxylase in an *Escherichia*

(56) References Cited

OTHER PUBLICATIONS

*coli* alcohol dehydrogenase and lactate dehydrogenase mutant," *Biotechnol. Prog.* 21(2):358-365 (2005).
Sanchez et al., "Novel pathway engineering design of the anaerobic central metabolic pathway in *Escherichia coli* to increase succinate yield and productivity," *Metab. Eng.* 7(3): 229-239 (2005).
Sanchez, et al., "Batch culture characterization and metabolic flux analysis of succinate-producing *Escherichia coli* strains," *Metab Eng.* 8(3):209-226 (2006).
Sanchez, et al., "Effect of different levels of NADH availability on metabolic fluxes of *Escherichia coli* chemostat cultures in defined medium," *J. Biotechnol.* 117(4):395-405.
Sankaranarayanan et al., "Preliminary x-ray crystallographic analysis of ornithine acetyltransferase (Rv1653) from Mycobacterium tuberculosis," *Acta Cryst.* F65:173-176.
Sanyai et al., "Biosyntehsis of pimeloyl-coA, a biotin precursor in *Escherichia coli*, follows a modified fatty acid synthesis pathway: It-labeling studies," *J. Am. Chem. Soc.* 116:2637-2638 (1994).
Sariaslani, "Development of a Combined biological and Chemical Process for Production of Industrial aromatics from Renewable Resources," *Annu. Rev. Microbiol.* 61:51-69 (2007).
Sass et al., "Folding of fumarase during mitochondrial import determines its dual targeting in yeast," *J. Biol. Chem.* 278(46):45109-45116 (2003).
Sato et al., "Poly[(R)-3-hydroxybutyrate] formation in Escherichia coli from glucose through an enoyl-CoA hydratase-mediated pathway," *J. Biosci. Bioeng.* 103(1):38-44.
Sauer et al., "Methanol:coenzyme M methyltransferase from Methanosarcina barkeri. Identification of the active-site histidine in the corrinoid-harboring subunit MtaC by site-directed mutagenesis," *Eur. J. Biochem.* 253(3):698-705 (1998).
Sauer et al., "Methanol:coenzyme M methyltransferase from Methanosarcina barkeri. Purification, properties and encoding genes of the corrinoid protein MT1," *Eur. J. Biochem.* 243(3):670-677 (1997).
Sauer, "Diels-Alder Reactions II: the Reaction Mechanism," *Angew Chem* 6:16-33.
Sauvageot et al., "Characterisation of the diol dehydratase pdu operon of Lactobacillus collinoides," *FEMS Microbiol. Lett.* 209:69-74 (2002).
Sawers et al., "Purification and properties of membrane-bound hydrogenase isoenzyme 1 from anaerobically grown *Escherichia coli* K12," *Eur. J. Biochem.* 156(2):265-275 (1986).
Sawers et al., "Characterization and physiological roles of membrane-bound hydrogenase isoenzymes from *Salmonella typhimurium*," *J. Bacteriol.* 168(1):398-404.
Sawers et al., "Differential expression of hydrogenase isoenzymes in *Escherichia coli* K12: evidence for a third isoenzyme," *J. Bacteriol.* 164(3):1324-1331 (1985).
Sawers, "The hydrogenases and formate dehydrogenases of *Escherichia coli*," *Antonie Van Leeuwenhoek* 66(1-3):57-88 (1994).
Saz et al., "The mechanism of the formation of a-methylbutyrate from carbohydrate by Ascaris lumbricoides muscle," *J. Biol. Chem.* 235:914-918 (1960).
Schadt et al., "2-Amino-2-deoxyisochorismate is a key intermediate in Bacillus subtilis p-aminobenzoic acid biosynthesis" *J Am. Chem. Soc.* 131:3481-3483 (2009).
Scharzer et al., "Nonribosomal peptides: from genes to products," *Nat. Prod. Rep.* 20:275-287 (2003).
Scher et al., "Maleate isomerase," *J. Biol. Chem.* 244:1878-1882 (1969).
Scherf et al., "Purification and properties of 4-hydroxybutyrate coenzyme a transferase from Clostridium aminobutyricum," *Appl. Environ. Microbiol.*, 57(9):2699-2702 (1991).
Scherf et al., "Purification and properties of an iron-sulfur and Fad-containing 4-hydroxybutyryl-CoA dehadratase/vinylacetyl-CoA A3 - 42-isomerase from Clostridium aminobutricum," *Eur. J. Biochem.* 215:421-429 (1993).
Scherf et al, "Succinate-ethanol fermentation in clostridium kluyveri: purification and characterisation of 4-hydroxybutyryl-CoA dehydratase/vinylacetyl-coA A3 - 42-isomerase," *Arch. Microbiol.* 161(3):239-245 (1994).
Schilling et al., "Genome-Scale Metabolic Model of Helicobacter pylori 26695," *J. Bacteriol.* 184:4582-4593 (2002).
Schilling et al., "Combining Pathway Analysis with Flux Balance Analysis for the Comprehensive Study of Metabolic Systems," *Biotechnol. Bioeng.* 71(4):286-306 (2000).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schilling et al., "Toward Metabolic Phenomics: Analysis of Genomic Data Using Flux Balances," *Biotechnol. Prog.* 15(3):288-295 (1999).
Schmid et al., "Plasmid-mediated uptake and metabolism of sucrose by Escherichia coli K-12," *J. Bacteriol.* 151(1):68-76 (1982).
Schmitzberger et al., "Structural constraints on protein self-processing in L-aspartate-a-decarboxylase," *EMBO J.* 22:6193-6204 (2003).
Schneider and Betz, Waxmonoester Fermentation in Euglena-Gracilis T. Factors Favoring the Synthesis of Odd-Numbered Fatty-Acids and Alcohols, Planta. 166:67-73.
Schneider et al., "Waxmonoester Fermentation in Euglena-Gracilis T Factors Favoring the Synthesis of Odd-Numbered Fatty-Acids and Alcohols," *Planta* 166:67-73 (1985).
Schneider et al., "The *Escherichia coli* gabDTPC operon: specific y-aminobutyrate catabolism and nonspecific induction," *J. Bacteriol.* 184:6976-6986 (2002).
Schnell et al., "Anaerobic degradation of aniline and dihydroxybenzenes by newly isolated sulfate-reducing bacteria and description of *Desulfobacterium anilini*," *Arch. Microbiol.* 152:556-563 (1989).
Schofield et al., "Substrate ambiguity and crystal structure of Pyrococcus furiosus 3-deoxy-D-arabino-heptulosonate-7-phosphate synthase: an ancestral 3-deoxyald-2-ulosonate-phosphate synthase?" *Biochemistry* 44(36):11950-11962 (2005).
Schomburg et al., "Ethanolamine Oxidase," in Springer handbook of enzymes: Class 1 : Oxidoreductases VII EC 1.4, vol. 22, 2nd ed., p. 320-323, New York (2005).
Schousboe et al., "Purification and Characterization of the 4-Aminobutyrate-2-Ketoglurate Transminase from Mouse Brain," *Biochem.* 2(15):2868-2873 (1973).
Schrock et al., "Preparation and Reactivity of Several Alkylidene Complexes of the Type W(Chr')(N--2, 6-C6H3-i-Pr2)(or)2 and Related Tungstacyclobutane complexes. Controlling Metathesis Activity through the Choice of Alkoxide Ligand," *J. Am. Chem. Soc.* 110:1423-1435 (1988).
Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).
Schurmann et al., Fructose-6-phosphate aldolase is a novel class I aldolase from *Escherichia coli* and is related to a novel group of bacterial transaldolases. *J. Biol. Chem.* 276(14): p. 11055-11061 (2001).
Schweiger and Buckel, "On the dehydration of (R)-lactate in the fermentation of alanine to propionat by Clostridium propionicum" *FEBS Lett.* 171:79-84 (1984).
Schweiger et al., "Purification of 2-hydroxyglutaryl-CoA dehydratase from Acidaminococcus fermentans. An iron-sulfur protein," *Eur. J. Biochem.* 169(2):441-448.
Scott et al., "Soluble y-aminobutyric-glutamic transaminase from Pseudomonas fluorescens," *J. Biol. Chem.* 234(4):932-936 (1959).
Scott "Discovering nature's diverse pathways to vitamin B12: a 35-year odyssey," *J. Org. Chem.* 68:2529-2539 (2003).
Seedorf et al., "The genome of Clostridium kluyveri, a strict anaerobe with unique metabolic features," *Proc. Natl. Acad. Sci. USA* 105(6):2128-2133 (2008).
Seffernick et al., "Melamine deaminase and Atrazine chlorohydrolase: 98 percent identical but functionally different," *J. Bacteriol.* 183 (8):2405-2410 (2001).
Segre et al., "Analysis of optimality in natural and perturbed metabolic networks," *Proc. Natl. Acad. Sci. USA* 99:15112-15117 (2002).

(56) References Cited

OTHER PUBLICATIONS

Seibert et al., "Characterization of a gene cluster encoding the maleylacetate reductase from Ralstonia eutropha 335T, and enzyme recruited for growth with 4-fluorobenzoate," *Microbiology* 150:463-472 (2004).
Seibert et al., "Characterization of the maleylacteate reductase MacA of Rhodococcus opacus 1CP and evidence for the presence of an isofunctional enzyme," *J. Bacteriol.* 180:3503-3508 (1998).
Seibert et al., "Purification and characterization of maleylacetate reductase from Alcaligenes eutrophys JMP134(pJP4)," *J. Bacteriol.* 175:6745-6754 (1993).
Sekimoto et al., "Cloning and molecular characterization of plant aldehyde oxidase," *J. Biol. Chem.* 272(24):15280-15285 (1997).
Selifonova et al., "Rapid evolution of novel traits in microorganisms," *Appl Environ. Microbiol.* 67:3645-3649 (2001).
Selmer et al., "Propionate CoA-transferase from Clostridium propionicum. Cloning of gene identification of glutamate 324 at the active site," *Eur. J. Biochem.* 269:372-380.
Seltzer, "Purification and properties of maleylacetone cis-trans isomerase from vibrio 01," *J. Biol. Chem.* 248:215-222 (1973).
Sen et al., "Developments in directed evolution for improving enzyme functions," *Appl. Biochem. Biotechnol.* 143:212-223 (2007).
Sennett et al., "Transmembrane transport of cobalamin in prokaryotic and eukaryotic cells," *Ann. Rev. Biochem.* 50:1053-1086 (1981).
Seravalli et al., "Evidence that NiNi acetyl-CoA synthase is active and that the CuNi enzyme is not," *Biochemistry* 43(13):3944-3955 (2004).
Seravalli et al., "Mechanism of transfer of the methyl group from (6S)-methyltetrahydrofolate to the corrinoid/iron-sulfur protein catalyzed by the methyltransferase from clostridium thermoaceticum: a key step in the Wood-Ljungdahl pathway of acetyl-CoA synthesis," *Biochemistry* 38(18):5728-5735 (1999).
Servos et al., "Molecular cloning and characterization of the aroD gene encoding 3-dehydroquinase from *Salmonella typhi*," *J. Gen. Microbiol.* 137(1):147-152 (1991).
Seyfried et al., "Cloning, Sequencing, and Overexpression of the Genes Encoding Coenzyme Biz-Dependent Glycerol Dehydratase of Citrobacter freundii," *J. Bacteriol.* 178(19):5793-5796 (1996).
Shafiani et al., "Cloning and characterization of aspartate-β-semialdehyde dehydrogenase from Mycobacterium tuberculosis H37 RV," *J. Appl. Microbiol.* 98:832-838.
Shah et al., "Repressible alkaline phosphatase of *Staphylococcus aureus*," *J. Bacteriol.* 94(3):780-781 (1967).
Shalel-Levanon et al., "Effect of ArcA and Fnr on the expression of genes related to the oxygen regulation and the glycolysis pathway in *Eschericiha coli* under microaerobic growth conditions," *Biotechnol. Bioeng.* 92(2):147-159 (2005).
Shames et al., "Interaction of Aspartate and Aspartate-derived Antimetabolites with the Enzymes of the Threonine Biosynthetic Pathway of *escherichia coli*," *J. Biol. Chem.* 258(24):15331-15339 (1984).
Shanley et al., "Cloning and expression of Acinetobacter calcoaceticus catBCDE genes in Pseudomonas putida and *Escherichia coli*," *J. Bacteriol.* 165:557-563 (1986).
Shao et al., "Random-priming in vitro recombination: an effective tool for directed evolution," *Nucleic Acids Res.* 26:681-683 (1998).
Sharma et al., "Menaquinone (Vitamin Iq Biosynthesis: Nucleotide Sequence and Expression of the menB Gene from *Escherichia coli*," *J. Bacteriol.* 174(15): 5057-5062.
Sheflyan et al., "Enzymatic Synthesis of 3-Deoxy-d-manno-octulosonate 8-phosphate, 3,5-Dideoxy-d-manno-octulosonate 8-phosphate and 3-Deoxy-d-altro-octulosonate 8-phosphate by 3-Deoxy-d-arabino-heptulosonate 7-phosphate Synthase," *J. Am. Chem. Soc.* 120:11027-11032 (1998).
Sheppard et al., "Purification and Properties of Nadh-Dependent 5,10-Methylenetetrahydrofolate Reductase (MetF) from *Escherichia coli*," *J. Bacteriol.* 181(3):718-725 (1999).
Shi et al., "The Structure of I-Aspartate Ammonia-Lyase from *Escherichia coli*," *Biochemistry* 36:9136-9144 (1997).

Shiba et al., "Engineering of the pyruate dehydrogenase bypass in Saccharomyces cerevisiae for high-level production of isoprenoids," *Metab. Eng,* 9:160-168 (2007).
Shibata et al., "Purification, characterization, and immunological properties of fumarase from Euglena gracilis var. bacillaris," *J. Bacteriol.* 164(2):762-768 (1985).
Shigeoka et al., "Characterization and molecular properties of 2-oxoglutarate decarboxylase from Euglena gracilis," *Arch. Biochem. Biophys.* 288:22-28 (1991).
Shigeoka et al., "The effect of thiamin on the activation of thiamin pyrophosphate-dependent 2-oxoglutarate decarboxylase in Euglena gracilis," *Biochem. J.* 292 (Pt 2):463-467 (1993).
Shigeoka et al., "Effect of L-glutamate on 2-oxoglutarate decarboxylase in Euglena gracilis," *Biochem. J.* 282( Pt 2):319-323 (1992).
Shimaoka et al, "Effects of edd and pgi Disruptions on Inosine Accumulation in *Escherichia coli*," *Biosci. Boitechnol. Biochem.* 69(7):1248-1255 (2005).
Shimoda et al., "Asymmetric Transformation of Enones with Synechococcus sp. Pcc 7942," *Bulletin of the Chemical Society of Japan* 77(12):2269-2272 (2004).
Shimomura et al., "3-hydroxyisobutyryl-CoA hydrolase," *Methods Enzymol.* 324:229-. 240 (2000).
Shimomura et al., "Purification and partial characterization of 3-hydroxyisobutyryl-coenzyme a hydrolase of rat liver," *J. Biol. Chem.* 269(19):14248-14253 (1994).
Shimoyama et al., "MmcBC in Pelotomaculum thermopropionicum represents a novel group of prokaryotic fumarases," *FEMS Microbiol Lett.* 270(2):207-213 (2007).
Shingler et al., "Nucleotide sequence and functional analysis of the complete phenol/3,4-dimethylphenol catabolic pathway of Pseudomonas sp. strain CF600," *J. Bacteriol.* 174(3):711-724 (1992).
Shlomi et al., "Regulatory on/off minimization of metabolic flux changes after genetic perturbations," *Proc. Natl. Acad. Sci. USA* 102:7695-7700 (2005).
Shukla et al., "Production of D(-)-lactate from sucrose and molasses," *Biotechnol. Lett.* 26(9):689-693 (2004).
Shuler et al., Operating Considerations for Bioreactors for Suspension and Immobilized Cultures, in Bioprocess Engineering: Basic Concepts, Prentice Hall, Inc., Upper Saddle. River, NJ., p. 245-247 (2002).
Sibilli et al., "Two regions of the bifunctional protein aspartokinase I-homoserine dehydrogenase I are connected by a short hinge," *J. Biol. Chem.* 256 (20):10228-10230.
Sieber et al., "Libraries of hybrid proteins from distantly related sequences," *Nat. Biotechnol.* 19:456-460 (2001).
Siebert et al., "Ubiquinone biosynthesis. Cloning of the genes coding for chorismate pyruvate-lyase and 4-hydroxybenzoate octaprenyl transferase from Escherichia coli," *FEBS. Lett.* 307(3):347-350 (1992).
Siegert et al., "Exchanging the substrate specificities of pyruvate decarboxylase from Zymomonas mobilis and benzoylformate decarboxylase from Pseudomonas putida," *Protein. Eng. Des. Sel.* 18:345-357 (2005).
Siew et al., "Localization and characteristics of rat liver mitochondrial aldehyde dehydrogenases," *Arch. Biochem. Biophys.* 176(2):638-649 (1976).
Sikorski et al., "A system of shuttle vectors and yeast host strains designed for efficient manipulation of DNA in Saccharomyces cerevisiae," *Genetics* 122(1):19-27 (1989).
Simanshu et al., "Structure and function of enzymes involved in the anaerobic degradation of L-threonine to propionate," *J. Biosci.* 32(6):1195-1206 (2007).
Simon et al., "Chiral Compounds Synthesized by Biocatalytic Reductions," *Angew. Chem. Int. Ed. Eng* 24:539-553 (1985).
Simonov et al.,"Application of Gas Chromatography and Gas Chromatography-Mass Spectrometry to the Detection ofr-Hydroxybutyric Acid and Its Precursors in Various Materials," *J. Anal. Chem.* 59:965-971 (2004).
Sinclair et al., Purification and characterization of the branched chain a-ketoacid dehydrogenase complex from Saccharomyces cerevisiae, *Biochem. Mol. Biol. Int.* 31(5):911-922 (1993).

(56) References Cited

OTHER PUBLICATIONS

Sipma et al., "Microbial Co conversions with applications in synthesis gas purification and bio-desulfurization," *Crit. Rev. Biotechnol.* 26:41-65 (2006).

Sivaraman et al., "Codon choice in genes depends on flanking sequence information-implications for theoretical reverse translation," *Nucleic Acids Res.* 36(3):e16 (2008).

Sjostrom et al., "Purification and characterisation of a plasminogen-binding protein from Haemophilus influenzae. Sequence determination reveals identity with aspartase," *Biochim. Biophys. Acta.* 1324(2):182-190 (1997).

Skarstedt et al., "Escherichia coli acetate kinase mechanism studied by net initial rate, equilibrium, and independent isotopic exchange kinetics," *J. Biol. Chem.* 251:6775-6783.

Slater et al., "Multiple I3-ketothiolases mediate poly03-hydroxyalkanoate) copolymer synthesis in Ralstonia eutropha," *J. Bacteriol.* 180(8):1979-1987 (1998).

Sloane et al., "Studies on the metabolism of p-aminobenzoic acid by Mycobacterium smegmatis," *J Biol. Chem.* 193:453-458 (1951).

Slock et al., "An apparent *Bacillus subtilis* folic acid biosynthetic operon containing pab, an amphibolic trpG gene, a third gene required for synthesis of para-aminobenzoic acid, and the dihydropteroate synthase gene," *J Bacteriol.* 172:7211-7226 (1990).

Smit et al., "Identification, cloning and characterization of Lactococcus lactis branched-chain a-keto acid decarboxylase involved in flavor formation," *Appl. Environ. Microbiol.* 71:303-311 (2005).

Smith et al., Catalysis of the oxidation of 1,4-cyclohexadiene to benzene by electroactive binuclear rhodium complexes, *Catalysis Lett.* 6:195-199 (1990).

Smith et al., "Purification, properties and kinetic mechanism of coenzyme A-linked aldehyde dehydrogenase from Clostridium kluyveri," *Arch. Biochem. Biophys.* 203:663-. 675 (1980).

Smith et al., "Purification and characteristics of a y-glutamyl kinase involved in *Escherichia coli* proline biosynthesis," *J. Bacteriol.* 157:545-551 (1984).

Smith et al., "Structural analysis of ligand binding and catalysis in chorismate lyase," *Arch. Biochem. Biophys.* 445(1):72-80 (2006).

Smith et al., "Fumarate metabolism and the microaerophily of Campylobacter species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Action polymerization induced by calspectin, a calmodulin-binding spectrin-like protein," *FEBS Lett* 148(2):221-225 (1982).

Soda et al.,"L-Lysine:a-ketoglutarate aminotransferase. II. Purification, crystallization, and properties," *J. Bacteriol.* 7:4110-4119 (1968).

Sohling et al., "Purification and characterization of a coenzyme-A-dependent succinate-semialdehyde dehydrogenase from Clostridium kluyveri," *Eur. J. Biochem.* 212:121-127.

Sohling and Gottschalk, "Molecular analysis of the anaerobic succinate degradation pathway in Clostridium kluyveri," *J. Bacteriol.* 178:871-880 (1996).

Soini et al., "High cell density media for *Escherichia coli* are generally designed for aerobic cultivations—consequences for large-scarle bioprocesses and shake flask cultures," *Microb. Cell. Fact.* 7:26 (2008).

Sokatch et al., "Purification of a Branched-Chain Keto Acid Dehydrogenase from Pseudomonas putida," *J. Bacteriol.* 148(2):647-652 (1981).

Somerville, "The Billion-Ton Biofuels Vision," *Science* 312(5778):1277 (2006).

Sone et al., "Nucleotide sequence and expression of the Enterobacter aerogenes a-acetolactate decarboxylase gene in brewer's yeast, " *Appl. Environ. Microbiol.* 54:38-42 (1988).

Song et al, "Effects of dissolved CO2 levels on the growth of *Mannheimia succinicproducens* and succinic acid production," Biotechnol. Bioeng. 98(6):1296-1304.

Song et al., "Construction of recombinant Escherichia coli strains producing poly (4-hydroxybutyric acid) homopolyester from glucose," *Wei Sheng Wu Xue.Bao.* 45:382-386.

Song et al., "Ultrasound-mediated DNA transfer for bacteria," *Nucl. Acids Res.* 35:e129.

Song et al., "Recovery of succinic acid produced by fermentation of a metabolically engineered Mannheimia succiniciproducens strain," *J. Biotechnol.* 132:445-452 (2007).

Song et al., "Structure, function, and mechanism of the phenylacetate pathway hot dog-fold thioesterase PaaI," *J. Biol. Chem.* 281(16):11028-11038 (2006).

Soucaille et al., "Butanol tolerance and autobacteriocin production by Clostridium acetobutylicum," *Curr. Microbiol.* 14:295-299 (1987).

Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek et al., "Purification and properties of *Escherichia coli* coenzyme A-transferase," *Arch. Biochem. Biophys.* 171(1):14-26 (1975).

St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," *J. Bacteriol.* 189:4764-4773.

Stadthagen et al., "p-Hydroxybenzoic acid synthesis in *Mycobacterium tuberculosis*," *J. Biol. Chem.* 280(49):40699-40706 (2005).

Stadtman, "The enzyme synthesis of β-alanyl coenzyme a," *J. Plant Chem. Soc.* 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of salmonella enerica on ethanolamine requires phosphotransacetylase (EutD) activity, and acetate recapture requires acetyl-CoA synthetase (ACS) and phosphotransacetylase (PTA) activities," *Microbiology* 151:3793-3801.

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

Starnes et al., "Threonine-sensitive aspartokinase-homoserine dehydrogenase complex, amino acid composition, molecular weight, and subunit composition of the complex," *Biochemistry* 11:677-687 (1973).

Steen et al., "Metabolic engineering of Saccharomyces cerevisiae for the production of n-butanol," *Microb. Cell Fact.* 7:36 (provided electronically by publisher as pp. 1-8) (2008).

Steffan et al., "Isolation and characterization of the yeast gene encoding the MDH3 isozyme of malate dehydrogenase," *J. Biol. Chem.* 267:24708-24715 (1992).

Steinbacher et al., "Enoate reductase family," in Flavins and Flavoproteins, Proceedings of the Fourteenth International Symposium, St. John's College, University of Cambridge, UK, Jul. 14-18 2002, Chapman et al., pp. 941-949, Rudolf Weber, Agency for Scientific Publications Berlin.

Steinbuchel et al., "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).

Steinbuchel et al., "A multifunctional fermentative alcohol dehydrogenase from the strict aerobe Alcaligenes eutrophus: purification and properties," *Eur. J. Biochem.* 141:555-. 564 (1984).

Steiner et al., "Long-term continuous evolution of acetate resistant Acetobacter aceti" *Biotechnol Bioeng.* 84:40-44 (2003).

Stemmer, "DNA shuffling by random fragmentation and reassembly: in vitro recombination for molecular evolution," *Proc. Natl. Acad. Sci. USA* 91:10747-10751.

Stemmer, "Rapid evolution of a protein in vitro by DNA shuffling," *Nature* 370:389-391.

Stim-Herndon et al., "Characterization of an acetyl-CoA C-acetyltransferase (thiolase) gene from Clostridium acetobutylicum ATCC 824," *Gene.* 154(1):81-85 (1995).

Stirling et al., "Purification and Properties of a Nicotinamide Adenine Dinucleotide-Linked Cyclohexanol Dehydrogenase from a nocardia Species," *Curr. Microbiol.* 4:37-40.

(56) References Cited

OTHER PUBLICATIONS

Stokell et al., "Probing the roles of key residues in the unique regulatory Nadh binding site of type II citrate synthase of *Escherichia coli*," *J. Biol. Chem.* 278:35435-35443 (2003).
Stols et al., "Production of succinic acid through overexpression of NAD±-dependent malic enzyme in an *Escherichia coli* mutant," *Appl. Environ. Microbiol.* 63(7):2695-2701.
Stols et al., "Expression of Ascaris suum malic enzyme in a mutant *Escherichia coli* allows production of succinic acid from glucose," *Appl. Biochem. Biotechnol.* 63-65: 153-158 (1997).
Stols et al., "New vectors for co-expression of proteins: Structure of Bacillus subtilis ScoAB obtained by High-throughput protocols," *Protein Expr. Purif.* 53:396-403 (2007).
Stoyan et al., "Cloning, sequencing and overexpression of the leucine dehydrogenase gene from Bacillus cereus," *J. Biotechnol.* 54:77-80 (1997).
Straathof et al., "Feasibility of acrylic acid production by fermentation," *Appl. Microbiol. Biotechnol.* 67:727-734 (2005).
Strauss et al., "Enzymes of a novel autotrophic CO2 fixation pathway in the phototrophic bacterium Chloroflexus aurantiacus, the 3-hydroxypropionate cycle," *Eur. J. Biochem.* 215:633-643 (1993).
Streit et al., "Biotin in microbes, the genes involved in its biosynthesis, its biochemical role and perspectives for biotechnological production," *Appl. Microbiol. Biotechnol.* 61:21-31 (2003).
Stringfellow et al., "Sequence of the *Escherichia coli* C homoprotocatechuic acid degradative operon completed with that of the 2,4-dihydroxyhept-2-ene-1,7-dioic acide aldolase-encoding gene (hpcH)," *Gene* 166:73-76 (1995). Stryer. Biochemistry. 3rd Ed. New York: W.H. Freeman and Company, p. 374-376.
Suarez De Mata et al., "Propionyl-CoA condensing enzyme from Ascaris muscle mitochondria. I. Isolation and characterization of multiple forms," *Arch. Biochem. Biophys.* 285(1):158-165 (1991).
Suarez De Mata et al., "Propionyl-CoA condensing enzyme from Ascaris muscle mitochondria. II. Coenzyme a modulation," *Arch. Biochem. Biophys.* 285:166-171 (1991).
Suda et al., "Purification and properties of a-ketodaipate reductase, a newly discovered enzyme from human placenta," *Arch. Biochem. Biophys.* 176(2):610-620 (1976).
Suda et al., "Subcellular localization and tissue distribution of a-ketoadipate reduction and oxidation in the rat," *Biochem. Biophys. Res. Commun.* 77(2):586-591 (1977).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of E.coli alcohol dehydrogenase YqhD: evidence of a covalently modified NADP coenzyme," *J. Mol. Biol.* 342(2):489-502 (2004).
Summers et al., "Choline Synthesis in Spinach in Relation to Salt Stress," *Plant Physiol.* 103(4):1269-1276 (1993).
Suthers et al., "Metabolic flux elucidation for large-scale models using 13C labeled isotopes," *Metab. Eng.* 9:387-405 (2007).
Suzuki et al., "Acetylputrescine deacetylase from Micrococcus luteus K-11," *Biochim. Biophys. Acta* 882:140-142 (1986).
Suzuki et al., "GriC and GriD Constitute a carboxylic acid reductase involved in grixazone biosynthesis in streptomyces griseus," *J. Antibiot.* 60(6):380-387 (2007).
Suzuki et al., "Properties and metabolic role of mesaconate hydratase of an aerobic bacterium," *J. Biochem.* 81:1917-1925 (1977).
Suzuki, "Phospotransacetylase of *Escherichia coli* B., activation by pyruvate and inhibition by Nadh and certain nucleotides," *Biochem. Biophys. Acta* 191:559-569.
Svensson et al., "Characterization and isolation of enzymes that hydrolyze short-chain acyl-CoA in rat-liver mitochondria," *Eur. J. Biochem.* 238(2):526-531 (1996).
Svetlitchnyi et al., "A functional Ni-Ni44Fe-451 cluster in the monomeric acetyl-CoA synthase from Carboxydothermus hydrogenoformans," *Proc. Natl. Acad. Sci. USA* 101(2):446-451 (2004).
Svetlitchnyi et al., "Two membrane-associated NiFeS-carbon monoxide dehydrogenases from the anaerobic carbon-monoxide-utilizing eubacterium Carboxydothermus hydrogenoformans," *J. Bacteriol.* 183(17):5134-5144 (2001).
Switzer, "Glutamate mutase," in Dolphin, D. ed., *Vitamin B12 (vol. 2: Biochemistry and. Medicine)*, Wiley-Interscience: New York, p. 289-305 (1982).
Tae-Kang et al., "Purification and characterization of a cyclohexanol dehydrogenase from Rhodococcus sp. TK6," *J. Microbiol. Biotechnol.* 12:39-45 (2002).
Tahlan et al., "Two sets of paralogous genes encode the enzymes involved in the early stages of clavulanic acid and clavam metabolite biosynthesis in Streptomyces clavuligerus," *Antimicrob. Agents Chemother.* 48(3):930-939 (2004).
Takacs et al., "Formate hydrogenlyase in the hyperthermophilic archaeon, Thermococcus litoralis," *BMC Microbiol.* 8:88 (2008).
Takagi et al, "Purification, crystallization, and molecular properties of aspartase from Pseudomonas fluorescens," *J. Biochem.* 96(2):545-552 (1984).
Takagi et al., "Isolation of a versatile Serratia marcescens mutant as a host and molecular cloning of the aspartase gene," *J. Bacteriol.* 161:1-6 (1985).
Takagi et al., "Cloning and nucleotide sequence of the aspartase gene of Pseudomonas fluorescens," *J. Biochem.* 100(3):697-705 (1986).
Takahashi et al., "Metabolic pathways for cytoxic and end product formation from glutamate- and aspartate-containing peptides by Porphyromonas gingivalis," *J. Bacteriol.* 182:4704-4710 (2000).
Takahashi et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis," *Proc. Natl. Acad. Sci. U. S. A.* 95(17):9879-9884 (1998).
Takahashi-Abbe et al., "Biochemical and functional properties of a pyruvate formate-lyase (PFL)-activating system in Streptococcus mutans," *Oral. Microbiol. Immunol.* 18:293-297 (2003).
Takanashi et al., "Characterization of a novel 3-hydroxybutyrate dehydrogenase from Ralstonia pickettii T1," *Antonie van Leeuwnhoek* 95(3):249-262 (2009).
Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).
Takatsuka et al., "Identification of the amino acid residues conferring substrate specificity upon Selenomonas ruminantium lysine decarboxylase," *Bioxci. Biotechnol. Biochem.* 63:1843-1846 (1999).
Takeo, "Existence and Properties of Two Malic Enzymes in *Escherichia coli* Especially of NAD-linked Enzyme," *J. Biochem.* 66:379-387 (1969).
Takigawa et al., "Probabilistic path ranking based on adjacent pairwise coexpression for metabolic transcripts analysis," *Bioinformatics* 24(2):250-257 (2008).
Tallant et al., "Coenzyme M methylase activity of the 480-kilodalton corrinoid protein from Methanosarcina barkeri," *J. Bacteriol.* 178(5):1295-1301 (1996).
Tallant et al., "Methylthiol:coenzyme M Methyltransferase from Methanosarcina barkeri, an enzyme of methanogenesis from dimethylsulfide and methylmercaptopropionate," *J. Bacteriol.* 179(22):6902-6911 (1997).
Tallant et al., "The MtsA subunit of the methylthiol:coenzyme M methyltransferase of Methanosarcina barkeri catalyses both half-reactions of corrinoid-dependent dimethylsulfide: coenzyme M methyl transfer," *J. Biol. Chem.* 276(6):4485-4493 (2001).
Tamaki et al., "Purification and properties of aldehyde dehydrogenase from Saccharomyces cerevisiae," *J. Biochem.* 82(1):73-79 (1977).
Tamaki et al., "Purification, properties, and sequencing of aminoisobutyrate aminotransferases from rat liver," *Methods Enzymol.* 324:376-389 (2000).
Tanaka et al., "Cloning and characterization of a human orthologue of testis-specific succinyl CoA: 3-oxo acid CoA transferase (Scot-t) cDNA," *Mol. Hum. Reprod.* 8:16-23.
Tanaka et al., "Lysine decarboxylase of Vibrio parahaemolyticus: kinetics of transcription and role in acid resistance," *J. Appl. Microbiol.* 104:1283-1293 (2008).

(56) References Cited

OTHER PUBLICATIONS

Tang et al., "Identification of a novel pyridoxal 5'-phosphaste binding site in adenosylcobalamin-dependent lysine 5,6-aminomutase from Porphyromonas gingivalis," *Biochemistry* 41(27):8767-8776 (2002).
Tang et al., "Microbial conversion of glycerol to 1,3-propanediol by an engineered strain of Escherichia coli," *Appl. Environ. Microbiol.* 75(6):1628-1634 (2009).
Tani et al., "Thermostable NADP(+)-dependent medium-chain alcohol dehydrogenase from Acinetobacter sp. strain M-1: purification and characterization and gene expression in *Escherichia coli*," *Appl. Environ. Microbiol.* 66(12):5231-5235 (2000).
Tanizawa et al., "The primary structure of thermostable D-amino acid aminotransferase from a thermophilic Bacillus species and its correlation with L-amino acid aminotransferases," *J. Biol. Chem.* 264(5):2450-2454 (1989).
Tanous et al., "Glutamate dehydrogenase activity can be transmitted naturally to Lactococcus lactis strains to stimulate amino acid conversion to aroma compounds," *Appl. Environ. Microbiol.* 72(2):1402-1409 (2006).
Tardif et al., "Electrotransformation studies in Clostridium cellulolyticum," *J. Ind. Microbiol. Biotechnol.* 27(5):271-274 (2001).
Taylor et al., "Nucleotide sequence of the Bacillus licheniformis ATCC 10716 dat gene and comparison of the predicted amino acid sequence with thos of other bacterial species," *Biochim. Biophys. Acta* 1350(1):38-40 (1997).
Tebbe et al., "Titanium-Catalyzed Olefin Metathesis," *J. Am. Chem. Soc.* 101(17):5074-. 5075 (1979).
Teipel et al., "The substrate specificity of fumarase," *J. Biol. Chem.* 243:5684-5694.
Ter Schure et al., "Pyruvate decarboxylase catalyzes decarboxylation of branched-chain 2-oxo acids but is not essential for fusel alcohol production by Saccharomyces cerevisiae," *Appl. Environ. Microbiol.* 64:1303-1307 (1998).
Teufel et al., "3-hydroxypropionyl-coenzyme a dehydratase and acryloyl-coenzyme a reductase, enzymes of the autotrophic 3-hydroxypropionate/4-hydroxybutyrate cycle in the Sulfolbales," *J. Bacteriol.* 191:4572-4581 (2009).
Thanos et al., "Electro-enzymic viologen-mediated stereospecific reduction of 2-enoates with free and immobilized enoate reductase on cellulose filters or modified carbon electrodes," *J. Biotechnol.* 6:13-29 (1987).
Thauer, "Microbiology. A Fifth Pathway of Carbon Fixation," *Science* 318:1732-1733.
Thomas et al., "Bimetallic nanocatalysts for the conversion of muconic acid to adipic acid," *Chem. Commun.* 21:1126-1127 (2003).
Thornton et al., "Primary structure of the monomer of the 12S subunit of transcarboxylase as deduced from Dna and characterizatio not the product expressed in *Escherichia coli*," *J. Bacteriol.* 175:5301-5308 (1993).
Thykaer, et al., "Metabolic network analysis of an adipoyl-7-Adca-producing strain of Penicillium chrysogenum: elucidation of adipate degradation," *Metab Eng,* 4(2):151-158.
Tian et al., "Variant tricarboxylic acid cycle in Mycobacterium tuberculosis: identification of a-ketoglutarate decarboxylase," *Proc. Natl. Acad. Sci. USA* 102:10670-10675 (2005).
Tischer et al., "Purification and Some Properties of a Hitherto-Unknown Enzyme Reducing the Carbon-Carbon Double Bond of a,(3-Unsaturated Carboxylate Anions," *Eur. J. Biochem.* 97(1):103-112 (1979).
Tobimatsu et al., "Molecular cloning, Sequencing and Characterization of the Genes for Adenosylcobalamin-dependent Diol Dehydratase of Klebsiella pneumoniae," *Biosci. Biotechnol. Biochem.* 62(9):1744-1777 (1998).
Tobimatsu et al., "Molecular cloning, Sequencing and Expression of the Genes Encoding Adenosylcobalamin-dependent Diol Dehydrase of Klebsiella oxytoca," *J. Biol. Chem.* 270(13):7142-7148 (1995).
Tobin et al., "Localization of the Lysine c-Aminotransferase (lat) and 6-(L-a-Aminoadipyl)-L-Cysteinyl-D-Valine Synthetase (pcbAB)

Genes from Streptomyces clavuligerus and Production of Lysine c-Aminotransferase Activity in *Escherichia coli*," *J. Bacteriol.* 173(19):6223-6229 (1991).
Tolentino et al., "A pH-regulated promoter for the expression of recombinant proteins in *Escherichia coli*," *Biotechnol. Lett.* 14:157-162. (1992).
Tomas et al., "Overexpression of groESL in Clostridium acetobutylicum Results in Increased Solvent Production and Tolerance, Prolonged Metabolism, and Changes in the Cell's Transcriptional Program," *Appl. Environ. Microbiol.* 69:4951-4965 (2003).
Toraya et al., "Substrate Specificity of Coenzyme 1312-Dependent Diol Dehydrase: Glycerol as Both a Good Substrate and a Potent Inactivator," *Biochem. Biophys. Res. Commun.* 69:475-480 (1976).
Toth et al., "The ald Gene, Encoding a coenzyme A-Acylating Aldehyde Dehydrogenase, Distinguishes Clostridium beijerinckii and Two Other Solvent-Producing Clostridia from Clostridium acetobutylicum," *App. Environ. Microbiol.* 65(11):4973-4980 (1999).
Tretter and Adam-Vizi, "Alpha-ketoglutarate dehydrogenase: a target and generator of oxidative stress," *Philos. Trans. R. Soc. B* 360:2335-2345 (2006).
Trower et al., "Isolation and Characterization of a Cyclohexane-Metabolizing Xanthobacter sp.," *Appl. Environ. Microbiol.* 49(5):1282-1289 (1985).
Truscott et al., "Mechanisms of protein import into mitochondria," *Curr. Biol.* 13(8):R326-R337 (2003).
Tsao et al., "Production of multifunctional organic acids from renewable resources," *Adv. Biochem. Eng. Biotechnol.* 65:243-280 (1999).
Tseng et al., "Metabolic Engineering of *Escherichia coli* for Enhanced Production of (R)-. And (S)-3-Hydroxybutyrate," *App. Environ. Microbiol.* 75(10):3137-3145 (2009).
Tseng et al., "Oxygen- and growth rate-dependent regulation of Escherichia coli fumarase (FumA, FumB, and FumC) activity," *J. Bacteriol.* 183(2):461-467 (2001).
Tsuji et al., "Purification and Properties of 4-Aminobenzoate Hydroxylase, a New Monooxygenase from Agaricus bisporus," *J. Biol. Chem.* 261(28):13203-13209 (1986).
Tsujimoto et al., "L-Lysine biosynthetic pathway of Methylophilus methylotrophus and construction of an L-Lysine producer," *J. Biotechnol.* 124:327-337 (2006).
Tucci et al., "A novel prokaryotic trans-2-enoyl-CoA reductase from the spirochete Treponema denticola," *FEBS Lett.* 581(8):1561-1566 (2007).
Tutino et al., "Expression of *Sulfolobus solfataricus trpE* and *trpG* genes in *E. coli*," *Biochem. Biophys. Res. Commun.* 230:306-310 (1997).
Twarog and Wolfe, "Role of butyryl phosphate in the energy metabolism of clostridium tetanomorphum," *J. Bacteriol.* 86:112-117 (1963).
Tweedy et al., "Metabolism of 3-(p-bromophenyl)-1-methoxy-l-methylurea (metobromuron) by selected soil microorganisms," *J. Agric. Food Chem.* 18(5):851-853.
Tyurin et al., "Electrotransformation of Clostridum acetobutylicum Atcc 824 using high-voltage radio frequency modulated square pulses," *J. Appl. Microbiol.* 88(2):220-227.
Tyurin, et al., "Electrotransformation of Clostridium thermocellum," *Appl Environ. Microbiol,* 70(2):883-890 (2004).
Tzagoloff et al., "PET genes of Saccharomyces cerevisiae," *Microbiol. Rev.* 54(3):211-225 (1990).
Uchiyama et al., "Identification of the 4-Hydroxycinnamate Decarboxylase (PAD) Gene of Klebsiella oxytoca," *Biosci. Biotechnol. Biochem.* 72: 116-123 (2008).
Ulaganathan et al., "Structure of Staphylococcus aureus 1,4-dihydroxy-2-naphthoyl-CoA synthase (MenB) in complex with acetoacetyl-CoA," *Acta Cryst* F63:908-913 (2007).
Umbarger et al., "Threonine deamination in *Escherichia coli*. II. Evidence fro two L-threonine deaminases," *J. Bacteriol.* 73(1):105-112 (1957).
Underwood et al., "Genetic Changes to Optimize Carbon Partitioning between Ethanol and Biosynthesis in Ethanologenic *Escherichia coli*," *App. Environ. Microbiol.* 68(12):6263-6272 (2002).

(56) References Cited

OTHER PUBLICATIONS

Urbance et al., "Evaluation of succinic acid continuous and repeat-batch biofilm fermentation by Actinobacillus succinogenes using plastic composite support bioreactors," *Appl. Microbiol. Biotechnol.* 65(6):664-670 (2004).
Url 1.eere.energy.gov/biomass/information_resources.html (printed Apr. 19, 2010).
Url http://wwwl.eere.energy.gov/biomass/information_resources.html (Aug. 21, 2007).
Url toxnet.nlm.nih.gov/cgi-bin/sis/search/f?./temp/—FwAsma:1:Basic (printed 02-172010).
Url web.archive.org/web/20080302001450/http://www.verenium.com/pp./Technology/EnzymeTech/TechEnzyTGR.html (printed Apr. 12, 2010).
Uttaro et al., "Purification and characterisation of a novel isopropanol dehydrogenase from Phytomonas sp.," *Mol. Biochem. Parasitol.* 85:213-219 (1997).
Vadali, et al., "Enhanced Isoamyl Acetate Production upon Manipulation of the Acetyl-. CoA node in *Escherichia coli*," *Biotech. Prog* 20:692-697 (2004).
Vadali, et al., "Production of isoamyl acetate in ackA-pta and/or ldh mutants of E. coli with overexpression of yeast ATF2," *Appl. Microbiol. Biotechnol.* 63:698-704 (2004).
Vadali, et al., "Cofactor engineering of intercellular CoA/acetyl-CoA and its effect on metabolic flux redistribution in *Escherichia coli*," *Metab Eng.* 6(2): 133-139 (2004).
Valdes-Hevia et al., "Isolation and characterization of the gene encoding phosphoenolpyruvate carboxykinase from Saccharomyces cerevisiae," *FEBS Lett.* 258:313-316 (1989).
Valentin et al., "Metabolic pathway for biosynthesis of poly(3-hydroxybutyrate-co-4-hydroxybutyrate) from 4-hydroxybutyrate by Alcaligenes eutrophus," *Eur. J. Biochem.* 227(1-2):43-60 (1995).
Valentine et al., "Purification and role of phosphotransbutyrylase," *J. Biol. Chem.* 235:1948-1952 (1960).
Vamecq et al., "The microsomal dicarboxylyl-CoA synthetase," *Biochem. J.* 230(3):683-693 (1985).
Van Beilen et al., "Cloning of Baeyer-Villiger monooxygenases from comamonas,. Xantherobacter and Rhodococcus using polymerase chain reaction with highly degenerate primers," *Environ. Microbiol.* 5(3):174-182 (2003).
Van Der Voorhorst et al., "Genetic and biochemcial characterization of a short-chain alcohol dehydrogenase from the hyperthermophilic archaeon Pyrococcus furiosus," *Eur. J. Biochem.* 268:3062-3068 (2001).
Van Der Westhuizen, et al., "Autolytic Activity and Butanol tolerance of Clostridium acetobutylicum," *Appl. Environ. Microbiol.* 44:1277-1281 (1982).
Van Grinsven et al., "Acetate:succinate CoA-transferase in the hydrogenosomes of Trichomonas vaginalis: identification and characterization," *J. Biol. Chem.* 283:1411-1418.
Van Loon et al., "Intracellular sorting of alcohol dehydregenase isoenzymes in yeast: a cytosolic location oreflects absence of an amino-terminal targeting sequence for the mitochondrion," *Embo J.* 5:161-165 (1986).
Van Maris et al., "Directed evolution of pyruvate decarboxylase-negative Saccharomyces cerevisiae, yielding a C2-independent, glucose-tolerant, and pyruvate-hyperproducing yeast," *Appl. Environ. Microbiol.* 70:159-166 (2004).
Van Mourik et al., "Functional analysis of a Campylobacter jejuni alkaline phosphatase secreted via the Tat export machinery," *Microbiology* 154(Pt 2):584-592 (2008).
Van Mullem et al., "Construction of a set of Saccharomyces cerevisiae vectors designed for recombinational cloning," *Yeast* 20(8):739-746 (2003).
Vandecasteele et al., "Aldehyde dehydrogenases from Pseudomonas aeruginosa," *Methods Enzymol.* 89 Pt D:484-490 (1982).
Vanderwinkel et al., "Growth of *Escherichia coli* on fatty acids: requirement for coenzyme a transferase activity," *Biochem. Biophys. Res. Commun.* 33(6):902-908.

Vanrolleghem et al., "Validation of a Metabolic Network for Saccharomyces cerevisiae Using Mixed Substrate Studies," *Biotechnol. Prog.* 12(4):434-448 (1996).
Varadarajan et al., "Catalytic Upgrading of Fermentation-Derived Organic Acids," *Biotechnol. Prog.* 15:845-854 (1999).
Vardar-Schara et al., "Metabolically engineered bacteria for producing hydrogen via fermentation," *Microbio. Biotechnol.* 1:107-125 (2008).
Varma et al., "Stoichiometric Flux Balance Models Quantitatively Predice Growth and Metabolic By-Product Secretion in Wild-Type Escherichia coli W3110," *Appl Env. Microbiol.* 60(10):3724-3731 (1994).
Varma et al., "Metabolic Flux Balancing: Basic Concepts, Scientific and Practical Use," *Biotechnol.* 12:994-998 (1994).
Varma et al., "Biochemical Production Capabilities of *Escherichia coli*," *Biotechnol. Bioeng.* 42:59-73 (1993).
Varma et al., "Stoichiometric Interpretation of *Escherichia coli* Glucose Catabolism under Various Oxygenation Rates," *Appl. Environ. Microbiol.* 59:2465-2473 (1993).
Vazquez et al., "Phosphtransbutyrylase expression in Bacillus megaterium," *Curr. Microbiol.* 42:345-349 (2001).
Vega et al., "The Biological Production of Ethanol from Synthesis Gas," *Appl. Biochem. Biotechnol.* 20/21:781-797 (1989).
Vellanki et al., "Expression of hepatitis B surface antigen in Saccharomyces cerevisiae utilizing glyceraldehyde-3-phosphate dehydrogenase promoter of Pichia pastoris," *Biotechnol. Lett.* 29(2):313-318 (2007).
Vemuri et al. "Succinate production in dual-phase *Escherichia coli* fermentations depends on the time of transition from aerobic to anaerobic conditions," *J. Ind. Microbiol. Biotechnol.* 28:325-332 (2002).
Vemuri et al., "Effects of growth mode and pyruvate carboxylase on succinic acid production by metabolically engineered strains of *Escherichia coli*," *Appl. Environ. Microbiol.* 68(4):1715-1727 (2002).
Venkitasubramanian et al. Biocatalysis in the Pharmaceitucal and Biotechnology Industires, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478- 485 (2007).
Verhaert et al., "Enzyme kinetics in reversed micelles. 2. Behaviour of enoate reductase," *Eur. J. Biochem.* 187:73-79 (1990).
Vernal et al., "Cloning and heterologous expression of a broad specificity aminotransferase of Leishmania mexicana promastigotes," *FEMS Microbiol. Lett.* 229:217-222 (2003).
Vernal et al., "Isolation partial characterization of a broad specificity aminotransferase from leishmania mexicana promastigotes," *Mol. Biochem. Parasitol.* 96:83-92 (1998).
Vey et al., "Structural basis for glycyl radical formation by pyruvate formate-lyase activating enzyme," *Proc. Natl. Acad. Sci USA* 105:16137-16141 (2008).
Victory et al., "A Non-Obvious Reaction Pathway in the Formation of 2-Aminobenzene-1,3-dicarbonitriles from a,(3-Unsaturated Ketones or Aldehydes," *Tetrahedron* 51(1):235-242 (1995).
Vijay et al., "Diels-Alder reactions between cyclic five-membered dienes and acetylene," *J. Mol. Struc.* 589-590:291-299 (2002).
Viola, "L-Aspartase: New Tricks From an Old Enzyme," *Adv. Enzymol. Relat. Areas. Mol. Biol.* 74:295-341 (2000).
Voellmy et al., "Role of 4-Aminobutyrate Aminotransferase in the Arginine Metabolism of Pseudomonas aeruginosa," *J. Bacteriol.* 128(3):722-729 (1976).
Voets et al., "Reduced intracellular ionic strength as the initial trigger for activation of endothelial volume-regulated anion channels," *Proc Natl Acad Sci U S.A* 96:5298-5303.
Volkert, et al., "The a(argF-lacZ)205(U169) Deletion Greatly Enhances Resistance to. Hydrogen Peroxide in Stationary-Phase *Escherichia coli*," *J. Bact.* 176(3):1297-1302.
Volkov et al., "Random chimeragenesis by heteroduplex recombination," *Methods Enzymol.* 328:456-463 (2000).
Volkov et al., "Recombination and chimeragenesis by in vitro heteroduplex formation and in vivo repair," *Nucleic Acids Res.* 27:e18 (1999).

(56) References Cited

OTHER PUBLICATIONS

Vrijbloed et al., "Insertional inactivation of methylmalonyl coenzyme a (CoA) mutase and isobutyryl-CoA mutase genes in Streptomyces cinnamonensis: influence on polyketide antibiotic biosynthesis," *J. Bacteriol.* 181(18):5600-5605 (1999).

Wakil et al., "Studies on the fatty acid oxidizing system of animal tissues. Vi. 13-Hydroxyacyl coenzyme a dehydrogenase," *J. Biol. Chem.* 207(2):631-638 (1954).

Walker et al., "Yeast pyruvate carboxylase: identification of two genes encoding isoenzymes," *Biochem. Biophys. Res. Commun.* 176:1210-1217 (2007).

Walter et al., "Molecular characterization of two Clostridium acetobutylicum ATCC 824 butanol dehydrogenase isozyme genes," *J. Bacteriol.* 174(22):7149-7158 (1992).

Walter et al., "Sequence and arrangement of two genes of the butyrate-synthesis pathway of Clostridium acetobutylicum ATCC 824," *Gene* 134(1):107-111 (1993).

Wang and Barker, "Purification and Properties of L-citramalate hydrolase," *J. Biol. Chem.* 244(10):2516-2526 (1969).

Wang et al., "Determination of the metal ion dependence and substrate specificty of a hydratase involve din the degradation pathway of biphenyl/chlorobiphenyl," *FEBS J.* 272:.966-974 (2005).

Wang et al, "Molecular cloning and functional identification of a novel phenylacetyl-CoA ligase gene from Penicillium chrysogenum," *Biochem. Biopyhs. Res. Commun.* 360(2):453-458 (2007).

Wang et al., "The primary structure of branched-chain a-oxo acid dehydrogenase from Bacillus subtilis and its similarity to other a-oxo acid dehydrogenases," *Eur. J. Biochem.* 213:1091-1099 (1993).

Wang et al., "Bioconversion of fumaric acid to succinic acid by recombinant E. coli," *App. Biochem. Biotechnol.* 70-72: 919-928 (1998).

Wang et al., "Cloning, Sequencing, and Expression of the Pyruvate Carboxylase Gene in Lactococcus lactis subsp. lactis C2," *App. Environ. Microbiol.* 66(3):1223-1227 (2000).

Wang et al., "Expression of galactose permease and pyruvate carboxylase in Escherichia coli ptsG mutant increases the growth rate and succinate yield under anaerobic conditions," *Biotechnol. Lett.* 28(2):89-93 (2006).

Wang et al., "Genome-scale in silico aided metabolic analysis and flux comparisons of Escherichia coli to improve succinate production," *Appl. Microbiol. Biotechnol.* 73(4):887-.

Wang et al., "Site-directed mutagenesis of the phosphorylatable serine (Ser8) in c4 phosphoenolpyruvate carboxylase from sorghum. The effect of negative charge at position 8," *J. Biol. Chem.* 267:16759-16762. (1992).

Wanner and Tressl, "Purification and characterization of two enone reductases from Saccharomyces cerevisia," *Eur. J. Biochem.* 255(1):271-278 (1998).

Ward et al., "Molecular analysis of the role of two aromatic aminotransferases and a broad-specificity aminotransferase in the aromatic amino acid metabolism of Pyococcus furiosus," *Archaea* 1:133-141 (2002).

Watanabe et al., "A novel a-ketoglutaric semialdehyde dehydrogenase: evolutionary insight into an alternative pathway of bacterial 1-arabinose metabolism," *J. Biol. Chem.* 281(39):28876-28888 (2006).

Weaver, "Structure of free fumarase C from *Escherichia coli*," *Acta Cryst* D61:1395-1401 (2005).

Weber and Falbe, "Oxo Synthesis Technology," Ind Eng Chem Res 62:33-37 (1970).

Weidner et al., "Molecular characterization of the Genes Encoding Pyruvate Formate-Lyase and Its Activating enzyme of clostridium pasteruianum," *J. Bacteriol.* 178(8):2440-. 2444 (1996).

Welch et al., "Purification and Characterization of the Nadh-Dependent Butanol Dehydrogenase from Clostridium acetobutylicum (ATCC 824)," *Arch. Biochem. Biophys.* 273(2):309-318 (1989).

Wengrovius et al., "Tungsten-Oxo Alkylidene Complexes as Olefin Metathesis Catalysts and the Crystal Structure of W(0)(CHCMe3)(PTt3)C121" *J. Am. Chem. Soc.* 102:4515-4516 (1980).

Westin et al., "The identification of a succinyl-CoA thioesterase suggests a novel pathway for succinate production in peroxisomes," *J. Biol. Chem.* 280(46):38125-38132.

Wexler et al., "A wide host-range metagenomic library from a waste water treatment plant yields a novel alcohol/aldehyde dehdrogenase," *Environ. Microbiol.* 7:1917-1926.

Whalen et al., "Analysis of an avtA::Mu dl(Ap lac) Mutant: Metabolic Role of Transaminase C," *J. Bacteriol.* 150(2):739-746 (1982).

Whalen et al., "Gratuitous repression of avtA in *Escherichia coli* and Salmonella typhimurium," *J. Bacteriol.* 158(2):571-574 (1984).

Whelan et al., "Nylon 6 (PA6)," Kunststof en Rubber, Wyt en Zonen Uitgevers. Rotterdam, Nl. 39(3):38-39 (1986).

Whisstock et al., "Prediction of protein function from protein sequence and structure," *Q. Rev. Biophysics.* 36(3):307-340 (2003).

White et al., "Long-chain alcohol production by yeasts," Yeast 5 Spec. No. S465-S470 (1989).

White et al., "The structural biology of type II fatty acid biosynthesis," *Ann. Rev. Biochem.* 74:791-831 (2005).

White, "Biosynthesis of methanopterin," *Biochemistry* 35(11):3447-3456 (1996).

Whitehead et al., "Cloning and expression in *Escherichia coli* of the gene for 10-formyltetrahydrofolate synthetase from Clostridium acidiurici ("Clostridium acidi-urici")," *J. Bacteriol.* 167:205-209 (1986).

Whitehead et al., "Nucleotide Sequence of the Clostridium acidiurici ("Clostridium acidi-urici") Gene for 10-Formyltetrahydrofolate Synthetase Shows Extensive Amino Acid Homology with the Trifunctional Enzyme Ci-Tetrahydrofolate Synthase from Saccharomyces cerevisiae," *J. Bacteriol.* 170(7):3255-3261 (1988).

Wiesenborn et al., "Coenzyme a Transferase from clostridium acetobutylicum ATCC 824 and Its Role in the Uptake of Acids," *Appl. Environ. Microbiol.* 55(2):323-329 (1989).

Wiesenborn et al., "Phosphotransbutyrylase from clostridium acetobutylicum Atcc 824 and its role in acidogenesis," *Appl. Environ. Microbiol.* 55:317-322 (1989).

Wilkie et al., "Recombinant expression, purification, and characterization of three isoenzymes of aspartate aminotransferase from Arabidopsis thaliana," *Protein Expr. Purif.* 12:381-389 (1998).

Wilks et al., "A specific, Highly Active Malate Dehydrogenase by Redesign of a Lactate Dehydrogenase Framework," *Science* 242:1541-1544 (1988).

Wilks et al., "Design of a Specific Phenyllactate Dehydrogenase by Peptide Loop Exchange on the Bacillus stearothermophilus Lactate Dehydrogenase Framework," *Biochemistry* 31:7802-7806 (1992).

Wilks et al., "Designs for a Broad Substrate Specificity Keto Acid Dehydrogenase," *Biochemistry* 29:8587-8591 (1990).

Willke and Vorlop, "Biotechnological production of itaconic acid," *Appl. Microbiol. Biotechnol.* 56(3-4):289-295 (2001).

Willke et al., "Industrial bioconversion of renewable resources as an alternative to conventional chemistry," *Appl. Microbiol. Biotechnol.* 66(2):131-142 (2004).

Winkler et al., "A new type of a multifunctional (3-oxidation enzyme in euglena," *Plant. Physiol.* 131(2):753-762 (2003).

Winzeler et al., "Functional Characterization of S. cerevisiae Genome by Gene Deletion and Parallel Analysis," *Science* 285:901-906 (1999).

Winzer et al., "Acetate kinase from Clostridium acetobutylicum: a highly specific enzyme that is actively transcribed during acidogenesis and solventogenesis," *Microbiology.* 143 (Pt 10):3279-3286 (1997).

Winzer et al., "Differential regulation of two thiolase genes from Clostridium acetobutylicum Dsm 792," *J. Mol. Microbiol. Biotechnol.* 2(4):531-541 (2000).

Witkowski et al., "Conversion of (3-ketoacyl synthase to a Malonyl Decarboxylase by replacement of the active cysteine with glutamine," *Biochemistry* 38:11643-11650 (1999).

Wittich and Walter, "Putrescine N-acetyltransferase in Onchocerca volvulus and Ascaris suum, an enzyme which is involved in polyamine degradation and release of N-acetylputrescine," *Mol. Biochem. Parasitol.* 38:13-17 (1990).

Wolff et al., "Purification and characterization of the oxygen-sensitive 4-hydroxybutanoate dehydrogenase from Clostridium kluyveri," *Protein Expr. Purif.* 6:206-212 (1995).

(56) References Cited

OTHER PUBLICATIONS

Wong et al., "Molecular Properties of Pyruvate Formate-Lyase Activating Enzyme," *Biochemistry* 32:14102-14110 (1993).
Wong et al., "Sequence saturation mutagenesis (SeSaM): a novel method for directed evolution," *Nucleic Acids Res* 32:e26 (2004).
Wong et al., "Sequence saturation mutagenesis with tunable mutation frequencies," *Anal. Biochem.* 341:187-189 (2005).
Wong et al., "Transversion-enriched sequence saturation mutagenesis (SeSaM-Tv±): a random mutagenesis method with consecutive nucleotide exchanges that complements the bias of error-prone Pcr," *Biotechnol. J.* 3:74-82 (2008).
Wood, "Life with Co or CO2 and H2 as a source of carbon and energy," *Fed. Amer. Societies Experi. Biol. J.* 5:156-163 (1991).
Woods, "Two biochemically distinct classes of fumarase in *Escherichia coli*," *Biochim. Biophys. Acta* 954(1):14-26 (1988).
Wu et al., "New insights into the evolutionary links relating to the 3-deoxy-D-arabino-heptulosonate 7-phosphate synthase subfamilies," *J Biol. Chem.* 281:4042-4048 (2006).
Wu et al., "Microbial synthesis of cis-cis-muconic acid by Sphingobacterium sp. Gcg generated from effluent of a styrene monomer (Sm) production plant," *Enzyme Microbial. Tech.* 35:598-604 (2004).
Wu et al., "Thermotoga maritima 3-deoxy-D-arabino-heptulosonate 7-phosphate (Dahp) synthase: the ancestral eubacterial Dahp synthase?" *J. Biol. Chem.* 278:27525-27531.
Wu et al., "Life in hot carbon monoxide: the complete genome sequence of Carboxydothermus hydrogenoformans Z-2901," *PLoS Genet,* 1(5):e65 (2005).
Wylie et al., "Nematode.net: a tool for navigating sequences from parasitic and free-living nematodes," *Nucleic Acids Res.* 32:D423-D426 (2004).
Wynn et al., "Chaperonins groEL and groES promote assembly of heterotetramers (a2(32) of mammalian mitochondrial branched-chain a-keto acid decarboxylase in *Escherichia coli*," J. Biol. Chem. 267:12400-12403 (1992).
Wynn et al., "Cloning and expression in Escherichia coli of mature Elfl subunit of bovine mitochondrial branched-chain a-keto acide dehydrogenase complex. Mapping of the Elfl-binding region on E2," *J. Biol. Chem.* 267:1881-1887 (1992).
Yabutani et al., "Analysis of 0-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," J. Biochem. 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from Hydrogenobacter thermophilus," *Extremophiles* 14:9-85 (2010).
Yamamoto et al., "Purification and Properties of Nadp-dependent Formate Dehydrogenase from Clostridium thermoaceticum, a tungsten-Selenium-Iron Protein," *J. Biol. Chem.* 258(3):1826-1832 (1983).
Yamano et al., "Construction of a brewer's yeast having a-acetolactate decarboxylase gene from acetobacter aceti sp. xylinum integrted in the genome," *J. Biotechnol.* 32:173-.
Yan et al., "Coenzyme A-acylating aldehyde dehydrogenase from Clostridium beijerinckii Nrrl B692," *Appl. Environ. Microbiol.* 56:2591-2599 (1990).
Yang et al, "Nucleotide sequence of the promoter and fadB gene of the fadBA operon and primary structure of the multifunctional fatty acid oxidation protein from *Escherichia coli*," *Biochem.* 30(27):6788-6795 (1991).
Yang et al., "Aspartate Dehydrogenase, a Novel Enzyme Identified from Structural and Functional Studies of TM1643," *J. Biol. Chem.* 278(10):8804-8808 (2003).

Yang et al., "Metabolic Flux Analysis of *Escherichia coli* Deficient in the Acetate Production Pathway and Expressing the Bacillus subtilis Acetolactate Synthase," *Metab. Eng.* 1(1):26-34 (1999).
Yang et al., "Nucleotide sequence of the fadA gene. Primary structure of 3-ketoacyl-coenzyme a thiolase from *Escherichia coli* and the structural organization of the fadAB operon," *J. Biol.Chem.* 266(24):16255 (1990).
Yang et al., "Nucleotide sequence of the fadA gene. Primary structure of 3-ketoacyl-coenzyme a thiolase from *Escherichia coli* and the structural organization of the fadAB operon," *J. Biol Chem.* 265(18):10424-10429 (1990).
Yang et al., "The effects of feed and intracellular pyruvate levels on the redistribution of metabolic fluxes in *Escherichia coli*," *Metab Eng.* 3(2):115-123 (2001).
Yang, "Location of the fadBA operon on the physical map of *Escherichia coli*," *J. Bacteriol.* 173(23):7405-7406 (1991).
Yang, et al., "Effect of inactivation of *nuo* and *ackA-pta* on redistribution of metabolic fluxes in *Escherichia coli*," *Biotechnol Bioeng.* 65(3):291-297 (1999).
Yang, et al., "Effect of Variation of Klebsiella pneumoniae Acetolactate Synthase Expression on Metabolic Flux Redistribution in *Escherichia coli*." *Biotechnol. Bioeng.* 69(2)150-159 (2000).
Yang, et al., "Redistribution of Metabolic Fluxes in *Escherichia coli* with Fermentative Lactate Dehydrogenase Overexpression and Deletion," *Metab. Eng.* 1:141-152 (1999).
Yanisch-Perron et al., "Improved M13 phage cloning vectors and host strains: nucleotide sequences of the M13mp18 and pUC19 vectors," *Gene* 33:103-19 (1985).
Yano et al., "Directed evolution of an aspartate aminotransferase with new substrate specificities," *Proc. Natl. Acad. Sci USA* 95:5511-5515 (1998).
Yarlett et al., "Trichomonas vaginalis: characterization of ornithine decarboxylase," *Biochem. J.* 293(Pt2):487-493 (1993).
Yeh a et al., "Evolutionarily Homologous a2132 Oligomeric Structures in β-Ketoadipate Sccinyl-CoA Transferases from Acinetobacter calcoaceticus and Pseudomonas putida, *J. Biol. Chem.* 256(4):1565-1569 (1981).
Ylianttila et al., "Crystal Structure of Yeasat Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of candida tropicalis (3R)-hydroxyacyl-CoA dehydrogenase," *Biochem. Biophys. Res. Commun.* 324:25-30 (2004).
Yoneyama et al., "Characteiization of a novel acid phosphatase from embryonic axes of kidney bean exhibiting vanadate-dependent chloroperoxidase active," *J. Biol. Chem.* 279(36)37477-37484 (2004).
Yoshida et al., "The Structures of L-Rhamnose Isomerase from Pseudomonas stutzeri in Complexes with L-Rhamnose and D-Allose Provide Insights into Broad Substrate Specificity," *J. Mol. Biol.* 365:1505-1516 (2007).
Yoshida et al., "Cloning and expression of the gene for hydroxypyruvate reductase (d-glycerate dehydrogenase from an obligate methylotroph Hyphomicrobium methylovorum GM2," *Eur. J. Biochem.* 223(3):727-732 (1994).
Yoshimoto, et al., "Isolation and Characterization of the ATF2 Gene Encoding Alcohol Acetyltransferase II in the Bottom Fermenting Yeast Saccharomyces pastorianus," *Yeast.* 15:409-417 (1999).
Yoshioka et al., "Ester formation by Alcohol Acetyltransferase from Brewers' Yeast," *Agric. Biol. Chem.* 45: 2183-2190 (1981).
Youngleson et al., "Homology between hydroxybutyryl and hydroxyacyl coenzyme a dehydrogenase enzymes from Clostridium acetobutylicum fermentation and vertebrate fatty acid (3-oxidation pathways," *J. Bacteriol.* 171(12):6800-6807 (1989).
Yun et al., "The genes for anabolic 2-oxoglutarate: ferredoxin oxidoreductse from hydrogenobacter thermophilus Tk-6," *Biochem. Biophys. Res. Commun.* 282(2):589-594.
Yun et al., "Enhancement of lactate and succinate formation in adhE or pta-ackA mutants of NADH dehydrogenase-deficient *Escherichia coli*," *J. Appl. Microbiol.* 99(6):1404-1412.

(56) References Cited

OTHER PUBLICATIONS

Yun et al., "w-Amino acid:pyruvate transaminase from Alcaligenes denitrificans Y2k-2: a new catalyst for kinetic resolution of (3-amino acids and amines," *Appl. Environ. Microbiol.* 70(4):2529-2534 (2004).

Zeiher and Randall, "Identification and characterization of Mitochondrial Acetyl-Coenzyme a Hydrolase from Pisum sativum L. Seedlings," *Plant. Physiol.* 94:20-27.

Zeikus et al., "Biotechnology of succinic acid production and markets for derived industrial products," *Appl. Microbiol. Biotechnol.* 51: 545-552 (1999).

Zelle et al., "Malic acid production by Saccharomyces cerevisiae: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the coenzyme 1312-dependent isobutyryl-CoA mutase from Streptomyces cinnamonensis," *J. Biol. Chem.* 273(11):6508-6517.

Zhang et al., "2-Oxoacid:Ferredoxin Oxidoreductase from the thermoacidophilic Archaeon, sulfolobus sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. USA* 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from Streptomyces coelicolor and Streptomyces avermitilis provide insights into the metabolism of small branched-chain fatty acids and marcrolide antibiotic production, "*Microbiol.* 145. (Pt 9):2323-2334 (1999).

Zhang et al., "Isolation and properties of a levo-lactonase from Fusarium proliferatum ECU2002: a robust biocatalyst for production of chiral lactones," *Appl Microbiol. Biotechnol* 75:1087-1094 (2007).

Zhang et al., "Molecular basis for the inhibition of the carboxyltransferase domain of acetyl-coenzyme-A carboxylase by haloxfop and dicofop," *Proc. Natl. Acad. Sci. USA.* 101:5910-5915 (2004).

Zhao et al., "A novel a-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by Rhizopus oryzae using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by Rhizopus oryzae ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. USA* 98:14802-14807 (2001).

Zhou et al., "Isolation, crystallization and preliminary X-ray analysis of a methanol-induced corrinoid protein from Moorella thermoacetica," *Acta Cryst* F61:537-540 (2005).

Zhu and Sadowski, "Cleavage-dependent ligation by the Flp recombinase. Characterization of a mutant Flp protein with an alteration in a catalytic amino acid," *J. Biol. Chem.* 270(39):23044-23054 (1995).

Zhuang, et al., "The YbgC protein encoded by the ybgC gene of the tol-pal gene cluster of Haemophilus influenzae catalyzes acyl-coenzyme a thioester hydrolysis," *FEBS Lett,* 516(1-3):161-163 (2002).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

\* cited by examiner

PRIMARY ALCOHOL PRODUCING ORGANISMS

This application is a continuation of U.S. patent application Ser. No. 16/233,018, filed Dec. 26, 2018, now abandoned, which is a continuation of U.S. patent application Ser. No. 14/987,489, filed Jan. 4, 2016, now U.S. Pat. No. 10,208,320, which is a continuation of U.S. patent application Ser. No. 13/168,833, filed Jun. 24, 2011, now U.S. Pat. No. 9,260,729, which is a continuation of U.S. patent application Ser. No. 12/398,996, filed Mar. 5, 2009, now U.S. Pat. No. 7,977,084, which claims priority under 35 U.S.C. § 119(e) to U.S. Provisional application Ser. No. 61/034,146, filed Mar. 5, 2008; U.S. Provisional application Ser. No. 61/090,171, filed Aug. 19, 2008; and U.S. Provisional application Ser. No. 61/110,500, filed Oct. 31, 2008, each of which the entire contents are incorporated herein by reference.

BACKGROUND OF THE INVENTION

This invention relates generally to biosynthetic processes and, more specifically to organisms having primary alcohol biosynthetic capability.

Primary alcohols are a product class of compounds having a variety of industrial applications which include a variety of biofuels and specialty chemicals. Primary alcohols also can be used to make a large number of additional industrial products including polymers and surfactants. For example, higher primary alcohols ($C_4$-$C_{20}$) and their ethoxylates are used as surfactants in many consumer detergents, cleaning products and personal care products worldwide such as laundry powders and liquids, dishwashing liquid and hard surface cleaners. They are also used in the manufacture of a variety of industrial chemicals and in lubricating oil additives. Long-chain primary alcohols, such as octanol and hexanol, have useful organoleptic properties and have long been employed as fragrance and flavor materials. Smaller chain ($C_4$-$C_8$) higher primary alcohols (e.g., butanol) are used as chemical intermediates for production of derivatives such as acrylates used in paints, coatings, and adhesives applications.

Primary alcohols are currently produced from, for example, hydrogenation of fatty acids, hydroformylation of terminal olefins, partial oxidation of n-paraffins and the Al-catalyzed polymerization of ethylene. Unfortunately, it is not commercially viable to produce primary alcohols directly from the oxidation of petroleum-based linear hydrocarbons (n-paraffins). This impracticality is because the oxidation of n-paraffins produces primarily secondary alcohols, tertiary alcohols or ketones, or a mixture of these compounds, but does not produce high yields of primary alcohols. Additionally, currently known methods for producing primary alcohols suffer from the disadvantage that they are restricted to feedstock which is relatively expensive, notably ethylene, which is produced via the thermal cracking of petroleum. In addition, current methods require several steps, and several catalyst types.

LCA production by microorganisms involves fatty acid synthesis followed by acyl-reduction steps. The universal fatty acid biosynthesis pathway found in most cells has been investigated for production of LCAs and other fatty acid derivatives. There is currently a great deal of improvement that can be achieved to provide more efficient biosynthesis pathways for LCA production with significantly higher theoretical product and energy yields.

Thus, there exists a need for alternative means for effectively producing commercial quantities of primary alcohols. The present invention satisfies this need and provides related advantages as well.

SUMMARY OF THE INVENTION

In some aspects, embodiments disclosed herein relate to a non-naturally occurring microbial organism having a microbial organism having a malonyl-CoA-independent fatty acid synthesis (FAS) pathway and an acyl-reduction pathway having at least one exogenous nucleic acid encoding a malonyl-CoA-independent FAS pathway enzyme expressed in sufficient amounts to produce a primary alcohol, the malonyl-CoA-independent FAS pathway having ketoacyl-CoA acyltransferase or ketoacyl-CoA thiolase, 3-hydroxyacyl-CoA dehydrogenase, enoyl-CoA hydratase and enoyl-CoA reductase, the acyl-reduction pathway having an acyl-CoA reductase and an alcohol dehydrogenase.

In other aspects, embodiments disclosed herein relate to a method for producing a primary alcohol. The method includes culturing a non-naturally occurring microbial organism have having a malonyl-CoA-independent fatty acid synthesis (FAS) pathway and an acyl-reduction pathway having at least one exogenous nucleic acid encoding a malonyl-CoA-independent FAS pathway enzyme expressed in sufficient amounts to produce a primary alcohol under substantially anaerobic conditions for a sufficient period of time to produce the primary alcohol, the malonyl-CoA-independent FAS pathway having ketoacyl-CoA acyltransferase or ketoacyl-CoA thiolase, 3-hydroxyacyl-CoA dehydrogenase, enoyl-CoA hydratase and enoyl-CoA reductase, the acyl-reduction pathway having an acyl-CoA reductase and an alcohol dehydrogenase.

In some aspects, embodiments disclosed herein relate to a non-naturally occurring microbial organism that includes one or more gene disruptions occurring in genes encoding enzymes that couple long-chain alcohol (LCA) production to growth of the non-naturally occurring microbial organism. In other embodiments, LCA production can be accomplished during non-growth phases using the same disruption strategies. The one or more gene disruptions reduce the activity of the enzyme, whereby the gene disruptions confer production of LCA onto the non-naturally occurring microbial organism.

In other aspects, embodiments disclosed herein relate to a method for producing LCA that includes culturing a non-naturally occurring microbial organism having one or more gene disruptions. The one or more gene disruptions occur in genes encoding an enzyme that confers LCA production in the organism.

In some aspects, embodiments disclosed herein relate to a non-naturally occurring eukaryotic organism, that includes one or more gene disruptions. The one or more gene disruptions occur in genes that encode enzymes such as a cytosolic pyruvate decarboxylase, a mitochondrial pyruvate dehydrogenase, a cytosolic ethanol-specific alcohol dehydrogenase and a mitochondrial ethanol-specific alcohol dehydrogenase. These disruptions confer production of long chain alcohols in the cytosol of the organism.

In some aspects, embodiments disclosed herein relate to a non-naturally occurring eukaryotic organism that includes one or more gene disruptions. The one or more gene disruptions occur in genes encoding enzymes such as a cytosolic pyruvate decarboxylase, a cytosolic ethanol-specific alcohol dehydrogenase, and a mitochondrial ethanol-specific alcohol dehydrogenase. These disruptions confer production of long chain alcohols in the mitochondrion of said organism.

In other aspects, embodiments disclosed herein relate to a method for producing long chain alcohols, including culturing these non-naturally occurring eukaryotic organisms.

DETAILED DESCRIPTION OF THE INVENTION

Figure 1:
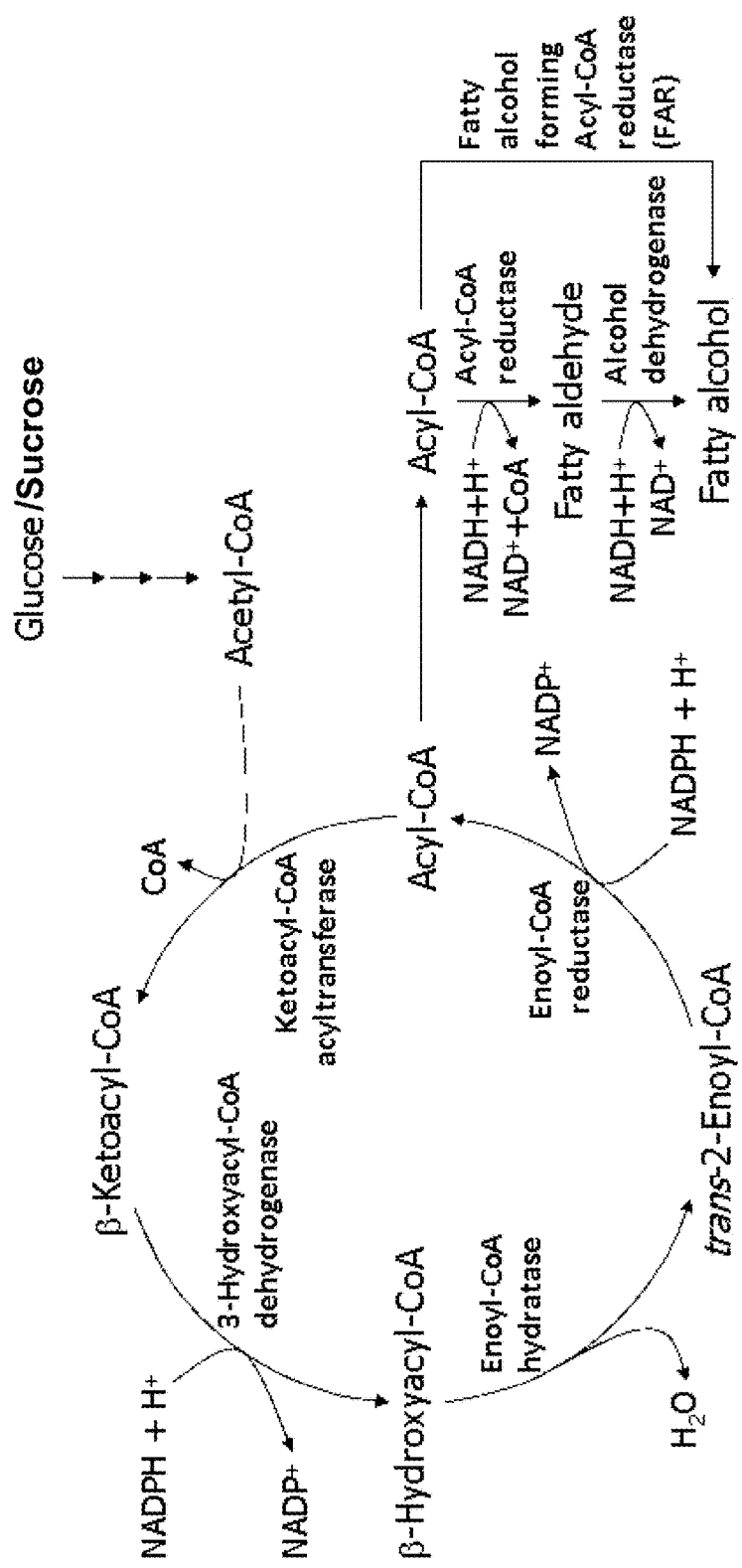
FIG. 1 shows the malonyl-CoA-independent fatty acid synthesis and reduction (MI-LCA) pathway to produce LCAs.

The invention is directed, in part, to recombinant microorganisms capable of synthesizing the primary alcohols using a malonyl-CoA-independent fatty acid synthesis and reduction pathway. The modified microorganisms of the invention also are capable of secreting the resultant primary alcohol into the culture media or fermentation broth for further manipulation or isolation. Recombinant microorganisms of the invention can be engineered to produce commercial quantities of a variety of different primary alcohols having different chain lengths between 4 (C4) and 24 (C24) or more carbon atoms. Production of primary alcohols through the modified pathways of the invention is particularly useful because it results in higher product and ATP yields than through naturally occurring biosynthetic pathways such as the well-documented malonyl-CoA dependent fatty acid synthesis pathway. Using acetyl-CoA as a C2 extension unit instead of malonyl-acyl carrier protein (malonyl-ACP) saves one ATP molecule per unit flux of acetyl-CoA entering the elongation cycle. The elongation cycle results in acyl-CoA instead of acyl-ACP, and precludes the need of the ATP-consuming acyl-CoA synthase reactions for the production of octanol and other primary alcohols. The primary alcohol producing organisms of the invention can additionally allow the use of biosynthetic processes to convert low cost renewable feedstock for the manufacture of chemical products.

In one specific embodiment, the invention utilizes a heterologous malonyl-CoA-independent fatty acid synthesis pathway coupled with an acyl-CoA reduction pathway to form primary alcohol species. The coupling of these two pathways will convert a carbon or energy source into acetyl-CoA, which is used as both primer and extension unit in biosynthetic elongation cycle. The elongation cycle includes ketoacyl-CoA thiolase (or ketoacyl-CoA acyltransferase), 3-hydroxyacyl-CoA dehydrogenase, enoyl-CoA hydratase and enoyl-CoA reductase. Each cycle results in the formation of an acyl-CoA extended by one $C_2$ unit compared to the acyl-CoA substrate entering the elongation cycle. Carbon chain-length of the primary alcohols can be controlled by chain-length specific enoyl-CoA reductase, ketoacyl-CoA thiolase and/or acyl-CoA reductase. Acyl-CoA products with desired chain-lengths are funneled into a reduction pathway and reduced through the combination of acyl-CoA reductase and alcohol dehydrogenase or the fatty alcohol forming acyl-CoA reductase to form desired primary alcohol. These reduction steps serve as another mechanism for control of chain length, for example, through the use of chain-length specific acyl-CoA reductases.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a malonyl-CoA-independent fatty acid biosynthetic pathway and enzymes within an acyl-reduction pathway.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "primary alcohol" is intended to mean an alcohol which has the hydroxyl radical connected to a primary carbon. The term includes an alcohol that possesses the group —$CH_2OH$ which can be oxidized so as to form a corresponding aldehyde and acid having the same number of carbon atoms. Alcohols include any of a series of hydroxyl compounds, the simplest of which are derived from saturated hydrocarbons, have the general formula $C_nH_{2n}+1OH$, and include ethanol and methanol. Exemplary primary alcohols include butanol, hexanol, heptanol, octanol, nananol, decanol, dodecanol, tetradecanol, and hexadecanol.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions, for example, in certain condensing enzymes, acts in acetyl or other acyl group transfer and in fatty acid synthesis and oxidation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acids that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

As used herein, the term "growth-coupled" when used in reference to the production of a biochemical is intended to mean that the biosynthesis of the referenced biochemical is a product produced during the growth phase of a microorganism. "Non-growth-coupled when used in reference to the production of a biochemical is intended to mean that the biosynthesis of the referenced biochemical is a product produced during a non-growth phase of a microorganism. Production of a biochemical product can be optionally obligatory to the growth of the organism.

As used herein, the term "metabolic modification" is intended to refer to a biochemical reaction that is altered from its naturally occurring state. Metabolic modifications can include, for example, elimination of a biochemical reaction activity by functional disruptions of one or more genes encoding an enzyme participating in the reaction. Sets of exemplary metabolic modifications are illustrated in Table 1. Individual reactions specified by such metabolic modifications and their corresponding gene complements are exemplified in Table 2 for *Escherichia coli*. Reactants and products utilized in these reactions are exemplified in Table 3.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation strategies that inactivate the encoded gene product. One particularly useful method of gene disruption is complete gene deletion because it reduces or eliminates the occurrence of genetic reversions in the non-naturally occurring microorganisms of the invention. The term "gene disruption" is also intended to mean a genetic alteration that lowers the activity of a given gene product relative to its activity in a wild-type organism. This attenuation of activity can be due to, for example, a deletion in a portion of the gene which results in a truncated gene product or any of various mutation strategies that render the encoded gene product less active than its natural form, replacement or mutation of the promoter sequence leading to lower or less efficient expression of the gene, culturing the organism under a condition where the gene is less highly expressed than under normal culture conditions, or introducing antisense RNA molecules that interact with complementary mRNA molecules of the gene and alter its expression.

As used herein, the term "stable" when used in reference to growth-coupled production of a biochemical product is intended to refer to microorganism that can be cultured for greater than five generations without loss of the coupling between growth and biochemical synthesis. Generally, stable growth-coupled biochemical production will be greater than 10 generations, particularly stable growth-coupled biochemical production will be greater than about 25 generations, and more particularly, stable growth-coupled biochemical production will be greater than 50 generations, including indefinitely. Stable growth-coupled production of a biochemical can be achieved, for example, by disruption of a gene encoding an enzyme catalyzing each reaction within a set of metabolic modifications. The stability of growth-coupled production of a biochemical can be enhanced through multiple disruptions, significantly reducing the likelihood of multiple compensatory reversions occurring for each disrupted activity.

Those skilled in the art will understand that the metabolic modifications exemplified herein are described with reference to *Escherichia coli* and *Saccharomyces cerevisae* genes and their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the *Escherichia coli* metabolic alterations exemplified herein can readily be applied to other species by incorporating the same or analogous gene disruptions in the other species. Such disruptions can include, for example, genetic alterations of species homologs, in general, and in particular, orthologs, paralogs or nonorthologous gene displacements.

As used herein, the term "confers production" refers not only to organisms that lack operational metabolic pathways for the production of LCAs, but also to organisms that may have some level of production of LCAs. Thus, an organism that already generates LCAs can benefit from improved production conferred onto the organism by the disruption of one or more genes.

As used herein, the term "eukaryotic organism" refers to any organism having a cell type having specialized organelles in the cytoplasm and a membrane-bound nucleus enclosing genetic material organized into chromosomes. The term is intended to encompass all eukaryotic organisms including eukaryotic microbial organisms such as yeast and fungi. The term also includes cell cultures of any eukaryotic species that can be cultured for the production of a biochemical where the eukaryotic species need not be a microbial organism. A "eukaryotic microbial organism," "microbial organism" or "microorganism" is intended to mean any eukaryotic organism that exists as a microscopic cell that is included within the domain of eukarya.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms of the invention having growth-coupled production of a biochemical, those skilled in the art will understand applying the teaching and guidance provided herein to a particular species that the identification of metabolic modifications should include identification and disruption of orthologs. To the extent that paralogs and/or nonorthologous gene displacements are present in the referenced microorganism that encode an enzyme catalyzing a similar or substantially similar metabolic reaction, those skilled in the art also can disrupt these evolutionarily related genes to ensure that any functional redundancy in enzymatic activities do not short circuit the designed metabolic modifications.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compared and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarly to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: -2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The non-naturally occurring microbial organisms of the invention can contain stable genetic alterations, which refer to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein are described with reference to *Euglena gracilis, E. coli* and *S. cerevisiae* genes and their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

In some embodiments, the invention provides a non-naturally occurring microbial organism having a malonyl-CoA-independent fatty acid synthesis (FAS) pathway and an acyl-reduction pathway having at least one exogenous nucleic acid encoding a malonyl-CoA-independent FAS pathway enzyme expressed in sufficient amounts to produce a primary alcohol, said malonyl-CoA-independent FAS pathway comprising ketoacyl-CoA acyltransferase or ketoacyl-CoA thiolase, 3-hydroxyacyl-CoA dehydrogenase, enoyl-CoA hydratase and enoyl-CoA reductase, said acyl-reduction pathway comprising an acyl-CoA reductase and an alcohol dehydrogenase.

Malonyl-CoA-independent fatty acid synthesis is a metabolic process used by photosynthetic flagellate such as *Euglena gracilis* (Inui et al., *Euro. J. Biochem.* 96:931-34 (1984). These single cell organisms exhibit both algae and protozoan characteristics and, depending on conditions, can utilize either light energy (photosynthesis) or chemical energy (eating) for biochemical processes. Under anaerobic conditions, *E. gracilis* converts paramylon, the reserve beta-1,2-glucan polysaccharide, into wax ester with concomitant generation of ATP, a phenomenon named wax ester fermentation (Inui et al., supra, 1982; Inui et al., Agricultural and Biological Chemistry 47:2669-2671 (1983)). Fatty acid synthesis through the malonyl-CoA-independent pathway results in a net gain of ATP, whereas other fatty acid synthesis systems can not support the net gain of ATP. ATP also can be produced under aerobic conditions (Inui et al., *Archives Biochemistry and Biophysics* 237:423-29 (1985)).

In the absence of oxygen, acetyl-CoA is generated from pyruvate via an oxygen-sensitive pyruvate:NADP+oxidoreductase (Inui et al., supra, 1984; Inui et al., supra, 1985; Inui et al., *Archives of Biochemistry and Biophysics* 280: 292-98 (1990); Inui et al., *Journal of Biological Chemistry* 262:9130-35 (1987)), and serves as the terminal electron acceptor of glucose oxidation via the malonyl-CoA-independent fatty acid synthesis to form wax ester (Inui et al., supra, (1985)). *E. gracilis* contains five different systems of fatty acid synthesis, including four fatty acid synthesis systems located in different compartments, and the mitochondrial malonyl-CoA-independent FAS system involved in anaerobic wax ester fermentation (Hoffmeister et al., *J. of Biological Chemistry* 280:4329-38 (2005)). The malonyl-CoA-independent FAS system has been shown to produce C8-C18 fatty acids. A fatty acid is reduced to alcohol, esterified with another fatty acid, and deposited in the cytosol as waxes (Inui et al., *Febs Letters* 150:89-93 (1982); Inui et al., *European Journal of Biochemistry* 142:121-126 (1984)). The wax can constitute approximately 50% of the total lipid in dark grown cells (Rosenberg, A., *Biochemistry* 2:1148 (1963)). A particularly useful embodiment of the invention harness the malonyl-CoA-independent fatty acid synthesis (FAS) system under anaerobic conditions to produce large quantities of alcohols using the modified biosynthetic pathways described herein.

The malonyl-CoA-independent fatty acid synthesis pathway is similar to the reversal of fatty acid oxidation and is referred as the fatty acid synthesis in mitochondria or acyl-carrier protein (ACP)-independent fatty acid synthesis as it is known in the art. Compared to the malonyl-CoA-dependent fatty acid synthesis (a.k.a. ACP dependent fatty acid synthesis; Smith et al., *Progress in Lipid Research* 42:289-317 (2003); White et al., *Annual Review of Biochemistry* 74:791-831 (2005)), there are several differences. First, acetyl-CoA is used as the extension unit instead of malonyl-ACP. Utilization of acetyl-CoA as elongation substrate in the malonyl-CoA-independent pathway eliminates the need for acetyl-CoA carboxylase complex (ACC), which converts acetyl-CoA to malonyl-CoA, and thus conserves one ATP molecule per unit flux of acetyl-CoA entering the elongation cycle. Second, all of the intermediates in the elongation cycle are attached to CoA instead of ACP. The elongation cycle can include (i) ketoacyl-CoA acyltransferase (or ketoacyl-CoA thiolase, EC 2.3.1.16), (ii) 3-hydroxyacyl-CoA dehydrogenase (EC 1.1.1.35 and 1.1.1.211), (iii) enoyl-CoA hydratase (EC 4.2.1.17 and 4.2.1.74), and (iv) enoyl-CoA reductase (EC 1.3.1.44 and 1.3.1.38). Third, the product from the elongation cycle is acyl-CoA, which can be utilized directly by acyl-CoA reductase, followed by a dehydrogenase for conversion to alcohol, or by fatty acid forming acyl-CoA reductase (FAR), which converts acyl-CoA directly to alcohol. Therefore, thioesterase and acyl-CoA synthase are not required for the production of primary alcohols, as is the case with the malonyl-CoA-dependent pathways.

For example, the microorganisms of the invention utilize the malonyl-CoA-independent fatty acid synthesis pathway coupled with the reduction of the fatty acid to form primary alcohol as illustrated in FIG. 1. The microorganism can additionally be modified to convert, for example, renewable feedstock to acetyl-CoA. In the bioengineered pathways of the invention, acetyl-CoA can be used as both a primer and an extension unit in the elongation cycle described above. At the end of each elongation cycle, an acyl-CoA is formed that is one C2 unit longer than the acyl-CoA entering the elongation cycle. Coupling the above synthesis pathway to a reduction pathway yields the primary alcohol products of the invention. Particularly useful is the coupling of acyl-CoA having a desired chain-length to a reduction pathway that uses the combination of chain-length specific acyl-CoA reductase (EC 1.2.1.50) and alcohol dehydrogenase (1.1.1.1) or the fatty alcohol forming acyl-CoA reductase (FAR, EC 1.1.1) to form desired primary alcohol. Carbon chain-length of the primary alcohols can be controlled by chain-length specific enoyl-CoA reductase, ketoacyl-CoA thiolase and/or acyl-CoA reductase.

The microorganisms of the invention having the coupled biosynthetic pathways described above can produce primary alcohols at very high levels. For example, the maximum theoretical yield for octanol using the malonyl-CoA-independent fatty acid biosynthetic pathway and the associated energetics were calculated by adding the malonyl-CoA-independent fatty acid synthesis, acyl-CoA reductase and alcohol dehydrogenase reactions to a predictive $E.$ $coli$ metabolic stoichiometric network using the in silico metabolic modeling system known in the art as SimPheny™ (see, for example, U.S. patent application Ser. No. 10/173,547, filed Jun. 14, 2002, and in International Patent Application No. PCT/US03/18838, filed Jun. 13, 2003). The model assumes that the secretion of octanol does not require energy. Table 4 shows the maximum theoretical yield for octanol under both aerobic and anaerobic conditions. The malonyl-CoA-independent fatty acid biosynthetic pathway is much more energy-efficient than the malonyl-CoA-dependent fatty acid synthesis pathways, and allows for a maximum theoretical yield of 0.5 mole octanol/mole of glucose and maximum ATP yield of 2.125 mole/mole of glucose under both aerobic and anaerobic conditions.

one, including all, nucleic acids encoding some or all of the enzymes for the complete pathway of malonyl-CoA independent FAS pathway enzymes. Some or all of the enzymes for acyl-reduction also can be exogenously expressed. Exogenous expression should be at levels sufficient to produce metabolically utilizable gene product and result in the production of a target primary alcohol or set of alcohols.

The biochemical reactions for formation of primary alcohols from a carbon or other energy source through a malonyl-CoA independent FAS pathway is shown in FIG. 1. The malonyl-CoA independent FAS pathway produces acyl-CoA. Concomitant utilization of this intermediate product to produce target primary alcohols by an acyl-reduction pathway also is shown in FIG. 1.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

Microbial organisms other than $Euglena$ $gracilis$ generally lack the capacity to synthesize acyl-CoA through a malonyl-CoA independent FAS pathway. Moreover, organisms having all of the requisite metabolic enzymatic capabilities are not known to produce acyl-CoA from the enzymes described and biochemical pathways exemplified herein. Rather, microorganisms having the enzymatic con-

TABLE 4

Comparison of the maximum theoretical yield of octanol using (1) the malonyl-CoA-independent fatty acid synthesis and acyl-reduction pathway and (2) the ACP-dependent fatty acid synthesis and pathway.

|  | Malonyl-CoA-independent fatty acid biosynthetic and reduction pathway | | Typical fatty acid biosynthetic and reduction pathway | |
| --- | --- | --- | --- | --- |
|  | Anaerobic | Aerobic | Anaerobic | Aerobic |
| Octanol Yield (mole/mole glucose) | 0.5 | 0.5 | 0.375 | 0.48 |
| Max ATP Yield @ max octanol yield (mole/mole glucose) | 2.125 | 2.125 | 0 | 0 |

A non-naturally occurring microbial organism of the invention employs combinations of metabolic reactions for biosynthetically producing a target primary alcohol or a target mixture of primary alcohols of the invention. The combination of metabolic reactions can be engineered in a variety of different alternatives to achieve exogenous expression of a malonyl-CoA-independent FAS pathway in sufficient amounts to produce a primary alcohol. The non-naturally occurring microbial organisms will express at least one exogenous nucleic acid encoding a malonyl-CoA-independent FAS pathway enzyme. In certain embodiments, the non-naturally occurring microbial organisms of the invention will be engineered to exogenously express more than stituents of malonyl-CoA independent FAS pathway operate to degrade short, medium, and long chain fatty-acyl-CoA compounds to acetyl-CoA. $E.$ $gracilis$, having a malonyl-CoA independent FAS pathway, utilizes this pathway to produce acylglycerols, trihydric sugar alcohols, phospholipids, wax esters and/or fatty acids. In contrast, the non-naturally occurring microbial organisms of the invention generate acyl-CoA as a product of the malonyl-CoA independent FAS pathway and funnel this product into an acyl-reduction pathway via favorable thermodynamic characteristics. Product biosynthesis of using the non-naturally occurring organisms of the invention is not only particularly useful for the production of primary alcohols, it also allows for the further biosynthesis of compounds using acyl-CoA and/or primary alcohols as an intermediate reactant.

The non-naturally occurring primary alcohol-producing microbial organisms of the invention are generated by ensuring that a host microbial organism includes functional capabilities for the complete biochemical synthesis of a malonyl-CoA independent fatty acid biosynthetic pathway and for an acyl-reduction pathway of the invention. Ensuring complete functional capabilities for both pathways will confer primary alcohol biosynthesis capability onto the host microbial organism. The enzymes participating in a malonyl-CoA independent FAS pathway include ketoacyl-CoA acyltransferase or ketoacyl-CoA thiolase, 3-hydroxyacyl-CoA dehydrogenase, enoyl-CoA hydratase and enoyl-CoA reductase. The enzymes participating in an acyl-reduction pathway include an acyl-CoA reductase and an alcohol dehydrogenase or an enzyme having dual reductase and dehydrogenase activity.

The non-naturally occurring microbial organisms of the invention can be produced by introducing expressible nucleic acids encoding one or more of the enzymes participating in the malonyl-CoA independent FAS and/or acyl-reduction pathways. Depending on the host microbial organism chosen for biosynthesis, nucleic acids for some or all of these biosynthetic pathways can be expressed. For example, if a chosen host is deficient in all of the enzymes in the malonyl-CoA independent FAS pathway, then expressible nucleic acids for each of the four enzymes ketoacyl-CoA acyltransferase or ketoacyl-CoA thiolase, 3-hydroxyacyl-CoA dehydrogenase, enoyl-CoA hydratase and enoyl-CoA reductase are introduced into the host for subsequent exogenous expression. Alternatively, for example, if the chosen host is deficient less than all four of the above enzymes, then all that is needed is to express nucleic acids encoding the deficient enzymes. For example, if a host is deficient in 3-hydroxyacyl-CoA dehydrogenase and enoyl-CoA hydratase a functionally complete malonyl-CoA independent FAS pathway can be engineererd by introduction of nucleic acids encoding these two enzymes.

In like fashion, where endogenous host biosynthetic machinery is complete for an acyl-reduction pathway, then genetic modification is unnecessary. However, if host capabilities are deficient in either or both of the acyl-CoA reductase and/or alcohol dehydrogenase activities, then introduction of the deficient activity by expression of an exogenous encoding nucleic acid is needed. Accordingly, depending on the malonyl-CoA independent FAS and acyl-reduction pathway constituents of a selected host microbial organism, the non-naturally occurring microbial organisms of the invention will include at least one exogenously expressed malonyl-CoA independent FAS pathway-encoding nucleic acid and up to all six malonyl-CoA independent FAS and acyl-reduction pathway encoding nucleic acids.

Given the teachings and guidance provided herein, those skilled in the art will understand that the number of encoding nucleic acids to introduce in an expressible form will parallel the malonyl-CoA independent FAS and acyl-reduction pathway deficiencies of the selected host microbial organism. Therefore, a non-naturally occurring microbial organism of the invention can have one, two, three, four, five or six encoding nucleic acids encoding the above enzymes constituting the malonyl-CoA independent FAS pathway, an acyl-reduction pathway or both the malonyl-CoA independent FAS and acyl-reduction biosynthetic pathways. In some embodiments, the non-naturally occurring microbial organisms also can include other genetic modifications that facilitate or optimize acyl-CoA and/or primary alcohol biosynthesis or that confer other useful functions onto the host microbial organism. One such other functionality can include, for example, augmentation of the synthesis of one or more of the malonyl-CoA independent FAS pathway precursors such as acetyl-CoA, β-ketoacyl-CoA, β-hydroxyacyl-CoA, trans-2-enoyl-CoA and/or fatty aldehyde.

In some embodiments, a non-naturally occurring microbial organism of the invention is generated from a host that contains the enzymatic capability to synthesize acyl-CoA through a malonyl-CoA independent FAS pathway, or having the capability to catalyze one or more of the enzymatic steps within the malonyl-CoA independent FAS and/or acyl-reduction pathways. In these specific embodiments it can be useful to increase the synthesis or accumulation of a malonyl-CoA independent FAS pathway product or an acyl-reduction pathway product to, for example, efficiently drive malonyl-CoA independent FAS and/or acyl-reduction pathway reactions toward primary alcohol production. Increased synthesis or accumulation can be accomplished by, for example, overexpression of nucleic acids encoding one or more of the above-described malonyl-CoA independent FAS and/or acyl-reduction pathway enzymes. Over expression of the desired pathway enzyme or enzymes can occur, for example, through exogenous expression of the endogenous gene or genes, or through exogenous expression of a heterologous gene or genes. Therefore, naturally occurring organisms can readily be generated to be non-naturally primary alcohol producing microbial organisms of the invention through overexpression of one, two, three, four, five or all six nucleic acids encoding a malonyl-CoA independent FAS and/or a acyl-reduction pathway enzymes. In addition, a non-naturally occurring organism can be generated by mutagenesis of an endogenous gene that results in an increase in activity of an enzyme in the malonyl-CoA independent FAS and/or acyl-reduction biosynthetic pathways.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. For example, activation of fadB, an *E. coli* gene having malonyl-CoA independent FAS activity corresponding to 3-hydroxyacyl-CoA dehydrogenase and enoyl-CoA hydratase activities can be accomplished by genetically knocking out a negative regulator, fadR, and co-expressing a heterologous ketothiolase (phaA from *Ralstonia eutropha*; Sato et al., *Journal of Bioscience and Bioengineering* 103: 38-44 (2007)). Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

Additionally, for example, if an endogenous enzyme or enzymes operate in a reverse direction to the desired malonyl-CoA independent FAS pathway, genetic modifications can be made to attenuate or eliminate such activities. For example, within the malonyl-CoA independent FAS pathway, the ketothiolase, dehydrogenase, and enoyl-CoA hydratase steps are reversible whereas the enoyl-CoA reductase step is primarily oxidative under physiological conditions (Hoffmeister et al., *Journal of Biological Chemistry* 280:4329-4338 (2005); Campbell, J. W. and J. E. Cronan, Jr., *J Bacteriol.* 184:3759-3764 (2002)). To accomplish reduction of a 2-enoyl-CoA intermediate a genetic modification can be introduced to attenuate or eliminate the reverse oxidative reaction.

Sources of encoding nucleic acids for a malonyl-CoA independent FAS and/or acyl-reduction pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. For example, the microbial organisms having primary alcohol biosynthetic production are exemplified herein with reference to an *E. coli* host. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite malonyl-CoA independent FAS and/or acyl-reduction biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of primary alcohols of the invention described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative malonyl-CoA independent FAS constituent enzyme or pathway exists in an unrelated species, primary alcohol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual genes usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize the primary alcohol products of the invention.

Encoding nucleic acids and species that can be used as sources for conferring malonyl-CoA independent FAS and/or acyl-reduction pathway capability onto a host microbial organism are exemplified further below. In one exemplary embodiment, the genes fadA and fadB encode a multienzyme complex that exhibits three constituent activities of the malonyl-CoA independent FAS pathway, namely, ketoacyl-CoA thiolase, 3-hydroxyacyl-CoA dehydrogenase, and enoyl-CoA hydratase activities (Nakahigashi, K. and H. Inokuchi, Nucleic Acids Research 18:4937 (1990); Yang et al., *Journal of Bacteriology* 173:7405-7406 (1991); Yang et al, Journal of Biological Chemistry 265:10424-10429 (1990); Yang et al., *Biochemistry* 30:6788-6795 (1990)). The fadI and fadJ genes encode similar activities which can substitute for the above malonyl-CoA independent FAS conferring genes fadA and fadB. These genes are naturally expressed under anaerobic conditions (Campbell and Cronan, supra, (2002)). The nucleic acid sequences for each of the above fad genes are well known in the art and can be accessed in the public databases such as Genbank using the following accession numbers.

| fadA | YP_026272.1 | *Escherichia coli* |
| fadB | NP_418288.1 | *Escherichia coli* |
| fadI | NP_416844.1 | *Escherichia coli* |
| fadJ | NP_416843.1 | *Escherichia coli* |
| fadR | NP_415705.1 | *Escherichia coli* |

Other exemplary genes for the ketothiolase step include atoB which can catalyze the reversible condensation of 2 acetyl-CoA molecules (Sato et al., supra, 2007), and its homolog yqeF. Non-*E. coli* genes that can be used include phaA from *R. eutropha* (Jenkins, L. S. and W. D. Nunn. *Journal of Bacteriology* 169:42-52 (1987)), and the two ketothiolases, thiA and thiB, from *Clostridium acetobutylicum* (Winzer et al., *Journal of Molecular Microbiology and Biotechnology* 2:531-541 (2000)). The sequences for these genes can be found at the following Genbank accession numbers:

| atoB | NP_416728.1 | *Escherichia coli* |
| yqeF | NP_417321.2 | *Escherichia coli* |
| phaA | YP_725941 | *Ralstonia eutropha* |
| thiA | NP_349476.1 | *Clostridium acetobutylicum* |
| thiB | NP_149242.1 | *Clostridium acetobutylicum* |

An exemplary gene from *E. coli* which can be used for conferring 3-hydroxyacyl-CoA dehydrogenase transformation activity is paaH (Ismail et al., *European Journal of Biochemistry* 270:3047-3054 (2003)). Non-*E. coli* genes applicable for conferring this activity include AAO72312.1 from *E. gracilis* (Winkler et al., *Plant Physiology* 131:753-762 (2003)), paaC from *Pseudomonas putida* (Olivera et al., PNAS USA 95:6419-6424 (1998)), paaC from *Pseudomonas fluorescens* (Di Gennaro et al., *Archives of Microbiology* 188:117-125 (2007)), and hbd from *C. acetobutylicum* (Atsumi et al., *Metabolic Engineering* (2007) and Boynton et al., *Journal of Bacteriology* 178:3015-3024 (1996)). The sequences for each of these exemplary genes can be found at the following Genbank accession numbers:

| paaH | NP_415913.1 | *Escherichia coli* |
| | AAO72312.1 | *Euglena gracilis* |
| paaC | NP_745425.1 | *Pseudomonas putida* |
| paaC | ABF82235.1 | *Pseudomonas fluorescens* |
| hbd | NP_349314.1 | *Clostridium acetobutylicum* |

Exemplary genes encoding the enoyl-CoA hydratase step include, for example, maoC (Park and Lee, Journal Bacteriology 185:5391-5397 (2003)), paaF (Ismail et al., *European Journal of Biochemistry* 270:3047-3054 (2003); Park and Lee, *Appl. Biochem. Biotechnol.* 113-116:335-346 (2004) and Park and Yup, *Biotechnol. Bioeng.* 86:681-686 (2004)), and paaG (Ismail et al., *European Journal of Biochemistry* 270:3047-3054 (2003); Park and Lee, *Appl. Biochem. Biotechnol.* 113-116:335-346 (2004) and Park and Yup, *Biotechnol. Bioeng.* 86:681-686 (2004)). Other genes which can be used to produce the gene product catalyzing this step, for example, paaA, paaB, and paaN from *P. putida* (Olivera et al., *PNAS USA* 95:6419-6424 (1998)) and *P. fluorescens* (Di Gennaro et al., *Archives of Microbiology* 188:117-125 (2007)). The gene product of crt from *C. acetobutylicum* also can be used (Atsumi et al., *Metabolic Engineering* (2007) and Boynton et al., *Journal of Bacteriology* 178: 3015-3024 (1996. The sequences for each of these exemplary genes can be found at the following Genbank accession numbers:

| maoC | NP_415905.1 | *Escherichia coli* |
|---|---|---|
| paaF | NP_415911.1 | *Escherichia coli* |
| paaG | NP_415912.1 | *Escherichia coli* |
| paaA | NP_745427.1 | *Pseudomonas putida* |
| paaA | ABF82233.1 | *Pseudomonas fluorescens* |
| paaB | NP_745426.1 | *Pseudomonas putida* |
| paaB | ABF82234.1 | *Pseudomonas fluorescens* |
| paaN | NP_745413.1 | *Pseudomonas putida* |
| paaN | ABF82246.1 | *Pseudomonas fluorescens* |
| crt | NP_349318.1 | *Clostridium acetobutylicum* |

An exemplary gene which can be introduced into a non-naturally occurring microbial organism of the invention to confer enoyl-CoA reductase activity is the mitochondrial enoyl-CoA reductase from *E. gracilis* Hoffmeister et al., supra (2005)). A construct derived from this sequence following the removal of its mitochondrial targeting leader sequence has been cloned and expressed in *E. coli*. This approach for heterologous expression of membrane targeted polypeptides in a soluble form is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents also can be employed to confer enoyl-CoA reductase activity (Tucci and Martin, *FEBS Letters* 581:1561-1566 (2007)). Butyryl-CoA dehydrogenase, encoded by bcd from *C. acetobutylicum*, is a further exemplary enzyme that can be used to confer enoyl-CoA reductase activity onto a host microbial organism of the invention (Atsumi et al., *Metabolic Engineering* (2007) and Boynton et al., *Journal of Bacteriology* 178: 3015-3024 (1996)). Alternatively, *E. coli* genes exhibiting this activity can be obtained using methods well known in the art (see, for example, Mizugaki et al., *Chemical & Pharmaceutical Bulletin* 30:206-213 (1982) and Nishimaki et al., *Journal of Biochemistry* 95:1315-1321 (1984)). The sequences for each of the above exemplary genes can be found at the following Genbank accession numbers:

| TER | Q5EU90.1 | *Euglena gracilis* |
|---|---|---|
| TDE0597 | NP_971211.1 | *Treponema denticola* |
| bcd | NP_349317.1 | *Clostridium acetobutylicum* |

At least three mitochondrial enoyl-CoA reductase enzymes exist in *E. gracilis* that similarly are applicable for use in the invention. Each enoyl-CoA reductase enzyme exhibits a unique chain length preference (Inui et al., *European Journal of Biochemistry* 142:121-126 (1984)), which is particularly useful for dictating the chain length of the desired primary alcohol products of the invention. EST's ELL00002199, ELL00002335, and ELL00002648, which are all annotated as mitochondrial trans-2-enoyl-CoA reductases, can be used to isolate these additional enoyl-CoA reductase genes as described further below.

Those skilled in the art also can obtain nucleic acids encoding any or all of the malonyl-CoA independent FAS pathway or acyl-reduction pathway enzymes by cloning using known sequences from available sources. For example, any or all of the encoding nucleic acids for the malonyl-CoA independent FAS pathway can be readily obtained using methods well known in the art from *E. gracilis* as this pathway has been well characterized in this organism. *E. gracilis* encoding nucleic acids can be isolated from, for example, an *E. gracilis* cDNA library using probes of known sequence. The probes can be designed with whole or partial DNA sequences from the following EST sequences from the publically available sequence database TBestDB (at URL bestdb.bcm.umontreal.ca). The nucleic acids generated from this process can be inserted into an appropriate expression vector and transformed into *E. coli* or other microorganisms to generate primary alcohol production organisms of the invention.

ketoacyl-CoA acyltransferase (or ketoacyl-CoA thiolase)
ELL00002550
ELL00002493
ELL00000789
3-hydroxyacyl-CoA dehydrogenase
ELL00000206
ELL00002419
ELL00006286
ELL00006656
enoyl-CoA hydratase
ELL00005926
ELL00001952
ELL00002235
ELL00006206
enoyl-CoA reductase
ELL00002199
ELL00002335
ELL00002648

Alternatively, the above EST sequences can be used to identify homologue polypeptides in GenBank through BLAST search. The resulting homologue polypeptides and their corresponding gene sequences provide additional encoding nucleic acids for transformation into *E. coli* or other microorganisms to generate the primary alcohol producing organisms of the invention. Listed below are exemplary homologue polypeptide and their gene accession numbers in GenBank which are applicable for use in the non-naturally occurring organisms of the invention.

| ketoacyl-CoA acyltransferase (or ketoacyl-CoA thiolase) | |
|---|---|
| YP_001530041 | *Desulfococcus oleovorans* Hxd3 |
| ZP_02133627 | *Desulfatibacillum alkenivorans* AK-01 |
| ZP_01860900 | *Bacillus* sp. SG-1 |
| YP_001511817 | *Alkaliphilus oremlandii* OhILAs |
| NP_781017 | *Clostridium tetani* E88 |
| YP_001646648 | *Bacillus weihenstephanensis* KBAB4 |
| YP_001322360 | *Alkaliphilus metalliredigens* QYMF |
| YP_001397054 | *Clostridium kluyveri* DSM 555 |
| NP_070026 | *Archaeoglobus fulgidus* DSM 4304 |
| YP_001585327 | *Burkholderia multivorans* ATCC 17616 |
| 3-hydroxyacyl-CoA dehydrogenase | |
| AAO72312 | *Euglena gracilis* |
| XP_001655993 | *Aedes aegypti* |
| NP_001011073 | *Xenopus tropicalis* |
| NP_001003515 | *Danio rerio* |
| XP_973042 | *Tribolium castaneum* |
| XP_001638329 | *Nematostella vectensis* |
| CAG11476 | *Tetraodon nigroviridis* |
| XP_787188 | *Strongylocentrotus purpuratus* |

-continued

| | | |
|---|---|---|
| XP_001749481 | *Monosiga brevicollis* MX1 | |
| NP_509584 | *Caenorhabditis elegans* | |
| XP_572875 | *Cryptococcus neoformans* var enoyl-CoA hydratase | |
| XP_844077 | *Trypanosoma brucei* | |
| XP_802711 | *Trypanosoma cruzi* strain CL Brener | |
| XP_806421 | *Trypanosoma cruzi* strain CL Brener. | |
| YP_001669856 | *Pseudomonas putida* GB-1 | |
| YP_641317 | *Mycobacterium* sp. MCS | |
| YP_959434 | *Marinobacter aquaeolei* VT8 | |
| ABK24445 | *Picea sitchensis* | |
| XP_640315 | *Dictyostelium discoideum* | |
| YP 633978 | *Myxococcus xanthus* DK 1622 | |
| YP_467905 | *Rhizobium etli* CFN 42 | |
| YP_419997 | *Magnetospirillum magneticum* AMB-1 | |
| YP_001172441 | *Pseudomonas stutzeri* A1501 enoyl-CoA reductase. | |
| XP_642118 | *Dictyostelium discoideum* AX4 | |
| XP_001639469 | *Nematostella vectensis* | |
| XP_001648220 | *Aedes aegypti* | |
| XP_974428 | *Tribolium castaneum* | |
| XP_535334 | *Canis lupus familiaris* (dog) | |
| NP_001016371 | *Xenopus tropicalis* | |
| XP_320682 | *Anopheles gambiae* str. PEST | |
| ZP_01645699 | *Stenotrophomonas maltophilia* | |
| XP_001679449 | *Caenorhabditis briggsae* AF16 | |
| ZP_01443601 | *Roseovarius* sp. HTCC2601 | |
| XP_395130 | *Apis mellifera* | |
| XP_001113746 | *Macaca mulatto* | |
| ZP_01485509 | *Vibrio cholerae* V51 | |
| ZP_02012479 | *Opitutaceae bacterium* TAV2 | |
| ZP_01163033 | *Photobacterium* sp. SKA34 | |
| YP_267463 | *Colwellia psychrerythraea* 34H | |
| ZP_01114282 | *Reinekea* sp. MED297 | |
| ZP_01732824 | *Flavobacteria bacterium* BAL38 | |

As described previously, after the malonyl-CoA independent elongation cycle, the resulting acyl-CoA can be reduced to produce a primary alcohol by either a single enzyme or pair of enzymes that exhibit acyl-CoA reductase and alcohol dehydrogenase activities. Exemplary genes that encode enzymes for catalyzing the reduction of an acyl-CoA to its corresponding aldehyde include the *Acinetobacter calcoaceticus* acr1 encoding a fatty acyl-CoA reductase (Reiser and Somerville, *Journal of Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and the sucD gene from *Clostridium kluyveri* (Sohling and Gottschalk, Journal Bacteriology 178:871-880 (1996)).

| acr1 | YP_047869.1 | *Acinetobacter calcoaceticus* |
|---|---|---|
| | AAC45217 | *Acinetobacter baylyi* |
| | BAB85476.1 | *Acinetobacter* sp. Strain M-1 |
| sucD | P38947.1 | *Clostridium kluyveri* |

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), ADH2 from *Saccharomyces cerevisiae* (Atsumi et al., *Nature* 451:86-89 (2008)), and yqhD from *E. coli* which has preference for molecules longer than $C_3$ (Sulzenbacher et al., *Journal of Molecular Biology* 342:489-502 (2004)).

| alrA | BAB12273.1 | *Acinetobacter* sp. Strain M-1 |
|---|---|---|
| ADH2 | NP_014032.1 | *Saccharymyces cerevisiae* |
| yqhD | NP_417484.1 | *Escherichia coli* |

Alternatively, the fatty acyl-CoA can be reduced in one step by a fatty alcohol forming acyl-CoA reductase or any other enzyme with dual acyl-CoA reductase and alcohol dehydrogenase activity. For example, the jojoba (*Simmondsia chinensis*) FAR encodes an alcohol-forming fatty acyl-CoA reductase and its overexpression in *E. coli* resulted in FAR activity and the accumulation of fatty alcohol (Metz et al., *Plant Physiology* 122:635-644 (2000)). The reductase with narrow substrate chain-length specificities will also function as additional control for product chain-length. Additional gene candidates include the *E. coli* adhE (Kessler et al., *FEBS Letters* 281:59-63 (2000)) and *C. acetobutylicum* bdh I and bdh II (Walter et al., *Journal of Bacteriology* 174:7149-7158 (1992)) which can reduce acetyl-CoA and butyryl-CoA to ethanol and butanol, respectively.

| FAR | AAD38039.1 | *Simmondsia chinensis* |
|---|---|---|
| adhE | NP_415757.1 | *Escherichia coli* |
| bdh I | NP_349892.1 | *Clostridium acetobutylicum* |
| bdh II | NP_349891.1 | *Clostridium acetobutylicum* |

In addition, the *E. gracilis* nucleic acid sequences encoding enzymes for the reduction step can be obtained and transformed into a host as described previously for the malonyl-CoA independent FAS pathway encoding nucleic acids. Isolated from an *E. gracilis* cDNA library using probes, designed with whole or partial DNA sequences from the following EST sequences from TBestDB (at URL bestdb.bcm.umontreal.ca) can be performed as described previously.

aldehyde dehydrogenase
ELL00002572
ELL00002581
ELL00000108

In addition to the above exemplary encoding nucleic acids, nucleic acids other than those within the malonyl-CoA independent FAS and/or acyl-reduction pathways of the invention also can be introduced into a host organism for further production of primary alcohols. For example, the *Ralstonia eutropha* BktB and PhbB genes catalyze the condensation of butyryl-CoA and acetyl-CoA to form β-keto-hexanoyl-CoA and the reduction of β-keto-hexanoyl-CoA to 3-hydroxy-hexanoyl-CoA (Fukui et al., *Biomacromolecules* 3:618-624 (2002)). To improve the production of primary alcohols, exogenous DNA sequences encoding for these specific enzymes can be expressed in the production host of interest. Furthermore, the above described enzymes can be subjected to directed evolution to generate improved versions of these enzymes with high activity and high substrate specificity. A similar approach also can be utilized with any or all other enzymatic steps in the primary alcohol producing pathways of the invention to, for example, improve enzymatic activity and/or specificity and/or to generate long chain alcohols of a predetermined chain length or lengths.

In addition, fatty acyl-CoA and fatty alcohols generated as described above can be applied to produce esters of various lengths. These esters can be formed between: 1) fatty acyl-CoA and short-chain alcohols such as methanol, ethanol, propanol, etc.; 2) fatty alcohols and short-chain acyl- CoA such as formyl-CoA, acetyl-CoA, and propionyl-CoA, etc.; 3) fatty acyl-CoA and fatty alcohols as shown in the following equations.

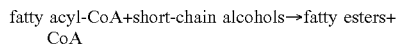

fatty acyl-CoA+short-chain alcohols→fatty esters+ CoA

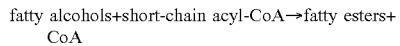

fatty alcohols+short-chain acyl-CoA→fatty esters+ CoA

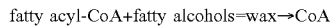

fatty acyl-CoA+fatty alcohols=wax→CoA

The fatty (or long-chain) alcohols can be synthesized intracellularly by the pathways described herein or can be added to the medium and taken up by the engineered microbe. Similarly, short-chain alcohols can be added to the medium or produced endogenously. Ethanol is an exemplary short chain alcohol that is naturally produced by many microorganisms including *Escherichia coli* and *Saccahyromyces cerevisiae*. Exemplary fatty esters include, but not limited to, fatty acid methyl esters (FAMEs), fatty acid ethyl esters (FAEEs), acetyl esters, and wax. Such molecules have broad applications including in food, personal care, coatings, surfactants, and biodiesel (Gerhard Knothe, Energy & Fuels 2008, 22, 1358-1364). Fatty esters, in this context, are differentiated from wax by the size of the hydrocarbon chain on each side of the ester bond. Waxes have long chain hydrocarbons on each side of the ester bond, whereas fatty esters have one short chain and one long chain hydrocarbon on each side of the ester bond, respectively.

The reactions to produce these esters can be catalyzed by enzymes with acyl-CoA:alcohol transacylase activities. Exemplary enzymes for catalyzing the formation of fatty esters include the acyl-CoA:fatty alcohol acyltransferase (wax ester synthase, WS, EC 2.3.1.75) and acetyl-CoA: alcohol 0-acetyltransferase (EC 2.3.1.84). Exemplary genes coding for these enzymes include the *Acinetobacter* sp. ADP1 atfA encoding a bifunctional enzyme with both wax ester synthase (WS) and acyl-CoA: diacylglycerol acyltransferase (DGAT) activities (Kalscheuer et al. A *J Biol Chem* 2003, 278: 8075-8082.); the *Simmondsia chinensis* gene AAD38041 encoding a WS required for the accumulation of waxes in jojoba seeds (Lardizabal et al. *Plant Physiology* 2000, 122: 645-655.); the *Alcanivorax borkumensis* atfA 1 and atfA2 encoding bifunctional WS/DGAT enzymes (Kalscheuer et al. *J Bacteriol* 2007, 189: 918-928.); the *Fragaria×ananassa* AAT encoding an alcohol acetyltransferasae (Noichinda et al. *Food Sci Technol Res* 1999, 5: 239-242.); the Rosa hybrid cultivar AAT1 encoding an alcohol acetyltransferase (Guterman et al. *Plant Mol Biol* 2006, 60: 555-563.); and the *Saccharomyces cerevisiae* ATF1 and ATF2 encoding alcohol acetyltransferases (Mason et al. *Yeast* 2000, 16: 1287-1298.).

| atfA | Q8GGG1 | *Acinetobacter* sp. ADP1 |
|---|---|---|
|  | AAD38041 | *Simmondsia chinensis* |
| atfA1 | YP_694462 | *Alcanivorax borkumensis* SK2 |
| atfA2 | YP_693524 | *Alcanivorax borkumensis* SK2 |
| AAT | AAG13130 | *Fragaria × ananassa* |
| AAT1 | Q5I6B5 | Rosa hybrid cultivar |
| ATF1 | P40353 | *Saccharomyces cerevisiae* |
| ATF2 | P53296 | *Saccharomyces cerevisiae* |

Host microbial organisms can be selected from, and the non-naturally occurring microbial organisms generated in, for example, bacteria, yeast, fungus or any of a variety of other microorganisms applicable to fermentation processes. Exemplary bacteria include species selected from *E. coli, Rhodococcus opacus, Ralstonia eutropha, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, Pseudomonas putida* and *E. gracilis*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

Methods for constructing and testing the expression levels of a non-naturally occurring primary alcohol-producing host can be performed, for example, by recombinant and detection methods well known in the art. Such methods can be found described in, for example, Sambrook et al., *Molecular Cloning: A Laboratory Manual*, Third Ed, Cold Spring Harbor Laboratory, New York (2001); Ausubel et al., *Current Protocols in Molecular Biology*, John Wiley and Sons, Baltimore, Md. (1999). For example, nucleic acids encoding enzymes in the malonyl-CoA independent FAS and/or acyl-reduction pathway can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, for example, mitochondrial genes will encode an N-terminal targeting signals, which can be removed before transformation into host cells. For exogenous expression in yeast or other eukaryotic cells, genes can be expressed in the cytosol without the addition of the targeting sequence, or alternatively, can be targeted to mitochondrion with the addition of mitochondrial targeting signal functional in the host organism. Furthermore, genes can be subjected for codon optimization with techniques well known in the art, to achieve optimal expression of the one or more malonyl-CoA independent FAS and/or acyl-reduction pathway gene products.

An expression vector or vectors can be constructed to harbor one or more malonyl-CoA independent FAS and/or acyl-reduction pathway encoding nucleic acids operably linked to expression control sequences functional in the host organism. Expression vectors applicable for use in the microbial host organisms of the invention include, for example, plasmids, phage vectors, viral vectors and artificial chromosomes. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous nucleic acids encoding are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous DNA sequences involved in a metabolic or synthetic pathway will be confirmed using methods well known in the art.

Primary alcohol production can be detected and/or monitored using methods well known to those skilled in the art. For example, final product of primary alcohol and/or intermediates such as acyl-CoA and organic acids can be analyzed by HPLC, GC-MS and LC-MS. For example, primary alcohols can be separated by HPLC using a Spherisorb 5 ODS1 column and a mobile phase of 70% 10 mM phosphate buffer (pH=7) and 30% methanol, and detected using a UV detector at 215 nm (Hennessy et al. 2004, J. Forensic Sci. 46(6):1-9). The release or secretion of primary alcohol into the culture medium or fermentation broth also can be detected using these procedures. Activities of one or more enzymes in the malonyl-CoA independent FAS and/or acyl-reduction pathway also can be measured using methods well known in the art.

The non-naturally occurring microbial organisms of the invention are constructed using methods well known in the art as exemplified above to exogenously express at least one nucleic acid encoding a malonyl-CoA independent FAS pathway enzyme in sufficient amounts to produce primary alcohol. Following the teachings and guidance provided herein, the non-naturally occurring microbial organisms of the invention can achieve biosynthesis of greater than that which can be synthesized in naturally occurring organisms. Generally, the intracellular concentration of, for example, octanol is about 54 µg/L and decanol is about 148 µg/L.

As described further below, one exemplary growth condition for achieving biosynthesis of primary alcohols includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The invention further provides a method for the production of primary alcohols. The method includes culturing a non-naturally occurring microbial organism have having a malonyl-CoA-independent fatty acid synthesis (FAS) pathway and an acyl-reduction pathway comprising at least one exogenous nucleic acid encoding a malonyl-CoA-independent FAS pathway enzyme expressed in sufficient amounts to produce a primary alcohol under substantially anaerobic conditions for a sufficient period of time to produce said primary alcohol, said malonyl-CoA-independent FAS pathway comprising ketoacyl-CoA acyltransferase or ketoacyl-CoA thiolase, 3-hydroxyacyl-CoA dehydrogenase, enoyl-CoA hydratase and enoyl-CoA reductase, said acyl-reduction pathway comprising an acyl-CoA reductase and an alcohol dehydrogenase.

Any of the non-naturally occurring microbial organisms described previously can be cultured to produce the biosynthetic products of the invention. For example, the primary alcohol producers can be cultured for the biosynthetic production of its engineered target primary alcohol. The primary alcohol can be isolated or isolated and further utilized in a wide variety of products and procedures.

In some embodiments, culture conditions include anaerobic or substantially anaerobic growth or maintenance conditions. Exemplary anaerobic conditions have been described previously and are well known in the art. Exemplary anaerobic conditions for fermentation processes are described below and are well known in the art. Any of these conditions can be employed with the non-naturally occurring microbial organisms as well as other anaerobic conditions well known in the art.

The culture conditions can include, for example, liquid culture procedures as well as fermentation and other large scale culture procedures. As described further below in the Examples, particularly useful yields of the biosynthetic products of the invention can be obtained under anaerobic or substantially anaerobic culture conditions. Exemplary growth procedures include, for example, fed-batch fermentation and batch separation; fed-batch fermentation and continuous separation, or continuous fermentation and continuous separation. All of these processes are well known in the art.

Fermentation procedures are particularly useful for the biosynthetic production of commercial quantities of primary alcohols. Generally, and as with non-continuous culture procedures, the continuous and/or near-continuous production of primary alcohols will include culturing a non-naturally occurring primary alcohol producing organism of the invention in sufficient neutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods.

Fermentation procedures are well known in the art. Briefly, fermentation for the biosynthetic production of primary alcohol products of the invention can be utilized in, for example, fed-batch fermentation and batch separation; fed-batch fermentation and continuous separation, or continuous fermentation and continuous separation. Examples of batch and continuous fermentation procedures well known in the art are exemplified further below in the Examples.

In a further embodiment, the primary alcohol producing microbial organisms of the invention utilize renewable feedstocks and carbon-containing gas as carbon sources for growth. Employing these alternative materials as a feedstock is particularly useful because they are beneficial from an environmental standpoint and lower production costs of bioprocess-derived products such as the primary alcohols of the invention.

Renewable feedstocks useful for growth of the primary alcohol producing organisms of the invention, including fermentation processes with the modified organisms of the invention, can include any regenerative raw material which can be used by the cell as a supply a carbon or other energy source. In general, renewable feedstock are derived from living organisms or their metabolic byproducts including material derived from biomass, often consisting of under-utilized components like chaff. Agricultural products specifically grown for use as renewable feedstocks and useful in the methods of the invention include, for example, corn, soybeans and cotton; flaxseed and rapeseed; sugar cane and palm oil. Renewable feedstocks that can be used therefore include an array of carbohydrates, fats and proteins derived from agricultural and/or animal matter which can be harnessed by the primary alcohol producing organisms of the invention as a source for carbon.

Plant-derived biomass which is available as an energy source on a sustainable basis includes, for example, herbaceous and woody energy crops, agricultural food and feed crops, agricultural crop wastes and residues, wood wastes and residues, aquatic plants, and other waste materials including some municipal wastes (see, for example, the URL 1.eere.energy.gov/biomass/information_resources.html, which includes a database describing more than 150 exemplary kinds of biomass sources). Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of a wide variety of primary alcohols.

In addition to renewable feedstocks such as those exemplified above, the primary alcohol producing microbial organisms of the invention also can be modified for growth on syngas as its source of carbon. In this specific embodiment, one or more proteins or enzymes are expressed in the primary alcohol producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

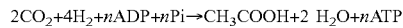

$$2CO_2 + 4H_2 + nADP + nPi \rightarrow CH_3COOH + 2\ H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided above for introducing a sufficient number of encoding nucleic acids to complete the either or both the malonyl-CoA independent FAS and/or the acyl-reduction pathway, those skilled in the art will understand that the same engineering design also can be performed with respect to introducing at least the nucleic acids encoding the Wood-Ljungdahl enzymes absent in the host organism. Therefore, introduction of one or more encoding nucleic acids into the microbial organisms of the invention such that the modified organism contains the complete Wood-Ljungdahl pathway will confer syngas utilization ability.

The invention is also directed, in part, to the design and creation of cells and organisms having growth-coupled production of LCA. In one embodiment, the invention utilizes optimization-based approaches based on in silico stoichiometric model of *Escherichia coli* metabolism that identify metabolic designs for optimal production of LCA. A bilevel programming framework, OptKnock, is applied within an iterative algorithm to predict multiple sets of gene disruptions, that collectively result in the growth-coupled production of LCA. The results described herein indicate that combinations of strategically placed gene deletions or functional disruptions of genes significantly improve the LCA production capabilities of *Escherichia coli* and other cells or organisms. The strain design strategies are equally applicable if an organism other than *E. coli* is chosen as the production host, even if the organism naturally lacks the activity or exhibits low activity of a subset of the gene products marked for disruption. In those cases, disruptions must only be introduced to eliminate or lessen the enzymatic activities of the gene products that are naturally present in the chosen production host. Growth-coupled production of LCA for the in silico designs are confirmed by construction of strains having the designed metabolic genotype. These metabolically engineered cells or organisms also can be subjected to adaptive evolution to further augment growth-coupled product production.

The invention is also directed, in part, to the design and creation of cells and organisms that produce long chain alcohols, LCAs based on in silico stoichiometric model of *Saccharomyces cerevisiae* metabolism. One skilled in the art will recognize the ability to also produce LCAs by non-growth-coupled production by providing a non-producing growth phase, followed by a non-growth production phase, for example. The results described herein indicate that combinations of gene deletions or functional disruptions of genes significantly improve the LCA production capabilities of *Saccharomyces cerevisaie* and other cells of eukaryotic organisms and eukaryotic microbial organisms. The strain design pathways are equally applicable if a eukaryotic microbial organism other than *S. cerevisiae* is chosen as the production host, even if the organism naturally lacks the activity or exhibits low activity of a subset of the gene products marked for disruption. In the latter case, disruptions can be introduced to eliminate or lessen the enzymatic activities of the gene products that are naturally present in the chosen production host. In some embodiments, growth-coupled production of LCA for the in silico determined metabolic pathways is confirmed by construction of strains having the designed metabolic genotype. These metabolically engineered cells or organisms can also be subjected to adaptive evolution to further augment growth-coupled product production. In some embodiments, the engineered cells or organisms can also incorporate additional copies of beneficial genes to increase flux through a particular metabolic pathway. Alternatively, exogenous gene insertions from another organism can be used to install functionality that is not present in the host organism.

In some embodiments, the designed LCA production pathway utilizes a malonyl-CoA-independent fatty acid synthesis pathway coupled with reduction of the fatty acid to form primary alcohol as shown in FIG. 1. The malonyl-CoA independent LCA production pathway (MI-LCA pathway) comprises the malonyl-CoA-independent fatty acid synthesis steps and the acyl-CoA reduction steps. An engineered microorganism possessing the MI-LCA pathway will convert low cost renewable feedstocks, such as glucose and sucrose, to acetyl-CoA through glycolysis. Acetyl-CoA then is used as both primer and extension units in an elongation cycle that involves the ketoacyl-CoA thiolase, 3-hydroxyacyl-CoA dehydrogenase, enoyl-CoA hydratase, and enoyl-CoA reductase. At the end of each elongation cycle, an acyl-CoA is formed that is one $C_2$ unit longer than the acyl-CoA entering the elongation cycle. The acyl-CoA with a desired chain-length is then reduced through the combination of acyl-CoA reductase and alcohol dehydrogenase or the fatty alcohol forming acyl-CoA reductase to form the desired primary alcohol. The carbon chain-length of the LCA can be controlled by chain-length specific enoyl-CoA reductase, ketoacyl-CoA thiolase, and/or acyl-CoA reductase.

The MI-LCA pathway has the advantage of better product and ATP yields than that through the typical energy-intensive fatty acid synthesis pathways for LCA production. For example, the maximum theoretical yield for dodecanol (Cu) using the MI-LCA pathway is 0.333 mol per mol of glucose consumed under both aerobic and anaerobic conditions:

$$3C_6H_{12}O_6 \rightarrow C_{12}H_{26}O + 6CO_2 + 5H_2O$$

Additionally, the energy and redox characteristics of the MI-LCA pathway make it suited for the creation of strains that couple LCA production to growth using OptKnock algorithms (Burgard, A. P., P. Pharkya, and C. D. Maranas, *Optknock: a bilevel programming framework for identifying gene knockout strategies for microbial* strain *optimization.* Biotechnol Bioeng, 2003. 84(6): p. 647-57; Pharkya, P., A. P. Burgard, and C. D. Maranas, *Exploring the overproduction of amino acids using the bilevel optimization framework OptKnock.* Biotechnol Bioeng, 2003. 84(7): p. 887-99; Pharkya, P., A. P. Burgard, and C. D. Maranas, *OptStrain: a computational framework for redesign of microbial production systems.* Genome Res, 2004. 14(11): p. 2367-76.). The resulting growth-coupled production strains will be inherently stable, self-optimizing, and suited for batch, fed-batch, and continuous process designs.

In some embodiments, the invention is directed to an integrated computational and engineering platform for developing metabolically altered microorganism strains having enhanced LCA producing characteristics. Strains identified via the computational component of the platform are put into actual production by genetically engineering the predicted metabolic alterations which lead to the enhanced production of LCA. Production of the desired product is coupled to optimal growth of the microorganism to optimize yields of this product during fermentation. In yet another embodiment, strains exhibiting growth-coupled production of LCA are further subjected to adaptive evolution to further augment product biosynthesis. The levels of growth-coupled product production following adaptive evolution also can be predicted by the computational component of the system where, in this specific embodiment, the elevated product levels are realized only following evolution.

In some embodiments, the invention provides a non-naturally occurring microbial organism, that includes one or more gene disruptions. The disruptions occur in genes encoding an enzyme that couples LCA production to growth of the organism when the gene disruption reduces the activity of the enzyme, such that the gene disruptions confer stable growth-coupled production of LCA onto the non-naturally occurring organism.

In particular embodiments, the invention provides a non-naturally occurring eukaryotic organism, that includes one or more gene disruptions. The one or more gene disruptions occur in genes that encode enzymes that include, for example a cytosolic pyruvate decarboxylase, a mitochondrial pyruvate dehydrogenase, a cytosolic ethanol-specific alcohol dehydrogenase or a mitochondrial ethanol-specific alcohol dehydrogenase. These gene disruptions confer production of long chain alcohols in the cytosol or mitochondrion (vide infra) of the organism.

Further, the present invention provides methods of producing such non-naturally microbial organisms having stable growth-coupled production of LCA. For LCA production, for example, the method includes: (a) identifying in silico a set of metabolic modifications requiring LCA production during cell growth, and (b) genetically modifying a microorganism to contain the set of metabolic modifications requiring LCA production.

One consideration for bioprocessing is whether to use a batch or continuous fermentation scheme. One difference between the two schemes that will influence the amount of product produced is the presence of a preparation, lag, and stationary phase for the batch scheme in addition to the exponential growth phase. In contrast, continuous processes are kept in a state of constant exponential growth and, if properly operated, can run for many months at a time. For growth-associated and mixed-growth-associated product formation, continuous processes provide much higher productivities (i.e., dilution rate times cell mass) due to the elimination of the preparation, lag, and stationary phases. For example, given the following reasonable assumptions:

Monod kinetics (i.e., $\mu = \mu_m \cdot S/(K_s+S)$)

$\mu_m = 1.0 \text{ hr}^{-1}$ final cell concentration/initial cell concentration=20

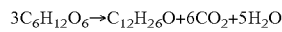

feed concentration of limiting nutrient$\gg$Ks increased productivity from a continuous process has been estimated at 8-fold, Shuler et al, *Prentice Hall*, Inc.: Upper Saddle River, N.J., 245-247.

Despite advantages in productivity, many more batch processes are in operation than continuous processes for a number of reasons. First, for non-growth associated product formation (e.g., penicillin), the productivity of a batch system may significantly exceed that of a continuous process because the latter would have to operate at very low dilution rates. Next, production strains generally have undergone modifications to their genetic material to improve their biochemical or protein production capabilities. These specialized strains are likely to grow less rapidly than their parental complements whereas continuous processes such as those employing chemostats (fermenters operated in continuous mode) impose large selection pressures for the fastest growing cells. Cells containing recombinant DNA or carrying point mutations leading to the desired overproduction phenotype are susceptible to back-mutation into the original less productive parental strain. It also is possible for strains having single gene deletions to develop compensatory mutations that will tend to restore the wild-type growth phenotype. The faster growing cells usually out-compete their more productive counterparts for limiting nutrients, drastically reducing productivity. Batch processes, on the other hand, limit the number of generations available by not reusing cells at the end of each cycle, thus decreasing the probability of the production strain reverting back to its wild-type phenotype. Finally, continuous processes are more difficult to operate long-term due to potential engineering obstacles such as equipment failure and foreign organism contamination. The consequences of such failures also are much more considerable for a continuous process than with a batch culture.

For small-volume production of specialty chemicals and/or proteins, the productivity increases of continuous processes rarely outweigh the risks associated with strain stability and reliability. However, for the production of large-volume, growth-associated products such as LCA, the increases in productivity for a continuous process can result in significant economic gains when compared to a batch process. Although the engineering obstacles associated with continuous bioprocess operation would always be present, the strain stability concerns can be overcome through metabolic engineering strategies that reroute metabolic pathways to reduce or avoid negative selective pressures and favor production of the target product during the exponential growth phase.

One computational method for identifying and designing metabolic alterations favoring growth-coupled production of a product is the OptKnock computational framework, Burgard et al., *Biotechnol Bioeng*, 84: 647-57 (2003). OptKnock is a metabolic modeling and simulation program that suggests gene disruption strategies that result in genetically stable microorganisms which overproduce the target product. Specifically, the framework examines the complete metabolic and/or biochemical network of a microorganism in order to suggest genetic manipulations that force the desired biochemical to become a byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production.

Figure 2:
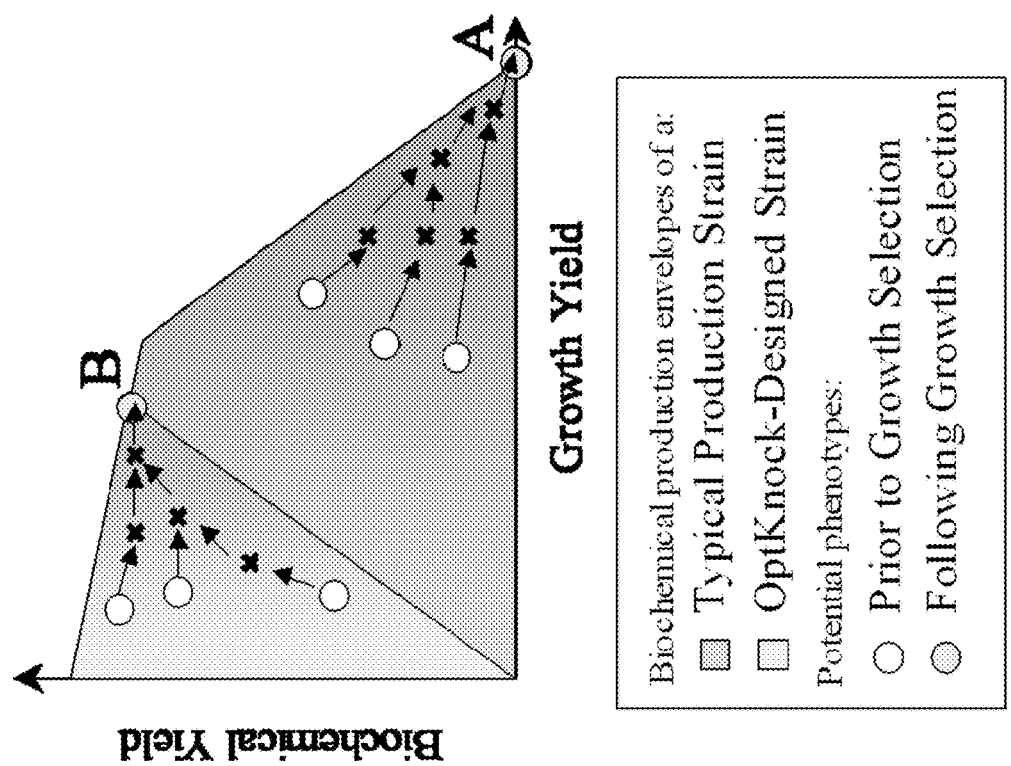
FIG. 2 shows the contrasted hypothetical production envelopes of an OptKnock-designed strain against a typical non-growth-coupled production strain. The potential evolutionary trajectories of the OptKnock strain lead to a high producing phenotype.

The concept of growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources. Thus, enhanced rates of biochemical production will necessarily result in sub-maximal growth rates. The disruptions suggested by OptKnock are designed to restrict the allowable solution boundaries forcing a change in metabolic behavior from the wild-type strain as depicted in FIG. 2. Although the actual solution boundaries for a given strain will expand or contract as the substrate uptake rate(s) increase or decrease, each experimental point should lie within its calculated solution boundary. Plots such as these enable one to visualize how close strains are to their performance limits or, in other words, how much room is available for improvement. The OptKnock framework has already been able to identify promising gene disruption strategies for biochemical overproduction, (Burgard, A. P., P. Pharkya, and C. D. Maranas, *Biotechnol Bioeng*, 84(6):647-657 (2003); Pharkya, P., A. P. Burgard, and C. D. Maranas, *Biotechnol Bioeng*, 84(7):887-899 (2003)) and establishes a systematic framework that will naturally encompass future improvements in metabolic and regulatory modeling frameworks.

Lastly, when gene deletions are constructed there is a negligible possibility of the designed strains reverting to their wild-type states because the genes selected by OptKnock are to be completely removed from the genome.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or disruptions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic alterations favoring growth-coupled production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.*

71:286-306 (2000) and Schilling et al., *Biotech. Prog.* 15:288-295 (1999), can be used to determine such phenotypic capabilities.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *S. cerevisiae* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement growth-coupled production of a biochemical product. Such metabolic modeling and simulation methods include, for example, the computational systems exemplified above as SimPheny® and OptKnock. For simplicity in illustrating the invention, the methods and strains will be described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to couple growth to the production of a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. As shown in FIG. 2, the production of a desired biochemical generally is in direct competition with biomass formation for intracellular resources. Under these circumstances, enhanced rates of biochemical production will necessarily result in sub-maximal growth rates. The disruptions suggested by the above metabolic modeling and simulation programs such as OptKnock are designed to restrict the allowable solution boundaries forcing a change in metabolic behavior from the wild-type strain as depicted in FIG. 2. Although the actual solution boundaries for a given strain will expand or contract as the substrate uptake rate(s) increase or decrease, each experimental point will lie within its calculated solution boundary. Plots such as these enable accurate predictions of how close the designed strains are to their performance limits which also indicates how much room is available for improvement.

The OptKnock mathematical framework is exemplified herein for pinpointing gene disruptions leading to growth-coupled biochemical production as illustrated in FIG. 2. The procedure builds upon constraint-based metabolic modeling which narrows the range of possible phenotypes that a cellular system can display through the successive imposition of governing physico-chemical constraints, Price et al., *Nat Rev Microbiol*, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows:

$$\text{maximize } v_{cellular\ objective}$$

$$\text{subject to } \sum_{j=1}^{M} S_{ij} v_j = 0, \forall\, i \in N$$

$$v_{substrate} = v_{substrate\_uptake} \text{ mmol/gDW} \cdot \text{hr } \forall\, i \in \{\text{limiting substrate}(s)\}$$

$$v_{atp} \geq v_{atp\_main} \text{mmol/gDW} \cdot \text{hr}$$

$$v_j \geq 0, \forall\, j \in \{\text{irrev. reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol Bioeng*, 74: 364-375 (2001), Burgard et al., *Biotechnol Prog*, 17: 791-797 (2001). These binary variables, $$y_j = \begin{cases} 1, \text{ if reaction flux } v_j \text{ is active} \\ 0, \text{ if reaction flux } v_j \text{ is not active} \end{cases}, \forall\, j \in M$$

assume a value of 1 if reaction j is active and a value of 0 if it is inactive. The following constraint, $$v_j^{min} \cdot y_j \leq v_j \leq v_j^{max} \cdot y_j, \forall j \in M$$

ensures that reaction flux $v_j$ is set to zero only if variable $y_j$ is equal to zero. Alternatively, when y is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab Eng,* 5: 264-76 (2003).

Optimal gene/reaction disruptions are identified by solving a bilevel optimization problem that chooses the set of active reactions ($y_j=1$) such that an optimal growth solution for the resulting network overproduces the chemical of interest. Schematically, this bilevel optimization problem is illustrated in FIG. 2. Mathematically, this bilevel optimization problem is expressed as the following bilevel mixed-integer optimization problem:

$$\begin{aligned}
&\underset{y_j}{\text{maximize}} \quad v_{chemical} \quad &\text{(OptKnock)}\\
&\left\{\begin{array}{ll}
\text{subject to} & \underset{v_j}{\text{maximize}} \quad v_{biomass}\\
& \text{subject to} \quad \sum_{j=1}^{M} S_{ij} v_j = 0 \quad \forall\, i \in N\\
& \qquad v_{substrate} = v_{substrate\_uptake} \quad \forall\, i \in \{\text{limiting substrate}(s)\}\\
& \qquad v_{atp} \geq v_{atp\_main}\\
& v_{biomass} \geq v_{biomass}^{target}
\end{array}\right.\\
&v_j^{min} \cdot y_j \leq v_j \leq v_j^{max} \cdot y_j, \;\forall\, j \in M\\
&\sum_{j \in M^{forward}} (1 - y_j) = K\\
&y_j \in \{0, 1\}, \;\forall\, j \in M
\end{aligned}$$

where $v_{chemical}$ is the production of the desired target product, for example LCA or other biochemical product, and K is the number of allowable knockouts. Note that setting K equal to zero returns the maximum biomass solution of the complete network, while setting K equal to one identifies the single gene/reaction knockout ($y_j=0$) such that the resulting network involves the maximum overproduction given its maximum biomass yield. The final constraint ensures that the resulting network meets a minimum biomass yield. Burgard et al., *Biotechnol Bioeng,* 84: 647-57 (2003), provide a more detailed description of the model formulation and solution procedure. Problems containing hundreds of binary variables can be solved in the order of minutes to hours using CPLEX 8.0, *GAMS: The Solver Manuals.* 2003: GAMS Development Corporation, accessed via the GAMS, Brooke et al., *GAMS Development Corporation* (1998), modeling environment on an IBM RS6000-270 workstation. The OptKnock framework has already been able to identify promising gene disruption strategies for biochemical overproduction, Burgard et al., *Biotechnol Bioeng,* 84: 647-57 (2003), Pharkya et al., *Biotechnol Bioeng,* 84: 887-899 (2003), and establishes a systematic framework that will naturally encompass future improvements in metabolic and regulatory modeling frameworks.

Any solution of the above described bilevel OptKnock problem will provide one set of metabolic reactions to disrupt. Elimination of each reaction within the set or metabolic modification can result in LCA as a product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve growth-coupled LCA production are implemented in the target cell or organism by functional disruption of at least one gene encoding each metabolic reaction within the set. As described previously, one particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the product coupling are desired or when genetic reversion is less likely to occur.

To identify additional productive solutions to the above described bilevel OptKnock problem which lead to further sets of reactions to disrupt or metabolic modifications that can result in the growth-coupled production of LCA, or other biochemical products, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that couples product biosynthesis to growth. For example, if a previously identified growth-coupled metabolic modification specifies reactions 1, 2, and 3 for disruption, then the following constraint prevents the same reactions from being simultaneously considered in subsequent solutions: $y_1+y_2+y_3 \geq 1$. The integer cut method is well known in the art and can be found described in, for example, reference, Burgard et al., *Biotechnol Prog,* 17: 791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to growth-coupled production of a product, a modification of the integer cut method was employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single disruptions are considered and the two parameter sets, objstore$_{iter}$ and ystore$_{iter,j}$, are introduced to store the objective function ($v_{chemical}$) and reaction on-off information ($y_j$), respectively, at each iteration, iter. The following constraints are then successively added to the OptKnock formulation at each iteration.

$$v_{chemical} \geq \text{objstore}_{iter} + \varepsilon - M \cdot \Sigma_{j \in ystore_{iter,j}=0} y_j$$

In the above equation, $\varepsilon$ and M are a small and a large numbers, respectively. In general, $\varepsilon$ can be set at about 0.01 and M can be set at about 1000. However, numbers smaller and/or larger then these numbers also can be used. M ensures that the constraint can be binding only for previously identified disruption strategies, while $\varepsilon$ ensures that adding disruptions to a previously identified strategy must lead to an increase of at least $\varepsilon$ in biochemical production at optimal growth. The approach moves onto double disruptions whenever a single disruption strategy fails to improve upon the wild-type strain. Triple disruptions are then considered when no double disruption strategy improves upon the wild-type strain, and so on. The end result is a ranked list, represented as desired biochemical production at optimal growth, of distinct disruption strategies that differ from each other by at least one disruption. This optimization procedure as well as the identification of a wide variety of reaction sets that, when disrupted, lead to the growth-coupled production of a biochemical product are exemplified in detail further below. Given the teachings and guidance provided herein, those skilled in the art will understand that the methods and metabolic engineering designs exemplified herein are applicable to the coupling of cell or microorganism growth to any biochemical product.

Employing the methods exemplified above, the methods of the invention enable the construction of cells and organisms that couple the production of a target biochemical product to growth of the cell or organism engineered to harbor the identified genetic alterations. In this regard, metabolic alterations have been identified that obligatorily couple the production of LCA to organism growth. Microbial organism strains constructed with the identified metabolic alterations produce elevated levels of LCA during the exponential growth phase. These strains can be beneficially used for the commercial production of LCA in continuous fermentation process without being subjected to the negative selective pressures described previously.

Therefore, the methods of the invention provide a set of metabolic modifications that are identified by an in silico method selected from OptKnock. The set of metabolic modifications can include functional disruption of one or more metabolic reactions including, for example, disruption by gene deletion. For LCA production metabolic modifications can be selected from the set of metabolic modifications listed in Table 1.

Also provided is a method of producing a non-naturally occurring microbial organism having stable growth-coupled production of LCA. The method includes: (a) identifying in silico a set of metabolic modifications requiring LCA production during exponential growth; (b) genetically modifying an organism to contain the set of metabolic modifications requiring product production, and culturing the genetically modified organism. Culturing can include adaptively evolving the genetically modified organism under conditions requiring product production. The methods of the invention are applicable to bacterium, yeast and fungus as well as a variety of other cells and microorganism. Exemplary bacteria include species selected from *E. coli, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary eukaryotic organisms include species selected from *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae,* and *Pichia pastoris*.

A microbial organism produced by the methods of the invention is further provided. Additionally, the invention provides a non-naturally occurring microbial organism comprising one or more gene disruptions encoding an enzyme associated with growth-coupled production of LCA and exhibiting stable growth-coupled production of these products. The non-naturally occurring microbial organism of the invention includes one or more gene disruptions occurring in genes encoding an enzyme obligatorily coupling LCA production to growth of the microbial organism when the gene disruption reduces an activity of the enzyme, whereby the one or more gene disruptions confers stable growth-coupled production of LCA onto the non-naturally occurring microbial organism.

The non-naturally occurring microbial organism can have one or more gene disruptions included in a metabolic modification listed in Table 1. The one or more gene disruptions can be a deletion. The non-naturally occurring microbial organism of the invention can be selected from a group of microbial organism having a metabolic modification listed in Tables 1. Non-naturally occurring microbial organisms of the invention include bacteria, yeast, fungus, or any of a variety of other microorganisms applicable to fermentation processes. Exemplary bacteria include species selected from *E. coli, A. succiniciproducens, A. succinogenes, M. succiniciproducens, R. etli, Bacillus subtilis, C. glutamicum, G. oxydans, Z. mobilis, L. lactis, L. plantarum, S. coelicolor, C. acetobutylicum, P. fluorescens,* and *P. putida*. Exemplary eukaryotic organisms include species selected from *S. cerevisiae, S. pombe, K lactis, K. marxianus, A. terreus, A. niger, R. arrhizus, R. oryzae,* and *P. pastoris*.

The microbial organisms having growth-coupled LCA production are exemplified herein with reference to an *Escherichia coli* genetic background. However, with the complete genome sequence available for now more than 550 species (with more than half of these available on public databases such as the NCBI), including 395 microorganism genomes and a variety of yeast, fungi, plant, and mammalian genomes, the identification of an alternate species homolog for one or more genes, including for example, orthologs, paralogs and nonorthologous gene displacements, and the interchange of genetic alterations between organisms is routine and well known in the art. Accordingly, the metabolic alterations enabling growth-coupled production of LCA described herein with reference to a particular organism such as *Escherichia coli* can be readily applied to other microorganisms. Given the teachings and guidance provided herein, those skilled in the art will know that a metabolic alteration exemplified in one organism can be applied equally to other organisms.

As described previously, homologues can include otholags and/or nonorthologous gene displacements. In some instances, such as when a substitute metabolic pathway exists in the species of interest, functional disruption can be accomplished by, for example, deletion of a paralog that catalyzes a similar, yet non-identical metabolic reaction which replaces the referenced reaction. Because certain differences among metabolic networks between different organisms, those skilled in the art will understand that the actual genes disrupted between different organisms may differ. However, the given the teachings and guidance provided herein, those skilled in the art also will understand that the methods of the invention can be applied to all microorganisms to identify the cognate metabolic alterations between organisms and to construct an organism in a species of interest that will enhance the coupling of LCA biosynthesis to growth.

The invention will be described herein with general reference to the metabolic reaction, reactant or product thereof, or with specific reference to one or more genes associated with the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene also constitutes a reference to the corresponding encoded enzyme and the reaction it catalyzes as well as the reactants and products of the reaction. As described previously and further below, exemplary reactions, reaction nomenclature, reactants, products, cofactors and genes encoding enzymes catalyzing a reaction involved in the growth-coupled production of LCA are set forth in Tables 2 and 3.

The invention provides non naturally occurring microbial organisms having growth-coupled production of LCA. Product production is obligatorily linked to the exponential growth phase of the microorganism by genetically altering the metabolic pathways of the cell. The genetic alterations make the desired product a product during the growth phase. Sets of metabolic alterations or transformations that result in elevated levels of LCA biosynthesis are exemplified in Table 1, respectively. Each alteration within a set corresponds to the requisite metabolic reaction that should be functionally disrupted. Functional disruption of all reactions within each set results in the production of LCA by the engineered strain during the growth phase. The corresponding reactions to the referenced alterations and the gene or genes that potentially encode them in *Escherichia coli*, are set forth in Table 2. The various metabolites, their abbreviations and location are set forth in Table 3.

For example, for each strain exemplified in Table 1, the metabolic alterations that can be generated for growth coupled LCA production are shown in each row. These alterations include the functional disruption of from one to six or more reactions. In particular, 995 strains are exemplified in Table 1 that have non-naturally occurring metabolic genotypes. Each of these non-naturally occurring alterations result in an enhanced level of LCA production during the exponential growth phase of the microbial organism compared to a wild-type strain, under appropriate culture conditions. Appropriate conditions include, for example, those exemplified further below in the Example I such as particular carbon sources or reactant availabilities and/or adaptive evolution.

Given the teachings and guidance provided herein, those skilled in the art will understand that to disrupt an enzymatic reaction it is necessary to disrupt the catalytic activity of the one or more enzymes involved in the reaction. Disruption can occur by a variety of means including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or destroyed.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the growth-coupled product production.

Herein below are described the designs identified for increasing LCA production in *Escherichia coli*. The Opt- Knock algorithm identified designs based on a stoichiometric model of *Escherichia coli* metabolism. Assumptions include (i) a glucose uptake rate of 10 mmol/gdw/hr; (ii) anaerobic or microaerobic conditions; and (iii) a minimum non-growth associated maintenance requirement of 3 mmol/gdw/hr. Dodecanol, a $C_{12}$ molecule, was chosen as an exemplary long chain alcohol whose production can be coupled to growth following the teachings of this invention. Although glucose was assumed to be the growth substrate, it is understood that the strategies are applicable to any substrate including glucose, sucrose, xylose, arabinose, or glycerol. The complete set of growth-coupled LCA productions designs are listed in Table 1. The enzyme names, their abbreviations, and the corresponding reaction stoichiometries are listed in Table 2. Finally, metabolites names corresponding to the abbreviations in the reaction equations are listed in Table 3. Although the designs were identified using a metabolic model of *E. coli* metabolism, and the gene names listed in Table 2 are specific to *E. coli*, the method of choosing the metabolic engineering strategies and also the designs themselves are applicable to any LCA-producing organism. Thus the designs are essentially lists of enzymatic transformations whose activity must be either eliminated, attenuated, or initially absent from a microorganism to enable the growth coupled production of long chain alcohols.

One criterion for prioritizing the final selection of designs was the growth-coupled yield of dodecanol. To examine this, production cones were constructed for each strategy by first maximizing and, subsequently minimizing the dodecanol yields at different rates of biomass formation (as described in the previous section). If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the dodecanol in the calculated range, including the lowest amount at the bottommost point of the vertical line. Such designs were given a lower priority. A short list of the highest priority OptKnock designs is provided here in Table I which represents a subset of the designs of Table 1.

TABLE I

| Design | Enzyme activity | Abbreviation | Other notes |
|---|---|---|---|
| I | Acetaldehyde-CoA dehydrogenase | ADHEr | |
| | D-lactate dehydrogenase | LDH_D | |
| II | Acetaldehyde-CoA dehydrogenase | ADHEr | Design I + PFL |
| | D-lactate dehydrogenase | LDH_D | |
| | Pyruvate formate lyase | PFLi | |
| III | Acetaldehyde-CoA dehydrogenase | ADHEr | Design II + FRD2 |
| | D-lactate dehydrogenase | LDH_D | |
| | Pyruvate formate lyase | PFLi | |
| | Fumarate reductase | FRD2 | |
| IV | Acetaldehyde-CoA dehydrogenase | ADHEr | Design II + FUM |
| | D-lactate dehydrogenase | LDH_D | |
| | Pyruvate formate lyase | PFLi | |
| | Fumarase | FUM | |
| V | Acetaldehyde-CoA dehydrogenase | ADHEr | Design II + MDH |
| | D-lactate dehydrogenase | LDH_D | |
| | Pyruvate formate lyase | PFLi | |
| | Malate dehydrogenase | MDH | |
| VI | Acetaldehyde-CoA dehydrogenase | ADHEr | Design III + GLUDy |
| | D-lactate dehydrogenase | LDH_D | |
| | Pyruvate formate lyase | PFLi | |
| | Fumarate reductase | FRD2 | |
| | Glutamate dehydrogenase | GLUDy | |
| VII | Acetaldehyde-CoA dehydrogenase | ADHEr | Design IV + GLUDy |
| | D-lactate dehydrogenase | LDH_D | |
| | Pyruvate formate lyase | PFLi | |
| | Fumarase | FUM | |
| | Glutamate dehydrogenase | GLUDy | |
| VIII | Acetaldehyde-CoA dehydrogenase | ADHEr | Design V + GLUDy |
| | D-lactate dehydrogenase | LDH_D | |
| | Pyruvate formate lyase | PFLi | |
| | Malate dehydrogenase | MDH | |
| | Glutamate dehydrogenase | GLUDy | |
| IX | Acetaldehyde-CoA dehydrogenase | ADHEr | Design III + THD2 |
| | D-lactate dehydrogenase | LDH_D | |
| | Pyruvate formate lyase | PFLi | |
| | Fumarate reductase | FRD2 | |
| | NAD(P) transhydrogenase | THD2 | |
| X | Acetaldehyde-CoA dehydrogenase | ADHEr | Design IV + THD2 |
| | D-lactate dehydrogenase | LDH_D | |
| | Pyruvate formate lyase | PFLi | |
| | Fumarase | FUM | |
| | NAD(P) transhydrogenase | THD2 | |
| XI | Acetaldehyde-CoA dehydrogenase | ADHEr | Design V + THD2 |
| | D-lactate dehydrogenase | LDH_D | |
| | Pyruvate formate lyase | PFLi | |
| | Malate dehydrogenase | MDH | |
| | NAD(P) transhydrogenase | THD2 | |

TABLE I-continued

| Design | Enzyme activity | Abbreviation | Other notes |
|---|---|---|---|
| XII | Acetaldehyde-CoA dehydrogenase | ADHEr | Design I + PTAr and/or ACKr |
| | D-lactate dehydrogenase | LDH_D | |
| | Phosphotransacetylase and/or Acetate kinase | PTAr and/or ACKr | |
| XIII | Acetaldehyde-CoA dehydrogenase | ADHEr | Design XII + FRD2 |
| | D-lactate dehydrogenase | LDH_D | |
| | Phosphotransacetylase and/or Acetate kinase | PTAr and/or ACKr | |
| | Fumarate reductase | FRD2 | |
| XIV | Acetaldehyde-CoA dehydrogenase | ADHEr | Design XII + FUM |
| | D-lactate dehydrogenase | LDH_D | |
| | Phosphotransacetylase and/or Acetate kinase | PTAr and/or ACKr | |
| | Fumarase | FUM | |
| XV | Acetaldehyde-CoA dehydrogenase | ADHEr | Design XII + MDH |
| | D-lactate dehydrogenase | LDH_D | |
| | Phosphotransacetylase and/or Acetate kinase | PTAr and/or ACKr | |
| | Malate dehydrogenase | MDH | |
| XVI | Acetaldehyde-CoA dehydrogenase | ADHEr | Design I + FRD |
| | D-lactate dehydrogenase | LDH_D | |
| | Fumarate reductase | FRD2 | |
| XVII | Acetaldehyde-CoA dehydrogenase | ADHEr | Design I + FUM |
| | D-lactate dehydrogenase | LDH_D | |
| | Fumarase | FUM | |
| XVIII | Acetaldehyde-CoA dehydrogenase | ADHEr | Design I + MDH |
| | D-lactate dehydrogenase | LDH_D | |
| | Malate dehydrogenase | MDH | |
| XIX | Acetaldehyde-CoA dehydrogenase | ADHEr | Design XVI + ATPS4r |
| | D-lactate dehydrogenase | LDH_D | |
| | Fumarate reductase | FRD2 | |
| | ATP synthase | ATPS4r | |
| XX | Acetaldehyde-CoA dehydrogenase | ADHEr | Design XVII + ATPS4r |
| | D-lactate dehydrogenase | LDH_D | |
| | Fumarase | FUM | |
| | ATP synthase | ATPS4r | |
| XXI | Acetaldehyde-CoA dehydrogenase | ADHEr | Design XVIII +ATPS4r |
| | D-lactate dehydrogenase | LDH_D | |
| | Fumarate reductase | MDH | |
| | ATP synthase | ATPS4r | |

Figure 3:
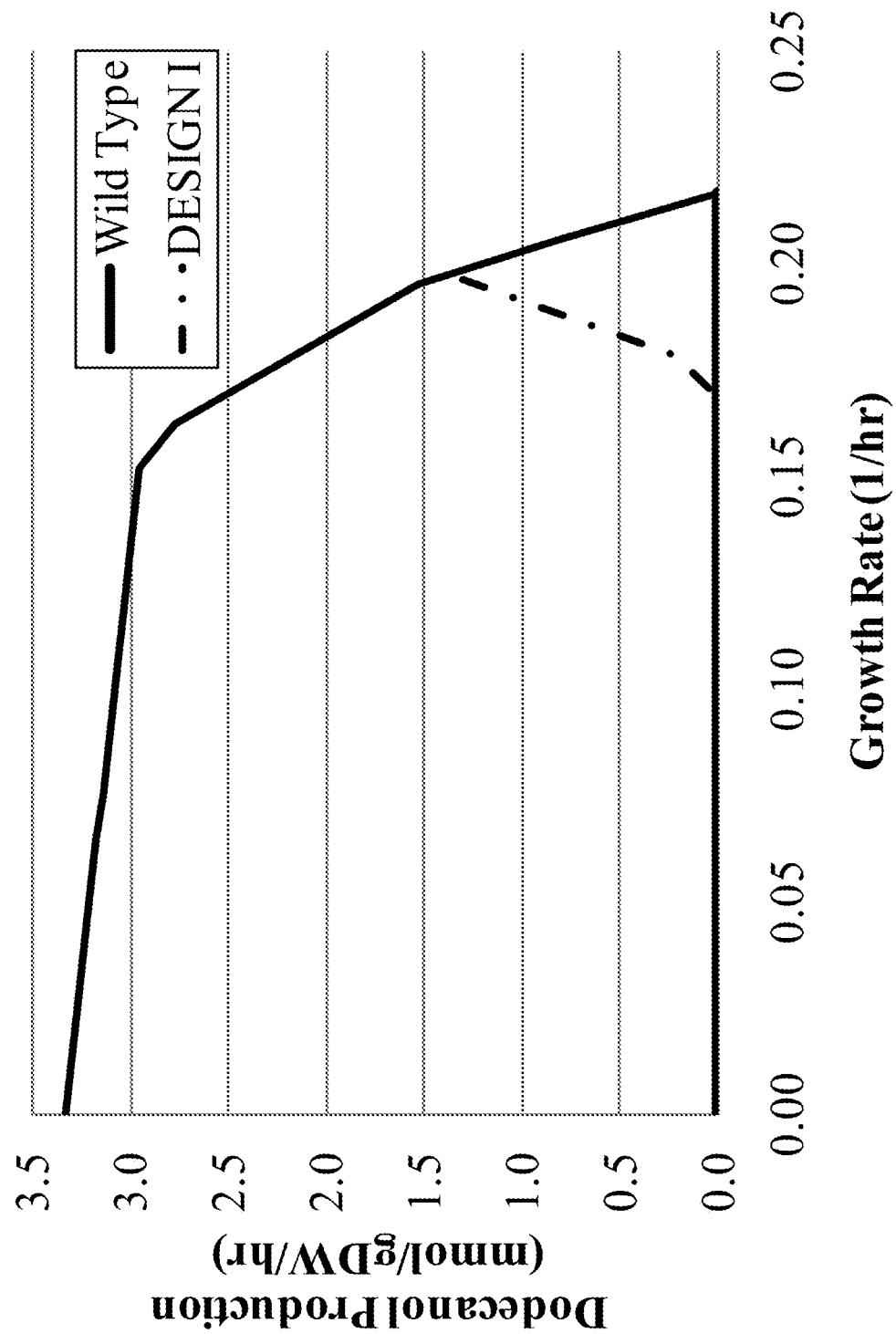
FIG. 3 shows the growth-coupled LCA production characteristics of strain design I (alternating dotted and dashed) compared with those of wild-type E. coli (black). A glucose uptake rate of 10 mmol/gDW/hr is assumed.
Figure 4:
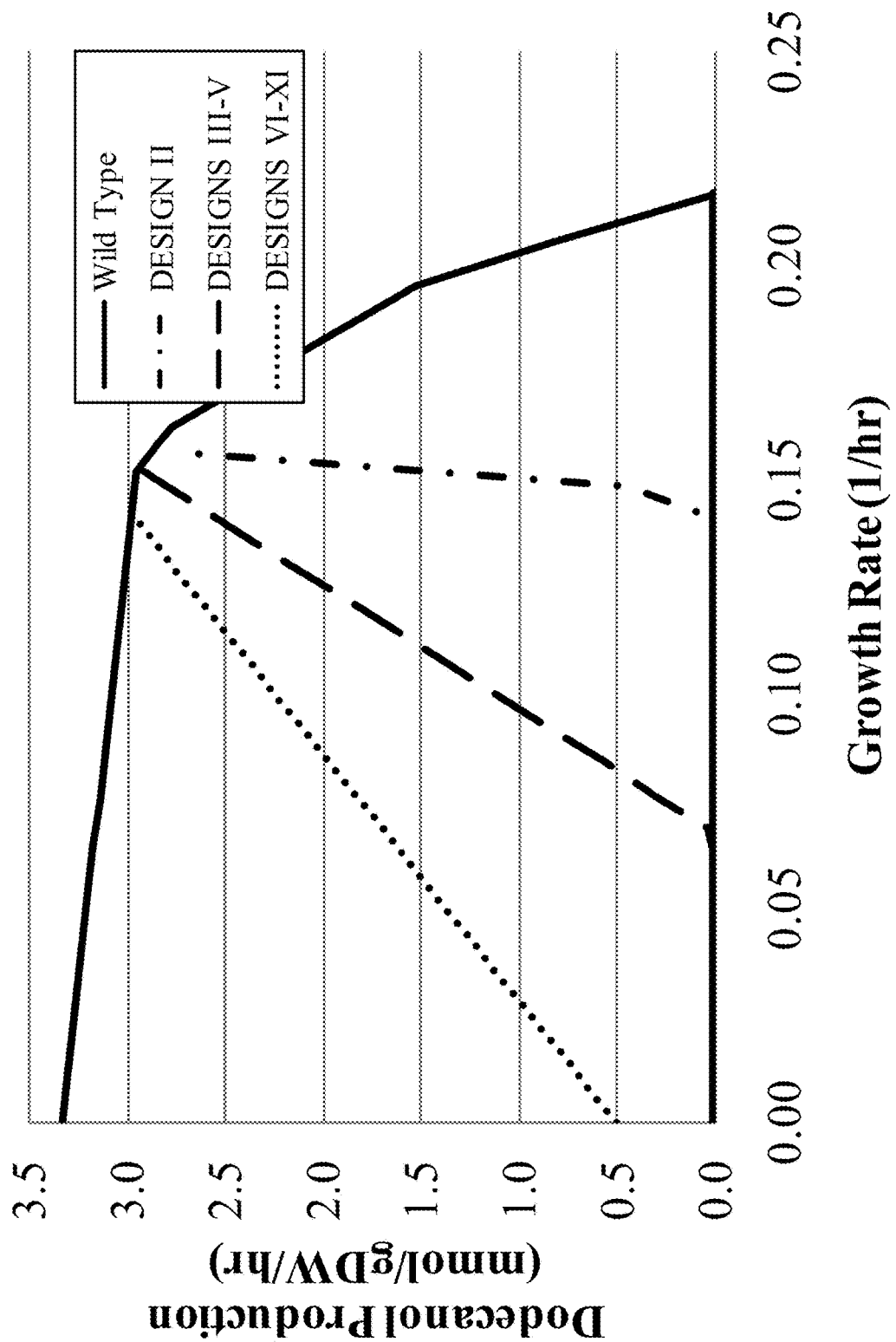
FIG. 4 shows the growth-coupled LCA production characteristics of strain designs II (alternating dotted and dashed), III-V (dashed), and VI-XI (dotted) compared with those of wild-type E. coli (black). A glucose uptake rate of 10 mmol/gDW/hr is assumed.

All growth coupled designs in this document build upon Design I which calls for the joint disruption of acetylaldehyde-CoA dehydrogenase (ADHEr) and lactate dehydrogenase (LDH_D) activities to reduce the formation of ethanol and lactate, respectively. A dodecanol yield of 0.14 mol/mol glucose is predicted to be attained upon achieving a maximum growth rate of 0.20 l/hr (Design I, FIG. 3). Design II specifies the removal, attenuation, or absence of ADHEr, LDH_D, and pyruvate formate lyase (PFLi) and is predicted to result in a dodecanol yield of 0.28 mol/mol glucose at maximum growth as shown in FIG. 4. A tighter coupling of LCA production to growth is attained by the further disruption of fumarate reductase (FRD2), fumarase (FUM), or malate dehydrogenase (MDH) activity as indicated by the solution boundary of Designs III-V in FIG. 4. An even tighter coupling of production to growth is attained by the further disruption of glutamate dehydrogenase (GLUDy) or NADP transhydrogenase (THD2) activity as shown in solution boundary of Designs VI-XI in FIG. 4. Designs VI-XI actually require a non-insignificant yield of LCA, specifically, 0.05 mol dodecanol/mol glucose, to enable a minimal amount of cell growth.

Figure 5:
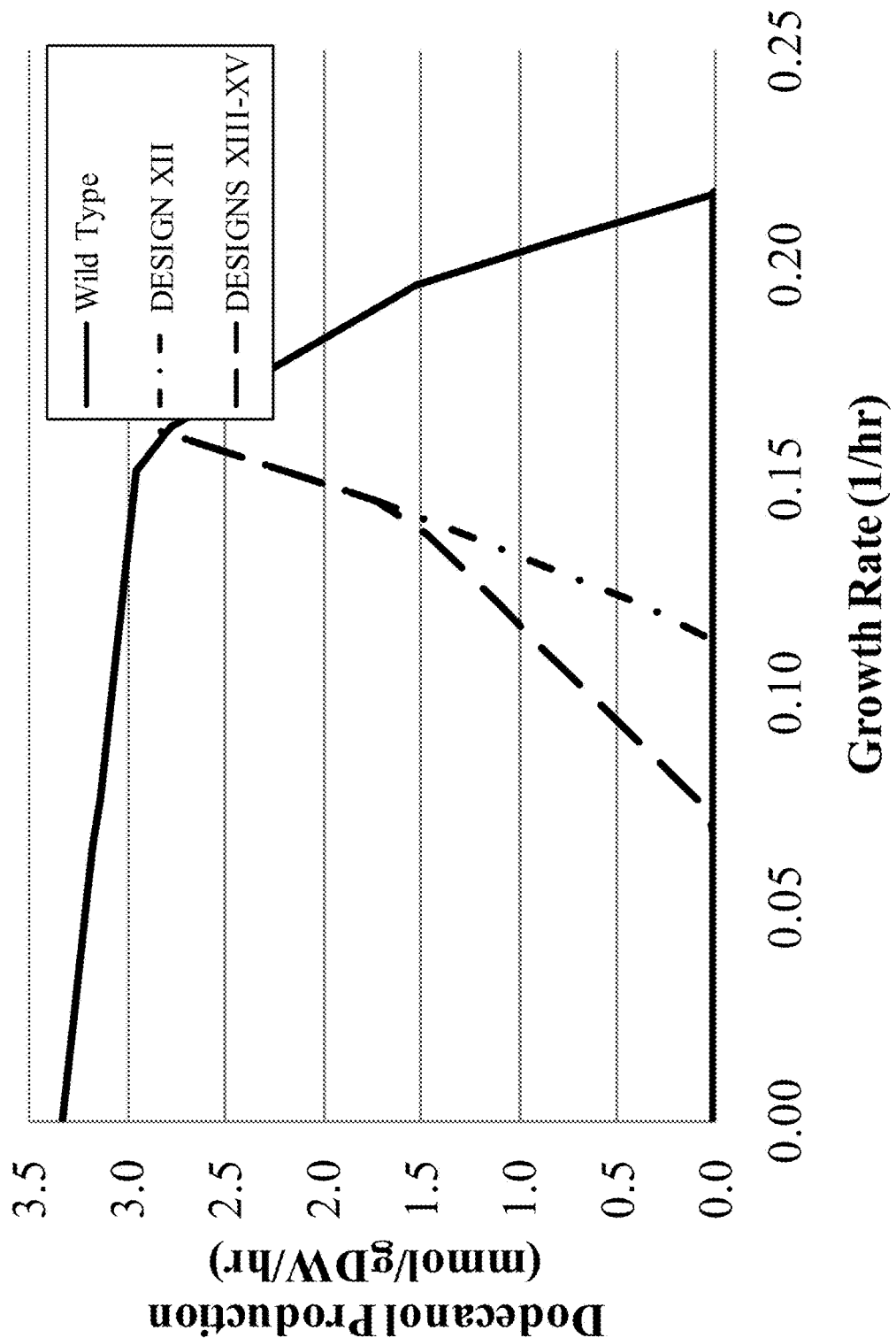
FIG. 5 shows the growth-coupled LCA production characteristics of strain designs XII (alternating dotted and dashed) and XIII-XV (dashed) compared with those of wild-type E. coli (black). A glucose uptake rate of 10 mmol/gDW/hr is assumed.
Figure 6:
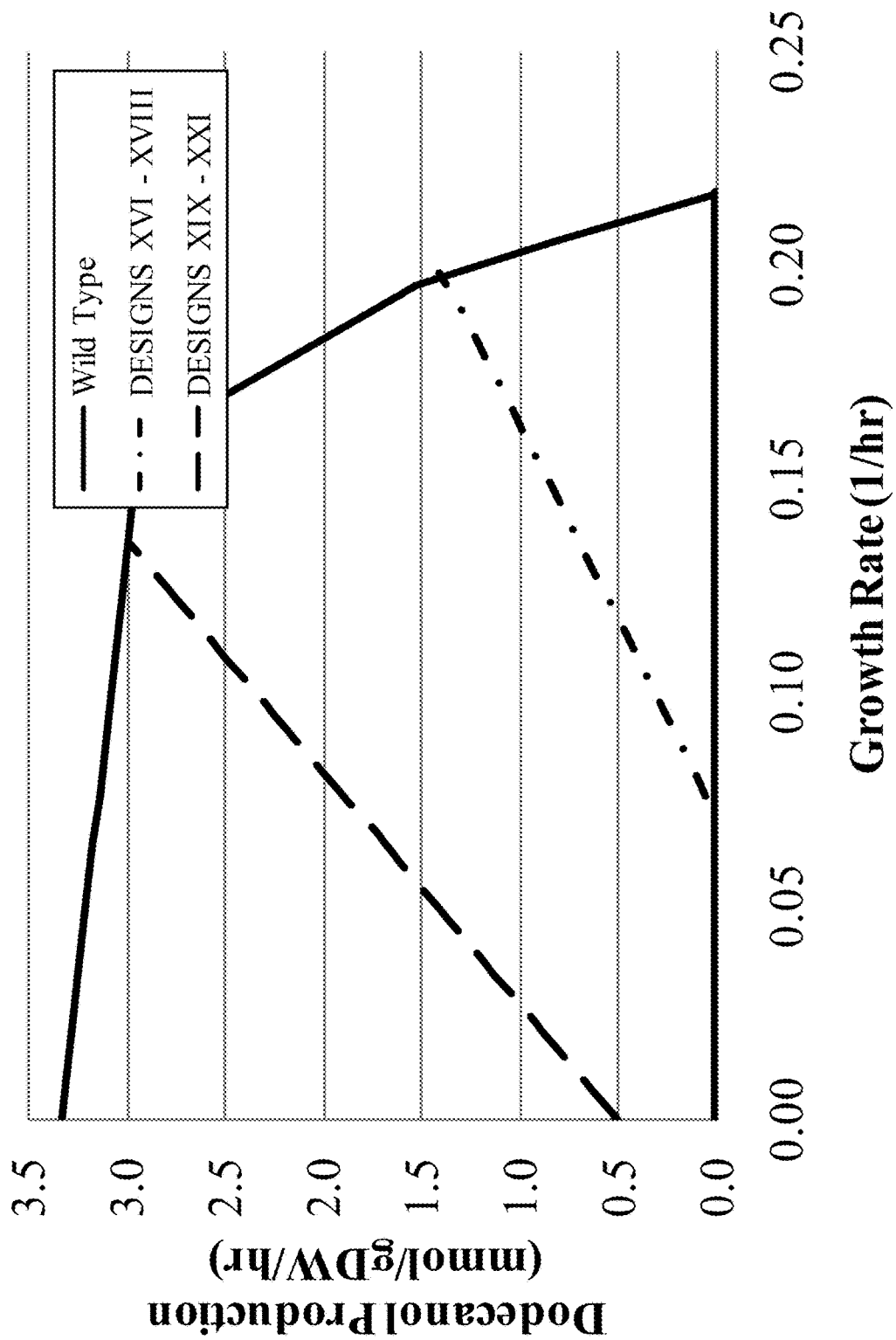
FIG. 6 shows the growth-coupled LCA production characteristics of strain designs XVI-XVIII (alternating dotted and dashed) and XIX-XXI (dashed) compared with those of wild-type E. coli (black). A glucose uptake rate of 10 mmol/gDW/hr is assumed.

Design XII calls for the disruption of phosphotransacetylase (PTAr) and/or acetate kinase (ACKr) activity in addition to ADHEr and LDH_D to prevent or lessen the production of acetate, ethanol, and lactate, respectively. A dodecanol yield of 0.28 mol/mol is required to attain a maximum growth rate of 0.16 l/hr assuming a glucose uptake rate of 10 mmol/gDW/hr as shown in FIG. 5. A tighter coupling of LCA production to growth is attained by the further disruption of FRD2, FUM, or MDH as indicated by the solution boundary of Designs XIII-XV. Designs XVI-XVIII specify that the disruption of FRD2, FUM, or MDH activity in addition to ADHEr and LDH_D results in a tighter coupling of dodecanol production to cell growth as compared to Design I as shown in FIG. 6. Further disrupting ATP synthase activity in designs XIX-XXI is predicted to result in a dodecanol yield of 0.30 mol/mol at a maximum growth rate of 0.13 l/hr as shown in FIG. 6. The disruption of this activity forces the organism to rely on the MI-LCA pathway for energy generation. Accordingly, a minimum dodecanol yield of 0.05 mol/mol is required for any growth to be attained assuming that the organism lacks the activities listed in Designs XIX-XXI.

Figure 7:
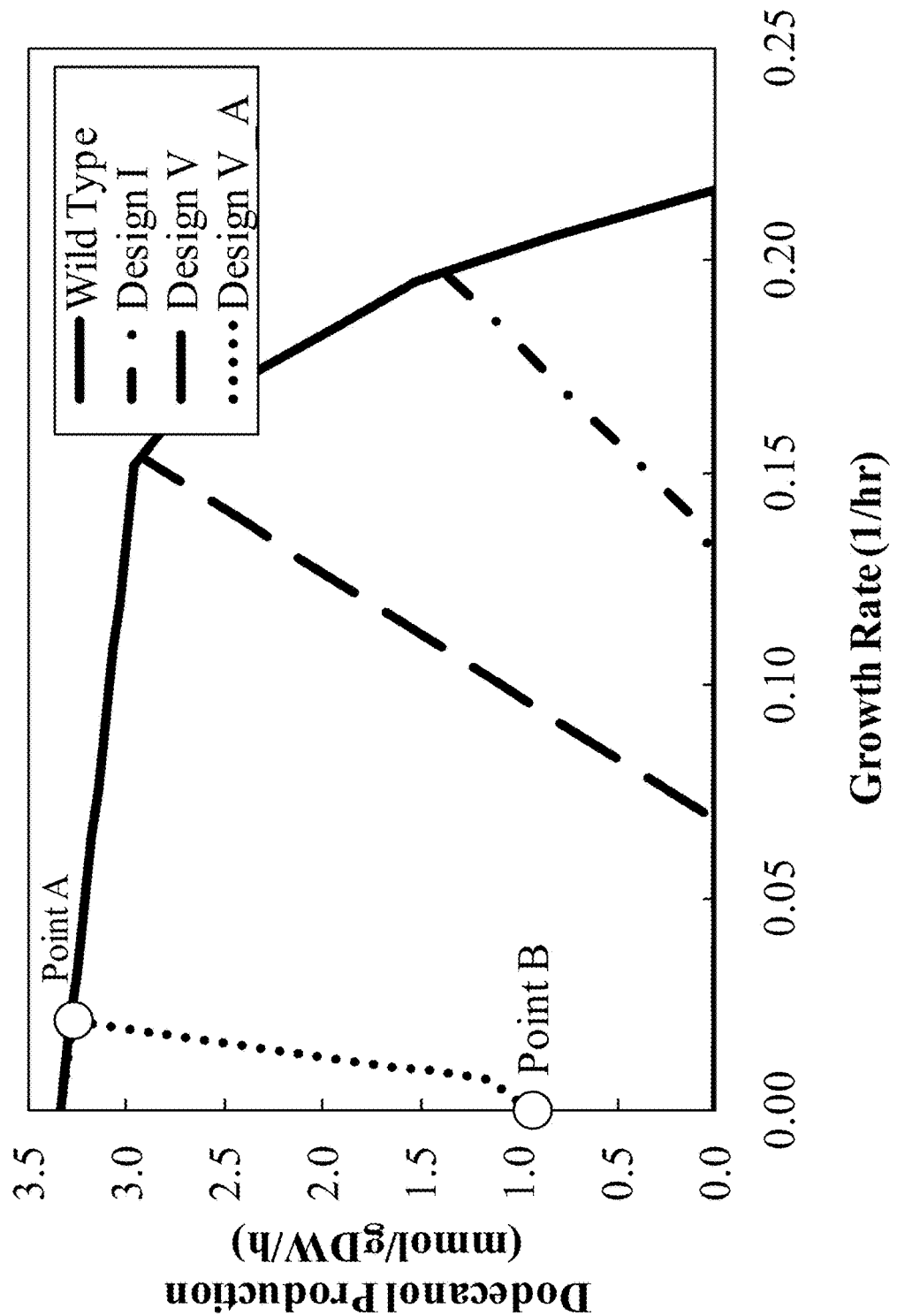
FIG. 7 shows the growth-coupled LCA production characteristics of Designs I (alternating dotted and dashed), V (dashed), and V_A (dotted) compared with those of wild-type E. coli (black). A glucose uptake rate of 10 mmol/gDW/hr is assumed. Point A refers to the dodecanol production rate at maximum growth of a strain engineered according to design V_A and point B refers to the minimal dodecanol production rate required for growth.

It is understood that the disruption of certain activities in addition to those listed by Designs I-XXI can lead to even higher production yields as illustrated in the following examples. Design V_A involves disruption of Acetaldehyde-CoA dehydrogenase (ADHEr), lactate dehydrogenase (LDH_D), malate dehydrogenase (MDH), pyruvate formate lyase (PFLi), L-aspartase (ASPT), pyruvate kinase (PYK), glucose 6-phosphate dehydrogenase (G6PDHy), and dihydroxyacetone phosphotransferase (DHAPT). Upon addition of the MI-LCA pathway, an engineered strain containing disruptions in these activities is predicted to have a growth-coupled dodecanol yield of 0.327 mol/mol glucose at the maximum growth rate of 0.02 l/hr (FIG. 7, point A). This corresponds to 98% of the maximum theoretical yield of 0.333 mol dodecanol/mol glucose. The maximum growth rate of such a strain is predicted to be approximately 10% of the wide type strain while a minimum dodecanol yield of 0.09 mol/mol is required for growth (FIG. 7, point B). A recombinant strain containing reduced activity of these functionalities can be constructed in a single step or in subsequent steps by, for example, disrupting 2-3 activities each step. For example, one can engineer *E. coli* for growth coupled LCA production by first removing genes encoding ADHEr and LDH_D activities resulting in Design I. Design V is then constructed by further deleting genes responsible for MDH and PFLi activities. Design V_A is then constructed by deleting genes encoding ASPT, PYK, G6PDHy, and DHAPT activities. Finally, note that several activities (i.e., 6-phosphogluconolactonase (PGL), phosphogluconate dehydratase (PGDHY), or 2-dehydro-3-deoxy-phosphogluconate aldolase (EDA)) can replace G6PDHy for disruption and yield the same characteristics as Design V_A.

Figure 8:
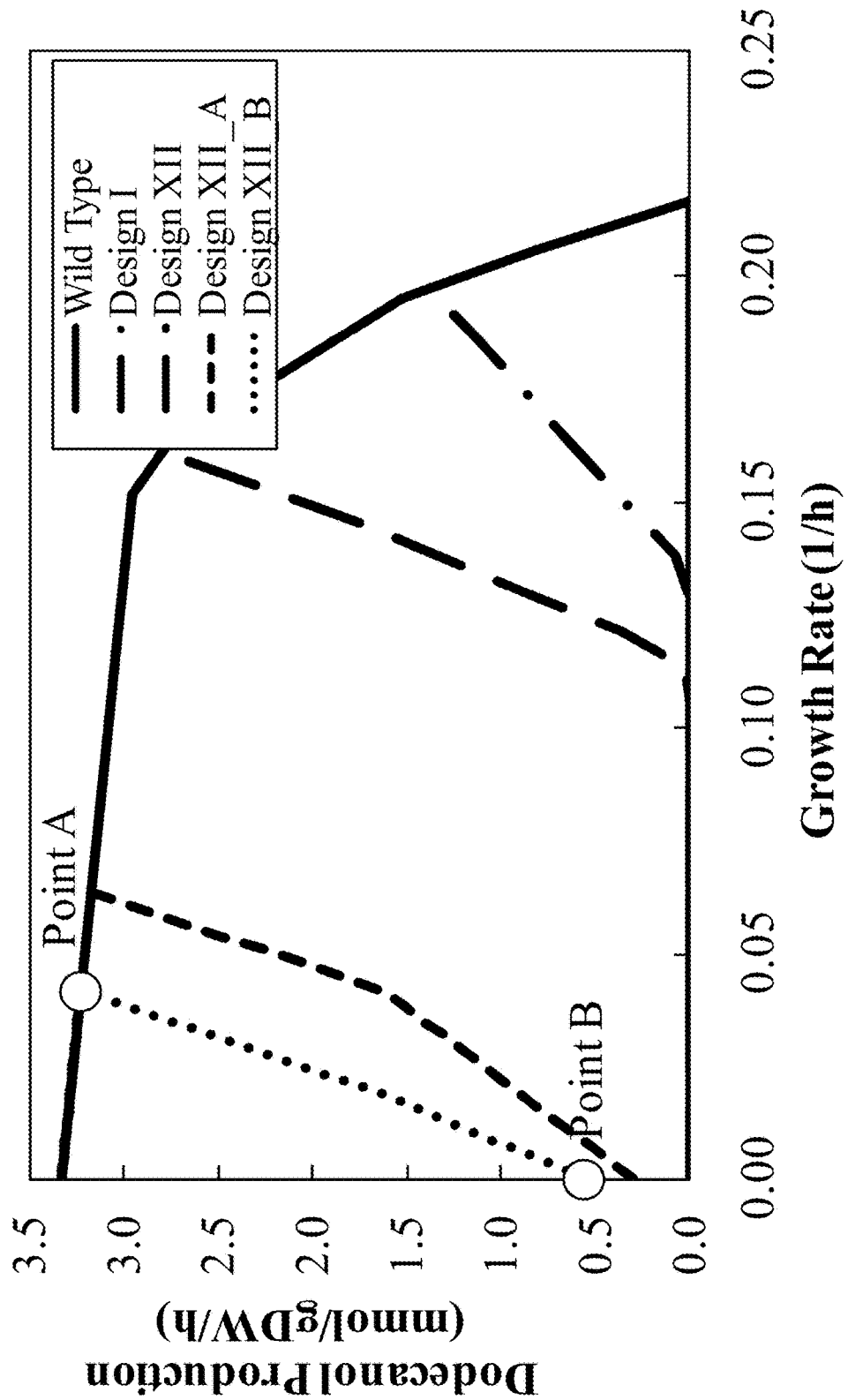
FIG. 8 shows the growth-coupled LCA production characteristics of Designs I (alternating dotted and dashed, XII (long dashed), XII_A (short dashed), and XII_B (dotted) compared with those of wild-type E. coli (black). A glucose uptake rate of 10 mmol/gDW/hr is assumed. Point A refers to the dodecanol production rate at maximum growth of a strain engineered according to design XII_B and point B refers to the minimal dodecanol production rate required for growth.

Design XII_A involves disruption of Acetaldehyde-CoA dehydrogenase (ADHEr), lactate dehydrogenase (LDH_D), acetate kinase (ACKr) and/or phosphotransacetylase (PTAr), glutamate dehydrogenase (NADP) (GLUDy), phosphogluconate dehydrogenase (PGDH), and glucose-6-phosphate isomerase (PGI). Design XII_B involves disruption of Acetaldehyde-CoA dehydrogenase (ADHEr), lactate dehydrogenase (LDH_D), acetate kinase (ACKr) and/or phosphotransacetylase (PTAr), glutamate dehydrogenase (NADP) (GLUDy), phosphogluconate dehydrogenase (PGDH), glucose-6-phosphate isomerase (PGI), and D-glucose transport via PEP:Pyr PTS (GLCpts). Upon addition of the MI-LCA pathway, an engineered strain lacking the activities specified by Design XII_B is predicted to have a growth-coupled dodecanol yield of 0.322 mol/mol glucose at the maximum growth rate of 0.04 l/hr (FIG. 8, point A). This corresponds to 97% of the maximum theoretical yield of 0.333 mol dodecanol/mol glucose. The maximum growth rate of such a strain is predicted to be approximately 20% of the wild type strain while a minimum dodecanol yield of 0.05 mol/mol is required for growth (FIG. 8, point B). A recombinant strain containing reduced activity of these functionalities can be constructed in a single step or in subsequent steps by, for example, removing additional activities each step. For example, one can engineer *E. coli* for growth coupled LCA production by first removing genes encoding ADHEr and LDH_D activities resulting in Design I. Design XII is then constructed by further deleting genes encoding PTAr and/or ACKr activities. Design XII_A is then constructed by deleting the genes responsible for GLUDy, PGDH, and PGI activities. Finally, Design XII_B is constructed by further deleting a gene essential for GLCpts activity.

Accordingly, the invention also provides a non-naturally occurring microbial organism having a set of metabolic modifications coupling LCA production to growth of the organism, the set of metabolic modifications includes disruption of one or more genes selected from the set of genes encoding proteins that include an acetylaldehyde-CoA dehydrogenase and a lactate dehydrogenase.

The present invention also provides a strain lacking the activities listed for Design I above that further lack at least one of the following activities: pyruvate formate lyase (PFLi), phosphotransacetylase (PTAr), acetate kinase (ACKr), fumarate reductase (FRD2), fumarase (FUM), or malate dehydrogenase (MDH) as exemplified by Designs II, XII, XVI, XVII, and XVIII.

In further embodiments, the invention provides a strain lacking the activities listed for Design II above and further lacks at least one of the following activities: fumarate reductase (FRD2), fumarase (FUM), or malate dehydrogenase (MDH) as exemplified by Designs III, IV, and V.

In still further embodiments, the invention provides strains lacking the activities listed for Designs III, IV, or V, above and further lack glutamate dehydrogenase (GLUDy) activity as exemplified by Designs VI, VII, and VIII.

The invention also provides strains lacking the activities listed for designs III, IV, or V, above and further lack NAD(P) transhydrogenase (THD2) activity as exemplified by Designs IX, X, and XI.

In yet further embodiments, the invention provides a strain lacking the activities listed for Design XII above and further lack at least one of the following activities: fumarate reductase (FRD2), fumarase (FUM), or malate dehydrogenase (MDH) as exemplified by Designs XIII, XIV, and XV.

Finally, the invention provides strains lacking the activities listed for designs XVI, XVII, and XVIII, above and further lack ATP synthase (ATPS4r) activity as exemplified by Designs XIX, XX, and XXI.

Herein below are described the pathways identified for increasing LCA production in *S. cerevisiae*. The OptKnock algorithm, described herein further below, identified designs based on a stoichiometric model of *Saccharomyces cerevisaie* metabolism. Assumptions include (i) a glucose uptake rate of 10 mmol/gdw/hr; (ii) anaerobic or microaerobic conditions; and (iii) a minimum non-growth associated maintenance requirement of 3 mmol/gdw/hr. Dodecanol, a $C_{12}$ molecule, was chosen as an exemplary long chain alcohol whose production can be coupled to growth following the teachings of this invention. Although glucose was assumed to be the growth substrate, it is understood that the methods are applicable to any substrate including glucose, sucrose, xylose, arabinose, or glycerol. Although the designs were identified using a metabolic model of *S. cerevisiae* metabolism the method of choosing the metabolic engineering pathways and also the designs themselves are applicable to any LCA-producing eukaryotic organism. Thus, the designs are essentially lists of enzymatic transformations whose activity must be either eliminated, attenuated, or initially absent from a microorganism to enable the production of long chain alcohols.

One criterion for prioritizing the final selection of pathways was the yield of dodecanol. To examine this, production cones were constructed for each set of pathways by first maximizing and, subsequently minimizing the dodecanol yields at different rates of biomass formation. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the dodecanol in the calculated range, including the lowest amount at the bottommost point of the vertical line. Such designs were given a lower priority.

The organisms of the present invention can be cultured in a substantially anaerobic culture medium or a microaerobic culture medium as detailed herein below further. Such organisms have one or more gene disruptions which may include complete deletion in some embodiments, or disruption by removal or changes in functional portions encoded by fragments of the entire gene.

In some embodiments, the present invention provides non-naturally occurring eukaryotic microbial organisms that produce LCAs in the cytosol. Note that cytosol herein refers to any compartment outside the mitochondrion. In such embodiments, one or more gene disruptions in the eukaryotic organism encoding an enzyme include, for example, a cytosolic pyruvate decarboxylase, a mitochondrial pyruvate dehydrogenase, a cytosolic ethanol-specific alcohol dehydrogenase and a mitochondrial ethanol-specific alcohol dehydrogenase. Exemplary genes endocing these enzymes include, for example, YLR044C, YLR134W, YGR087C, PDC3, YNL071W, YER178W, YBR221C, YGR193C, YFLO18C, YBR145W, YGL256W, YOL086C, YMR303, YMR083W, YPL088W, YAL061W, YMR318C, YCR105W, and YDL168W.

Other gene disruptions encoding an enzyme include, for example, a cytosolic malate dehydrogenase, a glycerol-3-phospate dehydrogenase shuttle, an external NADH dehydrogenase, and an internal mitochondrial NADH dehydrogenase can also be effected. Exemplary genes of the later include, for example, YOL126C, YDL022W, YOL059W, YIL155C, YMR145C, YDL085W, and YML120C.

These organisms can also include an exogenous nucleic acid encoding an enzyme in the cytosol including, for example, an acetyl-CoA synthetase (AMP-forming), an ADP-dependent acetate-CoA ligase, an acylating acetaldehyde dehydrogenase, a pyruvate dehydrogenase, a pyruvate: NADP oxidoreductase, and a pyruvate formate lyase, or their corresponding gene regulatory regions. An exogenous nucleic acid encoding a cytosolic transhydrogenase or its gene regulatory region can also be incorporated. In some embodiments these gene products may be natively expressed in the cytosol, while in other embodiments, they may be overexpressed by, for example, adding copies of the gene from the same source or from other organisms, or by introducing or changing gene regulatory regions. Such gene regulatory regions include, for example, alternate promoters, inducible promoters, variant promoters or enhancers to enhance gene expression. Functional disruption of negative regulatory elements such as repressors and/or silencers also can be employed to enhance gene expression. Similar modifications can be made to translation regulatory regions to enhance polypeptide synthesis and include, for example, substitution of a ribosome binding site with an optimal or consensus sequence and/or removing secondary structures.

These organisms maximize the availability of acetyl CoA, ATP and reducing equivalents (NADH) for dodecanol production. Acetyl CoA is the primary carbon precursor for the production of LCA via the proposed MI-LCA route. All the reactions enabling the formation of dodecanol via the malonyl-CoA independent pathway are operational in the cytosol. Specifically, ketoacyl-CoA thiolase, 3-hydroxyacyl-CoA dehydrogenase, enoyl-CoA hydratase, and enoyl-CoA reductase function in the appropriate direction to form acyl CoA which is then reduced to fatty aldehyde and dodecanol via acyl CoA reductase and alcohol dehydrogenase.

Introduction of the MI-LCA pathway in the cytosol prevented any flux through the native pyruvate dehydrogenase in silico. Under anaerobic conditions and in conditions where glucose concentrations are high in the medium, the capacity of this mitochondrial enzyme is very limited and there is no significant flux through it. However, in some embodiments, this enzyme can be deleted or attenuated to increase LCA production.

Figure 9A:
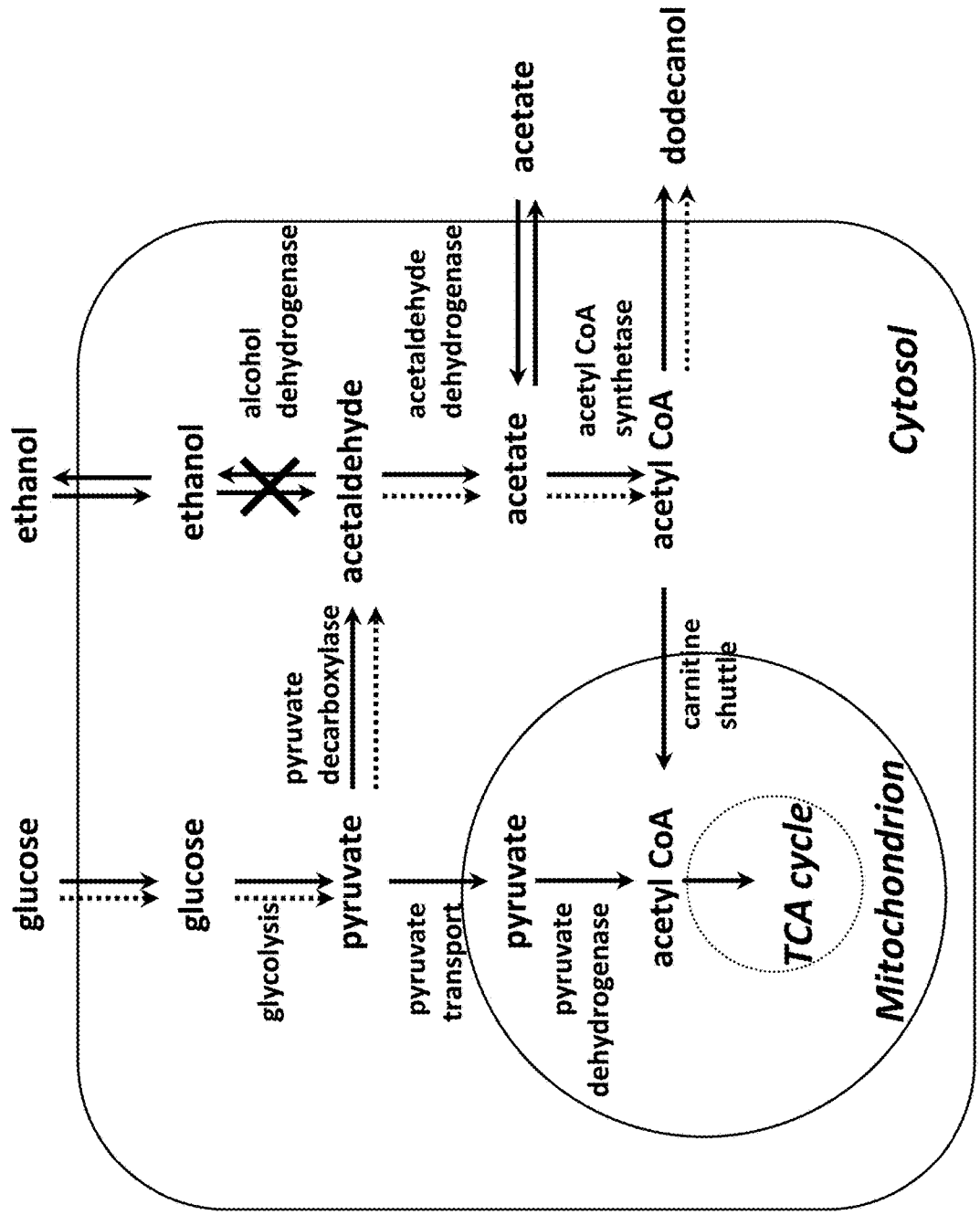
FIG. 9a shows the formation of dodecanol in the cytosol by relying on the AMP-forming acetyl CoA synthetase for the formation of acetyl CoA for dodecanol production. The dotted arrows depict the flow of the majority of the carbon flux in this production scenario.

In one embodiment, LCA production in the cytosol uses the AMP-forming acetyl-CoA synthetase. Dodecanol production in the cytosol relies on the native cell machinery to provide the precursors needed in LCA production. A majority of the pyruvate flux generated by glycolysis is channeled into the formation of acetyl CoA via the pyruvate dehydrogenase bypass comprised of the pyruvate decarboxylase, the acetaldehyde dehydrogenase and the AMP-forming acetyl-CoA synthetase (FIG. 9a). This bypass is reported to have significant flux through it even under aerobic conditions at high concentrations of glucose (Pronk et al., Yeast 12:1607-1633 (1996)).

The last step of the bypass that converts acetate into acetyl-CoA is catalyzed by acetyl-CoA synthetase, encoded by the ACS1 and ACS2 genes. Since ACS2 is constitutively expressed on glucose and is present in cytosol among other compartments, in some embodiments the non-naturally occurring eukarotyic organism is engineered to overexpress ACS2. In other embodiments the ACS2 gene is replaced with a mutant ACS from *Salmonellas enterica* (Genbank id NP_807785.1) that is not subject to post-translational modification and has higher activity in *S. cerevisiae* as compared to ACS1 or ACS2 (Shiba et al., *Metab Eng*. 9:160-168 (2007)).

The AMP-generating acetyl CoA synthetase uses two ATP equivalents for the conversion of each molecule of acetate into acetyl CoA (CoA+acetate+ATP→acetyl-CoA+PPi+AMP). Under anaerobic conditions, when energy is available only through substrate-level phosphorylation, the production of dodecanol via the AMP-forming acetyl CoA synthetase is not energetically favorable. Therefore, a small amount of oxygen is made available to the cell to fulfill its energetic requirements, simultaneously increasing the conversion of acetate into acetyl CoA.

Figure 9B:
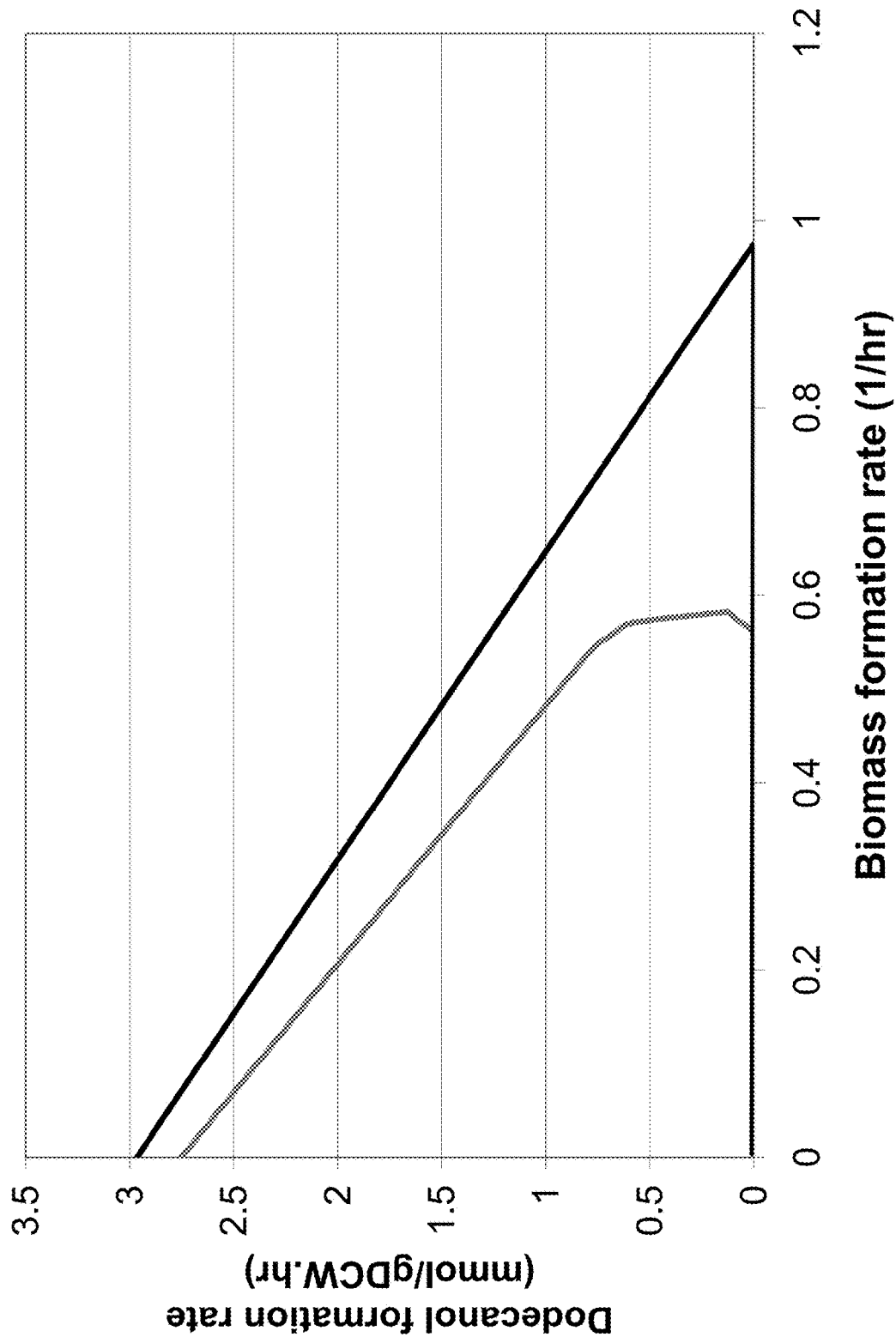
FIG. 9b shows the growth-coupled production envelopes for the production of dodecanol in S. cerevisiae in the scenario where acetyl CoA synthetase is used for acetyl CoA production in the cytosol. The black curve shows the production envelope for the wild-type network under aerobic conditions, and the dark gray curve shows the growth-coupled production characteristics for the mutant network. A glucose uptake rate of 10 mmol/gDCW·hr is assumed.

The production of dodecanol can be improved by disruption of ethanol-specific alcohol dehydrogenases to prevent acetyl-CoA and NADH from being used for ethanol production. Additionally, the production of LCA benefits from preventing NADH from being used in the respiratory electron-transport chain. Thus, disruptions in the internal mitochondrial NADH dehydrogenase, the glycerol-3-phosphate dehydrogenase shuttle (consisting of cytosolic NADH-linked glycerol-3-phosphate dehydrogenase and a membrane-bound glycerol-3-phosphate:ubiquinone oxidoreductase) (Bakker et al., *FEMS Microbiol*. Rev. 25:15-37 (2001)) and the external NADH dehydrogenase are introduced in some embodiments. Further, cytosolic malate dehydrogenase that can potentially draw NADH away from dodecanol production is also disrupted. A growth-coupled production envelope after imposing these disruptions is shown in dark gray in FIG. 9b and compared with the dodecanol production characteristics under aerobic conditions.

Figure 10A:
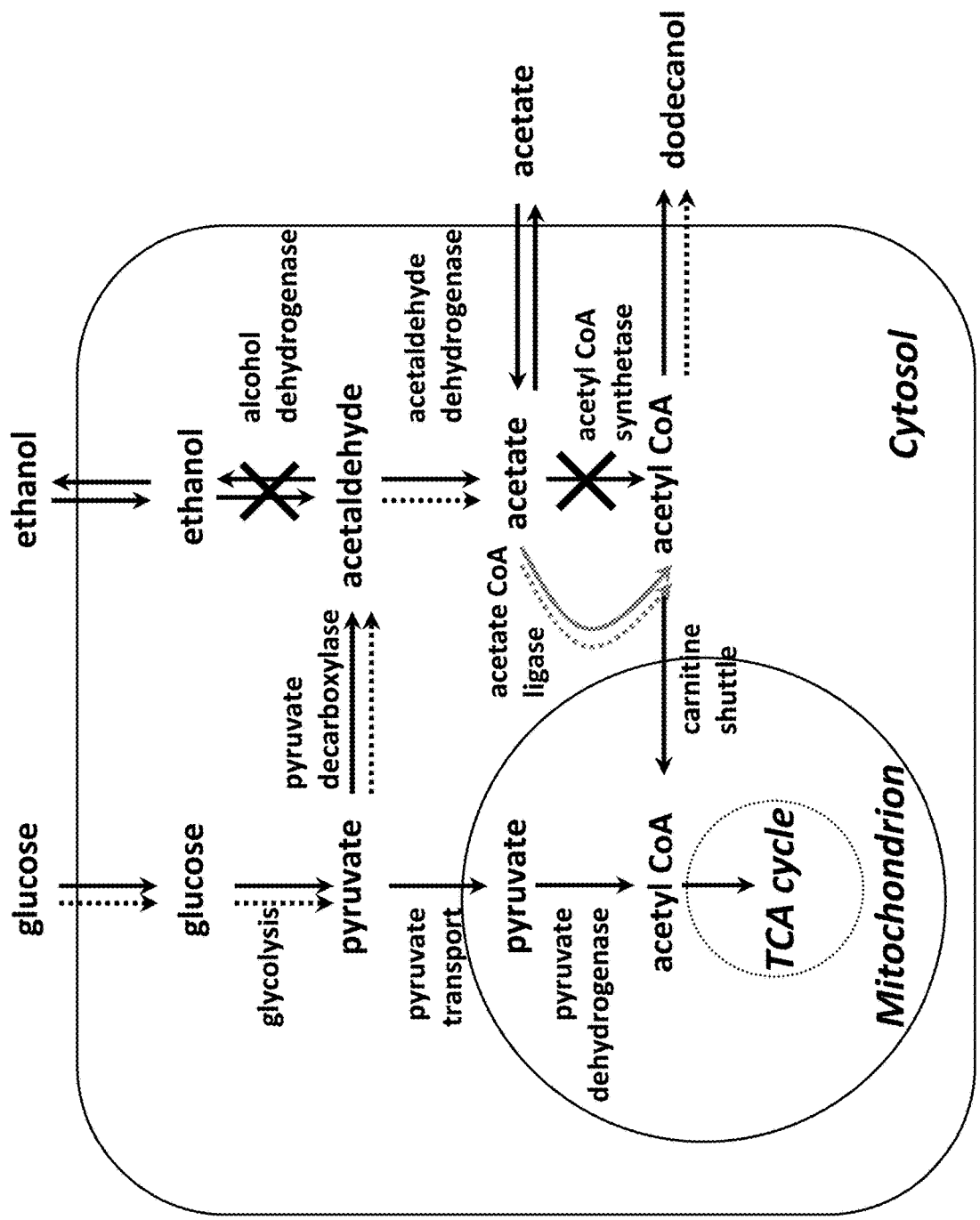
FIG. 10a shows the formation of dodecanol in the cytosol by relying on the ADP-forming acetate CoA ligase for the formation of acetyl CoA for dodecanol production. The gray arrow represents the addition of a heterologous enzyme. The dotted arrows depict the flow of the majority of the carbon flux in this production scenario.
Figure 10B:
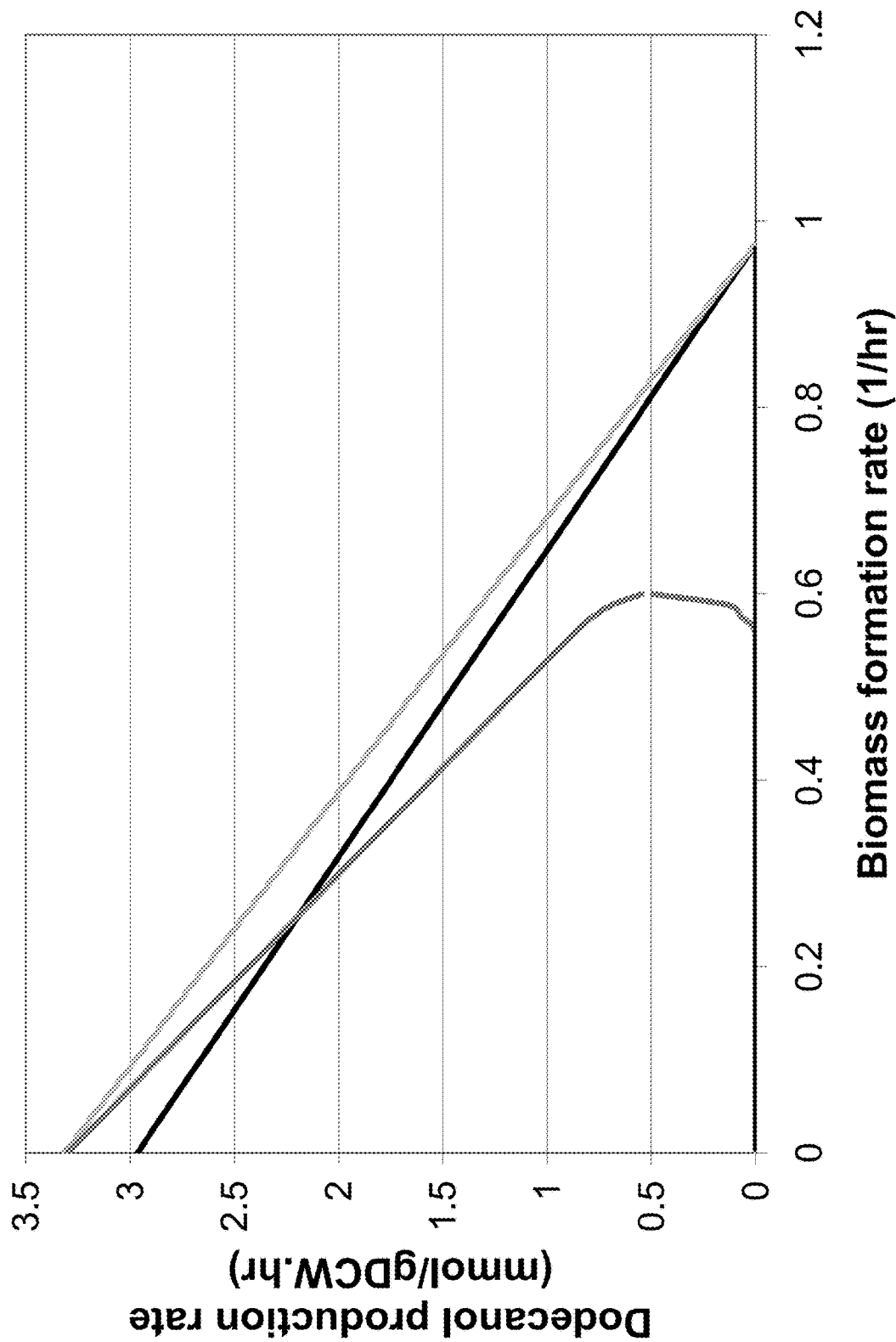
FIG. 10b shows the growth-coupled production envelopes for the production of dodecanol in S. cerevisiae in the scenario where acetate CoA ligase is employed for acetyl-CoA production in the cytosol. The black curve shows the production envelope for the wild-type network under aerobic conditions. The light gray curve shows the increase in feasible space after acetate CoA ligase is added to the network and the dark gray curve shows the growth-coupled production characteristics for the mutant network in the presence of oxygen. A glucose uptake rate of 10 mmol/gDCW·hr is assumed.

In some embodiments, the non-naturally occurring eukaryotic organism incorporates an exogenous gene encoding an ADP-forming acetate CoA ligase. In this embodiment, the AMP-forming acetyl CoA synthetase in the cytosol is replaced by the ADP-forming acetate CoA ligase (CoA+acetate+ATP→acetyl-CoA+Pi+ADP) (FIG. 10a). Exogenous genes to introduce acetate CoA ligase include, for example, acdA and acdB from *Pyrococcus furiosus* (Glasemacher et al., *Eur. J. Biochem*. 244:561-567 (1997)) (Mai and Adams, *J. Bacteriol*. 178: 5897-5903 (1996)). The introduction of this enzyme that uses one equivalent of ATP for formation of each molecule of acetyl CoA (as opposed to 2 ATP equivalents) allows the production of dodecanol to be energetically neutral. In this embodiment, a small amount of oxygen or other electron acceptor respiration is used to generate energy to support growth. Such small amounts of oxygen are referred to as microaerobic conditions, as described further below. In some embodiments, the ethanol-specific alcohol dehydrogenases is disrupted to prevent ethanol formation. In embodiments incorporating CoA ligase, one or more of the following knockouts can be introduced for LCA production: cytosolic malate dehydrogenase, glycerol-3-phospate dehydrogenase shuttle, the external NADH dehydrogenase, and the internal mitochondrial NADH dehydrogenase. The growth-coupled production after imposition of these disruptions is shown in FIG. 10b in dark gray. The black curve shows the production envelope for the wild-type strain under aerobic conditions and the light gray curve shows the envelope when the network is augmented with acetate-CoA ligase. Note the increase in the maximum theoretical yield of dodecanol after introduction of this enzyme.

Figure 11A:
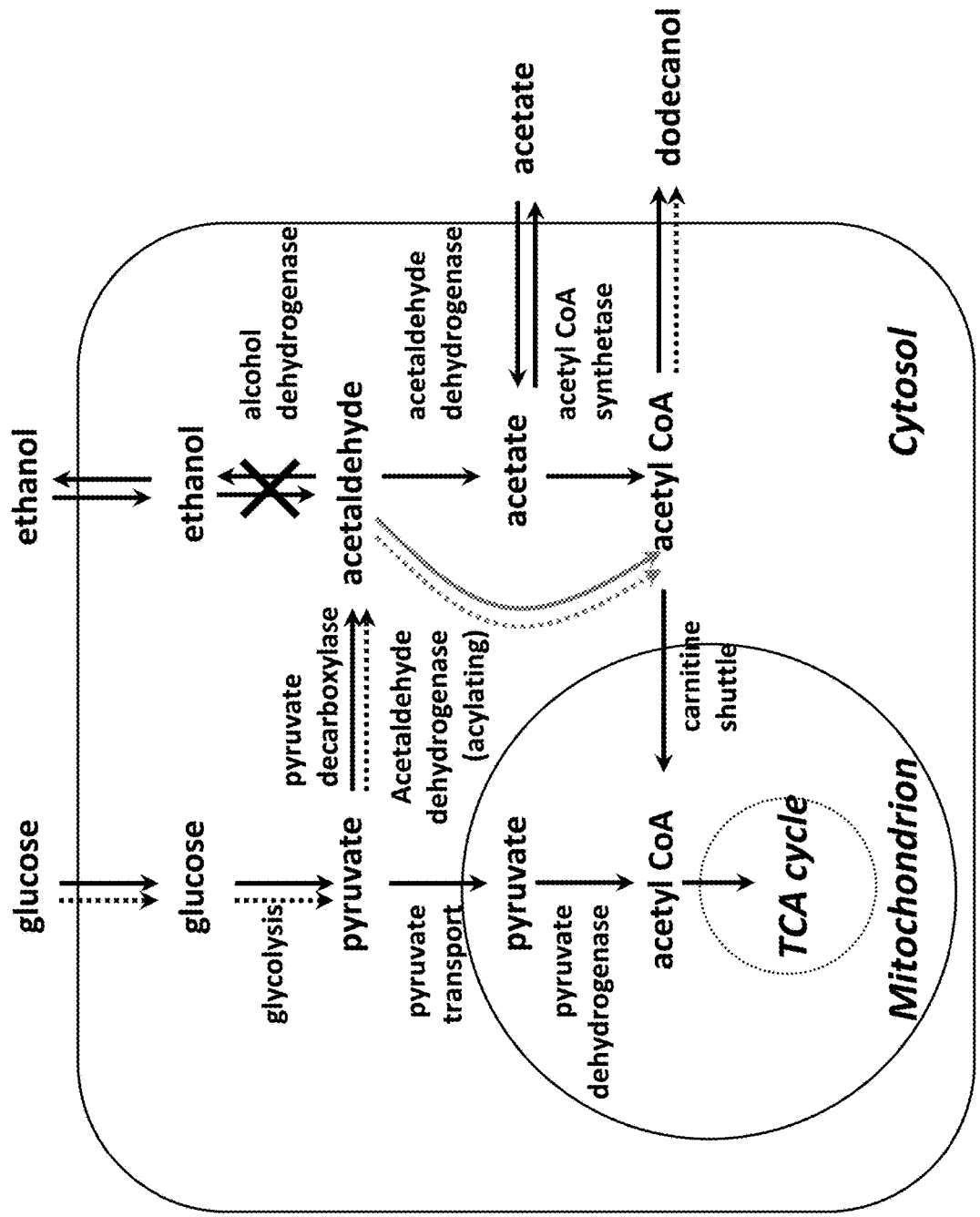
FIG. 11a shows the formation of dodecanol in the cytosol by relying on the acylating acetaldehyde dehydrogenase for the formation of acetyl CoA for dodecanol production. The gray arrow shows a heterologous enzyme. The dotted arrows depict the flow of the majority of the carbon flux in this production scenario.

In some embodiments, the non-naturally occurring eukaryotic organism incorporates an exogenous gene encoding an acylating acetaldehyde dehydrogenase. Improvement in the energetics of the dodecanol process can be accomplished by using the acylating acetaldehyde dehydrogenase (acetaldehyde+CoA+NAD→acetyl-CoA+NADH) for the conversion of acetaldehyde into acetyl CoA (FIG. 11a). The benefits of using this enzyme are that (i) no energy is expended for production of acetyl CoA, and (ii) one molecule of NADH is formed for every molecule of acetyl CoA formed. Thus, the reducing equivalents needed for the production of acetyl CoA can also be generated. The introduction of this enzyme allows production of LCA under anaerobic conditions.

Acylating acetaldehyde dehydrogenase has been reported in several bacteria, including Acetobacterium woodii (Mai and Adams, *J. Bacteriol.* 178:5897-5903 (1996)), *Clostridium kluyveri* (Seedorf et al., *Proc. Natl. Acad. Sci. U. S. A* 105:2128-2133 (2008); Smith and Kaplan, Arch. Biochem. Biophys. 203:663-675(1980)), *Clostridium beijerinckii* (Yan et al., *Appl. Environ. Microbiol* 56:2591-2599 (1990)), and in species of *Pseudomonas* such as strain CF600 (Lei et al., *Biochemistry* 47:6870-6882 (2008); Manjasetty et al., *Acta Crystallogr. D. Biol. Crystallogr.* 57:582-585 (2001)). The Genbank ids of genes are shown in Table 5 below.

TABLE 5

| Ald | YP_001394464.1 | *Clostridium kluyveri* |
|---|---|---|
| dmpF | CAA43226.1 | *Pseudomonas* sp. CF600 |
| bphG | BAA03892.1 | *Pseudomonas* sp |
| mhpD | NP_414884.1 | *Escherichia coli* K12 MG1655 |

In some embodiments each of the strains above can be supplemented with additional disruptions. Alternatively, some other enzymes not known to possess significant activity under the growth conditions can become active due to adaptive evolution or random mutagenesis and can also be disrupted.

Figure 11B:
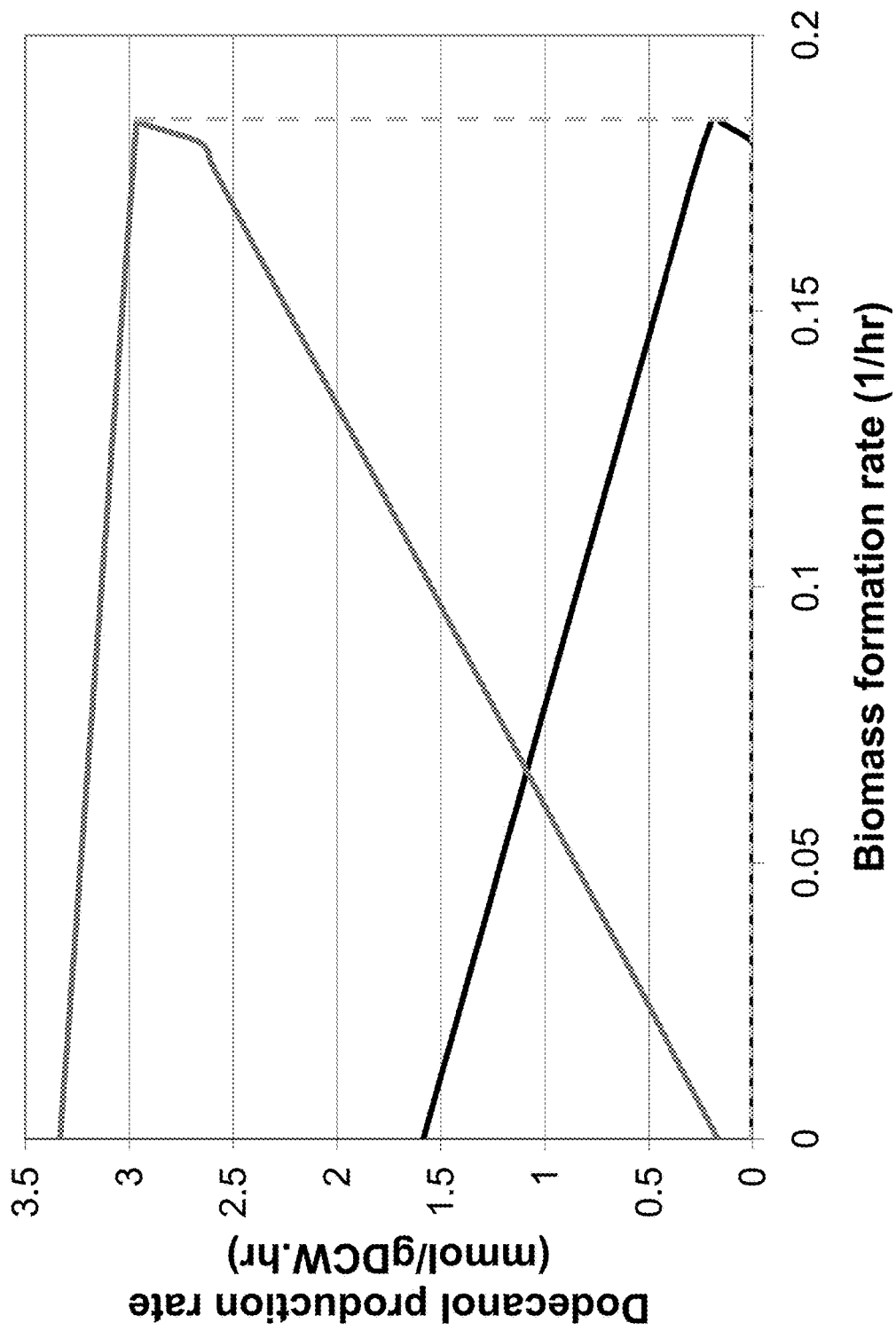
FIG. 11b shows the growth-coupled production envelopes for the anaerobic production of dodecanol in S. cerevisiae. The black curve shows the production capabilities for the wild-type network, the light gray dotted curve shows the production characteristics when acylating acetaldehyde dehydrogenase is added to the network and the dark gray curve shows the growth-coupling when alcohol dehydrogenase is deleted from the augmented network. Note the increase in the theoretical maximum when acylating acetaldehyde dehydrogenase is functional. A glucose uptake rate of 10 mmol/gDCW·hr is assumed.

The anaerobic growth-coupled production of dodecanol (or any LCA) can be accomplished by disrupting ethanol-specific alcohol dehydrogenase activity. The introduction of an acylating acetaldehyde dehydrogenase, with its favorable energetics, prevents or reduces carbon flux through the native acetaldehyde dehydrogenase and the acetyl-CoA synthetase. The production envelope is shown in FIG. 11b. The wild-type *S. cerevisiae* (black) network can form only small amounts of dodecanol as an byproduct of growth under anaerobic conditions. When the network is augmented with acylating dehydrogenase, there is an increase in the theoretical maximum yield in the network, but no growth-coupling is observed (dotted light gray curve). However, disruption of ethanol-specific alcohol dehydrogenase from the augmented network shows that dodecanol production is coupled to growth at the maximum feasible biomass in the network (dark gray curve).

Figure 12:
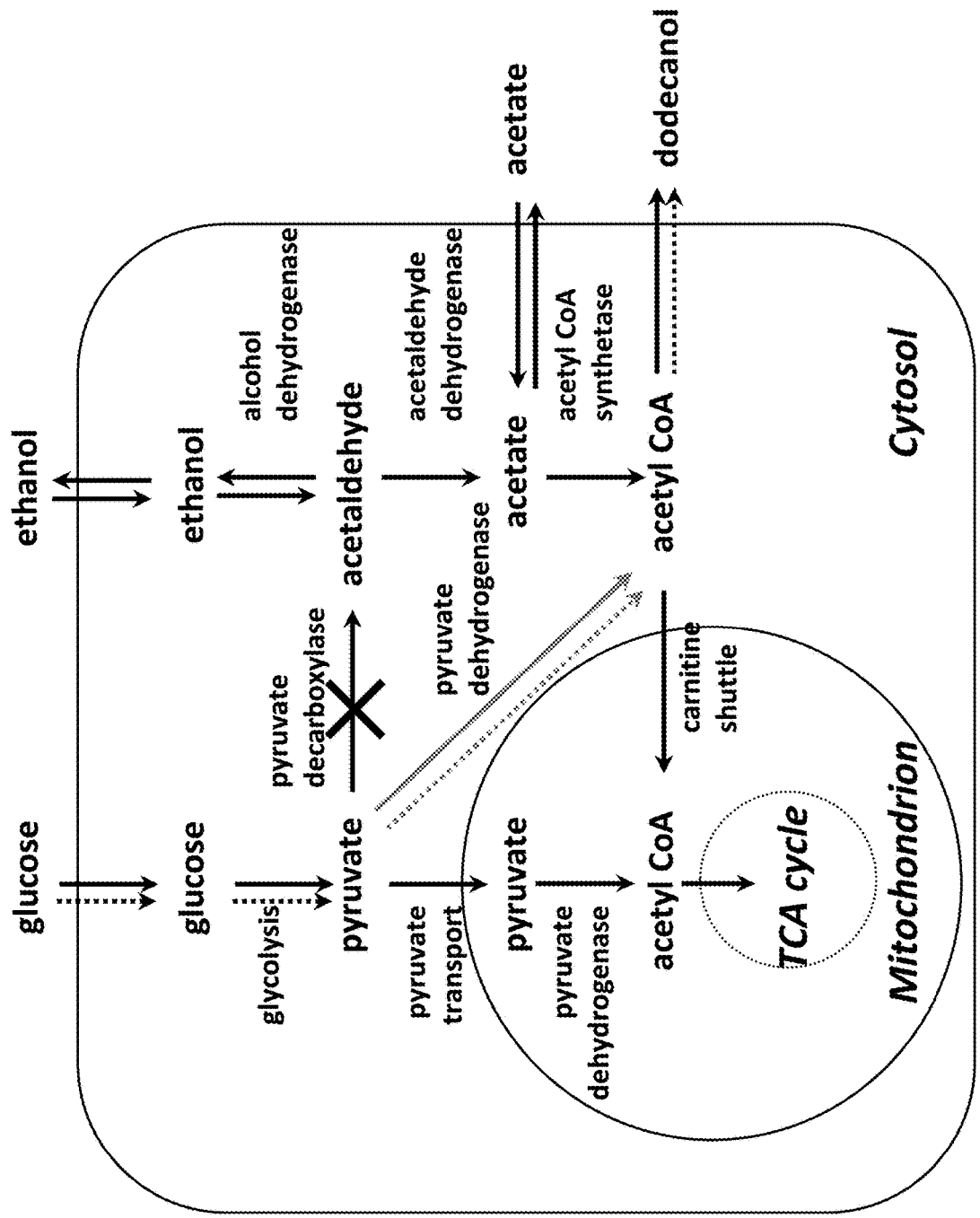
FIG. 12 shows the formation of dodecanol in the cytosol by relying on a cytosolic pyruvate dehydrogenase for acetyl CoA and NADH production. This can be accomplished by introducing a heterologous cytosolic enzyme (shown in gray) or by retargeting the native mitochondrial enzyme to the cytosol. The dotted arrows depict the flow of the majority of the carbon flux in this production scenario.

In some embodiments, the non-naturally occurring eukaryotic organism uses a cytosolic pyruvate dehydrogenase for dodecanol production. Cytosolic pyruvate dehydrogenase for generating the precursors for the MI-LCA pathway are shown in FIG. 12. In such embodiments, (i) pyruvate is directly converted into acetyl CoA in the cytosol without the expenditure of energy, and (ii) more reducing equivalents are available to the cell.

In some embodiments, the non-naturally occurring eukaryotic organism is engineered to retarget the native mitochondrial pyruvate dehydrogenase to the cytosol. In other embodiments, a heterologous cytosolic enzyme is introduced into the organism. The retargeting of an enzyme to a different compartment can be accomplished by changing the targeting sequence of the protein (van Loon and Young, *EMBO J* 5:161-165 (1986)). Disruption of the native pyruvate decarboxylase enables a majority of the carbon flux to be introduced into the cytosol for processing by cytosolic pyruvate dehydrogenase. This also allows the production of dodecanol under anaerobic conditions. The growth-coupled production envelope is similar to that depicted in FIG. 11b. Note that pyruvate decarboxylase is disrupted instead of alcohol dehydrogenase to achieve growth-coupling in the network.

Figure 13:
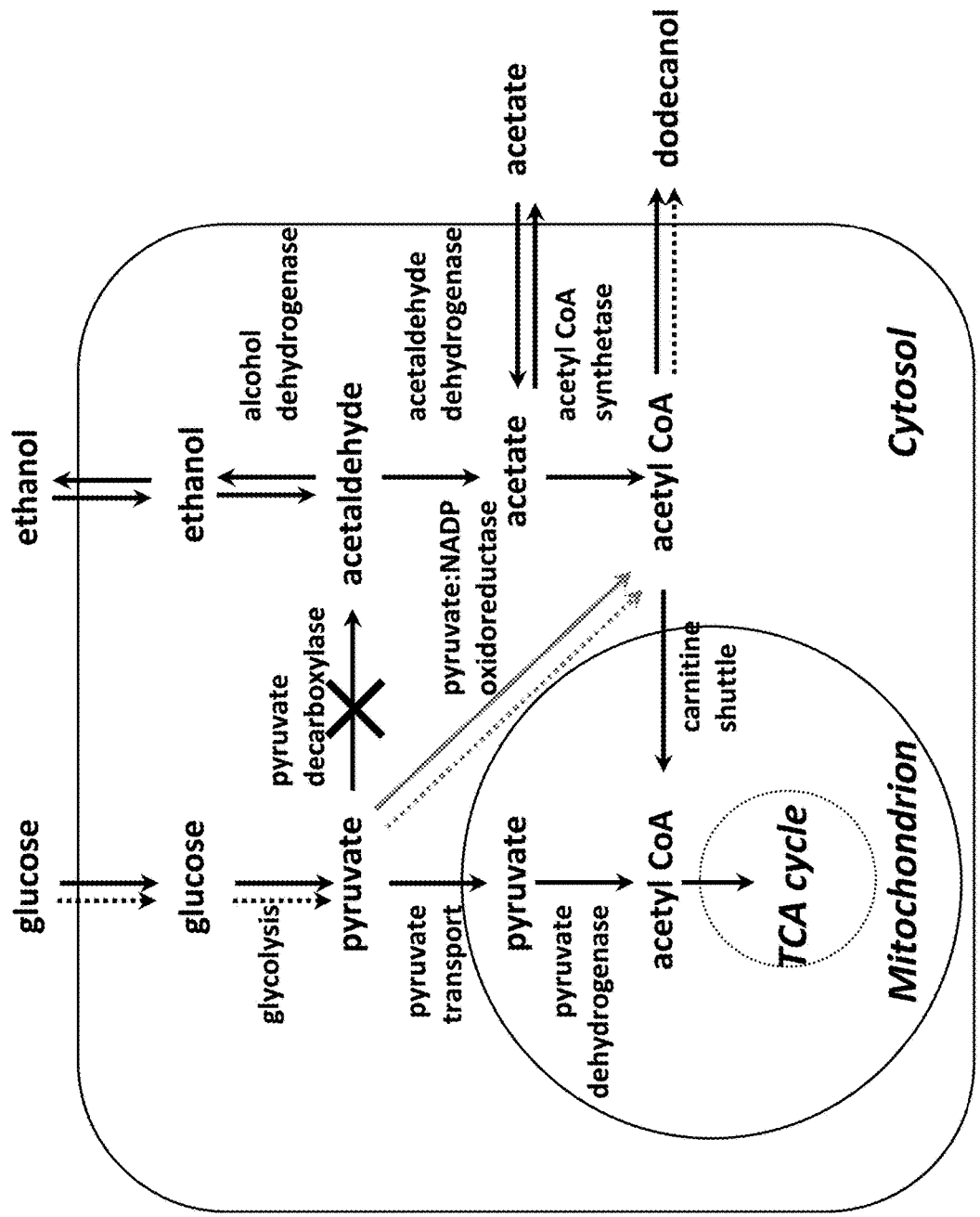
FIG. 13 shows the formation of dodecanol in the cytosol by relying on a cytosolic pyruvate:NADP oxidoreductase for acetyl CoA and NADH production. This can be accomplished by introducing a heterologous enzyme in the cytosol (shown in gray). The dotted arrows depict the flow of the majority of the carbon flux in this production scenario.

In some embodiments, the non-naturally occurring eukaryotic organism uses a cytosolic pyruvate:NADP oxidoreductase. Pyruvate: NADP oxidoreductase allows for the production of acetyl CoA and reducing equivalents in the cytosol as shown in FIG. 13. The addition of this enzyme allows for the production of acetyl CoA without expending energy that would otherwise have been required by acetyl CoA synthetase. The enzyme has been purified from the mitochondrion of *Euglena gracilis* and is oxygen-sensitive (Inui et al., *Journal of Biochemistry* 96:931-934 (1984); Inui et al., *Archives of Biochemistry and Biophysics* 237:423-429 (1985); Inui et al., *Archives of Biochemistry and Biophysics* 274:434-442 (1989); Inui et al., *Archives of Biochemistry and Biophysics* 280:292-298 (1990)). It is used for generating acetyl CoA from pyruvate, simultaneously producing NADPH. The corresponding gene is pno and its Genbank id is: CAC37628.1. It can be targeted to the cytosol by removing the mitochondrial targeting sequence. In some embodiments, a transhydrogenase is also added. This enzyme can be introduced as an exogenous gene from an organism such as *E. coli* to convert the generated NADPH into NADH (Nissen et al., *Yeast* 18:19-32 (2001)).

With its low ATP requirements, the pathway is energetically favorable even under anaerobic conditions. To prevent or reduce the utilization of NADH and pyruvate for ethanol production, pyruvate decarboxylase activity can be disrupted. This leads to a growth-coupled production of dodecanol similar to that shown in FIG. 11b.

Figure 14:
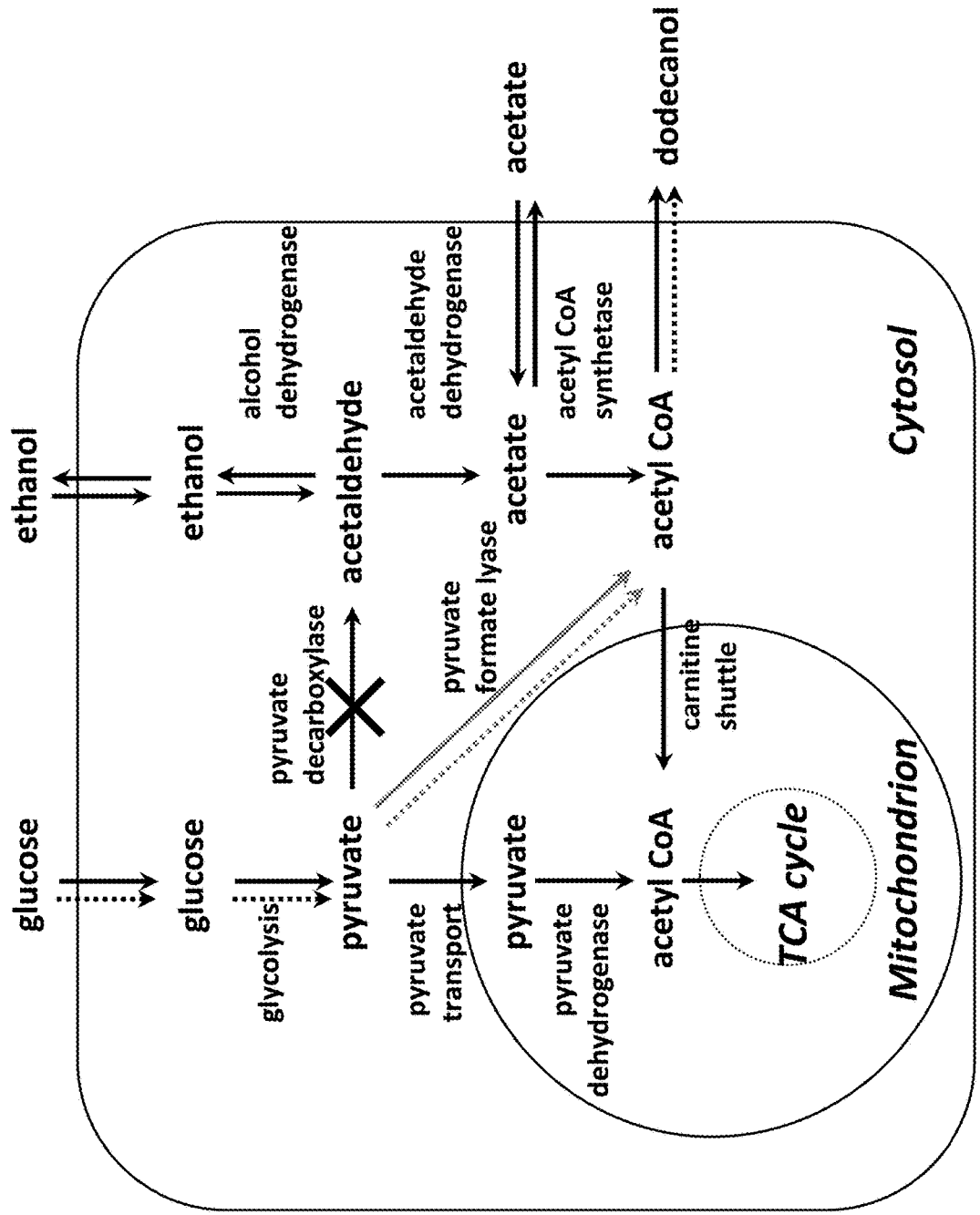
FIG. 14 shows the formation of dodecanol in the cytosol by the introduction of a heterologous pyruvate formate lyase (shown in gray) in the cytosol. The dotted arrows depict the flow of the majority of the carbon flux in this production scenario.

In some embodiments, a non-naturally occurring eukaryotic organism uses a pyruvate formate lyase. In such embodiments, a heterologous cytosolic pyruvate formate lyase (pfl) is used to generate both acetyl CoA and NADH as shown in FIG. 14. This enzyme is active typically under anaerobic conditions in organisms such as *E. coli*. The lack of energy requirement for conversion of pyruvate into acetyl CoA makes the production of dodecanol feasible under anaerobic conditions.

The conversion of pyruvate into acetyl CoA is accompanied by the production of formate. This is metabolized by the native formate dehydrogenase, leading to additional generation of reducing equivalents in stoichiometric quantities. In some embodiments that use this strain design, one or more of the three pyruvate decarboxylases, PDC1, PDC5 and PDC6, can be disrupted. The Genbank ids of exemplary genes encoding pyruvate formate lyase are shown in Table 6 below.

TABLE 6

| pflB | NP_415423.1 | *Escherichia coli* |
| pfl | YP_001588758. | *Lactococcus lactis* |
| pfl | YP_001394497.1 | *Clostridium kluyveri* |

The disruption of pyruvate decarboxylase along with the introduction of a heterologous pyruvate formate lyase in the network leads to a growth-coupled production of dodecanol. The production curve is similar to what is shown in FIG. 11b.

While the non-naturally occurring eukaryotic organisms described above produce LCAs in the cytosol, it is also possible to produce LCAs in the mitochondrion. Exemplary designs for the distribution of the carbon flux towards dodecanol production are detailed herein below. Organisms that produce LCAs in the mitochondrion include one or more disruptions in genes that encode enzymes such as a cytosolic pyruvate decarboxylase, a cytosolic ethanol-specific alcohol dehydrogenase, and amitochondrial ethanol-specific alcohol dehydrogenase. Exemplary genese encoding these enzymes include, for example, YLR044C, YLR134W, YGR087C, PDC3, YBR145W, YGL256W, YOL086C, YMR303, YMR083W, YPL088W, YAL061W, YMR318C, YCR105W, and YDL168W.

Other genes disruptions include those encoding an enzyme suchas a cytosolic malate dehydrogenase, glycerol-3-phospate dehydrogenase shuttle, catalyzed by, the external NADH dehydrogenase, and internal NADH dehydrogenase. Exemplary genes of the latter include, for example, YOL126C, YDL022W, YOL059W, YIL155C, YMR145C, YDL085W, and YML120C.

Organisms that produce LCAs in the mitochondrion can also include an exogenous nucleic acid encoding an enzyme such as a pyruvate dehydrogenase, a pyruvate: NADP oxidoreductase, a pyruvate formate lyase, an acylating acetaldehyde dehydrogenase, an acetate CoA ligase, and an AMP-forming acetyl CoA synthetase or their corresponding gene regulatory regions as described above. Additionally, such organisms benefit from enhanced NADH transporting shuttle systems for transport of NADH from the cytosol into the mitochondrion. Other exogenous nucleic acids encoding an enzyme that can be inserted in such organisms include a transhydrogenase, formate dehydrogenase, a pyruvate decarboxylase, and a pyruvate oxidase, all in the mitochondrion, or their corresponding gene regulatory regions.

Figure 15A:
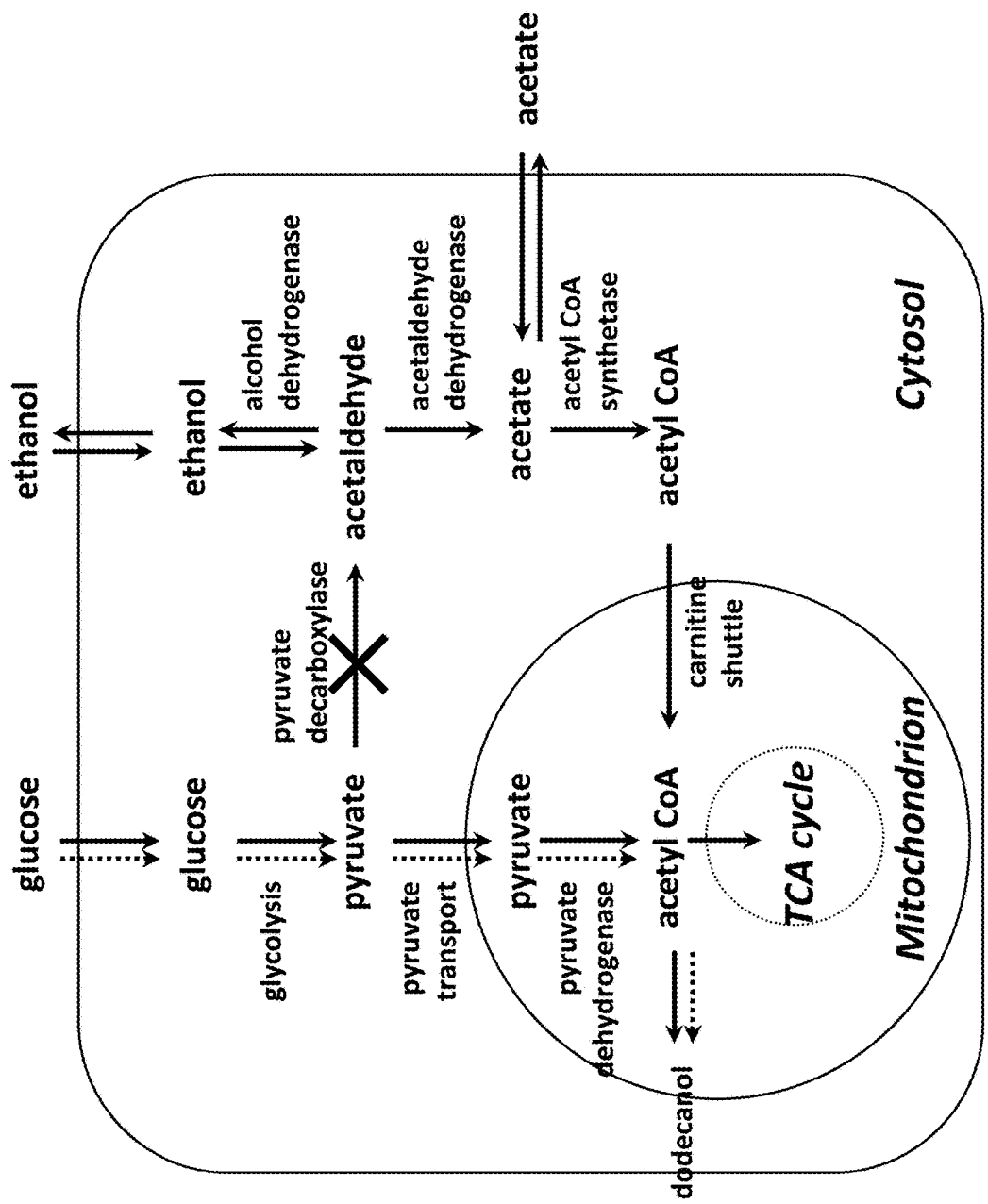
FIG. 15a shows the formation of dodecanol in the mitochondrion by using the pyruvate dehydrogenase for the formation of acetyl-CoA. The dotted arrows depict the flow of the majority of the carbon flux in this production scenario.

In one embodiment a mitochondrial pyruvate dehydrogenase is used in the non-naturally occurring eukaryotic organism. This can be the native pyruvate dehydrogenase which produces both acetyl CoA and NADH as shown in FIG. 15a. Since, there is no energy requirement for the conversion of pyruvate to acetyl CoA via this route; the production of dodecanol, for example, is energetically favorable even under anaerobic conditions.

Figure 15B:
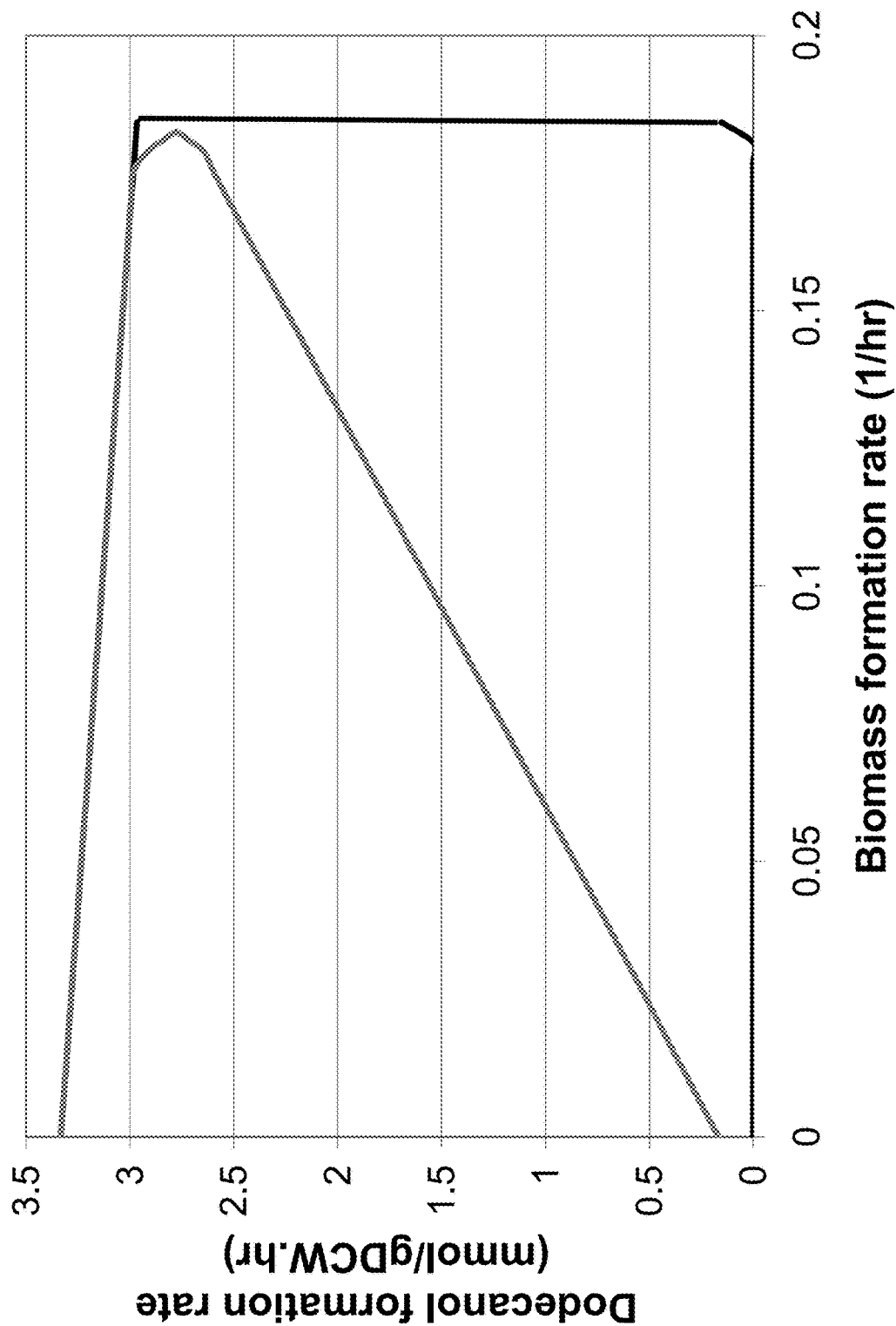
FIG. 15b shows the growth-coupled production envelopes for the production of dodecanol in S. cerevisiae mitochondrion. The black curve shows the production capabilities for the wild-type network under anaerobic conditions and the dark gray curve shows the production characteristics in the absence of oxygen when pyruvate decarboxylase is deleted from the network. A glucose uptake rate of 10 mmol/gDCW·hr is assumed.

The mitochondrial pyruvate dehydrogenase is known to be active in both aerobic and anaerobic conditions in *S. cerevisiae* (Pronk et al., *Yeast* 12:1607-1633 (1996)). In some embodiments the enzyme is overexpressed in its native or a heterologous form. The native enzyme can be overexpressed by using a stronger promoter. Additionally, mutations can be introduced aimed at increasing its activity under anaerobic conditions (Kim et al., *J. Bacteriol.* 190:3851-3858 (2008)). Reducing equivalents generated in the cytosol are made available in the mitochondrion for dodecanol production by using the redox shuttles present in *S. cerevisiae*. Note that these shuttles transport NADH into the mitochondrion for energy generation under respiratory conditions (Overkamp et al., *J. Bacteriol.* 182:2823-2830 (2000)). For growth-coupled production, pyruvate decarboxylase activity is disrupted to allow for pyruvate flux to be directed towards pyruvate dehydrogenase and to inhibit ethanol formation. The production curve for the mutant network is shown in FIG. 15b.

Figure 16:
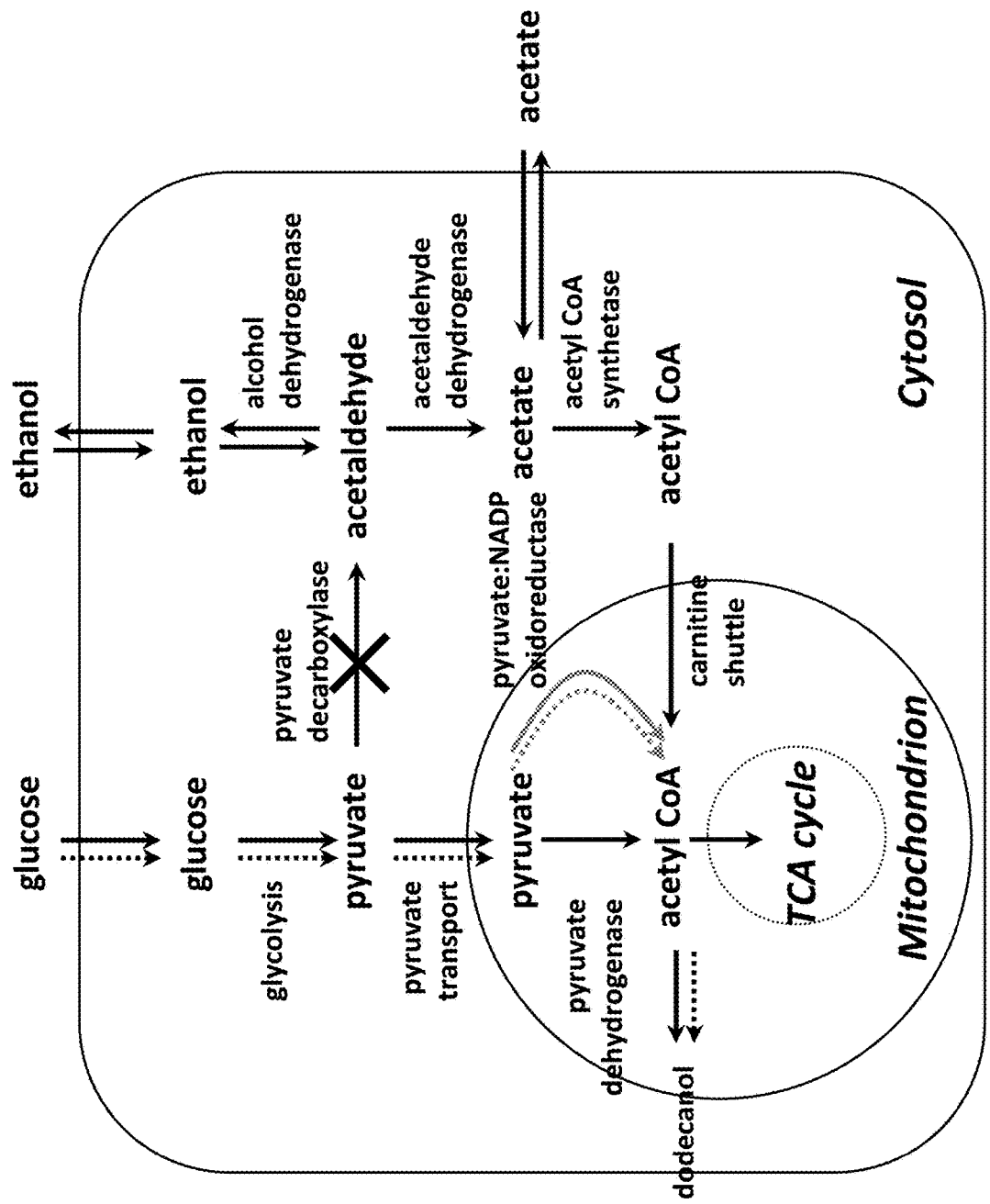
FIG. 16 shows the formation of dodecanol in the mitochondrion by using the pyruvate:NADP oxidoreductase for formation of acetyl CoA. The gray arrow shows the heterologous enzyme and the dotted arrows depict the flow of the majority of the carbon flux in this production scenario.

In some embodiments, a non-naturally occurring eukaryotic organism uses a heterologous pyruvate:NADP-oxidoreductase. The production of dodecanol in the mitochondrion can be achieved by introduction of the pyruvate: NADP oxidoreductase in the mitochondrion as shown in FIG. 16. This enzyme is purified from *E. gracilis*. Since the enzyme is naturally present in mitochondrion and is active under anaerobic conditions, it is possible to get high activity of the enzyme under anaerobic conditions. The introduction of this enzyme provides the precursor acetyl CoA for dodecanol production and also reducing equivalents. The NADPH generated by the enzyme is converted into NADH by a transhydrogenase, which can be introduced into the mitochondrion. For additional reducing equivalents, the redox shuttles need to transport NADH from the cytosol to the mitochondrion. The growth-coupled production of LCA using this enzyme can be obtained by disruption of pyruvate decarboxylase. The production curve of the mutant strain is very similar to the one shown in FIG. 15b.

Figure 17:
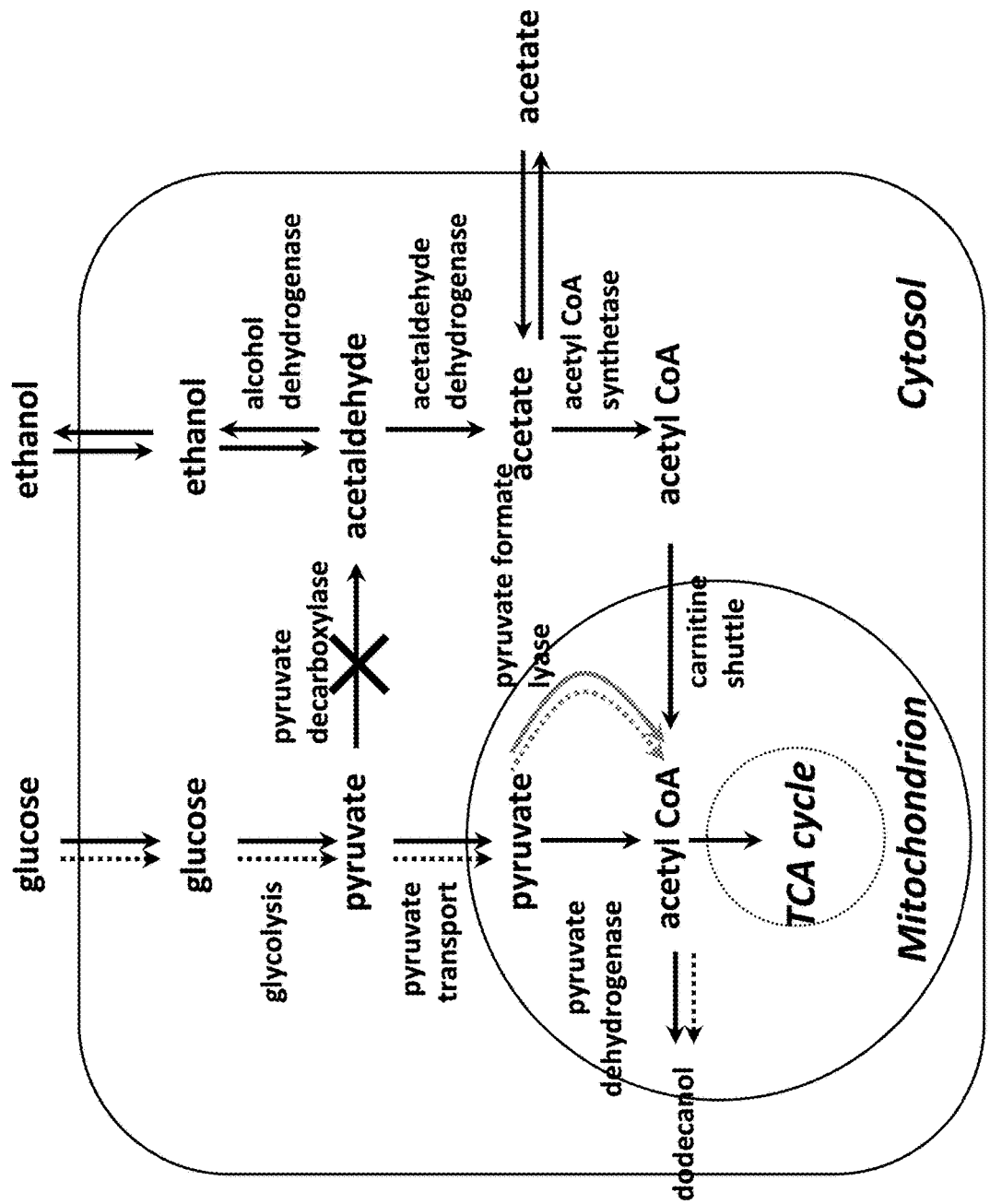
FIG. 17 shows the formation of dodecanol in the mitochondrion by using the pyruvate formate lyase for formation of acetyl CoA. The gray arrow shows the heterologous enzyme and the dotted arrows depict the flow of the majority of the carbon flux in this production scenario.

In some embodiments, a non-naturally occurring eukaryotic organism uses a heterologous pyruvate formate lyase. The production of dodecanol using a pyruvate formate lyase in mitochondrion is shown in FIG. 17. These genes have been outlined herein above. In such embodiments, the native formate dehydrogenase is retargeted to the mitochondrion to allow for further metabolizing formate and generating more reducing equivalents. This strain can be adopted to carry sufficient flux to sustain high yield and productivity of LCA production in the mitochondrion in the absence of oxygen.

Anaerobic growth conditions are feasible for the production of dodecanol using this strain design. Redox shuttles can be overexpressed to transport NADH generated in the cytosol to the mitochondrion. Production in this scenario is possible by disrupting the cytosolic pyruvate decarboxylase activity. The production characteristics of the mutant strain are similar to that shown in FIG. 15b.

Figure 18:
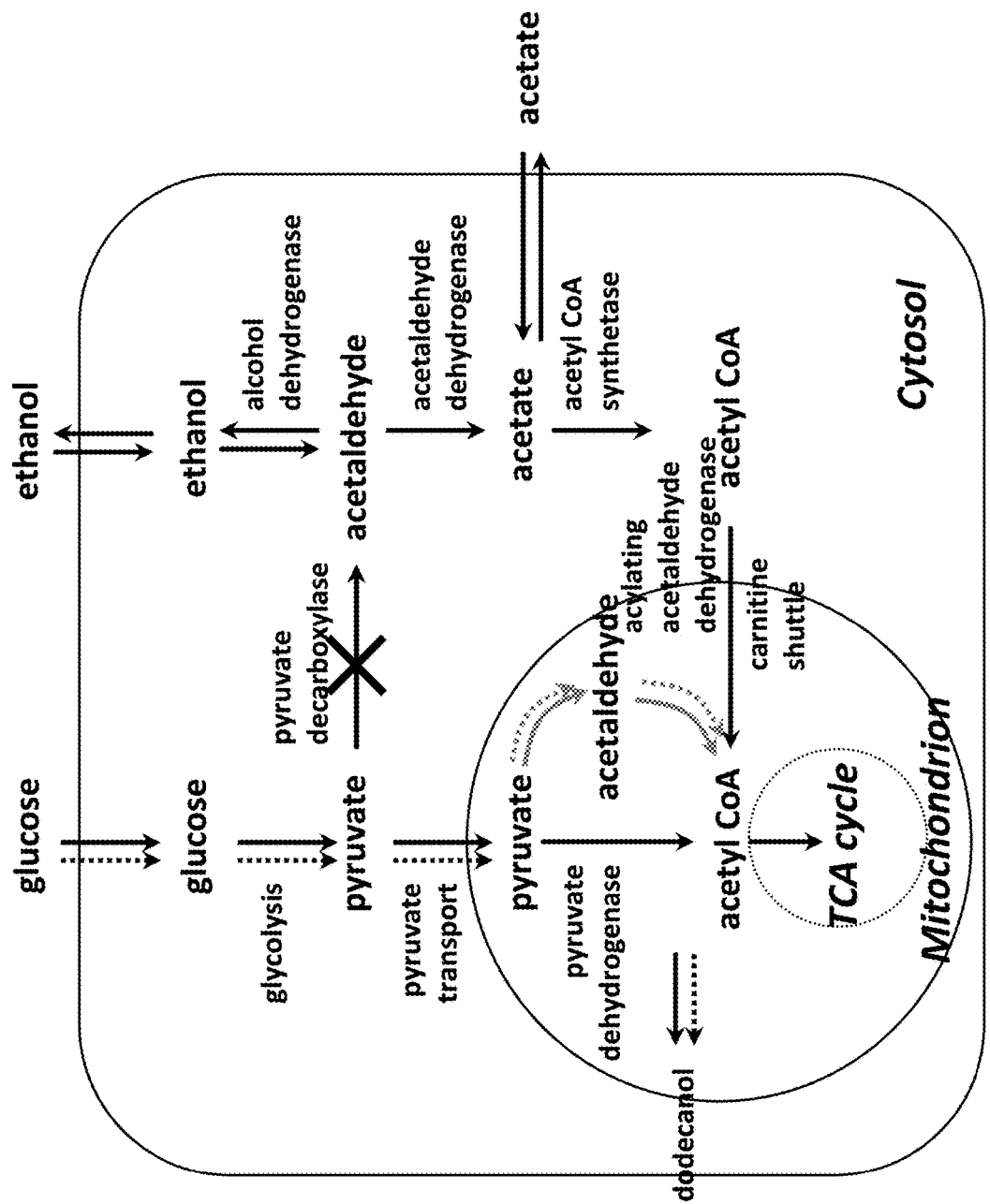
FIG. 18 shows the formation of dodecanol in the mitochondrion by adding the mitochondrial acylating acetaldehyde dehydrogenase. The gray arrow shows the heterologous enzyme(s) and the dotted arrows depict the flow of the majority of the carbon flux in this production scenario.

In some embodiments, a non-naturally occurring eukaryotic organism uses a heterologous acetaldehyde dehydrogenase (acylating). In such embodiments, an acylating acetaldehyde dehydrogenase is introduced into the mitochondrion to provide both acetyl-CoA and NADH for LCA production as shown in FIG. 18. A pyruvate decarboxylase isozyme is retargeted to the mitochondrion to convert pyruvate into acetaldehyde in some embodiments. The expression of these two activities in the mitochondrion is equivalent to the activity of pyruvate dehydrogenase. The growth-coupled production curve is the same as that shown in FIG. 15b. The growth-coupled production strain has the native mitochondrial acetaldehyde dehydrogenase (Pronk et al., *Yeast* 12:1607-1633 (1996)) and the cytosolic pyruvate decarboxylase disrupted in some embodiments. In other embodiments, the mitochondrial ethanol-specific alcohol dehydrogenase is also disrupted to prevent the conversion of acetaldehyde into ethanol.

In some embodiments, a non-naturally occurring eukaryotic organism uses a mitochondrial acetyl CoA synthetase (AMP-forming). As discussed above, the expression of this enzyme requires oxygen for favorable energetics. ACS1, an isozyme of acetyl CoA synthetase is expressed in *S. cerevisiae* in the mitochondrion under aerobic conditions but is repressed by glucose. This enzyme can be mutated to eliminate the repression or a heterologous enzyme that is expressed under the conditions of interest can be introduced. Additionally, pyruvate decarboxylase also can be expressed in the mitochondrion to form acetate. *S. cerevisiae*, for example, already possesses a mitochondrial acetaldehyde dehydrogenase (Pronk et al., *Yeast* 12:1607-1633 (1996)). Alternatively, enzymes such as pyruvate oxidase can be heterologously expressed to convert pyruvate into acetate. One such enzyme candidate is pyruvate oxidase from *E. coli* (Genbank id: NP_451392.1). This enzyme is naturally expressed in the presence of oxygen.

Figure 19A:
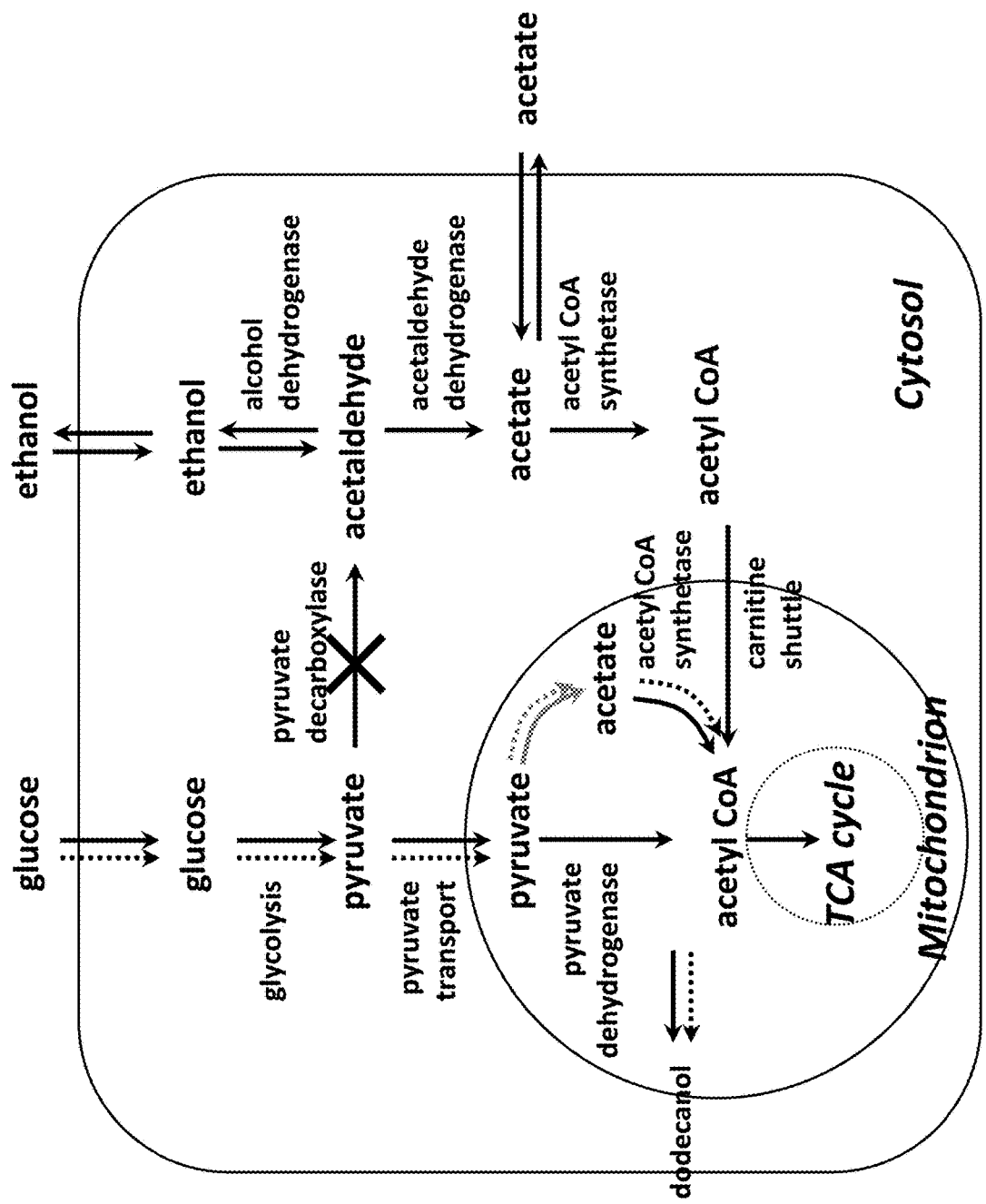
FIG. 19a shows the formation of dodecanol in the mitochondrion by using the acetyl CoA synthetase for formation of acetyl CoA. The gray arrow shows the heterologous enzyme(s) and the dotted arrows depict the flow of the majority of the carbon flux in this production scenario.
Figure 19B:
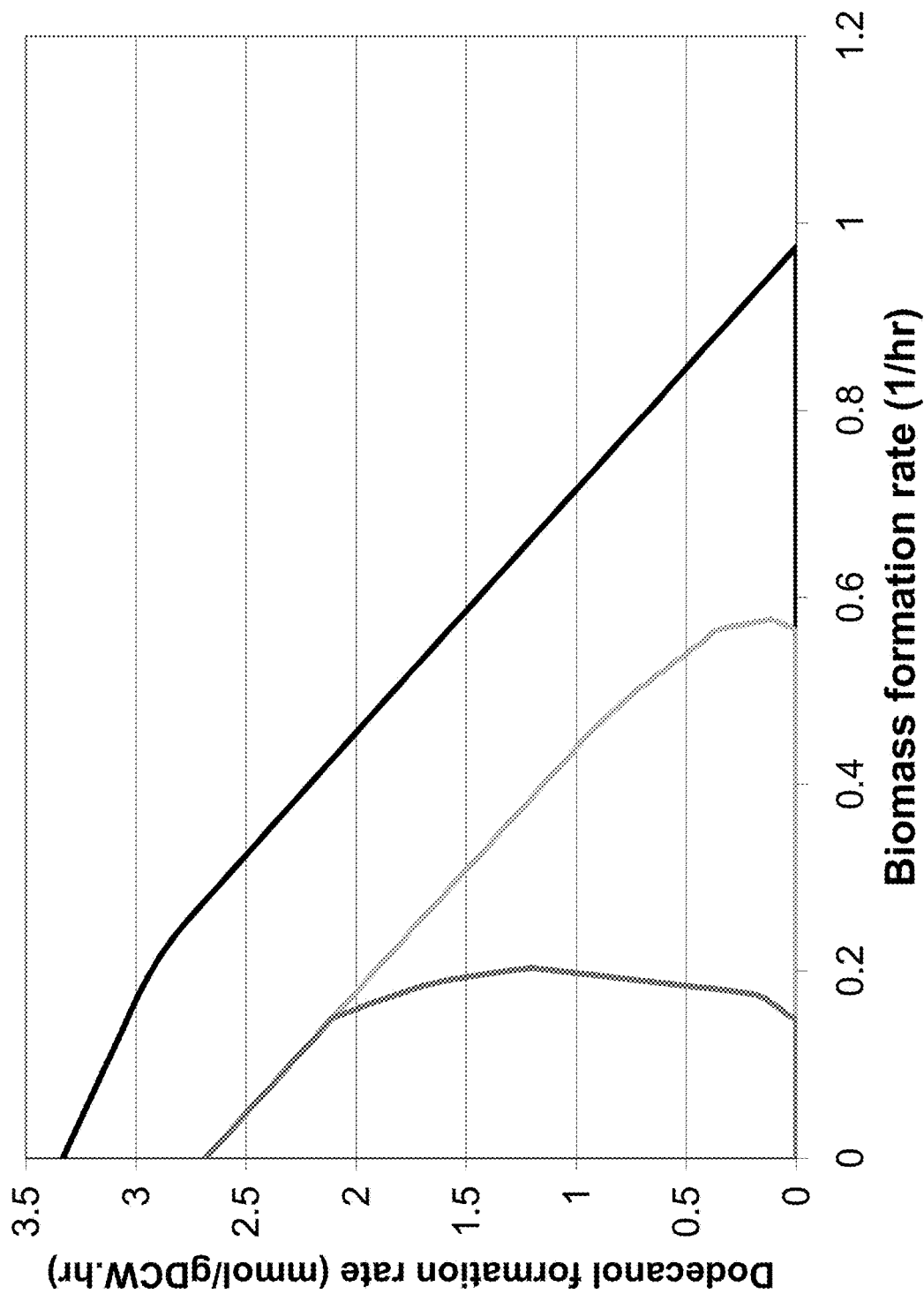
FIG. 19b shows the growth-coupled production envelopes for the production of dodecanol in S. cerevisiae mitochondrion when acetyl-CoA is formed through the mitochondrial acetyl-CoA synthetase. The black curve shows the production envelope for the wild-type network under aerobic conditions, the light dark gray curve shows the production characteristics when the deletions have been imposed upon the network. The growth coupling can be improved further (dark gray curve) when flux through the oxidative part of the pentose phosphate pathway is decreased. A glucose uptake rate of 10 mmol/gDCW·hr is assumed.

The production of LCA using this strain design benefits from one or more of the following disrupted enzymes: cytosolic malate dehydrogenase, the glycerol-3-phospate dehydrogenase shuttle, the external NADH dehydrogenase, and the internal mitochondrial NADH dehydrogenase. The glycerol-3-phosphate shuttle is comprised of the cytosolic glycerol-3-phosphate dehydrogenase and the membrane-bound glycerol-3-phosphate:ubiquionone oxidoreductase, with the latter also functioning as the mitochondrial glycerol-3-phosphate dehydrogenase. In some embodiments, the mitochondrial ethanol-specific alcohol dehydrogenase is also disrupted to prevent or reduce the conversion of acetaldehyde into ethanol. The production curve for the wild type strain with a mitochondrial pyruvate decarboxylase added to the network is shown in black in FIG. 19*b*. This curve is shown for aerobic conditions. The production characteristics when the aforementioned disruptions are imposed on the network are shown in light gray. The downregulation of the oxidative part of the pentose phosphate pathway, especially the committing step, glucose-6-phosphate dehydrogenase, further improves the LCA production characteristics of the network.

Figure 20:
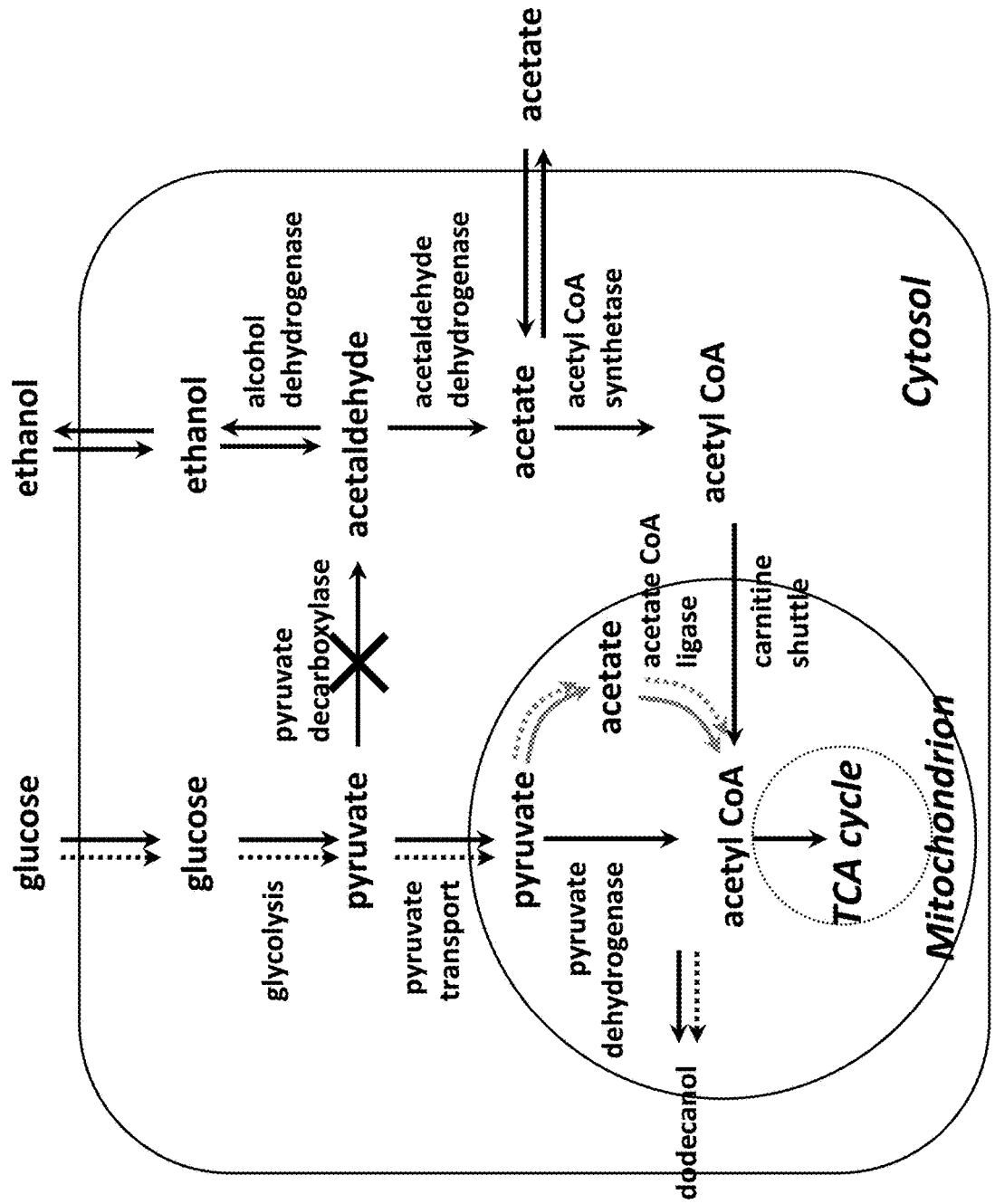
FIG. 20 shows the formation of dodecanol in the mitochondrion by using the acetate CoA ligase for formation of acetyl CoA. The gray arrows show the heterologous enzyme(s) and the dotted arrows depict the flow of the majority of the carbon flux in this production scenario

In some embodiments, a non-naturally occurring eukaryotic organism uses a mitochondrial acetate CoA ligase (ADP-forming). Mitochondrial LCA production can also be accomplished using an acetate-CoA ligase to convert acetate into acetyl-CoA as shown in FIG. 20. As described above, the use of this enzyme is energetically favorable and LCA production is energetically neutral unless oxygen is supplied. The mitochondrial expression of pyruvate decarboxylase is used in such embodiments. LCA production is obtained by imposing disruptions in cytosolic malate dehydrogenase, the glycerol-3-phospate dehydrogenase shuttle, the external NADH dehydrogenase, and the internal NADH dehydrogenase. The down-regulation of the oxidative part of the pentose phosphate pathway further improves the growth-coupled production characteristics to yield a production curve similar to the one shown in FIG. 19*b*. In some embodiments, the mitochondrial ethanol-specific alcohol dehydrogenase is also disrupted to prevent or reduce the conversion of acetaldehyde into ethanol.

The design strategies described herein are useful not only for enhancing growth-coupled production, but they are also well-suited for enhancing non-growth coupled production because they link the production of long chain alcohols to energy generation and/or redox balance. Exemplary non-growth coupled production methods include implementing an aerobic growth phase followed by an anaerobic production phase. For example, Vemuri et al. *J. Ind. Microbiol. Biotechnol.* (6):325-332, (2002) describe a dual-phase process for the production of succinate in *E. Coli*. Okino et al. *Appl. Microbiol. Biotechnol.* Sep. 6. (2008) [Currently available in online edition]. describe a similar non-growth couple production process in a strain of *Corynebacterium glutamicum* strain.

Another such method involves withholding an essential nutrient from a propogated cell culture, thereby limiting growth, but not precluding production as described in Durner et al. *Appl. Environ. Microbiol.* (8):3408-3414 (2000). Yet another strategy aimed at decoupling growth from production involves replacing the growth substrate with another compound that is more slowly metabolizable as described in Altamirano et al. *Biotechnol. Bioeng.* 76:351-360 (2001). Growth decoupled-product formation can also be brought about by specific genetic modifications as described in Blombach et al. *Appl. Microbiol. Biotechnol.* 79:471-9 (2008).

Some microbial organisms capable of LCA production are exemplified herein with reference to an *Saccharomyces cerevisaie* genetic background. However, with the complete genome sequence available now for more than 550 species (with more than half of these available on public databases such as the NCBI), including 395 microorganism genomes and a variety of yeast, fungi, plant, and mammalian genomes, the identification of an alternate species homolog for one or more genes, including for example, orthologs, paralogs and nonorthologous gene displacements, and the interchange of genetic alterations between eukaryotic organisms is routine and well known in the art. Accordingly, the metabolic alterations enabling production of LCA described herein with reference to a particular organism such as *Saccharomyces cerevisaie* can be readily applied to other microorganisms. Given the teachings and guidance provided herein, those skilled in the art will know that a metabolic alteration exemplified in one organism can be applied equally to other organisms.

The methods of the invention are applicable to various eukarotic organisms such as yeast and fungus. The yeast can include *S. cerevisiae* and *Rhizopus arrhizus*, for example. Exemplary eukaryotic species include those selected from *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae, Candida albicans, Candida boidinii* and *Pichia pastoris*. Additionally, select cells from larger eukaryotic organisms are also applicable to methods of the present invention.

Genes can be inserted into *S. cerevisiae*, using several methods; some of these are plasmid-based whereas others allow for the incorporation of the gene in the chromosome. The latter approach employs an integrative promoter based expression vector, for example, the pGAPZ or the pGAPZα vector based on the GAP promoter. The expression vector constitutes the GAP promoter, the HIS4 wild-type allele for integration and the 3' AOX transcription termination region of *P. pastoris* in addition to a KanMX cassette, flanked by loxP sites enabling removal and recycling of the resistance marker. The vectors are commercially available from Invitrogen. The details of which are elaborated in the Example below.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, alcohols, and other organic acid byproducts in the culture supernatant will be determined by analytical methods including HPLC using an HPX-87H column (BioRad), or GC-MS, and used to calculate uptake and secretion rates. All experiments are performed with triplicate cultures.

The invention also provides a method for producing long chain alcohols by culturing the non-naturally occurring eukaryotic organism described herein above. The one or more gene disruptions occur in genes encoding an enzyme to coupling long chain alcohol production to growth of the organism when the gene disruption reduces an activity of the enzyme. The one or more gene disruptions confers stable growth-coupled production of long chain alcohols onto the organism. In alternate embodiments the gene disruptions can enhance LCA production in a non-growth dependent manner.

Each of the strains presented herein may be supplemented with additional disruptions if it is determined that the predicted strain designs do not sufficiently couple the formation of LCAs with biomass formation. However, the list of gene disruption sets provided here serves as an excellent starting point for the construction of high-yielding growth-coupled LCA production strains.

Each of the proposed strains can be supplemented with additional disruptions if it is determined that the predicted strain designs do not sufficiently couple the formation of the product with biomass formation. Alternatively, some other enzymes not known to possess significant activity under the growth conditions can become active due to adaptive evolution or random mutagenesis and can also be disrupted. However, the list of gene disruption sets provided here serves as a starting point for construction of high-yielding growth-coupled LCA production strains.

The non-naturally occurring microbial organisms of the invention can be employed in the growth-coupled production of LCA. Essentially any quantity, including commercial quantities, can be synthesized using the growth-coupled LCA producers of the invention. Because the organisms of the invention obligatorily couple LCA to continuous growth or near-continuous growth processes are particularly useful for biosynthetic production of LCA. Such continuous and/or near continuous growth processes are described above and exemplified below in the Example I. Continuous and/or near-continuous microorganism growth processes also are well known in the art. Briefly, continuous and/or near-continuous growth processes involve maintaining the microorganism in an exponential growth or logarithmic phase. Procedures include using apparatuses such as the Evolugator™ evolution machine (Evolugate LLC, Gainesville, Fla.), fermentors and the like. Additionally, shake flask fermentation and grown under microaerobic conditions also can be employed. Given the teachings and guidance provided herein those skilled in the art will understand that the growth-coupled LCA producing microorganisms can be employed in a variety of different settings under a variety of different conditions using a variety of different processes and/or apparatuses well known in the art.

Generally, the continuous and/or near-continuous production of LCA will include culturing a non-naturally occurring growth-coupled LCA producing organism of the invention in sufficient nutrients and medium to sustain and/or nearly sustain growth in an exponential phase. Continuous culture under such conditions can be grown, for example, for a day, 2, 3, 4, 5, 6 or 7 days or more. Additionally, continuous cultures can include time durations of 1 week, 2, 3, 4 or 5 or more weeks and up to several months. It is to be understood that the continuous and/or near-continuous culture conditions also can include all time intervals in between these exemplary periods. In particular embodiments, culturing is conducted in a substantially anaerobic culture medium.

LCA can be harvested or isolated at any time point during the continuous and/or near-continuous culture period exemplified above. As exemplified below, the longer the microorganisms are maintained in a continuous and/or near-continuous growth phase, the proportionally greater amount of LCA can be produced.

Therefore, the invention provides a method for producing LCA that includes culturing a non-naturally occurring microbial organism that includes one or more gene disruptions. The disruptions can occur in genes encoding an enzyme to coupling LCA production to growth of the microorganism when the gene disruption reduces an activity of the enzyme, such that the disruptions confer stable growth-coupled production of LCA onto the non-naturally microbial organism.

In some embodiments, the gene disruption can include a complete gene deletion. In some embodiments other means to disrupt a gene include, for example, frameshifting by omission or addition of oligonucleotides or by mutations that render the gene inoperable. One skilled in the art will recognize the advantages of gene deletions, however, because of the stability it may confer to the non-naturally occurring organism from reverting to its wild-type. In particular, the gene disruptions are selected from the gene set that includes genes detailed herein above.

The metabolic engineering strategies listed in this disclosure assume that the organism can produce long chain alcohols via the malonyl-CoA independent pathway. The construction of a recombinant host organism capable of producing long chain alcohols via the malonyl-CoA independent pathway involves engineering a non-naturally occurring microbial organism having a malonyl-CoA-independent fatty acid synthesis (FAS) pathway and an acyl-reduction pathway having at least one exogenous nucleic acid encoding a malonyl-CoA-independent FAS pathway enzyme expressed in sufficient amounts to produce a primary alcohol. Such a malonyl-CoA-independent FAS pathway includes a ketoacyl-CoA acyltransferase or ketoacyl-CoA thiolase, 3-hydroxyacyl-CoA dehydrogenase, enoyl-CoA hydratase and enoyl-CoA reductase. The acyl-reduction pathway includes an acyl-CoA reductase and an alcohol dehydrogenase.

In order to validate the computational predictions presented herein, the strains must be constructed, evolved, and tested. *Escherichia coli* K-12 MG1655 housing the MI-LCA pathway will serve as the strain into which the disruptions will be introduced. The disruptions will be constructed by incorporating in-frame deletions using homologous recombination via the λ Red recombinase system of Datsenko and Wanner (Datsenko, K. A. and B. L. Wanner, *One-step inactivation of chromosomal genes in Escherichia coli K*-12 *using PCR products*. Proc Natl Acad Sci USA, 2000. 97(12): p. 6640-5.). The approach involves replacing a chromosomal sequence (i.e., the gene targeted for removal) with a selectable antibiotic resistance gene, which itself is later removed. Knockouts are integrated one by one into the recipient strain. No antibiotic resistance markers remain after each deletion allowing accumulation of multiple mutations in each target strain. The deletion technology completely removes the gene targeted for removal so as to substantially reduce the possibility of the constructed mutants reverting back to the wild-type.

As intermediate strains are being constructed, strain performance will be quantified by performing shake flask fermentations. Anaerobic conditions will be obtained by sealing the flasks with a rubber septum and then sparging the medium with nitrogen. For strains where growth is not observed under strict anaerobic conditions, microaerobic conditions can be applied by covering the flask with foil and poking a small hole for limited aeration. All experiments are performed using M9 minimal medium supplemented with glucose unless otherwise stated. Pre-cultures are grown overnight and used as inoculum for a fresh batch culture for which measurements are taken during exponential growth. The growth rate is determined by measuring optical density using a spectrophotometer (600 nm), and the glucose uptake rate by monitoring carbon source depletion over time. LCAs, ethanol, and organic acids are analyzed by GC-MS or HPLC using routine procedures. Triplicate cultures are grown for each strain.

The performance of select strains is tested in anaerobic, pH-controlled batch fermentations. This enables reliable quantification of the growth, glucose uptake, and formation rates of all products, as well as ensuring that the accumulation of acidic fermentation products will not limit cell growth. In addition, it allows accurate determination of LCA volumetric productivity and yield, two important parameters in benchmarking strain performance. Fermentations are carried out in 1-L bioreactors with 600 mL working volume, equipped with temperature and pH control. The reactor is continuously sparged with $N_2$ at approximately 0.5 L/min to ensure that DO levels remain below detection levels. The culture medium is the same as described above, except that the glucose concentration is increased in accordance with the higher cell density achievable in a fermentation vessel.

Chemostat experiments will be conducted to obtain a direct measure of how the switch in fermentation mode from batch to continuous affects LCA yield and volumetric productivity. The bioreactors described above using batch mode are operated in chemostat mode through continuous supply of medium and removal of spent culture. The inlet flow rate is set to maintain a constant dilution rate of 80% of the maximum growth rate observed for each strain in batch, and the outlet flow is controlled to maintain level. Glucose is the limiting nutrient in the medium, and set to achieve the desired optical density in the vessel.

The recombinant strains are initially expected to exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong, S. S. and B. O. Palsson, *Metabolic gene-deletion strains of Escherichia coli evolve to computationally predicted growth phenotypes*. Nat Genet, 2004. 36(10): p. 1056-8.). The OptKnock-generated strains are adaptively evolved in triplicate (running in parallel) due to differences in the evolutionary patterns witnessed previously in *E. coli* (Fong, S. S. and B. O. Palsson, *Metabolic gene-deletion strains of Escherichia coli evolve to computationally predicted growth phenotypes*. Nat Genet, 2004. 36(10): p. 1056-8; Fong, S. S., J. Y. Marciniak, and B. O. Palsson, *Description and interpretation of adaptive evolution of Escherichia coli K-12 MG1655 by using a genome-scale in silico metabolic model*. J Bacteriol, 2003. 185(21): p. 6400-8; Ibarra, R. U., J. S. Edwards, and B. O. Palsson, *Escherichia coli K-12 undergoes adaptive evolution to achieve in silico predicted optimal growth*. Nature, 2002. 420(6912): p. 186-189.) that could potentially result in one strain having superior production qualities over the others. Evolutions are run for a period of 2-6 weeks, depending upon the rate of growth improvement attained. In general, evolutions are stopped once a stable phenotype is obtained. The growth-coupled biochemical production concept behind the OptKnock approach results in the generation of genetically stable overproducers.

The engineered strains can be characterized by measuring the growth rate, the substrate uptake rate, and the product/byproduct secretion rate. Cultures are grown overnight and used as inoculum for a fresh batch culture for which measurements are taken during exponential growth. The growth rate can be determined by measuring optical density using a spectrophotometer (A600). Concentrations of glucose and other organic acid byproducts in the culture supernatant are determined by HPLC using an HPX-87H column (BioRad), and used to calculate uptake and secretion rates. All experiments are performed with triplicate cultures.

Following the adaptive evolution process, the new strains are characterized again by measuring the growth rate, the substrate uptake rate, and the product/byproduct secretion rate. These results will be compared to the OptKnock predictions by plotting actual growth and production yields along side the production envelopes in the above figures. The most successful OptKnock design/evolution combinations are chosen to pursue further, and are characterized in lab-scale batch and continuous fermentations. The growth-coupled biochemical production concept behind the OptKnock approach should also result in the generation of genetically stable overproducers. Thus, the cultures are maintained in continuous mode for one month to evaluate long-term stability. Periodic samples are taken to ensure that yield and productivity are maintained throughout the experiment.

As previously mentioned, one computational method for identifying and designing metabolic alterations favoring biosynthesis of a desired product is the OptKnock computational framework (Burgard et al., *Biotechnol. Bioeng.* 84:647-657 (2003)). The framework examines the complete metabolic and/or biochemical network of a microorganism in order to suggest genetic manipulations that force the desired biochemical to become a byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or disruptions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as a product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene disruption combinations that force a coupling between biochemical production and cell growth based on network stoichiometry. The identification of optimal gene/reaction disruptions requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *Escherichia coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene disruptions leading to the growth-coupled production of a desired product. Further, the solution of the bilevel OptKnock problem provides only one set of disruptions. To enumerate all meaningful solutions, that is, all sets of disruptions leading to growth-coupled production formation, an optimization technique, termed integer cuts, can be implemented. This entails iteratively solving the OptKnock problem with the incorporation of an additional constraint referred to as an integer cut at each iteration, as discussed above.

Adaptive evolution is a powerful experimental technique that can be used to increase growth rates of mutant or engineered microbial strains, or of wild-type strains growing under unnatural environmental conditions. It is especially useful for strains designed via the OptKnock formalism, which results in growth-coupled product formation. Therefore, evolution toward optimal growing strains will indirectly optimize production as well. Unique strains of *E. coli* K-12 MG1655 were created through gene knockouts and adaptive evolution. (Fong, S. S. and B. O. Palsson, *Nat. Genet.* 36:1056-1058 (2004).) In this work, all adaptive evolutionary cultures were maintained in prolonged exponential growth by serial passage of batch cultures into fresh medium before the stationary phase was reached, thus rendering growth rate as the primary selection pressure. The genes that were selected for this knockout study were ackA, frdA, pckA, ppc, tpiA, and zwf Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (i.e., within 10%) at predicting the post-evolution growth rate of the knockout strains in 38 out of the 50 cases examined. Furthermore, a combination of OptKnock design with adaptive evolution has led to improved lactic acid production strains. (Fong, S. S., A. P. Burgard, C. D. Herring, E. M. Knight, F. R. Blattner, C. D. Maranas, and B. O. Palsson, *Biotechnol Bioeng* 91:643-648 (2005).) The guidance of these teachings relevant to *E. coli* can be applied to other organisms.

There are a number of developed technologies for carrying out adaptive evolution. Exemplary methods are provided herein below. In some embodiments, optimization of a non-naturally occurring organism of the present invention includes subject the use of any of the these adaptive evolution techniques.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature, (Lenski, R. E. and M. Travisano, *Proc Natl Acad Sci US. A.* 91:6808-6814 (1994).) in experiments which clearly demonstrated consistent improvement in reproductive rate over period of years. In the experiments performed in the Palsson lab described above, transfer is usually performed during exponential phase, so each day the transfer volume is precisely calculated to maintain exponential growth through the next 24 hour period. This process is usually done manually, with considerable labor investment, and is subject to contamination through exposure to the outside environment. Furthermore, since such small volumes are transferred each time, the evolution is inefficient and many beneficial mutations are lost. On the positive side, serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate. (Dykhuizen, D. E., *Methods Enzymol.* 613-631 (1993).) The potential power of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less sticky individuals including those that have higher reproductive rates, thus obviating the intended purpose of the device. (Chao, L. and G. Ramsdell *J. Gen. Microbiol* 20:132-138 (1985).) One possible way to overcome this drawback is the implementation of a device with two growth chambers, which periodically undergo transient phases of sterilization, as described in the patent by the Pasteur Institute (Marliere and Mutzel, U.S. Pat. No. 6,686,194, filed 1999).

Evolugator™ is a continuous culture device developed by Evolugate, LLC (Gainesville, Fla.) exhibits significant time and effort savings over traditional evolution techniques. (de Crecy, E., Metzgar, D., Allen, C., Penicaud, M., Lyons, B., Hansen, C. J., de Crecy-Lagard, V. *Appl. Microbiol. Biotechnol.* 77:489-496 (2007).) The cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%.

It is understood that modifications which do not substantially affect the activity of the various embodiments of this invention are also included within the definition of the invention provided herein. Accordingly, the following examples are intended to illustrate but not limit the present invention.

Example I

Primary Alcohol Biosynthesis

This Example describes the generation of a microbial organism capable of producing primary alcohols using a malonyl-CoA independent FAS metabolic pathway and acyl-reduction metabolic pathways.

*Escherichia coli* is used as a target organism to engineer a malonyl-CoA-independent FAS and acyl-reduction pathway as shown in FIG. 1. *E. coli* provides a good host for generating a non-naturally occurring microorganism capable of producing primary alcohol, such as octanol. *E. coli* is amenable to genetic manipulation and is known to be capable of producing various products, like ethanol, effectively under anaerobic conditions.

To generate an *E. coli* strain engineered to produce primary alcohol, nucleic acids encoding the enzymes utilized in the malonyl-CoA-independent FAS and acyl-reduction pathway as described previously, are expressed in *E. coli* using well known molecular biology techniques (see, for example, Sambrook, supra, 2001; Ausubel supra, 1999; Roberts et al., supra, 1989). In particular, the fadI/fadJ genes (NP_416844.1 and NP_416843.1), encoding the multienzyme complex with ketoacyl-CoA thiolase, 3-hydroxyacyl-CoA dehydrogenase, and enoyl-CoA hydratase activities under anaerobic conditions, and the TDE0597 (NP_971211.1), encoding enoyl-CoA reductase, are cloned into the pZE13 vector (Expressys, Ruelzheim, Germany) under the PA1/lacO promoter. The acr1 gene (YP_047869.1), encoding acyl-CoA reductase, and the alrA gene (BAB12273.1), encoding alcohol dehydrogenase, are cloned into the pZA33 vector (Expressys, Ruelzheim, Germany) under the PA1/lacO promoter. The two sets of plasmids are transformed into *E. coli* strain MG1655 to express the proteins and enzymes required for the malonyl-CoA-independent FAS and acyl-reduction pathway.

The resulting genetically engineered organism is cultured in glucose containing medium following procedures well known in the art (see, for example, Sambrook et al., supra, 2001). The expression of malonyl-CoA-independent FAS and acyl-reduction pathway genes is corroborated using methods well known in the art for determining polypeptide expression or enzymatic activity, including for example, Northern blots, PCR amplification of mRNA, immunoblotting. Enzymatic activities of the expressed enzymes are confirmed using assays specific for the individually activities (see, for example, Tucci, supra, 2007; Hoffmeister et al., 2005; Inui et al., supra, 1984; Winkler, 2003; Tani, 2000; Reiser, 1997; Ishige, 2000). The ability of the engineered *E. coli* strain to produce primary alcohol, such as octanol is confirmed using HPLC, gas chromatography-mass spectrometry (GCMS) or liquid chromatography-mass spectrometry (LCMS).

Microbial strains engineered to have a functional malonyl-CoA-independent FAS and acyl-reduction pathway is further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of primary alcohols. One modeling method is the bilevel optimization approach, OptKnock (Burgard et al., *Biotechnol. Bioengineer.* 84:647-657 (2003)), which is applied to select gene knockouts that collectively result in better production of primary alcohols. Adaptive evolution also can be used to generate better producers of, for example, the acetyl-CoA intermediate or the primary alcohol product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the primary alcohol producer to further increase their production.

For large-scale production of primary alcohols, the above malonyl-CoA independent FAS pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Isolation of the product primary alcohol is performed based their insolubility in water. In particular, a two-phase fermentation process is used for separation of these product alcohols where they can either form a separate phase or be readily extracted in an organic phase from the fermentation broth. Residual cells and any other insoluble impurities are removed by filtration, allowing a continuous or semi-continuous fermentation process.

Example II

Microorganisms Having Growth-Coupled Production of LCA

This Example describes the construction in silico designed strains for the growth-coupled production of LCA.

E. coli K-12 MG1655 serves as the wild-type strain into which the disruptions are introduced. The disruptions are constructed by incorporating in-frame deletions using homologous recombination via the λ Red recombinase system of Datsenko and Wanner. (Datsenko, K. A. and B. L. Wanner, *Proc Natl Acad Sci USA.*, 97(12):6640-5 (2000).) The approach involves replacing a chromosomal sequence (i.e., the gene targeted for removal) with a selectable antibiotic resistance gene, which itself is later removed. Knockouts are integrated one by one into the recipient strain. No antibiotic resistance markers will remain after each deletion allowing accumulation of multiple mutations in each target strain. The deletion technology completely removes the gene targeted for removal so as to substantially reduce the possibility of the constructed mutants reverting back to the wild-type.

As described further below, one exemplary growth condition for achieving biosynthesis of LCA includes anaerobic culture or fermentation conditions. In certain embodiments, the non-naturally occurring microbial organism of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, LCA, and other organic acid byproducts in the culture supernatant are determined by HPLC using an HPX-87H column (BioRad), and are used to calculate uptake and secretion rates. All experiments are performed with triplicate cultures.

The recombinant strains can exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model. (Fong, S. S. and B. O. Palsson, *Nat Genet,* 36(10):1056-8 (2004).) These teachings can be applied to *Escherichia coli*.

Should the OptKnock predictions prove successful; the growth improvements brought about by adaptive evolution will be accompanied by enhanced rates of LCA production. The OptKnock-generated strains are adaptively evolved in triplicate (running in parallel) due to differences in the evolutionary patterns witnessed previously in *E. coli* (Fong, S. S. and B. O. Palsson, Nat Genet, 36(10):1056-8 (2004); Fong, S. S., J. Y. Marciniak, and B. O. Palsson, J Bacteriol, 185(21):6400-8 (2003); Ibarra, R. U., J. S. Edwards, and B. O. Palsson, *Nature,* 420(6912):186-189 (2002)) that could potentially result in one strain having superior production qualities over the others. Evolutions are run for a period of 2-6 weeks, depending upon the rate of growth improvement attained. In general, evolutions are stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The evolutions are performed in triplicate due to differences in the evolutionary patterns witnessed previously Donnelly et al., *Appl Biochem Biotechnol* 70-72: 187-98 (1998); Vemuri et al., *Appl Environ Microbiol* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%.

In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology. Evolugator™ is a continuous culture device that exhibits significant time and effort savings over traditional evolution techniques. (de Crecy et al., *Appl. Microbiol. Biotechnol.* 77:489-496 (2007)).

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Example III

Microorganisms Having Growth-Coupled Production of LCA

This Example describes the construction in silico designed strains for the growth-coupled production of LCA.

Gene deletions are introduced into *S. cerevisiae* by homologous recombination of the gene interrupted by the KanMX cassette, flanked by loxP sites enabling removal and recycling of the resistance marker (e.g. URA3) (Wach, A., et al., *PCR-based gene targeting in Saccharomyces cerevisiae*, in *Yeast Gene Analysis*, M. F. Tuite, Editor. 1998, Academic Press: San Diego). Starting with a loxP-kanMX-loxP sequence on a plasmid, an artificial construct with this sequence flanked by fragments of the gene of interest are created by PCR using primers containing both 45-50 bp target sequence followed by a region homologous to the above cassette. This linear DNA is transformed into wild-type *S. cerevisiae*, and recombinants are selected by geneticin resistance (Wach, A., et al. supra]. Colonies are purified and tested for correct double crossover by PCR. To remove the KanMX marker, a plasmid containing the Cre recombinase and bleomycin resistance are introduced, promoting recombination between the loxP sites (Gueldener, U., et al., *Nucleic Acids Res.* e23 (2002))]. Finally, the resulting strain is cured of the Cre plasmid by successive culturing on media without any antibiotic present. The final strain will have a markerless gene deletion, and thus the same method can be used to introduce multiple deletions in the same strain.

The strains are constructed, evolved, and tested by methods disclosed herein. Genes can be inserted into *S. cerevisiae*, for example, using several methods. These methods can be plasmid-based whereas others allow for the incorporation of the gene in the chromosome. The latter approach employs an integrative promoter based expression vector, for example, the pGAPZ or the pGAPZα vector based on the GAP promoter. The expression vector constitutes the GAP promoter, the HIS4 wild-type allele for integration and the 3' AOX transcription termination region of *P. pastoris* in addition to a KanMX cassette, flanked by loxP sites enabling removal and recycling of the resistance marker. Both of these vectors are commercially available from Invitrogen (Carlsbad, Calif.).

The method entails the synthesis and amplification of the gene of interest with suitable primers, followed by the digestion of the gene at a unique restriction site, such as that created by the EcoRI/XhoI enzymes (Vellanki et al., Biotechnol. Lett. 29:313-318 (2007)). The gene is inserted at the EcoRI and XhoI sites in the expression vector, downstream of the GAP promoter. The gene insertion is verified by PCR and/or DNA sequence analysis. The recombinant plasmid is then linearized with NarI for histidine integration, purified and integrated into the chromosomal DNA of *S. cerevisiae* using an appropriate transformation method. The cells are plated on the YPD medium with the appropriate selection marker (e.g., kanamycin) and incubated for 2-3 days. The transformants will then be analyzed for the requisite gene insert by colony PCR.

To remove the antibiotic marker, a plasmid containing the Cre recombinase is introduced, promoting recombination between the loxP sites (Gueldener et al., supra). Finally, the resulting strain is cured of the Cre plasmid by successive culturing on media without any antibiotic present. The final strain will have a markerless gene deletion, and thus the same method can be used to introduce multiple insertions in the same strain.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, alcohols, and other organic acid byproducts in the culture supernatant are determined by analytical methods including HPLC using an HPX-87H column (BioRad), or GC-MS, and used to calculate uptake and secretion rates. All experiments are performed with triplicate cultures.

The knockout strains are initially anticipated to exhibit suboptimal growth rates until their metabolic networks have adjusted to their missing functionalities. To enable this adjustment, the strains will be adaptively evolved. By subjecting the strains to adaptive evolution, cellular growth rate becomes the primary selection pressure and the mutant cells will be compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model. The growth improvements brought about by adaptive evolution can be accompanied by enhanced rates of LCA production. The OptKnock-generated strains can be adaptively evolved in triplicate (running in parallel) due to differences in the evolutionary patterns witnessed previously in *E. coli* that could potentially result in one strain having superior production qualities over the others. Evolutions can be run for a period of 2-6 weeks, or longer depending upon the rate of growth improvement attained. In general, evolutions can be stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The evolutions are performed in triplicate due to differences in the evolutionary patterns witnessed previously Donnelly et al., *Appl Biochem Biotechnol.* 70-72: 187-98 (1998); Vemuri et al., *Appl Environ Microbiol.* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness. In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology.

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Described herein above, is the application of the OptKnock methodology for generating useful gene disruption targets. Multiple disruption strategies were enumerated for establishing the coupling between LCA production and *Escherichia coli* growth. This methodology is applicable to a wide variety of cells and microorganisms other than *Escherichia coli* and also can utilize metabolic modeling and simulation systems other than OptKnock.

The combined computational and engineering platform described herein is generally applicable to any stoichiometric model organism and the teachings and guidance provided herein will allow those skilled in the art to design and implement sets of genetic manipulations for metabolic alterations that lead to the growth-coupled production of any biochemical product.

Throughout this application various publications have been referenced within parentheses. The disclosures of these publications in their entireties are hereby incorporated by reference in this application in order to more fully describe the state of the art to which this invention pertains.

The present disclosure provides gene disruption strategies for growth-coupled production of LCA in *Escherichia coli* under anaerobic conditions. The suggested strategies can increase product yields significantly over the reported yields for each of these products. A comprehensive list of the strategies is listed in Table 1 for LCA production. The associated genes and stoichiometries for each of the reaction disruption are catalogued in Table 2. Table 3 lists metabolite abbreviations and their corresponding names along with their location.

TABLE 1

The list of all disruption strategies identified by OptKnock that are most likely to provide growth-coupled LCA produciton.

| | | | | | | | | |
|---|---|---|---|---|---|---|---|---|
| 1 | ADHEr | LDH_D | ASPT | MDH | PFLi | PGDHY | PYK | DHAPT |
| 2 | ADHEr | LDH_D | ASPT | MDH | PFLi | PGL | PYK | DHAPT |
| 3 | ADHEr | LDH_D | ASPT | G6PDHy | MDH | PFLi | PYK | DHAPT |
| 4 | ADHEr | LDH_D | ASPT | EDA | MDH | PFLi | PYK | DHAPT |
| 5 | ADHEr | LDH_D | GLCpts | GLUDy | PGDH | PGI | PTAr | |
| 6 | ADHEr | LDH_D | ACKr | GLCpts | GLUDy | PGDH | PGI | |
| 7 | ADHEr | LDH_D | GLCpts | GLUDy | PGI | PTAr | TAL | |
| 8 | ADHEr | LDH_D | GLCpts | GLUDy | PGI | PTAr | TKT1 | |
| 9 | ADHEr | LDH_D | ACKr | GLCpts | GLUDy | PGI | TKT1 | |
| 10 | ADHEr | LDH_D | ACKr | GLCpts | GLUDy | PGI | TAL | |
| 11 | ADHEr | LDH_D | FBA | GLCpts | GLUDy | PTAr | | |
| 12 | ADHEr | LDH_D | GLCpts | GLUDy | PTAr | TPI | | |
| 13 | ADHEr | LDH_D | ACKr | GLCpts | GLUDy | TPI | | |
| 14 | ADHEr | LDH_D | GLCpts | GLUDy | PFK | PTAr | | |
| 15 | ADHEr | LDH_D | ACKr | FBA | GLCpts | GLUDy | | |
| 16 | ADHEr | LDH_D | ACKr | GLCpts | GLUDy | PFK | | |
| 17 | ADHEr | LDH_D | ACKr | GLCpts | GLUDy | PGI | RPE | |
| 18 | ADHEr | LDH_D | GLCpts | GLUDy | PGI | PTAr | RPE | |
| 19 | ADHEr | LDH_D | GLCpts | GLUDy | PGI | PTAr | TKT2 | |
| 20 | ADHEr | LDH_D | ACKr | GLCpts | GLUDy | PGI | TKT2 | |
| 21 | ADHEr | LDH_D | ACKr | GLCpts | PGDH | PGI | | |
| 22 | ADHEr | LDH_D | GLCpts | PGDH | PGI | PTAr | | |
| 23 | ADHEr | LDH_D | ACKr | GLCpts | PGI | TKT1 | | |
| 24 | ADHEr | LDH_D | ACKr | GLCpts | PGI | TAL | | |
| 25 | ADHEr | LDH_D | GLCpts | PGI | PTAr | TAL | | |
| 26 | ADHEr | LDH_D | GLCpts | PGI | PTAr | TKT1 | | |
| 27 | ADHEr | LDH_D | ACKr | GLCpts | PFK | | | |
| 28 | ADHEr | LDH_D | ACKr | GLCpts | TPI | | | |
| 29 | ADHEr | LDH_D | ACKr | FBA | GLCpts | | | |
| 30 | ADHEr | LDH_D | FBA | GLCpts | PTAr | | | |
| 31 | ADHEr | LDH_D | GLCpts | PFK | PTAr | | | |
| 32 | ADHEr | LDH_D | GLCpts | PTAr | TPI | | | |

TABLE 1-continued

The list of all disruption strategies identified by OptKnock that are most likely to provide growth-coupled LCA produciton.

| # | | | | | | |
|---|---|---|---|---|---|---|
| 33 | ADHEr | LDH_D | ACKr | GLCpts | PGI | RPE |
| 34 | ADHEr | LDH_D | GLCpts | PGI | PTAr | RPE |
| 35 | ADHEr | LDH_D | FRD2 | GLCpts | GLUDy | PFLi | PGI |
| 36 | ADHEr | LDH_D | ACKr | GLCpts | PGI | TKT2 |
| 37 | ADHEr | LDH_D | GLCpts | PGI | PTAr | TKT2 |
| 38 | ADHEr | LDH_D | FRD2 | GLCpts | GLUDy | PFLi | TPI |
| 39 | ADHEr | LDH_D | FBA | FRD2 | GLCpts | GLUDy | PFLi |
| 40 | ADHEr | LDH_D | FRD2 | GLCpts | GLUDy | PFK | PFLi |
| 41 | ADHEr | LDH_D | ASPT | ATPS4r | FUM | NADH6 | PGI |
| 42 | ADHEr | LDH_D | ASPT | ATPS4r | MDH | NADH6 | PGI |
| 43 | ADHEr | LDH_D | ASPT | ATPS4r | MDH | NADH6 | PFK |
| 44 | ADHEr | LDH_D | ASPT | ATPS4r | FBA | FUM | NADH6 |
| 45 | ADHEr | LDH_D | ASPT | ATPS4r | FUM | NADH6 | TPI |
| 46 | ADHEr | LDH_D | ASPT | ATPS4r | MDH | NADH6 | TPI |
| 47 | ADHEr | LDH_D | ASPT | ATPS4r | FBA | MDH | NADH6 |
| 48 | ADHEr | LDH_D | ASPT | ATPS4r | FUM | NADH6 | PFK |
| 49 | ADHEr | LDH_D | FUM | GLCpts | GLUDy | PFLi | PGI |
| 50 | ADHEr | LDH_D | GLCpts | GLUDy | MDH | PFLi | PGI |
| 51 | ADHEr | LDH_D | GLCpts | PFLi | PGI | SUCD4 |
| 52 | ADHEr | LDH_D | GLCpts | NADH6 | PFLi | PGI |
| 53 | ADHEr | LDH_D | FRD2 | GLCpts | PFLi | PGI |
| 54 | ADHEr | LDH_D | ACKr | GLUDy | HEX1 | PGDH | PGI |
| 55 | ADHEr | LDH_D | GLUDy | HEX1 | PGDH | PGI | PTAr |
| 56 | ADHEr | LDH_D | FUM | GLCpts | GLUDy | PFK | PFLi |
| 57 | ADHEr | LDH_D | FBA | FUM | GLCpts | GLUDy | PFLi |
| 58 | ADHEr | LDH_D | GLCpts | GLUDy | MDH | PFK | PFLi |
| 59 | ADHEr | LDH_D | FUM | GLCpts | GLUDy | PFLi | TPI |
| 60 | ADHEr | LDH_D | FBA | GLCpts | GLUDy | MDH | PFLi |
| 61 | ADHEr | LDH_D | GLCpts | GLUDy | MDH | PFLi | TPI |
| 62 | ADHEr | LDH_D | GLCpts | NADH6 | PFLi | TPI |
| 63 | ADHEr | LDH_D | FRD2 | GLCpts | PFLi | TPI |
| 64 | ADHEr | LDH_D | FBA | FRD2 | GLCpts | PFLi |
| 65 | ADHEr | LDH_D | FBA | GLCpts | NADH6 | PFLi |
| 66 | ADHEr | LDH_D | FBA | GLCpts | PFLi | SUCD4 |
| 67 | ADHEr | LDH_D | FRD2 | GLCpts | PFK | PFLi |
| 68 | ADHEr | LDH_D | GLCpts | PFLi | SUCD4 | TPI |
| 69 | ADHEr | LDH_D | GLCpts | PFK | PFLi | SUCD4 |
| 70 | ADHEr | LDH_D | GLCpts | NADH6 | PFK | PFLi |
| 71 | ADHEr | LDH_D | ASPT | GLCpts | MDH | PFLi | PGI |
| 72 | ADHEr | LDH_D | ASPT | FUM | GLCpts | PFLi | PGI |
| 73 | ADHEr | LDH_D | ASPT | ATPS4r | MDH | PGI | PPS |
| 74 | ADHEr | LDH_D | ASPT | ATPS4r | FUM | PGI | PPS |
| 75 | ADHEr | LDH_D | GLUDy | HEX1 | PGI | PTAr | TAL |
| 76 | ADHEr | LDH_D | ACKr | GLUDy | HEX1 | PGI | TAL |
| 77 | ADHEr | LDH_D | ACKr | GLUDy | HEX1 | PGI | TKT1 |
| 78 | ADHEr | LDH_D | GLUDy | HEX1 | PGI | PTAr | TKT1 |
| 79 | ADHEr | LDH_D | ACKr | GLUDy | HEX1 | TPI |
| 80 | ADHEr | LDH_D | ACKr | GLUDy | HEX1 | PFK |
| 81 | ADHEr | LDH_D | GLUDy | HEX1 | PTAr | TPI |
| 82 | ADHEr | LDH_D | GLUDy | HEX1 | PFK | PTAr |
| 83 | ADHEr | LDH_D | ACKr | FBA | GLUDy | HEX1 |
| 84 | ADHEr | LDH_D | FBA | GLUDy | HEX1 | PTAr |
| 85 | ADHEr | LDH_D | ASPT | GLCpts | MDH | PFLi | TPI |
| 86 | ADHEr | LDH_D | ASPT | FBA | GLCpts | MDH | PFLi |
| 87 | ADHEr | LDH_D | ASPT | GLCpts | MDH | PFK | PFLi |
| 88 | ADHEr | LDH_D | ASPT | FUM | GLCpts | PFK | PFLi |
| 89 | ADHEr | LDH_D | ASPT | FUM | GLCpts | PFLi | TPI |
| 90 | ADHEr | LDH_D | ASPT | FBA | FUM | GLCpts | PFLi |
| 91 | ADHEr | LDH_D | GLUDy | HEX1 | PGI | PTAr | RPE |
| 92 | ADHEr | LDH_D | ACKr | GLUDy | HEX1 | PGI | RPE |
| 93 | ADHEr | LDH_D | ASPT | ATPS4r | FUM | GLUDy | PGI |
| 94 | ADHEr | LDH_D | ASPT | ATPS4r | GLUDy | MDH | PGI |
| 95 | ADHEr | LDH_D | ASPT | ATPS4r | FBA | MDH | PPS |
| 96 | ADHEr | LDH_D | ASPT | ATPS4r | FUM | PFK | PPS |
| 97 | ADHEr | LDH_D | ASPT | ATPS4r | MDH | PFK | PPS |
| 98 | ADHEr | LDH_D | ASPT | ATPS4r | MDH | PPS | TPI |
| 99 | ADHEr | LDH_D | ASPT | ATPS4r | FUM | PPS | TPI |
| 100 | ADHEr | LDH_D | ASPT | ATPS4r | FBA | FUM | PPS |
| 101 | ADHEr | LDH_D | ACKr | GLUDy | HEX1 | PGI | TKT2 |
| 102 | ADHEr | LDH_D | GLUDy | HEX1 | PGI | PTAr | TKT2 |
| 103 | ADHEr | LDH_D | ASPT | ATPS4r | FBA | FUM | GLUDy |
| 104 | ADHEr | LDH_D | ASPT | ATPS4r | GLUDy | MDH | PFK |
| 105 | ADHEr | LDH_D | ASPT | ATPS4r | FBA | GLUDy | MDH |
| 106 | ADHEr | LDH_D | ASPT | ATPS4r | FUM | GLUDy | TPI |
| 107 | ADHEr | LDH_D | ASPT | ATPS4r | FUM | GLUDy | PFK |
| 108 | ADHEr | LDH_D | ASPT | ATPS4r | GLUDy | MDH | TPI |
| 109 | ADHEr | LDH_D | ACKr | GLUDy | PGDH | PGI |

TABLE 1-continued

The list of all disruption strategies identified by OptKnock that are most likely to provide growth-coupled LCA produciton.

| | | | | | | |
|---|---|---|---|---|---|---|
| 110 | ADHEr | LDH_D | GLUDy | PGDH | PGI | PTAr |
| 111 | ADHEr | LDH_D | ACKr | GLUDy | PGI | TAL |
| 112 | ADHEr | LDH_D | GLUDy | PGI | PTAr | TKT1 |
| 113 | ADHEr | LDH_D | ACKr | GLUDy | PGI | TKT1 |
| 114 | ADHEr | LDH_D | GLUDy | PGI | PTAr | TAL |
| 115 | ADHEr | LDH_D | ACKr | GLUDy | TPI | |
| 116 | ADHEr | LDH_D | GLUDy | PFK | PTAr | |
| 117 | ADHEr | LDH_D | FBA | GLUDy | PTAr | |
| 118 | ADHEr | LDH_D | ACKr | FBA | GLUDy | |
| 119 | ADHEr | LDH_D | ACKr | GLUDy | PFK | |
| 120 | ADHEr | LDH_D | GLUDy | PTAr | TPI | |
| 121 | ADHEr | LDH_D | ACKr | GLUDy | PGI | RPE |
| 122 | ADHEr | LDH_D | GLUDy | PGI | PTAr | RPE |
| 123 | ADHEr | LDH_D | GLUDy | PGI | PTAr | TKT2 |
| 124 | ADHEr | LDH_D | ACKr | GLUDy | PGI | TKT2 |
| 125 | ADHEr | LDH_D | HEX1 | PGDH | PGI | PTAr |
| 126 | ADHEr | LDH_D | ACKr | HEX1 | PGDH | PGI |
| 127 | ADHEr | LDH_D | ASPT | ATPS4r | CBMK2 | FUM | PGI |
| 128 | ADHEr | LDH_D | ASPT | ATPS4r | CBMK2 | MDH | PGI |
| 129 | ADHEr | LDH_D | HEX1 | PGI | PTAr | TAL |
| 130 | ADHEr | LDH_D | HEX1 | PGI | PTAr | TKT1 |
| 131 | ADHEr | LDH_D | ACKr | HEX1 | PGI | TKT1 |
| 132 | ADHEr | LDH_D | ACKr | HEX1 | PGI | TAL |
| 133 | ADHEr | LDH_D | GLUDy | HEX1 | PFLi | PGI | SUCD4 |
| 134 | ADHEr | LDH_D | FRD2 | GLUDy | HEX1 | PFLi | PGI |
| 135 | ADHEr | LDH_D | GLUDy | HEX1 | NADH6 | PFLi | PGI |
| 136 | ADHEr | LDH_D | ACKr | FBA | HEX1 | |
| 137 | ADHEr | LDH_D | FBA | HEX1 | PTAr | |
| 138 | ADHEr | LDH_D | HEX1 | PFK | PTAr | |
| 139 | ADHEr | LDH_D | ACKr | HEX1 | PFK | |
| 140 | ADHEr | LDH_D | ACKr | HEX1 | TPI | |
| 141 | ADHEr | LDH_D | HEX1 | PTAr | TPI | |
| 142 | ADHEr | LDH_D | HEX1 | PGI | PTAr | RPE |
| 143 | ADHEr | LDH_D | ACKr | HEX1 | PGI | RPE |
| 144 | ADHEr | LDH_D | ASPT | ATPS4r | CBMK2 | FBA | FUM |
| 145 | ADHEr | LDH_D | ASPT | ATPS4r | CBMK2 | FBA | MDH |
| 146 | ADHEr | LDH_D | ASPT | ATPS4r | CBMK2 | MDH | TPI |
| 147 | ADHEr | LDH_D | ASPT | ATPS4r | CBMK2 | FUM | PFK |
| 148 | ADHEr | LDH_D | ASPT | ATPS4r | CBMK2 | FUM | TPI |
| 149 | ADHEr | LDH_D | ASPT | ATPS4r | CBMK2 | MDH | PFK |
| 150 | ADHEr | LDH_D | FBA | GLUDy | HEX1 | NADH6 | PFLi |
| 151 | ADHEr | LDH_D | GLUDy | HEX1 | NADH6 | PFK | PFLi |
| 152 | ADHEr | LDH_D | FBA | GLUDy | HEX1 | PFLi | SUCD4 |
| 153 | ADHEr | LDH_D | FRD2 | GLUDy | HEX1 | PFK | PFLi |
| 154 | ADHEr | LDH_D | GLUDy | HEX1 | PFK | PFLi | SUCD4 |
| 155 | ADHEr | LDH_D | GLUDy | HEX1 | NADH6 | PFLi | TPI |
| 156 | ADHEr | LDH_D | FBA | FRD2 | GLUDy | HEX1 | PFLi |
| 157 | ADHEr | LDH_D | GLUDy | HEX1 | PFLi | SUCD4 | TPI |
| 158 | ADHEr | LDH_D | FRD2 | GLUDy | HEX1 | PFLi | TPI |
| 159 | ADHEr | LDH_D | GLUDy | HEX1 | MDH | PFLi | PGI |
| 160 | ADHEr | LDH_D | FUM | GLUDy | HEX1 | PFLi | PGI |
| 161 | ADHEr | LDH_D | HEX1 | PGI | PTAr | TKT2 | |
| 162 | ADHEr | LDH_D | ACKr | HEX1 | PGI | TKT2 | |
| 163 | ADHEr | LDH_D | ATPS4r | GLUDy | HEX1 | MDH | PFK |
| 164 | ADHEr | LDH_D | ATPS4r | FBA | GLUDy | HEX1 | MDH |
| 165 | ADHEr | LDH_D | ATPS4r | GLUDy | HEX1 | MDH | TPI |
| 166 | ADHEr | LDH_D | ATPS4r | FBA | FUM | GLUDy | HEX1 |
| 167 | ADHEr | LDH_D | ATPS4r | FUM | GLUDy | HEX1 | PFK |
| 168 | ADHEr | LDH_D | ATPS4r | FUM | GLUDy | HEX1 | TPI |
| 169 | ADHEr | LDH_D | FBA | FUM | GLUDy | HEX1 | PFLi |
| 170 | ADHEr | LDH_D | FUM | GLUDy | HEX1 | PFLi | TPI |
| 171 | ADHEr | LDH_D | GLUDy | HEX1 | MDH | PFLi | TPI |
| 172 | ADHEr | LDH_D | GLUDy | HEX1 | MDH | PFK | PFLi |
| 173 | ADHEr | LDH_D | FBA | GLUDy | HEX1 | MDH | PFLi |
| 174 | ADHEr | LDH_D | FUM | GLUDy | HEX1 | PFK | PFLi |
| 175 | ADHEr | LDH_D | ATPS4r | FUM | GLUDy | HEX1 | PGI |
| 176 | ADHEr | LDH_D | ATPS4r | GLUDy | HEX1 | MDH | PGI |
| 177 | ADHEr | LDH_D | ASPT | ATPS4r | MDH | PGI | |
| 178 | ADHEr | LDH_D | ASPT | ATPS4r | FUM | PGI | |
| 179 | ADHEr | LDH_D | ATPS4r | GLUDy | MDH | NADH6 | PGI |
| 180 | ADHEr | LDH_D | ATPS4r | FUM | GLUDy | NADH6 | PGI |
| 181 | ADHEr | LDH_D | ATPS4r | GLUDy | HEX1 | PGDH | PGI |
| 182 | ADHEr | LDH_D | PGDH | PGI | PTAr | | |
| 183 | ADHEr | LDH_D | ACKr | PGDH | PGI | | |
| 184 | ADHEr | LDH_D | ATPS4r | GLUDy | HEX1 | PFLi | PGI |
| 185 | ADHEr | LDH_D | ASPT | ATPS4r | MDH | TPI | |
| 186 | ADHEr | LDH_D | ASPT | ATPS4r | FUM | TPI | |

TABLE 1-continued

The list of all disruption strategies identified by OptKnock that are most likely to provide growth-coupled LCA produciton.

| | | | | | | |
|---|---|---|---|---|---|---|
| 187 ADHEr | LDH_D | ASPT | ATPS4r | MDH | PFK | |
| 188 ADHEr | LDH_D | ASPT | ATPS4r | FBA | FUM | |
| 189 ADHEr | LDH_D | ASPT | ATPS4r | FBA | MDH | |
| 190 ADHEr | LDH_D | ASPT | ATPS4r | FUM | PFK | |
| 191 ADHEr | LDH_D | ACKr | PGI | TKT1 | | |
| 192 ADHEr | LDH_D | PGI | PTAr | TAL | | |
| 193 ADHEr | LDH_D | PGI | PTAr | TKT1 | | |
| 194 ADHEr | LDH_D | ACKr | PGI | TAL | | |
| 195 ADHEr | LDH_D | ATPS4r | FBA | GLUDy | MDH | NADH6 |
| 196 ADHEr | LDH_D | ATPS4r | GLUDy | MDH | NADH6 | PFK |
| 197 ADHEr | LDH_D | ATPS4r | GLUDy | MDH | NADH6 | TPI |
| 198 ADHEr | LDH_D | ATPS4r | FUM | GLUDy | NADH6 | TPI |
| 199 ADHEr | LDH_D | ATPS4r | FUM | GLUDy | NADH6 | PFK |
| 200 ADHEr | LDH_D | ATPS4r | FBA | FUM | GLUDy | NADH6 |
| 201 ADHEr | LDH_D | ATPS4r | GLUDy | HEX1 | PGI | TAL |
| 202 ADHEr | LDH_D | ATPS4r | GLUDy | HEX1 | PGI | TKT1 |
| 203 ADHEr | LDH_D | ATPS4r | GLUDy | HEX1 | PFK | |
| 204 ADHEr | LDH_D | ATPS4r | GLUDy | HEX1 | TPI | |
| 205 ADHEr | LDH_D | ATPS4r | FBA | GLUDy | HEX1 | |
| 206 ADHEr | LDH_D | GLUDy | PTAr | PYK | SUCD4 | |
| 207 ADHEr | LDH_D | ACKr | GLUDy | PYK | SUCD4 | |
| 208 ADHEr | LDH_D | FRD2 | GLUDy | PTAr | PYK | |
| 209 ADHEr | LDH_D | ACKr | FRD2 | GLUDy | PYK | |
| 210 ADHEr | LDH_D | FDH2 | GLUDy | NADH6 | PTAr | PYK |
| 211 ADHEr | LDH_D | ACKr | FDH2 | GLUDy | NADH6 | PYK |
| 212 ADHEr | LDH_D | PFK | PTAr | | | |
| 213 ADHEr | LDH_D | ACKr | TPI | | | |
| 214 ADHEr | LDH_D | ACKr | FBA | | | |
| 215 ADHEr | LDH_D | PTAr | TPI | | | |
| 216 ADHEr | LDH_D | FBA | PTAr | | | |
| 217 ADHEr | LDH_D | ACKr | PFK | | | |
| 218 ADHEr | LDH_D | FRD2 | GLUDy | PFLi | PGI | |
| 219 ADHEr | LDH_D | GLUDy | PFLi | PGI | PRO1z | SUCD4 |
| 220 ADHEr | LDH_D | ACKr | PGI | RPE | | |
| 221 ADHEr | LDH_D | PGI | PTAr | RPE | | |
| 222 ADHEr | LDH_D | ACKr | PGI | TKT2 | | |
| 223 ADHEr | LDH_D | PGI | PTAr | TKT2 | | |
| 224 ADHEr | LDH_D | ATPS4r | GLUDy | HEX1 | PGI | RPE |
| 225 ADHEr | LDH_D | FRD2 | GLUDy | PFLi | TPI | |
| 226 ADHEr | LDH_D | FRD2 | GLUDy | PFK | PFLi | |
| 227 ADHEr | LDH_D | FBA | FRD2 | GLUDy | PFLi | |
| 228 ADHEr | LDH_D | GLUDy | PFK | PFLi | PRO1z | SUCD4 |
| 229 ADHEr | LDH_D | GLUDy | PFLi | PRO1z | SUCD4 | TPI |
| 230 ADHEr | LDH_D | FBA | GLUDy | PFLi | PRO1z | SUCD4 |
| 231 ADHEr | LDH_D | GLUDy | MDH | PFLi | PGI | SUCD4 |
| 232 ADHEr | LDH_D | FUM | GLUDy | NADH6 | PFLi | PGI |
| 233 ADHEr | LDH_D | GLUDy | MDH | NADH6 | PFLi | PGI |
| 234 ADHEr | LDH_D | FUM | GLUDy | PFLi | PGI | SUCD4 |
| 235 ADHEr | LDH_D | ASPT | GLUDy | MDH | PFLi | PGI |
| 236 ADHEr | LDH_D | ASPT | FUM | GLUDy | PFLi | PGI |
| 237 ADHEr | LDH_D | ATPS4r | GLUDy | HEX1 | PGI | TKT2 |
| 238 ADHEr | LDH_D | FUM | GLUDy | PFK | PFLi | SUCD4 |
| 239 ADHEr | LDH_D | GLUDy | MDH | NADH6 | PFK | PFLi |
| 240 ADHEr | LDH_D | FUM | GLUDy | PFLi | SUCD4 | TPI |
| 241 ADHEr | LDH_D | FUM | GLUDy | NADH6 | PFK | PFLi |
| 242 ADHEr | LDH_D | FBA | FUM | GLUDy | PFLi | SUCD4 |
| 243 ADHEr | LDH_D | GLUDy | MDH | PFLi | SUCD4 | TPI |
| 244 ADHEr | LDH_D | GLUDy | MDH | PFK | PFLi | SUCD4 |
| 245 ADHEr | LDH_D | FBA | FUM | GLUDy | NADH6 | PFLi |
| 246 ADHEr | LDH_D | FBA | GLUDy | MDH | PFLi | SUCD4 |
| 247 ADHEr | LDH_D | FBA | GLUDy | MDH | NADH6 | PFLi |
| 248 ADHEr | LDH_D | GLUDy | MDH | NADH6 | PFLi | TPI |
| 249 ADHEr | LDH_D | FUM | GLUDy | NADH6 | PFLi | TPI |
| 250 ADHEr | LDH_D | ASPT | ATPS4r | FUM | NADH6 | PYK |
| 251 ADHEr | LDH_D | ASPT | ATPS4r | MDH | NADH6 | PYK |
| 252 ADHEr | LDH_D | GLCpts | GLUDy | PFLi | PGI | PTAr |
| 253 ADHEr | LDH_D | ACKr | GLCpts | GLUDy | PFLi | PGI |
| 254 ADHEr | LDH_D | ASPT | FBA | GLUDy | MDH | PFLi |
| 255 ADHEr | LDH_D | ASPT | GLUDy | MDH | PFK | PFLi |
| 256 ADHEr | LDH_D | ASPT | FBA | FUM | GLUDy | PFLi |
| 257 ADHEr | LDH_D | ASPT | GLUDy | MDH | PFLi | TPI |
| 258 ADHEr | LDH_D | ASPT | FUM | GLUDy | PFLi | TPI |
| 259 ADHEr | LDH_D | ASPT | FUM | GLUDy | PFK | PFLi |
| 260 ADHEr | LDH_D | ME2 | PGL | PTAr | PYK | SUCD4 |
| 261 ADHEr | LDH_D | FRD2 | G6PDHy | ME2 | PTAr | PYK |
| 262 ADHEr | LDH_D | ACKr | ME2 | PGL | PYK | SUCD4 |
| 263 ADHEr | LDH_D | ACKr | FRD2 | ME2 | PGL | PYK |

TABLE 1-continued

The list of all disruption strategies identified by OptKnock that are most likely to provide growth-coupled LCA produciton.

| # | | | | | | | |
|---|---|---|---|---|---|---|---|
| 264 | ADHEr | LDH_D | FRD2 | ME2 | PGL | PTAr | PYK |
| 265 | ADHEr | LDH_D | G6PDHy | ME2 | PTAr | PYK | SUCD4 |
| 266 | ADHEr | LDH_D | ACKr | FRD2 | G6PDHy | ME2 | PYK |
| 267 | ADHEr | LDH_D | ACKr | G6PDHy | ME2 | PYK | SUCD4 |
| 268 | ADHEr | LDH_D | G6PDHy | MDH | PTAr | PYK | SUCD4 |
| 269 | ADHEr | LDH_D | ACKr | G6PDHy | MDH | NADH6 | PYK |
| 270 | ADHEr | LDH_D | FRD2 | G6PDHy | MDH | PTAr | PYK |
| 271 | ADHEr | LDH_D | FRD2 | MDH | PGL | PTAr | PYK |
| 272 | ADHEr | LDH_D | ACKr | G6PDHy | MDH | PYK | SUCD4 |
| 273 | ADHEr | LDH_D | ACKr | MDH | PGL | PYK | SUCD4 |
| 274 | ADHEr | LDH_D | MDH | NADH6 | PGL | PTAr | PYK |
| 275 | ADHEr | LDH_D | ACKr | MDH | NADH6 | PGL | PYK |
| 276 | ADHEr | LDH_D | ACKr | FRD2 | G6PDHy | MDH | PYK |
| 277 | ADHEr | LDH_D | MDH | PGL | PTAr | PYK | SUCD4 |
| 278 | ADHEr | LDH_D | ACKr | FRD2 | MDH | PGL | PYK |
| 279 | ADHEr | LDH_D | G6PDHy | MDH | NADH6 | PTAr | PYK |
| 280 | ADHEr | LDH_D | ATPS4r | GLUDy | NADH6 | PGI | |
| 281 | ADHEr | LDH_D | FUM | GLUDy | PTAr | PYK | |
| 282 | ADHEr | LDH_D | ACKr | GLUDy | MDH | PYK | |
| 283 | ADHEr | LDH_D | ACKr | FUM | GLUDy | PYK | |
| 284 | ADHEr | LDH_D | GLUDy | MDH | PTAr | PYK | |
| 285 | ADHEr | LDH_D | ATPS4r | HEX1 | PGDH | PGI | |
| 286 | ADHEr | LDH_D | ATPS4r | GLUDy | NADH6 | TPI | |
| 287 | ADHEr | LDH_D | ATPS4r | GLUDy | NADH6 | PFK | |
| 288 | ADHEr | LDH_D | ATPS4r | FBA | GLUDy | NADH6 | |
| 289 | ADHEr | LDH_D | HEX1 | PFLi | PGI | | |
| 290 | ADHEr | LDH_D | ASPT | ATPS4r | GLUDy | MDH | PYK |
| 291 | ADHEr | LDH_D | ASPT | ATPS4r | FUM | GLUDy | PYK |
| 292 | ADHEr | LDH_D | ATPS4r | HEX1 | PGI | TKT1 | |
| 293 | ADHEr | LDH_D | ATPS4r | HEX1 | PGI | TAL | |
| 294 | ADHEr | LDH_D | ATPS4r | HEX1 | PFK | | |
| 295 | ADHEr | LDH_D | ATPS4r | FBA | HEX1 | | |
| 296 | ADHEr | LDH_D | ATPS4r | HEX1 | TPI | | |
| 297 | ADHEr | LDH_D | HEX1 | PFLi | TPI | | |
| 298 | ADHEr | LDH_D | HEX1 | PFK | PFLi | | |
| 299 | ADHEr | LDH_D | FBA | HEX1 | PFLi | | |
| 300 | ADHEr | LDH_D | ATPS4r | HEX1 | PGI | RPE | |
| 301 | ADHEr | LDH_D | ACKr | GLUDy | NADH6 | PGI | PYK |
| 302 | ADHEr | LDH_D | GLUDy | NADH6 | PGI | PTAr | PYK |
| 303 | ADHEr | LDH_D | ATPS4r | HEX1 | PGI | TKT2 | |
| 304 | ADHEr | LDH_D | ACKr | FRD2 | PYK | | |
| 305 | ADHEr | LDH_D | ACKr | PYK | SUCD4 | | |
| 306 | ADHEr | LDH_D | FRD2 | PTAr | PYK | | |
| 307 | ADHEr | LDH_D | PTAr | PYK | SUCD4 | | |
| 308 | ADHEr | LDH_D | ACKr | FDH2 | NADH6 | PYK | |
| 309 | ADHEr | LDH_D | FDH2 | NADH6 | PTAr | PYK | |
| 310 | ADHEr | LDH_D | ATPS4r | NADH6 | PGI | | |
| 311 | ADHEr | LDH_D | ACKr | GLCpts | PFLi | PGI | |
| 312 | ADHEr | LDH_D | GLCpts | PFLi | PGI | PTAr | |
| 313 | ADHEr | LDH_D | FRD2 | GLUDy | PFLi | PYK | |
| 314 | ADHEr | LDH_D | ATPS4r | FUM | GLUDy | PGDH | PGI |
| 315 | ADHEr | LDH_D | ATPS4r | GLUDy | MDH | PGDH | PGI |
| 316 | ADHEr | LDH_D | FUM | GLUDy | PFLi | PGI | |
| 317 | ADHEr | LDH_D | GLUDy | MDH | PFLi | PGI | |
| 318 | ADHEr | LDH_D | ATPS4r | FBA | NADH6 | | |
| 319 | ADHEr | LDH_D | ATPS4r | NADH6 | PFK | | |
| 320 | ADHEr | LDH_D | ATPS4r | NADH6 | TPI | | |
| 321 | ADHEr | LDH_D | ATPS4r | FBA | FUM | GLUDy | |
| 322 | ADHEr | LDH_D | ATPS4r | FUM | GLUDy | PFK | |
| 323 | ADHEr | LDH_D | ATPS4r | FBA | GLUDy | MDH | |
| 324 | ADHEr | LDH_D | ATPS4r | GLUDy | MDH | TPI | |
| 325 | ADHEr | LDH_D | ATPS4r | FUM | GLUDy | TPI | |
| 326 | ADHEr | LDH_D | ATPS4r | GLUDy | MDH | PFK | |
| 327 | ADHEr | LDH_D | FRD2 | G6PDHy | ME2 | PFLi | PYK |
| 328 | ADHEr | LDH_D | FRD2 | ME2 | PFLi | PGL | PYK |
| 329 | ADHEr | LDH_D | EDA | FRD2 | ME2 | PFLi | PYK |
| 330 | ADHEr | LDH_D | FRD2 | ME2 | PFLi | PGDHY | PYK |
| 331 | ADHEr | LDH_D | GLUDy | MDH | PFK | PFLi | |
| 332 | ADHEr | LDH_D | FBA | GLUDy | MDH | PFLi | |
| 333 | ADHEr | LDH_D | GLUDy | MDH | PFLi | TPI | |
| 334 | ADHEr | LDH_D | FBA | FUM | GLUDy | PFLi | |
| 335 | ADHEr | LDH_D | FUM | GLUDy | PFLi | TPI | |
| 336 | ADHEr | LDH_D | FUM | GLUDy | PFK | PFLi | |
| 337 | ADHEr | LDH_D | PFLi | PGI | SUCD4 | | |
| 338 | ADHEr | LDH_D | FRD2 | PFLi | PGI | | |
| 339 | ADHEr | LDH_D | NADH6 | PFLi | PGI | | |
| 340 | ADHEr | LDH_D | FRD2 | MDH | PFLi | PGL | PYK |

TABLE 1-continued

The list of all disruption strategies identified by OptKnock that are most likely to provide growth-coupled LCA produciton.

| | | | | | | | |
|---|---|---|---|---|---|---|---|
| 341 ADHEr | LDH_D | FRD2 | G6PDHy | MDH | PFLi | PYK | |
| 342 ADHEr | LDH_D | FRD2 | MDH | PFLi | PGDHY | PYK | |
| 343 ADHEr | LDH_D | EDA | FRD2 | MDH | PFLi | PYK | |
| 344 ADHEr | LDH_D | ACKr | ASPT | MDH | PYK | | |
| 345 ADHEr | LDH_D | ASPT | MDH | PTAr | PYK | | |
| 346 ADHEr | LDH_D | ACKr | ASPT | FUM | PYK | | |
| 347 ADHEr | LDH_D | ASPT | FUM | PTAr | PYK | | |
| 348 ADHEr | LDH_D | ATPS4r | GLUDy | MDH | PGI | | |
| 349 ADHEr | LDH_D | ATPS4r | FUM | GLUDy | PGI | | |
| 350 ADHEr | LDH_D | FBA | PFLi | SUCD4 | | | |
| 351 ADHEr | LDH_D | FRD2 | PFK | PFLi | | | |
| 352 ADHEr | LDH_D | PFLi | SUCD4 | TPI | | | |
| 353 ADHEr | LDH_D | FBA | FRD2 | PFLi | | | |
| 354 ADHEr | LDH_D | PFK | PFLi | SUCD4 | | | |
| 355 ADHEr | LDH_D | FRD2 | PFLi | TPI | | | |
| 356 ADHEr | LDH_D | NADH6 | PFLi | TPI | | | |
| 357 ADHEr | LDH_D | FBA | NADH6 | PFLi | | | |
| 358 ADHEr | LDH_D | NADH6 | PFK | PFLi | | | |
| 359 ADHEr | LDH_D | ASPT | MDH | PFLi | PGI | | |
| 360 ADHEr | LDH_D | ASPT | FUM | PFLi | PGI | | |
| 361 ADHEr | LDH_D | ASPT | GLUDy | MDH | PFLi | PYK | |
| 362 ADHEr | LDH_D | ASPT | FUM | GLUDy | PFLi | PYK | |
| 363 ADHEr | LDH_D | ASPT | ATPS4r | CBMK2 | FUM | PYK | |
| 364 ADHEr | LDH_D | ASPT | MDH | PFLi | TPI | | |
| 365 ADHEr | LDH_D | ASPT | FUM | PFLi | TPI | | |
| 366 ADHEr | LDH_D | ASPT | FBA | MDH | PFLi | | |
| 367 ADHEr | LDH_D | ASPT | FBA | FUM | PFLi | | |
| 368 ADHEr | LDH_D | ASPT | MDH | PFK | PFLi | | |
| 369 ADHEr | LDH_D | ASPT | FUM | PFK | PFLi | | |
| 370 ADHEr | LDH_D | ACKr | NADH6 | PGI | PYK | | |
| 371 ADHEr | LDH_D | NADH6 | PGI | PTAr | PYK | | |
| 372 ADHEr | LDH_D | ASPT | ATPS4r | FUM | PYK | | |
| 373 ADHEr | LDH_D | ASPT | ATPS4r | MALS | MDH | PYK | |
| 374 ADHEr | LDH_D | ASPT | ATPS4r | ICL | MDH | PYK | |
| 375 ADHEr | LDH_D | GLUDy | PFLi | PGDH | PGI | | |
| 376 ADHEr | LDH_D | ATPS4r | GLUDy | PFLi | PGI | | |
| 377 ADHEr | LDH_D | FBA | GLUDy | PFLi | | | |
| 378 ADHEr | LDH_D | GLUDy | PFLi | TPI | | | |
| 379 ADHEr | LDH_D | GLUDy | PFK | PFLi | | | |
| 380 ADHEr | LDH_D | GLUDy | PFLi | PGI | TAL | | |
| 381 ADHEr | LDH_D | GLUDy | PFLi | PGI | TKT1 | | |
| 382 ADHEr | LDH_D | GLUDy | PFLi | PRO1z | PYK | SUCD4 | |
| 383 ADHEr | LDH_D | GLUDy | MDH | NADH6 | PFLi | PYK | |
| 384 ADHEr | LDH_D | GLUDy | MDH | PFLi | PYK | SUCD4 | |
| 385 ADHEr | LDH_D | FUM | GLUDy | PFLi | PYK | SUCD4 | |
| 386 ADHEr | LDH_D | FUM | GLUDy | NADH6 | PFLi | PYK | |
| 387 ADHEr | LDH_D | GLUDy | PFLi | PGI | | | |
| 388 ADHEr | LDH_D | EDA | MDH | PFLi | PYK | SUCD4 | |
| 389 ADHEr | LDH_D | MDH | PFLi | PGDHY | PYK | SUCD4 | |
| 390 ADHEr | LDH_D | MDH | PFLi | PGL | PYK | SUCD4 | |
| 391 ADHEr | LDH_D | G6PDHy | MDH | PFLi | PYK | UCD4 | |
| 392 ADHEr | LDH_D | ATPS4r | GLUDy | MDH | NADH6 | PYK | |
| 393 ADHEr | LDH_D | ATPS4r | FUM | GLUDy | NADH6 | PYK | |
| 394 ADHEr | LDH_D | ACKr | AKGD | ATPS4r | GLUDy | PYK | |
| 395 ADHEr | LDH_D | AKGD | ATPS4r | GLUDy | PTAr | PYK | |
| 396 ADHEr | LDH_D | FRD2 | PFLi | PYK | | | |
| 397 ADHEr | LDH_D | ALAR | PFLi | PRO1z | PYK | SUCD4 | |
| 398 ADHEr | LDH_D | DAAD | PFLi | PRO1z | PYK | SUCD4 | |
| 399 ADHEr | LDH_D | PFLi | PGDH | PGI | | | |
| 400 ADHEr | LDH_D | ATPS4r | PFLi | PGI | | | |
| 401 ADHEr | LDH_D | ATPS4r | FUM | GLUDy | PFLi | PYK | |
| 402 ADHEr | LDH_D | ATPS4r | GLUDy | MDH | PFLi | PYK | |
| 403 ADHEr | LDH_D | PFLi | TPI | | | | |
| 404 ADHEr | LDH_D | FBA | PFLi | | | | |
| 405 ADHEr | LDH_D | PFK | PFLi | | | | |
| 406 ADHEr | LDH_D | ASPT | FUM | PFLi | PYK | | |
| 407 ADHEr | LDH_D | ASPT | MDH | PFLi | PYK | | |
| 408 ADHEr | LDH_D | PFLi | PGI | TKT1 | | | |
| 409 ADHEr | LDH_D | PFLi | PGI | TAL | | | |
| 410 ADHEr | LDH_D | ASPT | ATPS4r | FUM | GLUDy | NADH6 | |
| 411 ADHEr | LDH_D | ASPT | ATPS4r | GLUDy | MDH | NADH6 | |
| 412 ADHEr | LDH_D | G6PDHy | ME2 | PFLi | PYK | SUCD4 | |
| 413 ADHEr | LDH_D | EDA | ME2 | PFLi | PYK | SUCD4 | |
| 414 ADHEr | LDH_D | ME2 | PFLi | PGDHY | PYK | SUCD4 | |
| 415 ADHEr | LDH_D | ME2 | PFLi | PGL | PYK | SUCD4 | |
| 416 ADHEr | LDH_D | MDH | NADH6 | PFLi | PGDHY | PYK | |
| 417 ADHEr | LDH_D | G6PDHy | MDH | NADH6 | PFLi | PYK | |

TABLE 1-continued

The list of all disruption strategies identified by OptKnock that are most likely to provide growth-coupled LCA produciton.

| | | | | | | |
|---|---|---|---|---|---|---|
| 418 | ADHEr | LDH_D | EDA | MDH | NADH6 | PFLi | PYK |
| 419 | ADHEr | LDH_D | MDH | NADH6 | PFLi | PGL | PYK |
| 420 | ADHEr | LDH_D | ASPT | ATPS4r | CBMK2 | MDH | NADH6 |
| 421 | ADHEr | LDH_D | ASPT | ATPS4r | CBMK2 | FUM | NADH6 |
| 422 | ADHEr | LDH_D | CBMK2 | PFLi | PGI | RPE | |
| 423 | ADHEr | LDH_D | ASNS2 | GLU5K | PFLi | PGI | RPE |
| 424 | ADHEr | LDH_D | ASNS2 | G5SD | PFLi | PGI | RPE |
| 425 | ADHEr | LDH_D | ASPT | ATPS4r | GLUDy | MDH | PTAr |
| 426 | ADHEr | LDH_D | ASPT | ATPS4r | FUM | GLUDy | PTAr |
| 427 | ADHEr | LDH_D | PFLi | PGI | | | |
| 428 | ADHEr | LDH_D | ASPT | ATPS4r | FUM | GLUDy | |
| 429 | ADHEr | LDH_D | ASPT | ATPS4r | GLUDy | MDH | |
| 430 | ADHEr | LDH_D | ACKr | AKGD | ATPS4r | PYK | |
| 431 | ADHEr | LDH_D | AKGD | ATPS4r | PTAr | PYK | |
| 432 | ADHEr | LDH_D | ASPT | ATPS4r | MDH | NADH6 | |
| 433 | ADHEr | LDH_D | ASPT | ATPS4r | FUM | NADH6 | |
| 434 | ADHEr | LDH_D | G6PDHy | GLCpts | GLUDy | PTAr | |
| 435 | ADHEr | LDH_D | ACKr | GLCpts | GLUDy | PGL | |
| 436 | ADHEr | LDH_D | GLCpts | GLUDy | PGDH | PTAr | |
| 437 | ADHEr | LDH_D | GLCpts | GLUDy | PGL | PTAr | |
| 438 | ADHEr | LDH_D | ACKr | G6PDHy | GLCpts | GLUDy | |
| 439 | ADHEr | LDH_D | ACKr | GLCpts | GLUDy | PGDH | |
| 440 | ADHEr | LDH_D | GLCpts | GLUDy | PTAr | TKT1 | |
| 441 | ADHEr | LDH_D | GLCpts | GLUDy | PTAr | TAL | |
| 442 | ADHEr | LDH_D | ACKr | GLCpts | GLUDy | TKT1 | |
| 443 | ADHEr | LDH_D | ACKr | GLCpts | GLUDy | TAL | |
| 444 | ADHEr | LDH_D | ACKr | GLCpts | GLUDy | RPE | |
| 445 | ADHEr | LDH_D | GLCpts | GLUDy | PTAr | RPE | |
| 446 | ADHEr | LDH_D | ACKr | GLCpts | GLUDy | TKT2 | |
| 447 | ADHEr | LDH_D | GLCpts | GLUDy | PTAr | TKT2 | |
| 448 | ADHEr | LDH_D | GLCpts | PGDH | PTAr | THD2 | |
| 449 | ADHEr | LDH_D | G6PDHy | GLCpts | PTAr | THD2 | |
| 450 | ADHEr | LDH_D | ACKr | G6PDHy | GLCpts | THD2 | |
| 451 | ADHEr | LDH_D | ACKr | GLCpts | PGL | THD2 | |
| 452 | ADHEr | LDH_D | ACKr | GLCpts | PGDH | THD2 | |
| 453 | ADHEr | LDH_D | GLCpts | PGL | PTAr | THD2 | |
| 454 | ADHEr | LDH_D | ACKr | GLCpts | THD2 | TKT1 | |
| 455 | ADHEr | LDH_D | ACKr | GLCpts | TAL | THD2 | |
| 456 | ADHEr | LDH_D | GLCpts | PTAr | TAL | THD2 | |
| 457 | ADHEr | LDH_D | GLCpts | PTAr | THD2 | TKT1 | |
| 458 | ADHEr | LDH_D | ASPT | ATPS4r | MDH | | |
| 459 | ADHEr | LDH_D | ASPT | ATPS4r | FUM | | |
| 460 | ADHEr | LDH_D | GLCpts | PTAr | RPE | THD2 | |
| 461 | ADHEr | LDH_D | ACKr | GLCpts | RPE | THD2 | |
| 462 | ADHEr | LDH_D | ACKr | ATPS4r | PYK | SUCOAS | |
| 463 | ADHEr | LDH_D | ATPS4r | PTAr | PYK | SUCOAS | |
| 464 | ADHEr | LDH_D | FRD2 | GLCpts | GLUDy | PFLi | |
| 465 | ADHEr | LDH_D | GLCpts | PTAr | THD2 | TKT2 | |
| 466 | ADHEr | LDH_D | ACKr | GLCpts | THD2 | TKT2 | |
| 467 | ADHEr | LDH_D | FRD2 | GLCpts | PFLi | THD2 | |
| 468 | ADHEr | LDH_D | ACKr | GLUDy | PGDH | THD2 | |
| 469 | ADHEr | LDH_D | GLUDy | PGL | PTAr | THD2 | |
| 470 | ADHEr | LDH_D | G6PDHy | GLUDy | PTAr | THD2 | |
| 471 | ADHEr | LDH_D | GLUDy | PGDH | PTAr | THD2 | |
| 472 | ADHEr | LDH_D | ACKr | GLUDy | PGL | THD2 | |
| 473 | ADHEr | LDH_D | ACKr | G6PDHy | GLUDy | THD2 | |
| 474 | ADHEr | LDH_D | FRD2 | GLUDy | PFLi | THD2 | |
| 475 | ADHEr | LDH_D | GLUDy | PTAr | THD2 | TKT1 | |
| 476 | ADHEr | LDH_D | GLUDy | PTAr | TAL | THD2 | |
| 477 | ADHEr | LDH_D | ACKr | GLUDy | TAL | THD2 | |
| 478 | ADHEr | LDH_D | ACKr | GLUDy | THD2 | TKT1 | |
| 479 | ADHEr | LDH_D | ACKr | GLCpts | PGDH | | |
| 480 | ADHEr | LDH_D | ACKr | GLCpts | PGL | | |
| 481 | ADHEr | LDH_D | GLCpts | PGDH | PTAr | | |
| 482 | ADHEr | LDH_D | GLCpts | PGL | PTAr | | |
| 483 | ADHEr | LDH_D | ACKr | G6PDHy | GLCpts | | |
| 484 | ADHEr | LDH_D | G6PDHy | GLCpts | PTAr | | |
| 485 | ADHEr | LDH_D | GLUDy | PTAr | RPE | THD2 | |
| 486 | ADHEr | LDH_D | ACKr | GLUDy | RPE | THD2 | |
| 487 | ADHEr | LDH_D | GLCpts | GLUDy | PTAr | | |
| 488 | ADHEr | LDH_D | ACKr | GLCpts | GLUDy | | |
| 489 | ADHEr | LDH_D | GLCpts | PTAr | TKT1 | | |
| 490 | ADHEr | LDH_D | GLCpts | PTAr | TAL | | |
| 491 | ADHEr | LDH_D | ACKr | GLCpts | TAL | | |
| 492 | ADHEr | LDH_D | ACKr | GLCpts | TKT1 | | |
| 493 | ADHEr | LDH_D | NADH6 | PFLi | PTAr | PYK | |
| 494 | ADHEr | LDH_D | ACKr | NADH6 | PFLi | PYK | |

TABLE 1-continued

The list of all disruption strategies identified by OptKnock that are most likely to provide growth-coupled LCA produciton.

| | | | | | | |
|---|---|---|---|---|---|---|
| 495 | ADHEr | LDH_D | ACKr | GLUDy | THD2 | TKT2 |
| 496 | ADHEr | LDH_D | GLUDy | PTAr | THD2 | TKT2 |
| 497 | ADHEr | LDH_D | ACKr | GLCpts | RPE | |
| 498 | ADHEr | LDH_D | GLCpts | PTAr | RPE | |
| 499 | ADHEr | LDH_D | ACKr | GLCpts | TKT2 | |
| 500 | ADHEr | LDH_D | GLCpts | PTAr | TKT2 | |
| 501 | ADHEr | LDH_D | ACKr | GLUDy | PGDH | |
| 502 | ADHEr | LDH_D | GLUDy | PGL | PTAr | |
| 503 | ADHEr | LDH_D | ACKr | GLUDy | PGL | |
| 504 | ADHEr | LDH_D | ACKr | G6PDHy | GLUDy | |
| 505 | ADHEr | LDH_D | GLUDy | PGDH | PTAr | |
| 506 | ADHEr | LDH_D | G6PDHy | GLUDy | PTAr | |
| 507 | ADHEr | LDH_D | GLUDy | PTAr | TKT1 | |
| 508 | ADHEr | LDH_D | ACKr | GLUDy | TKT1 | |
| 509 | ADHEr | LDH_D | ACKr | GLUDy | TAL | |
| 510 | ADHEr | LDH_D | GLUDy | PTAr | TAL | |
| 511 | ADHEr | LDH_D | GLUDy | PTAr | RPE | |
| 512 | ADHEr | LDH_D | ACKr | GLUDy | RPE | |
| 513 | ADHEr | LDH_D | GLUDy | PTAr | TKT2 | |
| 514 | ADHEr | LDH_D | ACKr | GLUDy | TKT2 | |
| 515 | ADHEr | LDH_D | PGDH | PTAr | THD2 | |
| 516 | ADHEr | LDH_D | ACKr | PGDH | THD2 | |
| 517 | ADHEr | LDH_D | G6PDHy | PTAr | THD2 | |
| 518 | ADHEr | LDH_D | PGL | PTAr | THD2 | |
| 519 | ADHEr | LDH_D | ACKr | PGL | THD2 | |
| 520 | ADHEr | LDH_D | ACKr | G6PDHy | THD2 | |
| 521 | ADHEr | LDH_D | PTAr | TAL | THD2 | |
| 522 | ADHEr | LDH_D | ACKr | THD2 | TKT1 | |
| 523 | ADHEr | LDH_D | ACKr | TAL | THD2 | |
| 524 | ADHEr | LDH_D | PTAr | THD2 | TKT1 | |
| 525 | ADHEr | LDH_D | PTAr | RPE | THD2 | |
| 526 | ADHEr | LDH_D | ACKr | RPE | THD2 | |
| 527 | ADHEr | LDH_D | FRD2 | GLUDy | PFLi | |
| 528 | ADHEr | LDH_D | GLUDy | PFLi | PRO1z | SUCD4 |
| 529 | ADHEr | LDH_D | FRD2 | GLCpts | PFLi | |
| 530 | ADHEr | LDH_D | PTAr | THD2 | TKT2 | |
| 531 | ADHEr | LDH_D | ACKr | THD2 | TKT2 | |
| 532 | ADHEr | LDH_D | ACKr | GLCpts | | |
| 533 | ADHEr | LDH_D | GLCpts | PTAr | | |
| 534 | ADHEr | LDH_D | FRD2 | PFLi | THD2 | |
| 535 | ADHEr | LDH_D | ATPS4r | FUM | GLUDy | |
| 536 | ADHEr | LDH_D | ATPS4r | GLUDy | MDH | |
| 537 | ADHEr | LDH_D | FUM | GLCpts | PFLi | SUCD4 |
| 538 | ADHEr | LDH_D | GLCpts | MDH | PFLi | SUCD4 |
| 539 | ADHEr | LDH_D | FUM | GLUDy | PFLi | SUCD4 |
| 540 | ADHEr | LDH_D | GLUDy | MDH | PFLi | SUCD4 |
| 541 | ADHEr | LDH_D | GLUDy | MDH | NADH6 | PFLi |
| 542 | ADHEr | LDH_D | FUM | GLUDy | NADH6 | PFLi |
| 543 | ADHEr | LDH_D | MDH | PFLi | SUCD4 | THD2 |
| 544 | ADHEr | LDH_D | FUM | PFLi | SUCD4 | THD2 |
| 545 | ADHEr | LDH_D | ASPT | FUM | GLCpts | PFLi |
| 546 | ADHEr | LDH_D | ASPT | GLCpts | MDH | PFLi |
| 547 | ADHEr | LDH_D | ASPT | FUM | GLUDy | PFLi |
| 548 | ADHEr | LDH_D | ASPT | GLUDy | MDH | PFLi |
| 549 | ADHEr | LDH_D | GLCpts | PFLi | SUCD4 | THD2 |
| 550 | ADHEr | LDH_D | PGDH | PTAr | | |
| 551 | ADHEr | LDH_D | PGL | PTAr | | |
| 552 | ADHEr | LDH_D | ACKr | PGL | | |
| 553 | ADHEr | LDH_D | G6PDHy | PTAr | | |
| 554 | ADHEr | LDH_D | ACKr | G6PDHy | | |
| 555 | ADHEr | LDH_D | ACKr | PGDH | | |
| 556 | ADHEr | LDH_D | ASPT | FUM | PFLi | THD2 |
| 557 | ADHEr | LDH_D | ASPT | MDH | PFLi | THD2 |
| 558 | ADHEr | LDH_D | ACKr | GLUDy | | |
| 559 | ADHEr | LDH_D | GLUDy | PTAr | | |
| 560 | ADHEr | LDH_D | PTAr | TAL | | |
| 561 | ADHEr | LDH_D | ACKr | TAL | | |
| 562 | ADHEr | LDH_D | ACKr | TKT1 | | |
| 563 | ADHEr | LDH_D | PTAr | TKT1 | | |
| 564 | ADHEr | LDH_D | ACKr | RPE | | |
| 565 | ADHEr | LDH_D | PTAr | RPE | | |
| 566 | ADHEr | LDH_D | GLCpts | GLUDy | PFLi | SUCD4 |
| 567 | ADHEr | LDH_D | FUM | GLCpts | GLUDy | PFLi |
| 568 | ADHEr | LDH_D | GLCpts | GLUDy | MDH | PFLi |
| 569 | ADHEr | LDH_D | ACKr | TKT2 | | |
| 570 | ADHEr | LDH_D | PTAr | TKT2 | | |
| 571 | ADHEr | LDH_D | GLUDy | PFLi | SUCD4 | THD2 |

TABLE 1-continued

The list of all disruption strategies identified by OptKnock that are most likely to provide growth-coupled LCA produciton.

| | | | | | | |
|---|---|---|---|---|---|---|
| 572 | ADHEr | LDH_D | FUM | GLUDy | PFLi | THD2 |
| 573 | ADHEr | LDH_D | GLUDy | MDH | PFLi | THD2 |
| 574 | ADHEr | LDH_D | GLCpts | GLUDy | NADH6 | PFLi |
| 575 | ADHEr | LDH_D | ATPS4r | GLUDy | NADH6 | PFLi |
| 576 | ADHEr | LDH_D | GLCpts | MDH | PFLi | THD2 |
| 577 | ADHEr | LDH_D | FUM | GLCpts | PFLi | THD2 |
| 578 | ADHEr | LDH_D | ACKr | CBMK2 | FRD2 | PFLi |
| 579 | ADHEr | LDH_D | CBMK2 | FRD2 | PFLi | PTAr |
| 580 | ADHEr | LDH_D | MDH | PTAr | SUCD4 | |
| 581 | ADHEr | LDH_D | FRD2 | MDH | PTAr | |
| 582 | ADHEr | LDH_D | ACKr | MDH | SUCD4 | |
| 583 | ADHEr | LDH_D | ACKr | FRD2 | MDH | |
| 584 | ADHEr | LDH_D | FDH2 | MDH | NADH6 | PTAr |
| 585 | ADHEr | LDH_D | ACKr | FDH2 | MDH | NADH6 |
| 586 | ADHEr | LDH_D | GLCpts | NADH6 | PFLi | THD2 |
| 587 | ADHEr | LDH_D | GLCpts | PFLi | SUCD4 | |
| 588 | ADHEr | LDH_D | GLCpts | NADH12 | NADH6 | PFLi |
| 589 | ADHEr | LDH_D | ATPS4r | FUM | PGL | |
| 590 | ADHEr | LDH_D | ATPS4r | MDH | PGDH | |
| 591 | ADHEr | LDH_D | ATPS4r | FUM | PGDH | |
| 592 | ADHEr | LDH_D | ATPS4r | FUM | G6PDHy | |
| 593 | ADHEr | LDH_D | GLCpts | MDH | NADH6 | PFLi |
| 594 | ADHEr | LDH_D | FUM | GLCpts | NADH6 | PFLi |
| 595 | ADHEr | LDH_D | FRD2 | PFLi | | |
| 596 | ADHEr | LDH_D | ALAR | PFLi | PRO1z | SUCD4 |
| 597 | ADHEr | LDH_D | DAAD | PFLi | PRO1z | SUCD4 |
| 598 | ADHEr | LDH_D | ACKr | | | |
| 599 | ADHEr | LDH_D | PTAr | | | |
| 600 | ADHEr | LDH_D | FUM | PFLi | SUCD4 | |
| 601 | ADHEr | LDH_D | MDH | PFLi | SUCD4 | |
| 602 | ADHEr | LDH_D | FUM | NADH12 | NADH6 | PFLi |
| 603 | ADHEr | LDH_D | MDH | NADH12 | NADH6 | PFLi |
| 604 | ADHEr | LDH_D | ATPS4r | MDH | TKT1 | |
| 605 | ADHEr | LDH_D | ATPS4r | FUM | TKT1 | |
| 606 | ADHEr | LDH_D | ATPS4r | MDH | TAL | |
| 607 | ADHEr | LDH_D | ATPS4r | FUM | TAL | |
| 608 | ADHEr | LDH_D | ATPS4r | NADH6 | PFLi | PYK |
| 609 | ADHEr | LDH_D | ASPT | FUM | PFLi | |
| 610 | ADHEr | LDH_D | ASPT | MDH | PFLi | |
| 611 | ADHEr | LDH_D | ATPS4r | MDH | RPE | |
| 612 | ADHEr | LDH_D | ATPS4r | FUM | RPE | |
| 613 | ADHEr | LDH_D | PFLi | SUCD4 | THD2 | |
| 614 | ADHEr | LDH_D | NADH12 | NADH6 | PFLi | THD2 |
| 615 | ADHEr | LDH_D | FUM | NADH6 | PFLi | THD2 |
| 616 | ADHEr | LDH_D | MDH | NADH6 | PFLi | THD2 |
| 617 | ADHEr | LDH_D | ATPS4r | MDH | TKT2 | |
| 618 | ADHEr | LDH_D | ATPS4r | FUM | TKT2 | |
| 619 | ADHEr | LDH_D | GLCpts | NADH6 | PFLi | |
| 620 | ADHEr | LDH_D | GLUDy | NADH6 | PFLi | THD2 |
| 621 | ADHEr | LDH_D | GLUDy | PFLi | SUCD4 | |
| 622 | ADHEr | LDH_D | GLUDy | NADH12 | NADH6 | PFLi |
| 623 | ADHEr | LDH_D | FUM | GLUDy | PFLi | |
| 624 | ADHEr | LDH_D | GLUDy | MDH | PFLi | |
| 625 | ADHEr | LDH_D | ATPS4r | FUM | NADH6 | |
| 626 | ADHEr | LDH_D | ATPS4r | MDH | NADH6 | |
| 627 | ADHEr | LDH_D | ATPS4r | G6PDHy | GLUDy | NADH6 |
| 628 | ADHEr | LDH_D | ATPS4r | GLUDy | NADH6 | PGDH |
| 629 | ADHEr | LDH_D | ATPS4r | GLUDy | NADH6 | PGL |
| 630 | ADHEr | LDH_D | ATPS4r | MDH | PFLi | THD2 |
| 631 | ADHEr | LDH_D | ATPS4r | FUM | PFLi | THD2 |
| 632 | ADHEr | LDH_D | ATPS4r | GLUDy | NADH6 | TKT1 |
| 633 | ADHEr | LDH_D | ATPS4r | GLUDy | NADH6 | TAL |
| 634 | ADHEr | LDH_D | ATPS4r | GLUDy | PFLi | THD2 |
| 635 | ADHEr | LDH_D | GLCpts | MDH | PFLi | |
| 636 | ADHEr | LDH_D | FUM | GLCpts | PFLi | |
| 637 | ADHEr | LDH_D | GLUDy | NADH6 | PFLi | |
| 638 | ADHEr | LDH_D | ATPS4r | GLUDy | NADH6 | RPE |
| 639 | ADHEr | LDH_D | ATPS4r | GLUDy | NADH6 | TKT2 |
| 640 | ADHEr | LDH_D | FUM | PFLi | THD2 | |
| 641 | ADHEr | LDH_D | MDH | PFLi | THD2 | |
| 642 | ADHEr | LDH_D | NADH6 | PFLi | THD2 | |
| 643 | ADHEr | LDH_D | PFLi | SUCD4 | | |
| 644 | ADHEr | LDH_D | NADH12 | NADH6 | PFLi | |
| 645 | ADHEr | LDH_D | ATPS4r | NADH6 | PFLi | |
| 646 | ADHEr | LDH_D | FUM | NADH6 | PFLi | |
| 647 | ADHEr | LDH_D | MDH | NADH6 | PFLi | |
| 648 | ADHEr | LDH_D | ATPS4r | NADH6 | PGL | |

TABLE 1-continued

The list of all disruption strategies identified by OptKnock that are most likely to provide growth-coupled LCA produciton.

| | | | | | |
|---|---|---|---|---|---|
| 649 | ADHEr | LDH_D | ATPS4r | NADH6 | PGDH |
| 650 | ADHEr | LDH_D | ATPS4r | G6PDHy | NADH6 |
| 651 | ADHEr | LDH_D | ATPS4r | NADH6 | TAL |
| 652 | ADHEr | LDH_D | ATPS4r | NADH6 | TKT1 |
| 653 | ADHEr | LDH_D | CBMK2 | GLU5K | NADH6 | PFLi |
| 654 | ADHEr | LDH_D | CBMK2 | G5SD | NADH6 | PFLi |
| 655 | ADHEr | LDH_D | ASNS2 | CBMK2 | NADH6 | PFLi |
| 656 | ADHEr | LDH_D | ATPS4r | PFLi | THD2 |
| 657 | ADHEr | LDH_D | NADH6 | PFLi | |
| 658 | ADHEr | LDH_D | ATPS4r | NADH6 | RPE |
| 659 | ADHEr | LDH_D | ATPS4r | NADH6 | TKT2 |
| 660 | ADHEr | LDH_D | CBMK2 | FUM | G5SD | PFLi |
| 661 | ADHEr | LDH_D | CBMK2 | GLU5K | MDH | PFLi |
| 662 | ADHEr | LDH_D | CBMK2 | FUM | GLU5K | PFLi |
| 663 | ADHEr | LDH_D | CBMK2 | G5SD | MDH | PFLi |
| 664 | ADHEr | LDH_D | ASNS2 | CBMK2 | FUM | PFLi |
| 665 | ADHEr | LDH_D | ASNS2 | CBMK2 | MDH | PFLi |
| 666 | ADHEr | LDH_D | MDH | PFLi | |
| 667 | ADHEr | LDH_D | FUM | PFLi | |
| 668 | ADHEr | LDH_D | ATPS4r | GLUDy | PFLi | RPE |
| 669 | ADHEr | LDH_D | ATPS4r | GLUDy | PFLi | TAL |
| 670 | ADHEr | LDH_D | ATPS4r | GLUDy | PFLi | TKT1 |
| 671 | ADHEr | LDH_D | ATPS4r | GLUDy | PFLi | TKT2 |
| 672 | ADHEr | LDH_D | ATPS4r | GLUDy | PFLi | |
| 673 | ADHEr | LDH_D | ATPS4r | GLUDy | NADH6 | |
| 674 | ADHEr | LDH_D | ATPS4r | PFLi | RPE |
| 675 | ADHEr | LDH_D | ATPS4r | PFLi | TAL |
| 676 | ADHEr | LDH_D | ATPS4r | PFLi | TKT1 |
| 677 | ADHEr | LDH_D | ATPS4r | PFLi | TKT2 |
| 678 | ADHEr | LDH_D | ATPS4r | CBMK2 | PFLi |
| 679 | ADHEr | LDH_D | ATPS4r | PFLi | |
| 680 | ADHEr | LDH_D | ASPT | MDH | PGDHY | PYK |
| 681 | ADHEr | LDH_D | ASPT | EDA | MDH | PYK |
| 682 | ADHEr | LDH_D | ATPS4r | CBMK2 | NADH6 |
| 683 | ADHEr | LDH_D | ATPS4r | NADH6 | |
| 684 | ADHEr | LDH_D | ATPS4r | HEX1 | PGI | PPS |
| 685 | ADHEr | LDH_D | G6PDHy | ME2 | THD2 |
| 686 | ADHEr | LDH_D | ME2 | PGL | THD2 |
| 687 | ADHEr | LDH_D | ME2 | PGDH | PGDHY | THD2 |
| 688 | ADHEr | LDH_D | EDA | ME2 | PGDH | THD2 |
| 689 | ADHEr | LDH_D | EDA | ME2 | TAL | THD2 |
| 690 | ADHEr | LDH_D | ME2 | PGDHY | TAL | THD2 |
| 691 | ADHEr | LDH_D | ME2 | PGDHY | THD2 | TKT1 |
| 692 | ADHEr | LDH_D | EDA | ME2 | THD2 | TKT1 |
| 693 | ADHEr | LDH_D | ME2 | PGDHY | RPE | THD2 |
| 694 | ADHEr | LDH_D | EDA | ME2 | RPE | THD2 |
| 695 | ADHEr | LDH_D | MDH | PGL | THD2 |
| 696 | ADHEr | LDH_D | G6PDHy | MDH | THD2 |
| 697 | ADHEr | LDH_D | EDA | MDH | PGDH | THD2 |
| 698 | ADHEr | LDH_D | MDH | PGDH | PGDHY | THD2 |
| 699 | ADHEr | LDH_D | ME2 | PGDHY | THD2 | TKT2 |
| 700 | ADHEr | LDH_D | EDA | ME2 | THD2 | TKT2 |
| 701 | ADHEr | LDH_D | MDH | PGDHY | THD2 | TKT1 |
| 702 | ADHEr | LDH_D | EDA | MDH | THD2 | TKT1 |
| 703 | ADHEr | LDH_D | MDH | PGDHY | TAL | THD2 |
| 704 | ADHEr | LDH_D | EDA | MDH | TAL | THD2 |
| 705 | ADHEr | LDH_D | ATPS4r | GLUDy | HEX1 | PGI |
| 706 | ADHEr | LDH_D | MDH | PGDHY | RPE | THD2 |
| 707 | ADHEr | LDH_D | EDA | MDH | RPE | THD2 |
| 708 | ADHEr | LDH_D | MDH | PGDHY | THD2 | TKT2 |
| 709 | ADHEr | LDH_D | EDA | MDH | THD2 | TKT2 |
| 710 | ADHEr | LDH_D | ATPS4r | HEX1 | PGI |
| 711 | ADHEr | LDH_D | FRD2 | HEX1 | MDH | PGI |
| 712 | ADHEr | LDH_D | HEX1 | MDH | PGI | SUCD4 |
| 713 | ADHEr | LDH_D | HEX1 | PGI | SUCOAS |
| 714 | ADHEr | LDH_D | HEX1 | MDH | NADH6 | PGI |
| 715 | ADHEr | LDH_D | FUM | HEX1 | NADH6 | PGI |
| 716 | ADHEr | LDH_D | FRD2 | FUM | HEX1 | PGI |
| 717 | ADHEr | LDH_D | HEX1 | PGI | |
| 718 | ADHEr | LDH_D | SUCOAS | THD2 | |
| 719 | ADHEr | LDH_D | THD2 | | |
| 720 | ADHEr | LDH_D | GLCpts | SUCOAS | TKT2 | TPI |
| 721 | ADHEr | LDH_D | GLCpts | PFK | SUCOAS | TKT2 |
| 722 | ADHEr | LDH_D | FBA | GLCpts | SUCOAS | TKT2 |
| 723 | ADHEr | LDH_D | GLCpts | GLUDy | TKT2 | TPI |
| 724 | ADHEr | LDH_D | FBA | GLCpts | GLUDy | TKT2 |
| 725 | ADHEr | LDH_D | GLCpts | GLUDy | PFK | TKT2 |

TABLE 1-continued

The list of all disruption strategies identified by OptKnock that are most likely to provide growth-coupled LCA produciton.

| | | | | | | |
|---|---|---|---|---|---|---|
| 726 | ADHEr | LDH_D | GLCpts | PGI | SUCOAS | |
| 727 | ADHEr | LDH_D | GLCpts | GLUDy | PGI | |
| 728 | ADHEr | LDH_D | GLCpts | PFK | RPE | SUCOAS |
| 729 | ADHEr | LDH_D | GLCpts | RPE | SUCOAS | TPI |
| 730 | ADHEr | LDH_D | FBA | GLCpts | RPE | SUCOAS |
| 731 | ADHEr | LDH_D | GLCpts | GLUDy | RPE | TPI |
| 732 | ADHEr | LDH_D | FBA | GLCpts | GLUDy | RPE |
| 733 | ADHEr | LDH_D | GLCpts | GLUDy | PFK | RPE |
| 734 | ADHEr | LDH_D | FBA | GLUDy | SUCOAS | TKT2 |
| 735 | ADHEr | LDH_D | GLUDy | PFK | SUCOAS | TKT2 |
| 736 | ADHEr | LDH_D | GLUDy | SUCOAS | TKT2 | TPI |
| 737 | ADHEr | LDH_D | GLCpts | GLUDy | PFK | SUCOAS |
| 738 | ADHEr | LDH_D | GLCpts | GLUDy | SUCOAS | TPI |
| 739 | ADHEr | LDH_D | FBA | GLCpts | GLUDy | SUCOAS |
| 740 | ADHEr | LDH_D | GLCpts | PFK | TKT2 | |
| 741 | ADHEr | LDH_D | FBA | GLCpts | TKT2 | |
| 742 | ADHEr | LDH_D | GLCpts | TKT2 | TPI | |
| 743 | ADHEr | LDH_D | GLUDy | PGI | SUCOAS | |
| 744 | ADHEr | LDH_D | PGDHY | PGI | | |
| 745 | ADHEr | LDH_D | EDA | PGI | | |
| 746 | ADHEr | LDH_D | GLCpts | PGI | | |
| 747 | ADHEr | LDH_D | GLUDy | PFK | RPE | SUCOAS |
| 748 | ADHEr | LDH_D | GLUDy | RPE | SUCOAS | TPI |
| 749 | ADHEr | LDH_D | FBA | GLUDy | RPE | SUCOAS |
| 750 | ADHEr | LDH_D | GLCpts | RPE | TPI | |
| 751 | ADHEr | LDH_D | GLCpts | PFK | RPE | |
| 752 | ADHEr | LDH_D | a'FBA | GLCpts | RPE | |
| 753 | ADHEr | LDH_D | PFK | SUCOAS | TKT2 | |
| 754 | ADHEr | LDH_D | FBA | SUCOAS | TKT2 | |
| 755 | ADHEr | LDH_D | SUCOAS | TKT2 | TPI | |
| 756 | ADHEr | LDH_D | GLCpts | SUCOAS | TPI | |
| 757 | ADHEr | LDH_D | GLCpts | PFK | SUCOAS | |
| 758 | ADHEr | LDH_D | FBA | GLCpts | SUCOAS | |
| 759 | ADHEr | LDH_D | FBA | GLCpts | GLUDy | |
| 760 | ADHEr | LDH_D | GLCpts | GLUDy | TPI | |
| 761 | ADHEr | LDH_D | GLCpts | GLUDy | PFK | |
| 762 | ADHEr | LDH_D | GLUDy | PFK | TKT2 | |
| 763 | ADHEr | LDH_D | FBA | GLUDy | TKT2 | |
| 764 | ADHEr | LDH_D | GLUDy | TKT2 | TPI | |
| 765 | ADHEr | LDH_D | PGI | SUCOAS | | |
| 766 | ADHEr | LDH_D | GLUDy | PGI | | |
| 767 | ADHEr | LDH_D | ASPT | G6PDHy | MDH | PYK |
| 768 | ADHEr | LDH_D | ASPT | MDH | PGL | PYK |
| 769 | ADHEr | LDH_D | FBA | RPE | SUCOAS | |
| 770 | ADHEr | LDH_D | PFK | RPE | SUCOAS | |
| 771 | ADHEr | LDH_D | RPE | SUCOAS | TPI | |
| 772 | ADHEr | LDH_D | HEX1 | PFK | SUCOAS | TKT1 |
| 773 | ADHEr | LDH_D | FBA | HEX1 | SUCOAS | TAL |
| 774 | ADHEr | LDH_D | HEX1 | PFK | SUCOAS | TAL |
| 775 | ADHEr | LDH_D | HEX1 | SUCOAS | TKT1 | TPI |
| 776 | ADHEr | LDH_D | FBA | HEX1 | SUCOAS | TKT1 |
| 777 | ADHEr | LDH_D | HEX1 | SUCOAS | TAL | TPI |
| 778 | ADHEr | LDH_D | GLUDy | RPE | TPI | |
| 779 | ADHEr | LDH_D | FBA | GLUDy | RPE | |
| 780 | ADHEr | LDH_D | GLUDy | PFK | RPE | |
| 781 | ADHEr | LDH_D | GLUDy | HEX1 | TKT1 | TPI |
| 782 | ADHEr | LDH_D | GLUDy | HEX1 | PFK | TKT1 |
| 783 | ADHEr | LDH_D | FBA | GLUDy | HEX1 | TKT1 |
| 784 | ADHEr | LDH_D | GLUDy | HEX1 | TAL | TPI |
| 785 | ADHEr | LDH_D | FBA | GLUDy | HEX1 | TAL |
| 786 | ADHEr | LDH_D | GLUDy | HEX1 | PFK | TAL |
| 787 | ADHEr | LDH_D | GLUDy | SUCOAS | TPI | |
| 788 | ADHEr | LDH_D | GLUDy | PFK | SUCOAS | |
| 789 | ADHEr | LDH_D | FBA | GLUDy | SUCOAS | |
| 790 | ADHEr | LDH_D | FRD2 | PYK | SUCOAS | TKT2 |
| 791 | ADHEr | LDH_D | PYK | SUCD4 | SUCOAS | TKT2 |
| 792 | ADHEr | LDH_D | GLCpts | TPI | | |
| 793 | ADHEr | LDH_D | GLCpts | PFK | | |
| 794 | ADHEr | LDH_D | FBA | GLCpts | | |
| 795 | ADHEr | LDH_D | FRD2 | GLUDy | PYK | TKT2 |
| 796 | ADHEr | LDH_D | GLUDy | PYK | SUCD4 | TKT2 |
| 797 | ADHEr | LDH_D | PFK | TKT2 | | |
| 798 | ADHEr | LDH_D | FBA | TKT2 | | |
| 799 | ADHEr | LDH_D | TKT2 | TPI | | |
| 800 | ADHEr | LDH_D | CBMK2 | SUCOAS | TAL | TPI |
| 801 | ADHEr | LDH_D | CBMK2 | FBA | SUCOAS | TAL |
| 802 | ADHEr | LDH_D | CBMK2 | FBA | SUCOAS | TKT1 |

TABLE 1-continued

The list of all disruption strategies identified by OptKnock that are most likely to provide growth-coupled LCA produciton.

| | | | | | | |
|---|---|---|---|---|---|---|
| 803 | ADHEr | LDH_D | CBMK2 | PFK | SUCOAS | TAL |
| 804 | ADHEr | LDH_D | CBMK2 | PFK | SUCOAS | TKT1 |
| 805 | ADHEr | LDH_D | CBMK2 | SUCOAS | TKT1 | TPI |
| 806 | ADHEr | LDH_D | CBMK2 | FBA | HEX1 | SUCOAS |
| 807 | ADHEr | LDH_D | CBMK2 | HEX1 | SUCOAS | TPI |
| 808 | ADHEr | LDH_D | CBMK2 | HEX1 | PFK | SUCOAS |
| 809 | ADHEr | LDH_D | PGI | | | |
| 810 | ADHEr | LDH_D | HEX1 | PFK | TAL | |
| 811 | ADHEr | LDH_D | HEX1 | TAL | TPI | |
| 812 | ADHEr | LDH_D | FBA | HEX1 | TAL | |
| 813 | ADHEr | LDH_D | HEX1 | PFK | TKT1 | |
| 814 | ADHEr | LDH_D | HEX1 | TKT1 | TPI | |
| 815 | ADHEr | LDH_D | FBA | HEX1 | TKT1 | |
| 816 | ADHEr | LDH_D | PYK | RPE | SUCD4 | SUCOAS |
| 817 | ADHEr | LDH_D | FRD2 | PYK | RPE | SUCOAS |
| 818 | ADHEr | LDH_D | FRD2 | GLUDy | PYK | RPE |
| 819 | ADHEr | LDH_D | GLUDy | PYK | RPE | SUCD4 |
| 820 | ADHEr | LDH_D | RPE | TPI | | |
| 821 | ADHEr | LDH_D | PFK | RPE | | |
| 822 | ADHEr | LDH_D | FBA | RPE | | |
| 823 | ADHEr | LDH_D | SUCOAS | TPI | | |
| 824 | ADHEr | LDH_D | PFK | SUCOAS | | |
| 825 | ADHEr | LDH_D | FBA | SUCOAS | | |
| 826 | ADHEr | LDH_D | GLUDy | TPI | | |
| 827 | ADHEr | LDH_D | FBA | GLUDy | | |
| 828 | ADHEr | LDH_D | GLUDy | PFK | | |
| 829 | ADHEr | LDH_D | FRD2 | GLUDy | PYK | SUCOAS |
| 830 | ADHEr | LDH_D | GLUDy | PYK | SUCD4 | SUCOAS |
| 831 | ADHEr | LDH_D | HEX1 | MDH | PFK | SUCD4 |
| 832 | ADHEr | LDH_D | HEX1 | MDH | SUCD4 | TPI |
| 833 | ADHEr | LDH_D | FBA | HEX1 | MDH | SUCD4 |
| 834 | ADHEr | LDH_D | FRD2 | HEX1 | MDH | TPI |
| 835 | ADHEr | LDH_D | FBA | FRD2 | HEX1 | MDH |
| 836 | ADHEr | LDH_D | FRD2 | HEX1 | MDH | PFK |
| 837 | ADHEr | LDH_D | FRD2 | MDH | TKT1 | TPI |
| 838 | ADHEr | LDH_D | FRD2 | MDH | TAL | TPI |
| 839 | ADHEr | LDH_D | MDH | PFK | SUCD4 | TKT1 |
| 840 | ADHEr | LDH_D | MDH | PFK | SUCD4 | TAL |
| 841 | ADHEr | LDH_D | FBA | MDH | SUCD4 | TKT1 |
| 842 | ADHEr | LDH_D | FBA | MDH | SUCD4 | TAL |
| 843 | ADHEr | LDH_D | MDH | SUCD4 | TAL | TPI |
| 844 | ADHEr | LDH_D | FRD2 | MDH | PFK | TKT1 |
| 845 | ADHEr | LDH_D | FRD2 | MDH | PFK | TAL |
| 846 | ADHEr | LDH_D | FBA | FRD2 | MDH | TAL |
| 847 | ADHEr | LDH_D | MDH | SUCD4 | TKT1 | TPI |
| 848 | ADHEr | LDH_D | FBA | FRD2 | MDH | TKT1 |
| 849 | ADHEr | LDH_D | PYK | SUCD4 | TKT2 | |
| 850 | ADHEr | LDH_D | FRD2 | PYK | TKT2 | |
| 851 | ADHEr | LDH_D | FDH2 | NADH6 | PYK | TKT2 |
| 852 | ADHEr | LDH_D | CBMK2 | PFK | TAL | |
| 853 | ADHEr | LDH_D | CBMK2 | TAL | TPI | |
| 854 | ADHEr | LDH_D | CBMK2 | FBA | TKT1 | |
| 855 | ADHEr | LDH_D | CBMK2 | TKT1 | TPI | |
| 856 | ADHEr | LDH_D | CBMK2 | FBA | TAL | |
| 857 | ADHEr | LDH_D | CBMK2 | PFK | TKT1 | |
| 858 | ADHEr | LDH_D | CBMK2 | HEX1 | PFK | |
| 859 | ADHEr | LDH_D | CBMK2 | HEX1 | TPI | |
| 860 | ADHEr | LDH_D | CBMK2 | FBA | HEX1 | |
| 861 | ADHEr | LDH_D | GLU5K | TAL | TPI | |
| 862 | ADHEr | LDH_D | G5SD | TAL | TPI | |
| 863 | ADHEr | LDH_D | FBA | GLU5K | TKT1 | |
| 864 | ADHEr | LDH_D | G5SD | TKT1 | TPI | |
| 865 | ADHEr | LDH_D | G5SD | PFK | TKT1 | |
| 866 | ADHEr | LDH_D | GLU5K | PFK | TAL | |
| 867 | ADHEr | LDH_D | FBA | G5SD | TAL | |
| 868 | ADHEr | LDH_D | FBA | G5SD | TKT1 | |
| 869 | ADHEr | LDH_D | G5SD | PFK | TAL | |
| 870 | ADHEr | LDH_D | GLU5K | TKT1 | TPI | |
| 871 | ADHEr | LDH_D | GLU5K | PFK | TKT1 | |
| 872 | ADHEr | LDH_D | FBA | GLU5K | TAL | |
| 873 | ADHEr | LDH_D | GLU5K | HEX1 | TPI | |
| 874 | ADHEr | LDH_D | GLU5K | HEX1 | PFK | |
| 875 | ADHEr | LDH_D | G5SD | HEX1 | PFK | |
| 876 | ADHEr | LDH_D | FBA | G5SD | HEX1 | |
| 877 | ADHEr | LDH_D | FBA | GLU5K | HEX1 | |
| 878 | ADHEr | LDH_D | G5SD | HEX1 | TPI | |
| 879 | ADHEr | LDH_D | ASNS2 | PFK | TKT1 | |

TABLE 1-continued

The list of all disruption strategies identified by OptKnock that are most likely to provide growth-coupled LCA produciton.

| | | | | | |
|---|---|---|---|---|---|
| 880 | ADHEr | LDH_D | ASNS2 | TKT1 | TPI |
| 881 | ADHEr | LDH_D | ASNS2 | PFK | TAL |
| 882 | ADHEr | LDH_D | ASNS2 | FBA | TKT1 |
| 883 | ADHEr | LDH_D | ASNS2 | FBA | TAL |
| 884 | ADHEr | LDH_D | ASNS2 | TAL | TPI |
| 885 | ADHEr | LDH_D | ASNS2 | HEX1 | PFK |
| 886 | ADHEr | LDH_D | ASNS2 | FBA | HEX1 |
| 887 | ADHEr | LDH_D | ASNS2 | HEX1 | TPI |
| 888 | ADHEr | LDH_D | PYK | SUCD4 | SUCOAS | TKT1 |
| 889 | ADHEr | LDH_D | FRD2 | PYK | SUCOAS | TAL |
| 890 | ADHEr | LDH_D | PYK | SUCD4 | SUCOAS | TAL |
| 891 | ADHEr | LDH_D | FRD2 | PYK | SUCOAS | TKT1 |
| 892 | ADHEr | LDH_D | PYK | RPE | SUCD4 |
| 893 | ADHEr | LDH_D | FRD2 | PYK | RPE |
| 894 | ADHEr | LDH_D | FDH2 | NADH6 | PYK | RPE |
| 895 | ADHEr | LDH_D | GLUDy | MDH | PYK | TKT2 |
| 896 | ADHEr | LDH_D | FUM | GLUDy | PYK | TKT2 |
| 897 | ADHEr | LDH_D | GLCpts | GLUDy | SUCOAS | TKT2 |
| 898 | ADHEr | LDH_D | GLUDy | PYK | SUCD4 |
| 899 | ADHEr | LDH_D | FRD2 | GLUDy | PYK |
| 900 | ADHEr | LDH_D | FDH2 | GLUDy | NADH6 | PYK |
| 901 | ADHEr | LDH_D | FBA | | |
| 902 | ADHEr | LDH_D | TPI | | |
| 903 | ADHEr | LDH_D | PFK | | |
| 904 | ADHEr | LDH_D | PYK | SUCD4 | SUCOAS |
| 905 | ADHEr | LDH_D | FRD2 | PYK | SUCOAS |
| 906 | ADHEr | LDH_D | FDH2 | NADH6 | PYK | SUCOAS |
| 907 | ADHEr | LDH_D | FRD2 | ME2 | PGDHY | PYK |
| 908 | ADHEr | LDH_D | EDA | FRD2 | ME2 | PYK |
| 909 | ADHEr | LDH_D | FRD2 | ME2 | PGL | PYK |
| 910 | ADHEr | LDH_D | EDA | ME2 | PYK | SUCD4 |
| 911 | ADHEr | LDH_D | ME2 | PGDHY | PYK | SUCD4 |
| 912 | ADHEr | LDH_D | ME2 | PGL | PYK | SUCD4 |
| 913 | ADHEr | LDH_D | FRD2 | G6PDHy | ME2 | PYK |
| 914 | ADHEr | LDH_D | G6PDHy | ME2 | PYK | SUCD4 |
| 915 | ADHEr | LDH_D | MDH | NADH6 | PGDHY | PYK |
| 916 | ADHEr | LDH_D | MDH | PGL | PYK | SUCD4 |
| 917 | ADHEr | LDH_D | FRD2 | MDH | PGL | PYK |
| 918 | ADHEr | LDH_D | FRD2 | MDH | PGDHY | PYK |
| 919 | ADHEr | LDH_D | G6PDHy | MDH | PYK | SUCD4 |
| 920 | ADHEr | LDH_D | MDH | NADH6 | PGL | PYK |
| 921 | ADHEr | LDH_D | EDA | FRD2 | MDH | PYK |
| 922 | ADHEr | LDH_D | EDA | MDH | PYK | SUCD4 |
| 923 | ADHEr | LDH_D | MDH | PGDHY | PYK | SUCD4 |
| 924 | ADHEr | LDH_D | EDA | MDH | NADH6 | PYK |
| 925 | ADHEr | LDH_D | FRD2 | G6PDHy | MDH | PYK |
| 926 | ADHEr | LDH_D | G6PDHy | MDH | NADH6 | PYK |
| 927 | ADHEr | LDH_D | GLUDy | MDH | PYK | RPE |
| 928 | ADHEr | LDH_D | FUM | GLUDy | PYK | RPE |
| 929 | ADHEr | LDH_D | FRD2 | PYK | TAL |
| 930 | ADHEr | LDH_D | PYK | SUCD4 | TKT1 |
| 931 | ADHEr | LDH_D | PYK | SUCD4 | TAL |
| 932 | ADHEr | LDH_D | FRD2 | PYK | TKT1 |
| 933 | ADHEr | LDH_D | FDH2 | NADH6 | PYK | TAL |
| 934 | ADHEr | LDH_D | FDH2 | NADH6 | PYK | TKT1 |
| 935 | ADHEr | LDH_D | GLCpts | GLUDy | RPE | SUCOAS |
| 936 | ADHEr | LDH_D | GLUDy | MDH | PYK | SUCOAS |
| 937 | ADHEr | LDH_D | FUM | GLUDy | PYK | SUCOAS |
| 938 | ADHEr | LDH_D | FUM | GLUDy | NADH6 | PYK |
| 939 | ADHEr | LDH_D | GLUDy | MDH | NADH6 | PYK |
| 940 | ADHEr | LDH_D | GLCpts | SUCOAS | TKT2 |
| 941 | ADHEr | LDH_D | GLUDy | SUCOAS | TKT2 |
| 942 | ADHEr | LDH_D | ASPT | MDH | PYK | TKT2 |
| 943 | ADHEr | LDH_D | ASPT | FUM | PYK | TKT2 |
| 944 | ADHEr | LDH_D | FRD2 | PYK | | |
| 945 | ADHEr | LDH_D | PYK | SUCD4 | | |
| 946 | ADHEr | LDH_D | FDH2 | NADH6 | PYK |
| 947 | ADHEr | LDH_D | GLCpts | GLUDy | TKT2 |
| 948 | ADHEr | LDH_D | GLCpts | GLUDy | SUCOAS | TAL |
| 949 | ADHEr | LDH_D | GLCpts | GLUDy | SUCOAS | TKT1 |
| 950 | ADHEr | LDH_D | FUM | GLUDy | PYK |
| 951 | ADHEr | LDH_D | GLUDy | MDH | PYK |
| 952 | ADHEr | LDH_D | GLCpts | RPE | SUCOAS |
| 953 | ADHEr | LDH_D | ASPT | FUM | PYK | RPE |
| 954 | ADHEr | LDH_D | ASPT | MDH | PYK | RPE |
| 955 | ADHEr | LDH_D | GLUDy | RPE | SUCOAS |
| 956 | ADHEr | LDH_D | GLCpts | GLUDy | RPE |

TABLE 1-continued

The list of all disruption strategies identified by OptKnock that are most likely to provide growth-coupled LCA produciton.

| | | | | | | |
|---|---|---|---|---|---|---|
| 957 | ADHEr | LDH_D | ASPT | FUM | PYK | SUCOAS |
| 958 | ADHEr | LDH_D | ASPT | MDH | PYK | SUCOAS |
| 959 | ADHEr | LDH_D | GLCpts | GLUDy | SUCOAS | |
| 960 | ADHEr | LDH_D | ASPT | FUM | NADH6 | PYK |
| 961 | ADHEr | LDH_D | ASPT | MDH | NADH6 | PYK |
| 962 | ADHEr | LDH_D | SUCOAS | TKT2 | | |
| 963 | ADHEr | LDH_D | GLCpts | TKT2 | | |
| 964 | ADHEr | LDH_D | ASPT | MDH | PYK | TKT1 |
| 965 | ADHEr | LDH_D | ASPT | FUM | PYK | TAL |
| 966 | ADHEr | LDH_D | ASPT | MDH | PYK | TAL |
| 967 | ADHEr | LDH_D | ASPT | FUM | PYK | TKT1 |
| 968 | ADHEr | LDH_D | GLCpts | SUCOAS | TAL | |
| 969 | ADHEr | LDH_D | GLCpts | SUCOAS | TKT1 | |
| 970 | ADHEr | LDH_D | GLUDy | TKT2 | | |
| 971 | ADHEr | LDH_D | GLCpts | GLUDy | TKT1 | |
| 972 | ADHEr | LDH_D | GLCpts | GLUDy | TAL | |
| 973 | ADHEr | LDH_D | GLUDy | SUCOAS | TKT1 | |
| 974 | ADHEr | LDH_D | GLUDy | SUCOAS | TAL | |
| 975 | ADHEr | LDH_D | ASPT | MDH | PYK | |
| 976 | ADHEr | LDH_D | ASPT | FUM | PYK | |
| 977 | ADHEr | LDH_D | RPE | SUCOAS | | |
| 978 | ADHEr | LDH_D | GLCpts | RPE | | |
| 979 | ADHEr | LDH_D | GLCpts | SUCOAS | | |
| 980 | ADHEr | LDH_D | GLUDy | RPE | | |
| 981 | ADHEr | LDH_D | GLCpts | GLUDy | | |
| 982 | ADHEr | LDH_D | GLUDy | SUCOAS | | |
| 983 | ADHEr | LDH_D | TKT2 | | | |
| 984 | ADHEr | LDH_D | GLCpts | TAL | | |
| 985 | ADHEr | LDH_D | GLCpts | TKT1 | | |
| 986 | ADHEr | LDH_D | SUCOAS | TAL | | |
| 987 | ADHEr | LDH_D | SUCOAS | TKT1 | | |
| 988 | ADHEr | LDH_D | GLUDy | TKT1 | | |
| 989 | ADHEr | LDH_D | GLUDy | TAL | | |
| 990 | ADHEr | LDH_D | RPE | | | |
| 991 | ADHEr | LDH_D | GLCpts | | | |
| 992 | ADHEr | LDH_D | SUCOAS | | | |
| 993 | ADHEr | LDH_D | GLUDy | | | |
| 994 | ADHEr | LDH_D | TAL | | | |
| 995 | ADHEr | LDH_D | TKT1 | | | |

TABLE 2

A list of all the reaction stoichiometries and the associated genes known to be associated with the reactions identified for disruption in the strategies listed in Tables 1.

| Reaction Abbreviation | Reaction Name | Reaction Stoichiometry | Assigned Genes |
|---|---|---|---|
| ACKr | acetate kinase | [c]: ac + atp <==> actp + adp | b2296, b3115 |
| ADHEr | acetaldehyde-CoA dehydrogenase | [c]: accoa + (2) h + (2) nadh <==> coa + etoh + (2) nad | b1241 |
| AKGD | 2-oxoglutarate dehydrogenase | [c]: akg + coa + nad --> co2 + nadh + succoa | b0727, b0726, b0116 |
| ALAR | alanine racemase | [c]: ala-L <==> ala-D | b4053 |
| ASNS2 | asparagine synthetase | [c]: asp-L + atp + nh4 --> amp + asn-L + h + ppi | b3744 |
| ASPT | L-aspartase | [c]: asp-L --> fum + nh4 | b4139 |
| ATPS4r | ATP synthase (four protons for one ATP) | adp[c] + (4) h[e] + pi[c] <==> atp[c] + (3) h[c] + h2o[c] | b3738 + b3736 + b3737, b3739, b3734 + b3732 + b3735 + b3733 + b3731 |
| CBMK2 | Carbamate kinase | [c]: atp + co2 + nh4 --> adp + cbp + (2) h | b0323, b0521, b2874 |
| DAAD | D-Amino acid dehydrogenase | [c]: ala-D + fad + h2o --> fadh2 + nh4 + pyr | b1189 |
| EDA | 2-dehydro-3-deoxy-phosphogluconate aldolase | [c]: 2ddg6p --> g3p + pyr | b1850 |
| FBA | fructose-bisphosphate aldolase | [c]: fdp <==> dhap + g3p | b1773, b2097, b2925 |
| FDH2 | formate dehydrogenase (quinone-8: 2 protons) | for[c] + (3) h[c] + ubq8[c] --> co2[c] + (2) h[e] + ubq8h2[c] | b3893 + b3894 + b3892, b1476 + b1475 + b1474, b4079 |
| FRD2 | fumarate reductase | [c]: fum + mql8 --> mqn8 + succ | b4153 + b4152 + b4151 + b4154 |
| FUM | fumarase | [c]: fum + h2o <==> mal-L | b1612, b4122, b1611 |
| G5SD | glutamate-5-semialdehyde dehydrogenase | [c]: glu5p + h + nadph --> glu5sa + nadp + pi | b0243 |

TABLE 2-continued

A list of all the reaction stoichiometries and the associated genes known to be associated with the reactions identified for disruption in the strategies listed in Tables 1.

| Reaction Abbreviation | Reaction Name | Reaction Stoichiometry | Assigned Genes |
|---|---|---|---|
| G6PDHy | glucose 6-phosphate dehydrogenase | [c]: g6p + nadp <==> 6pgl + h + nadph | b1852 |
| GLCpts | D-glucose transport via PEP: Pyr PTS | glc-D[e] + pep[c] --> g6p[c] + pyr[c] | b1817, b1818, b2417, b1621, b2416, b1819, b1101, b2415 |
| GLU5K | glutamate 5-kinase | [c]: atp + glu-L --> adp + glu5p | b0242 |
| GLUDy | glutamate dehydrogenase (NADP) | [c]: glu-L + h2o + nadp <==> akg + h + nadph + nh4 | b1761 |
| HEX1 | hexokinase (D-glucose: ATP) | [c]: atp + glc-D --> adp + g6p + h | b2388 |
| ICL | Isocitrate lyase | [c]: icit --> glx + succ | b4015 |
| LDH_D | D-lactate dehydrogenase | [c]: lac-D + nad <==> h + nadh + pyr | b2133, b1380 |
| MALS | malate synthase | [c]: accoa + glx + h2o --> coa + h + mal-L | b4014, b2976 |
| MDH | malate dehydrogenase | [c]: mal-L + nad <==> h + nadh + oaa | b3236 |
| ME2 | malic enzyme (NADP) | [c]: mal-L + nadp --> co2 + nadph + pyr | b2463 |
| NADH12 | NADH dehydrogenase (ubiquinone-8) | [c]: h + nadh + ubq8 --> nad + ubq8h2 | b1109 |
| NADH6 | NADH dehydrogenase (ubiquinone-8 & 3.5 protons) | (4.5) h[c] + nadh[c] + ubq8[c] --> (3.5) h[e] + nad[c] + ubq8h2[c] | b2288 + b2277 + b2285 + b2278 + b2276 + b2286 + b2287 + b2279 + b2280 + b2284 + b2283 + b2282 + b2281 |
| PFK | phosphofructokinase | [c]: atp + f6p --> adp + fdp + h | b3916, b1723 |
| PFLi | pyruvate formate lyase | [c]: coa + pyr --> accoa + for | b3114, b3951 + b3952, b0902 + b2579 + b0903 |
| PGDH | phosphogluconate dehydrogenase | [c]: 6pgc + nadp --> co2 + nadph + ru5p-D | b2029 |
| PGDHY | phosphogluconate dehydratase | [c]: 6pgc --> 2ddg6p + h2o | b1851 |
| PGI | glucose-6-phosphate isomerase | [c]: g6p <==> f6p | b4025 |
| PGL | 6-phosphogluconolactonase | [c]: 6pgl + h2o --> 6pgc + h | b0767 |
| PPS | phosphoenolpyruvate synthase | [c]: atp + h2o + pyr --> amp + (2) h + pep + pi | b1702 |
| PRO1z | proline oxidase | [c]: fad + pro-L --> 1 pyr5c + fadh2 + h | b1014 |
| PTAr | phosphotransacetylase | [c]: accoa + pi <==> actp + coa | b2297 |
| PYK | pyruvate kinase | [c]: adp + h + pep --> atp + pyr | b1854, b1676 |
| RPE | ribulose 5-phosphate 3-epimerase | [c]: ru5p-D <==> xu5p-D | b4301, b3386 |
| SUCD4 | succinate dehyrdogenase | [c]: fadh2 + ubq8 <==> fad + ubq8h2 | b0723 + b0721 + b0724 + b0722 |
| SUCOAS | succinyl-CoA synthetase (ADP-forming) | [c]: atp + coa + succ <==> adp + pi + succoa | b0729 + b0728 |
| TAL | transaldolase | [c]: g3p + s7p <==> e4p + f6p | b2464, b0008 |
| THD2 | NAD(P) transhydrogenase | (2) h[e] + nadh[c] + nadp[c] --> (2) h[c] + nad[c] + nadph[c] | b1602 + b1603 |
| TKT1 | transketolase | [c]: r5p + xu5p-D <==> g3p + s7p | b2935, b2465 |
| TKT2 | transketolase | [c]: e4p + xu5p-D <==> f6p + g3p | b2935, b2465 |
| TPI | triose-phosphate isomerase | [c]: dhap <==> g3p | b3919 |

TABLE 3

List of the metabolite abbreviations, the corresponding names and locations of all the metabolites that participate in the reactions listed in Table 2.

| Metabolite Abbreviation | Compartment | Metabolite Name |
|---|---|---|
| 1pyr5c | Cytosol | 1-Pyrroline-5-carboxylate |
| 2ddg6p | Cytosol | 2-Dehydro-3-deoxy-D-gluconate 6-phosphate |
| 6pgc | Cytosol | 6-Phospho-D-gluconate |
| 6pgl | Cytosol | 6-phospho-D-glucono-1,5-lactone |
| ac | Cytosol | Acetate |
| accoa | Cytosol | Acetyl-CoA |
| actp | Cytosol | Acetyl phosphate |
| adp | Cytosol | ADP |
| akg | Cytosol | 2-Oxoglutarate |
| ala-D | Cytosol | D-Alanine |
| ala-L | Cytosol | L-Alanine |
| amp | Cytosol | AMP |
| asn-L | Cytosol | L-Asparagine |
| asp-L | Cytosol | L-Aspartate |
| atp | Cytosol | ATP |
| cbp | Cytosol | Carbamoyl phosphate |
| cit | Cytosol | Citrate |
| co2 | Cytosol | CO2 |
| coa | Cytosol | Coenzyme A |
| ctp | Cytosol | CTP |
| dha | Cytosol | Dihydroxyacetone |

TABLE 3-continued

List of the metabolite abbreviations, the corresponding
names and locations of all the metabolites that
participate in the reactions listed in Table 2.

| Metabolite Abbreviation | Compartment | Metabolite Name |
|---|---|---|
| dhap | Cytosol | Dihydroxyacetone phosphate |
| e4p | Cytosol | D-Erythrose 4-phosphate |
| etoh | Cytosol | Ethanol |
| f6p | Cytosol | D-Fructose 6-phosphate |
| fad | Cytosol | FAD |
| fadh2 | Cytosol | FADH2 |
| fdp | Cytosol | D-Fructose 1,6-bisphosphate |
| for | Cytosol | Formate |
| fum | Cytosol | Fumarate |
| g3p | Cytosol | Glyceraldehyde 3-phosphate |
| g6p | Cytosol | D-Glucose 6-phosphate |
| glc-D | Cytosol | D-Glucose |
| glc-D[e] | Extra-organism | D-Glucose |
| glu5p | Cytosol | L-Glutamate 5-phosphate |
| glu5sa | Cytosol | L-Glutamate 5-semialdehyde |
| glu-L | Cytosol | L-Glutamate |
| glx | Cytosol | Glyoxylate |
| h | Cytosol | H+ |
| h[e] | Extra-organism | H+ |
| h2 | Cytosol | H2 |
| h2o | Cytosol | H2O |
| icit | Cytosol | Isocitrate |
| k | Cytosol | K+ |
| lac-D | Cytosol | D-Lactate |
| mal-L | Cytosol | L-Malate |
| mql8 | Cytosol | Menaquinol 8 |
| mqn8 | Cytosol | Menaquinone 8 |
| nad | Cytosol | Nicotinamide adenine dinucleotide |
| nadh | Cytosol | Nicotinamide adenine dinucleotide - reduced |
| nadp | Cytosol | Nicotinamide adenine dinucleotide phosphate |
| nadph | Cytosol | Nicotinamide adenine dinucleotide phosphate - reduced |
| nh4 | Cytosol | Ammonium |
| o2 | Cytosol | O2 |
| oaa | Cytosol | Oxaloacetate |
| pep | Cytosol | Phosphoenolpyruvate |
| pi | Cytosol | Phosphate |
| ppi | Cytosol | Diphosphate |
| pro-L | Cytosol | L-Proline |
| pyr | Cytosol | Pyruvate |
| r5p | Cytosol | alpha-D-Ribose 5-phosphate |
| ru5p-D | Cytosol | D-Ribulose 5-phosphate |
| s7p | Cytosol | Sedoheptulose 7-phosphate |
| succ | Cytosol | Succinate |
| succoa | Cytosol | Succinyl-CoA |
| ubq8 | Cytosol | Ubiquinone-8 |
| ubq8h2 | Cytosol | Ubiquinol-8 |
| xu5p-D | Cytosol | D-Xylulose 5-phosphate |

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring eukaryotic organism, comprising at least two gene disruptions, said at least two gene disruptions comprise a first gene disruption occurring in a gene encoding an enzyme selected from the group consisting of a cytosolic pyruvate decarboxylase, a cytosolic ethanol-specific alcohol dehydrogenase, and a mitochondrial ethanol-specific alcohol dehydrogenase, and a second gene disruption occurring in a gene encoding an enzyme selected from the group consisting of a cytosolic malate dehydrogenase, a glycerol-3-phosphate dehydrogenase shuttle, an external NADH dehydrogenase, and an internal mitochondrial NADH dehydrogenase, wherein said at least two gene disruptions confers production of long chain alcohols in the mitochondrion of said organism.

2. The organism of claim 1, wherein production of long chain alcohols is growth-coupled.

3. The organism of claim 1, wherein production of long chain alcohols is not growth-coupled.

4. The organism of claim 1, wherein said first gene disruption is in a gene selected from the group consisting of YLR044C, YLR134W, YGR087C, PDC3, YBR145W, YGL256W, YOL086C, YMR303, YMR083W, YPL088W, YAL061W, YMR318C, YCR105W, and YDL168W.

5. The organism of claim 1, wherein said second gene disruption is in a gene selected from the group consisting of YOL126C, YDL022W, YOL059W, YIL155C, YMR145C, YDL085W, and YML120C.

6. The organism of claim 1, further comprising an exogenous nucleic acid encoding an enzyme in the mitochondrion selected from the group consisting of a pyruvate dehydrogenase, a pyruvate: NADP oxidoreductase, a pyruvate formate lyase, an acylating acetaldehyde dehydrogenase, an acetate CoA ligase, and an AMP-forming acetyl CoA synthetase; or a gene regulatory region thereof.

7. The organism of claim 6, further comprising enhanced NADH transporting shuttle systems for transport of NADH from the cytosol into the mitochondrion.

8. The organism of claim 6, further comprising an exogenous nucleic acid encoding an enzyme in the mitochondrion selected from the group consisting of a transhydrogenase, formate dehydrogenase, a pyruvate decarboxylase, and a pyruvate oxidase; or a gene regulatory region thereof.

9. The organism of claim 1, wherein said strain is in a substantially anaerobic culture medium.

10. The organism of claim 1, wherein said strain is in a microaerobic culture medium.

11. The organism of claim 1, wherein said organism is a yeast or a fungus.

12. The organism of claim 11, wherein said yeast is selected from the group consisting of *Saccharomyces* spp. including *Saccharomyces cerevisiae* and *Schizosaccharomyces pombe*, *Kluyveromyces* spp. including *Kluyveromyces lactis* and *Kluyveromyces marxianus*, and *Pichia* spp. including *Pichia pastoris*.

13. The organism of claim 12, wherein said yeast is *Saccharomyces cerevisiae*.

14. The organism of claim 11, wherein said fungus is selected from the group consisting of *Aspergillus* spp., including *Aspergillus terreus* and *Aspergillus niger*, and *Rhizopus* spp., including *Rhizopus arrhizus* and *Rhizopus oryzae*.

15. A method for producing long chain alcohols, comprising culturing a non-naturally occurring eukaryotic organism according to claim 1.

16. The method of claim 15, wherein production of long chain alcohols is growth-coupled.

17. The method of claim 15, wherein production of long chain alcohols is not growth-coupled.

18. The method of claim 15, wherein said first gene disruption is in a gene selected from the group consisting of YLR044C, YLR134W, YGR087C, PDC3, YBR145W, YGL256W, YOL086C, YMR303, YMR083W, YPL088W, YAL061W, YMR318C, YCR105W, and YDL168W.

19. The method of claim 15, wherein said second gene disruption is in a gene selected from the group consisting of YOL126C, YDL022W, YOL059W, YIL155C, YMR145C, YDL085W, and YML120C.

20. The method of claim 15, further comprising an exogenous nucleic acid encoding an enzyme in the mitochondrion selected from the group consisting of a pyruvate dehydrogenase, a pyruvate: NADP oxidoreductase, a pyruvate formate lyase, an acylating acetaldehyde dehydrogenase, an acetate CoA ligase, and an AMP-forming acetyl CoA synthetase;

or a gene regulatory region thereof.

21. The method of claim 20, further comprising enhanced NADH transporting shuttle systems for transport of NADH from the cytosol into the mitochondrion.

22. The method of claim 20, further comprising an exogenous nucleic acid encoding an enzyme in the mitochondrion selected from the group consisting of a transhydrogenase, formate dehydrogenase, a pyruvate decarboxylase, and a pyruvate oxidase;

or a gene regulatory region thereof.

23. The method of claim 15, wherein said organism is a yeast or a fungus.

24. The method of claim 23, wherein said yeast is selected from the group consisting of *Saccharomyces* spp. including *Saccharomyces cerevisiae* and *Schizosaccharomyces pombe, Kluyveromyces* spp. including *Kluyveromyces lactis* and *Kluyveromyces marxianus*, and *Pichia* spp. including *Pichia pastoris*.

25. The method of claim 24, wherein said yeast is *Saccharomyces cerevisiae*.

26. The method of claim 23, wherein said fungus is selected from the group consisting of *Aspergillus* spp., including *Aspergillus terreus* and *Aspergillus niger*, and *Rhizopus* spp., including *Rhizopus arrhizus* and *Rhizopus oryzae*.

27. The method of claim 15, wherein said strain is cultured in a substantially anaerobic medium.

28. The method of claim 15, wherein said strain is cultured in a microaerobic medium.

* * * * *